(12) United States Patent
Arora et al.

(10) Patent No.: US 7,456,200 B2
(45) Date of Patent: Nov. 25, 2008

(54) COMPOUNDS

(75) Inventors: Jalaj Arora, Cambridge (CA); Louise Edwards, Mississauga (CA); Methvin Isaac, Etoicoke (CA); Donald A. McLeod, Salt Lake City, UT (US); Abdelmalik Slassi, Mississauga (CA); Tomislav Stefanac, Burlington (CA); Thomas M. Stormann, Salt Lake City, UT (US); David Wensbo, Sodertalje (SE); Tao Xin, Woodbridge (CA); Helena Gyback, Sodertalje (SE); Martin Johansson, Sodertalje (SE); Annika Kers, Sodertalje (SE); John Malmberg, Sodertalje (SE); Alexander Minidis, Sodertalje (SE); Karin Oscarsson, Sodertalje (SE); Mangus Waldman, Sodertalje (SE); Ulrika Yngve, Sodertalje (SE); Christoffer Osterwall, Sodertalje (SE)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 11/274,611

(22) Filed: Nov. 14, 2005

(65) Prior Publication Data
US 2006/0122397 A1 Jun. 8, 2006

Related U.S. Application Data

(62) Division of application No. 10/637,012, filed on Aug. 8, 2003, now abandoned.

(60) Provisional application No. 60/402,040, filed on Aug. 9, 2002.

(51) Int. Cl.
A61K 31/44 (2006.01)
C07D 413/14 (2006.01)

(52) U.S. Cl. .................................. 514/340; 546/272.1

(58) Field of Classification Search .............. 546/272.1; 514/340
See application file for complete search history.

(56) References Cited

U.S. PATENT DOCUMENTS

| 3,740,434 | A | 6/1973 | Berkelhammer et al. |
| 3,816,426 | A | 6/1974 | Lee |
| 5,140,034 | A | 8/1992 | Baker et al. |
| 5,631,269 | A | 5/1997 | Broughton et al. |
| 2005/0272779 | A1 * | 12/2005 | Edwards et al. .............. 514/341 |
| 2007/0129408 | A1 * | 6/2007 | Minidis et al. .............. 514/341 |

FOREIGN PATENT DOCUMENTS

| EP | 0 377 457 | 7/1990 |
| EP | 0 397 365 | 11/1990 |
| EP | 0 422 369 | 4/1991 |
| EP | 0 438 230 B1 | 4/1997 |
| GB | 2 070 603 A | 9/1981 |
| WO | WO 98/57969 | 12/1998 |
| WO | WO 99/26927 | 6/1999 |
| WO | WO 00/35285 | 6/2000 |
| WO | WO 00/35913 | 6/2000 |
| WO | WO 00/63204 | 10/2000 |
| WO | WO 01/12627 A1 | 2/2001 |
| WO | WO 01/26656 A2 | 4/2001 |
| WO | WO 01/47918 | 7/2001 |
| WO | WO 02/24680 A1 | 3/2002 |
| WO | WO 02/46166 A1 | 6/2002 |
| WO | WO 03/008411 A1 | 1/2003 |
| WO | WO 2005/077345 | 8/2005 |
| WO | WO 2005/080397 | 9/2005 |

OTHER PUBLICATIONS

Shishue Chiou et al., "A Simplified Procedure for Preparing 3,5-Disubstituted-1,2,4-Oxadiazoles by Reaction of Amidoximes with Acyl Chlorides in Pyridine Solution", J. Heterocyclic Chem., 26, (1989), pp. 125-128.

Jong Chan Lee et al., "A Novel and Direct Synthesis of 2-Alkyl-5-Aryl Disubstituted Oxazoles", Tetrahedron Letters, vol. 38, No. 52, pp. 8959-8960, 1997.

Andrew J. Phillips et al., "Synthesis of Functionalized Oxazolines and Oxazoles with DAST and Deoxo-Fluor", Org. Lett., vol. 2, No. 8, 2000, pp. 1165-1168.

Stephen T. Meller et al., "Acute Mechanical Hyperalgesia is Produced by Coactivation of AMPA and Metabotropic Glutamate Receptors", NeuroReport, vol. 4, No. 7, Jul. 1993, pp. 879-882.

Norton P. Peet et al., "Factors Which Influence the Formation of Oxadiazoles from Anthranilhydrazides and Other Benzoylhydrazines", J. Heterocyclic Chem., vol. 21, 1807-1816 (1984).

Andrius Baskys, "Metabotropic receptors and 'slow' excitatory actions of glutamate agonists in the hippocampus", TINS, vol. 15, No. 3, 1992, pp. 92-96.

(Continued)

Primary Examiner—Rebecca L Anderson
(74) Attorney, Agent, or Firm—Birch Stewart Kolasch & Birch LLP

(57) ABSTRACT

The present invention relates to new compounds of formula I,

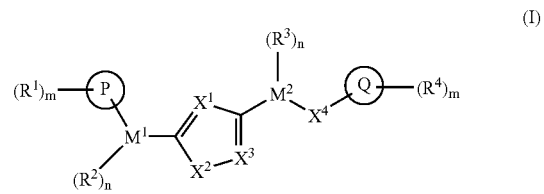

a process for their preparation and new intermediates prepared therein, pharmaceutical formulations containing compounds of the formula I and to the use of compounds of the formula I in therapy.

11 Claims, No Drawings

OTHER PUBLICATIONS

Darryle D. Schoepp et al., "Metabotropic glutamate receptors in brain function and pathology", TIPS, vol. 14, 1993, pp. 13-20.

Darryle D. Schoepp et al., "Novel Functions for Subtypes of Metabotropic Glutamate Receptors", Neurochem. Int. vol. 24, No. 5, pp. 439-449, 1994.

J.-P. Pin et al., "Review: Neurotransmitter receptors 1 The Metabotropic Glutamate Receptors: Structure and Functions", Neuropharmacology vol. 34, No. 1, pp. 1-26, 1995.

Shigetada Nakanishi, "Metabotropic Glutamate Receptors: Synaptic Transmission, Modulation, and Plasticity", Neuron, vol. 13, 1031-1037, Nov. 1994.

Thomas Knöpfel et al., "Metabotropic Glutamate Receptors: Novel Targets for Drug Development", Journal of Medicinal Chemistry, vol. 38, No. 9, Apr. 1995, pp. 1417-1426.

Jean-Philippe Pin et al., "Alternative splicing generates metabotropic glutamate receptors inducing different patterns of calcium release in *Xenopus oocytes*", Neurobiology, Proc. Natl. Acad. Sci. USA, vol. 89, pp. 10331-10335, Nov. 1992.

Cécile Joly et al., "Molecular, Functional and Pharmacological Characterization of the Metabotropic Glutamate Receptor Type 5 Splice Variants: Comparison with mGluR1", The Journal of Neuroscience, May 1995, vol. 15, No. 5, pp. 3970-3981.

"Trends in Pharmacological Sciences including Toxicological Sciences", Reference Edition, vol. 13, 1992, Elsevier Science Ltd.

"Meeting Reports: Angiosuppressive Therapy for Cancer", TIPS, vol. 15, Feb. 1994, pp. 33-36.

Zafar I. Bashir et al, "Induction of LTP in the hippocampus needs synaptic activation of glutamate metabotropic receptors", Nature, vol. 363, May 1993, pp. 347-350.

Z. A. Bortolotto et al., "A molecular switch activated by metabotropic glutamate receptors regulates induction of long-term potentiation", Nature. vol. 368, Apr. 1994, pp. 740-743.

Atsu Aiba et al, "Reduced Hippocampal Long-Term Potentiation and Context-Specific Deficit in Associative Learning in mGluR1 Mutant Mice", Cell, vol. 79, Oct. 1994, pp. 365-375.

Atsu Aiba et al., "Deficient Cerebellar Long-Term Depression and Impaired Motor Learning in mGluR1 Mutant Mice", Cell, vol. 79, Oct. 1994, 377-388.

Fabio Bordi et al., "Involvement of mGluR$_5$ on acute nociceptive transmission", Brain Research 871 (2000), pp. 223-233.

Michael Hollmann et al., "Cloned Glutamate Receptors" Annu. Rev. Neurosci., 1994, 17, 31-108.

Will P.J.M. Spooren et al., "Novel allosteric antagonists shed light on mglu$_5$ receptors and CNS disorders", TRENDS inj Pharmacological Sciences, vol. 22, No. 7, 2001, pp. 331-337.

Fabrizio Gasparini et al., "Allosteric modulators of group I metabotropic glutamate receptors: novel subtype-selective ligands and therapeutic perspectives", Neurosciences, 2002, pp. 43-49.

Volker Neugebauer, "Metabotropic glutamate receptors—important modulators of nociception and pain behavior" Pain , 98, 2002, pp. 1-8.

Ichiro Aramori et al., "Signal Transduction and Pharmacological Characteristics of a Metabotropic Glutamate Receptor, mGluR1, in Transfected CHO Cells", Neuron, vol. 8, Apr. 1992, pp. 757-765.

Yasuto Tanabe et al., "A Family of Metabotropic Glutamate Receptors", Neuron, vol. 8, 169-179, Jan. 1992.

Stephan Miller et al., "Growth Factor Upregulation of a Phosphoinositide-Coupled Metabotropic Glutamate Receptor in Cortical Astrocytes", The Journal of Neuroscience, 15(9), Sep. 1995, pp. 6103-6109.

Robert Balåzs et al., "Metabotropic Glutamate Receptor mGluR5 in astrocytes: Pharmacological Properties and Agonist Regulation", J. Neurochem., vol. 69, No. 1, 1997, pp. 151-163.

M. Schlosser, "Organometallics in Synthesis", A Manual, Edited by M. Schlosser, Universite de Lausanne, Lausanne, Switzerland, 1994, John Wiley & Sons Ltd., West Sussex England.

Rébecca F. Poulain et al., "Parallel synthesis of 1,2,4-oxadiazoles from carboxylic acids using an improved, uranium-based, activation", Tetrahedron Letters 42 (2001), pp. 1495-1498.

Anthony R. Gangloff et al., "Synthesis of 3,5-disubstituted-1,2,4-oxadiazoles using tetrabutylammonium fluoride as a mild and efficient catalyst", Tetrahedron Letters 42 (2001) 1441-1443.

Robert J. Mathvink et al., "Potent, Selective Human $\beta_3$ Adrenergic Receptor Agonists Containing a Substituted Indoline-5-Sulfonamide Pharmacophore", Bioorganic & Medicinal Chemistry Letters 9 (1999) 1869-1874.

Reiko Minakami et al, "Molecular Cloning and the Functional Expression of Two Isoforms of Human Metabotropic Glutamate Receptor Subtype 5", Biochemical and Biophysical Research Communications, vol. 199, No. 3, Mar. 1994, pp. 1136-1143.

Jae Nyoung Kim et al., "A Convenient Synthesis of Benzohydroximoyl Chlorides as Nitrile Oxide Precursors by HCl/ N,N-Dimethylformamide/Oxone System", J. Org. Chem. 1992, 57. pp. 6649-6650.

Chun-Sing Li et al., "Synthesis of pyran-4-ones from isoxazoles", Tetrahedron Letters 43 (2002) 3565-3568.

Branko S. Jursic et al., "Preparation of 5-substituted 2-Methyl-1,3,4-Oxadiazoles from 5-Substituted Tetrazoles and Acetic Anhydride", Synthetic Communications, 24(11), 1575-1582 (1994).

John Saunders et al., "Novel Quinuclidine—Based Ligands for the Muscarinic Cholinergic Receptor", J. Med. Chem. 1990, 33, 1128-1138.

Akio Kakefuda et al., "Discovery of 4,5-Diphenyl-1,2,4-triazole Derivatives as a Novel Class of Selective Antagonists for the Human $V_{1A}$ Receptor", Bioorganic & Medicinal Chemistry 10 (2002), 1905-1912.

Al-Talib et al., "A convenient synthesis of alky 1 and aryl substituted bis-1,3,4-oxadiazoles" Synth. Commun., vol. 20, No. 12 (1990), pp. 1811-1817.

Gunay et al., "5-Nitroimidazole derivatives as possible antibacterial and antifungal agents", IL Farmaco, vol. 54 (1999), pp. 826-831.

Holla et al., "Synthesis and antibacterial studies of a new series of 1,2-bis(1,3,4-oxadiazol-2-yl) ethanes . . . ", European Journal of medicinal Chemistry, Editions Scientifique Elsevier, Paris, vol. 35, No. 2, (2000), pp. 267-271.

Madronero et al., "Tetrazole analogues of arylthiazolylacetic acids. Synthesis and pharmacological study", European Journal of Medicinal Chemistry, vol. 9, No. 4, (1974), pp. 445-448.

Miyaura et al., "The Palladium-Catalyzed Cross-Coupling Reaction of Phenylboronic Acid with Haloarenes in the Presence of Bases", Synth Commun., vol. 11(7) (1981) pp. 513-520.

Srivastava et al., "Mass Spectra of 5,5'-(1,2-ethanediyl)bis [3-(aryl)-1,2,4-oxadiazoles]" Org. Mass Spectrom., vol. 26, No. 11, (1991), pp. 1017-1018.

Watkins et al., "Phenylglycine derivatives as antagonists of metabotropic glutamate receptors", Trends Pharmacol. Sci., vol. 15 (1994), pp. 33-36.

Database Crossfire Beilstein "Online" Accession No. 4885431 & Org Mass Spectrom. (1991), 26(11), 1017-1018, XP002264298.

Database Crossfire Beilstein "Online" Accession No. 4208871 XP002264299, & Synth Commun. (1990), 20(12), 1811-1817.

Database CHEMCATS "Online" Chem, Abstracts Service, Columbus, Ohio, US XP002264300 & "Maybridge HTS", May 14, 2004 Maybridge PLc, Tintagel, Cornwall, PL34 OHW, UK.

\* cited by examiner

COMPOUNDS

This application is a Divisional of co-pending application Ser. No. 10/637,012, filed on Aug. 8, 2003, the entire contents of which are hereby incorporated by reference and for which priority is claimed under 35 U. S. C. § 120.

FIELD OF THE INVENTION

The present invention relates to a new class of compounds, to pharmaceutical formulations containing said compounds and to the use of said compounds in therapy. The present invention further relates to the process for the preparation of said compounds and to new intermediates prepared therein.

BACKGROUND OF THE INVENTION

Glutamate is the major excitatory neurotransmitter in the mammalian central nervous system (CNS). Glutamate produces its effects on central neurons by binding to and thereby is activating cell surface receptors. These receptors have been divided into two major classes, the ionotropic and metabotropic glutamate receptors, based on the structural features of the receptor proteins, the means by which the receptors transduce signals into the cell, and pharmacological profiles.

The metabotropic glutamate receptors (mGluRs) are G protein-coupled receptors that activate a variety of intracellular second messenger systems following the binding of glutamate. Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels. Schoepp et al., *Trends Pharmacol. Sci.* 14:13 (1993), Schoepp, *Neurochem. Int.* 24:439 (1994), Pin et al., *Neuropharmacology* 34:1 (1995), Bordi and Ugolini, *Prog. Neurobiol.* 59:55 (1999).

Molecular cloning has identified eight distinct mGluR subtypes, termed mGluR1 through mGluR8. Nakanishi, *Neuron* 13:1031 (1994), Pin et al., *Neuropharmacology* 34:1 (1995), Knopfel et al, *J. Med. Chem.* 38:1417 (1995). Further receptor diversity occurs via expression of alternatively spliced forms of certain mGluR subtypes. Pin et al., *PNAS* 89:10331 (1992), Minakami et al., *BBRC* 199:1136 (1994), Joly et al., *J. Neurosci.* 15:3970 (1995).

Metabotropic glutamate receptor subtypes may be subdivided into three groups, Group I, Group II, and Group III mGluRs, based on amino acid sequence homology, the second messenger systems utilized by the receptors, and by their pharmacological characteristics. Group I mGluR comprises mGluR1, mGluR5 and their alternatively spliced variants. The binding of agonists to these receptors results in the activation of phospholipase C and the subsequent mobilization of intracellular calcium.

Attempts at elucidating the physiological roles of Group I mGluRs suggest that activation of these receptors elicits neuronal excitation. Various studies have demonstrated that Group I mGluRs agonists can produce postsynaptic excitation upon application to neurons in the hippocampus, cerebral cortex, cerebellum, and thalamus, as well as other CNS regions. Evidence indicates that this excitation is due to direct activation of postsynaptic mGluRs, but it also has been suggested that activation of presynaptic mGluRs occurs, resulting in increased neurotransmitter release. Baskys, *Trends Pharmacol. Sci.* 15:92 (1992), Schoepp, *Neurochem. Int.* 24:439 (1994), Pin et al., *Neuropharmacology* 34:1(1995), Watkins et al., *Trends Pharmacol. Sci.* 15:33 (1994).

Metabotropic glutamate receptors have been implicated in a number of normal processes in the mammalian CNS. Activation of mGluRs has been shown to be required for induction of hippocampal long-term potentiation and cerebellar long-term depression. Bashir et al., *Nature* 363:347 (1993), Bortolotto et al., *Nature* 368:740 (1994), Aiba et al., *Cell* 79:365 (1994), Aiba et al., *Cell* 79:377 (1994). A role for mGluR activation in nociception and analgesia also has been demonstrated, Meller et al., *Neuroreport* 4: 879 (1993), Bordi and Ugolini, *Brain Res.* 871:223 (1999). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex. Nakanishi, *Neuron* 13: 1031 (1994), Pin et al., *Neuropharmacology* 34:1, Knopfel et al., *J. Med. Chem.* 38:1417 (1995).

Further, Group I metabotropic glutamate receptors and mGluR5 in particular, have been suggested to play roles in a variety of pathophysiological processes and disorders affecting the CNS. These include stroke, head trauma, anoxic and ischemic injuries, hypoglycemia, epilepsy, neurodegenerative disorders such as Alzheimer's disease and pain. Schoepp et at, *Trends Pharmacol. Sci.* 14:13 (1993), Cunningham et al., *Life Sci.* 54:135 (1994), Hollman et al., *Ann. Rev. Neurosci.* 17:31 (1994), Pin et al., *Neuropharmacology* 34:1 (1995), Knopfel et al., *J. Med. Chem.* 38:1417 (1995), Spooren et al., *Trends Pharmacol. Sci.* 22:331 (2001), Gasparini et al. *Curr. Opin. Pharmacol.* 2:43 (2002), Neugebauer *Pain* 98:1 (2002). Much of the pathology in these conditions is thought to be due to excessive glutamate-induced excitation of CNS neurons. Because Group I mGluRs appear to increase glutamate-mediated neuronal excitation via postsynaptic mechanisms and enhanced presynaptic glutamate release, their activation probably contributes to the pathology. Accordingly, selective antagonists of Group I mGluR receptors could be therapeutically beneficial, specifically as neuroprotective agents, analgesics or anticonvulsants.

Recent advances in the elucidation of the neurophysiological roles of metabotropic glutamate receptors generally and Group I in particular, have established these receptors as promising drug targets in the therapy of acute and chronic neurological and psychiatric disorders and chronic and acute pain disorders. Because of their physiological and pathophysiological significance, there is a need for new potent mGluR agonists and antagonists that display a high selectivity for mGluR subtypes, particularly the Group I receptor subtype, most particularly the mGluR5 subtype.

The object of the present invention is to provide compounds exhibiting an activity at metabotropic glutamate receptors (mGluRs), especially at the mGluR5 receptor.

SUMMARY OF THE INVENTION

The present invention provides a compound of formula Ia

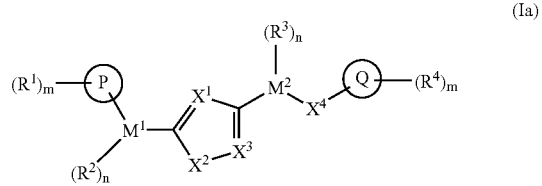

wherein:

P is selected from the group consisting of hydrogen, $C_{3-7}$alkyl or a 3- to 8-membered ring containing one or more atoms independently selected from C, N, O and S, which ring may optionally be fused with a 5- or 6-membered ring containing one or more atoms independently selected from the group consisting of C, N, O and S;

$R^1$ is selected from the group consisting of hydrogen, hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, $(CO)R^5$, $O(CO)R^5$, $O(CO)OR^5$, $O(CN)OR^5$, $C_{1-6}$alkyl$OR^5$, $OC_{2-6}$alkyl$OR^5$, $C_{1-6}$alkyl$(CO)R^5$, $OC_{1-6}$alkyl$(CO)R^5$, $C_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^6$, $OC_{2-6}$alkyl$NR^5R^6$, $C_{1-6}$alkyl$(CO)NR^5R^6$, $OC_{1-6}$alkyl$(CO)NR^5R^6$, $C_{0-6}$alkyl$NR^5(CO)R^6$, $OC_{2-6}$alkyl$NR^5(CO)R^6$, $C_{0-6}$alkyl$NR^5(CO)NR^5R^6$, $C_{0-6}$alkyl$SR^5$, $OC_{2-6}$alkyl$SR^5$, $C_{0-6}$alkyl$(SO)R^5$, $OC_{2-6}$alkyl$(SO)R^5$, $C_{0-6}$alkyl$SO_2R^5$, $OC_{2-6}$alkyl$SO_2R^5$, $C_{0-6}$alkyl$(SO_2)NR^5R^6$, $OC_{2-6}$alkyl$(SO_2)NR^5R^6$, $C_{0-6}$alkyl$NR^5(SO_2)R^6$, $OC_{2-6}$alkyl$NR^5(SO_2)R^6$, $C_{0-6}$alkyl$NR^5(SO_2)NR^5R^6$, $OC_{2-6}$alkyl$NR^5(SO_2)NR^5R^6$, $(CO)NR^5R^6$, $O(CO)NR^5R^6$, $NR^5OR^6$, $C_{0-6}$alkyl$NR^5(CO)OR^6$, $OC_{2-6}$alkyl$NR^5(CO)OR^6$, $SO_3R^5$ and a 5- or 6-membered ring containing one or more atoms independently selected from the group consisting of C, N, O and S, wherein said ring may be substituted by one or more A;

$M^1$ is selected from the group consisting of a bond, $C_{1-3}$alkyl, $C_{2-3}$alkenyl, $C_{2-3}$alkynyl, $C_{0-4}$alkyl$(CO)C_{0-4}$alkyl, $C_{0-3}$alkyl$OC_{0-3}$alkyl, $C_{0-3}$alkyl$(CO)NR^5$, $C_{0-3}$alkyl$(CO)NR^5C_{0-3}$alkyl, $C_{0-4}$alkyl$NR^5$, $C_{0-3}$alkyl$SC_{0-3}$alkyl, $C_{0-3}$alkyl$(SO)C_{0-3}$alkyl or $C_{0-3}$alkyl$(SO_2)C_{0-3}$alkyl; $R^2$ is selected from the group consisting of hydrogen, hydroxy, $C_{0-6}$alkylcyano, oxo, $=NR^5$, $=NOR^5$, $C_{1-4}$alkylhalo, halo, $C_{1-4}$alkyl, $O(CO)C_{1-4}$alkyl, $C_{1-4}$alkyl$(SO)C_{0-4}$alkyl, $C_{1-4}$alkyl$(SO_2)C_{0-4}$alkyl, $(SO)C_{0-4}$alkyl, $(SO_2)C_{0-4}$alkyl, $OC_{1-4}$alkyl, $C^{1-4}$alkyl$OR^5$ and $C_{0-4}$alkyl$NR^5R^6$;

$X^1$, $X^2$ and $X^3$ are independently selected from the group consisting of CR, CO, N, NR, O and S;

R is selected from the group consisting of hydrogen, $C_{0-3}$alkyl, halo, $C_{0-3}$alkyl$OR^5$, $C_{0-3}$alkyl$NR^5R^6$, $C_{0-3}$alkyl$(CO)OR^5$, $C_{0-3}$alkyl$NR^5R^6$ and $C_{0-3}$alkylaryl;

$M^2$ is selected from a group consisting of a bond, $C_{1-3}$alkyl, $C_{3-7}$cycloalkyl, $C_{2-3}$alkenyl, $C_{2-3}$alkynyl, $C_{0-4}$alkyl$(CO)C_{0-4}$alkyl, $C_{0-3}$alkyl$OC_{0-3}$alkyl, $C_{0-3}$alkyl$NR^5C_{1-3}$alkyl, $C_{0-3}$alkyl$(CO)NR^5$, $C_{0-4}$alkyl$NR^5$, $C_{0-3}$alkyl$SC_{0-3}$alkyl, $C_{0-3}$alkyl$(SO)C_{0-3}$alkyl and $C_{0-3}$alkyl$(SO_2)C_{0-3}$alkyl;

$R^3$ is selected from a group consisting of hydrogen, hydroxy, $C_{0-6}$alkylcyano, oxo, $=NR^5$, $=NOR^5$, $C_{1-4}$alkylhalo, halo, $C_{1-4}$alkyl, $O(CO)C_{1-4}$alkyl, $C_{1-4}$alkyl$(SO)C_{0-4}$alkyl, $C_{1-4}$alkyl$(SO_2)C_{0-4}$alkyl, $(SO)C_{0-4}$alkyl, $(SO_2)C_{0-4}$alkyl, $OC_{1-4}$alkyl, $C_{1-4}$alkyl$OR^5$ and $C_{0-4}$alkyl$NR^5R^6$;

$X^4$ is selected from the group consisting of $C_{0-4}$alkyl$R^5$, $C_{0-4}$alkyl$(NR^5R^6)$, $C_{0-4}$alkyl$(NR^5R^6)=N$, $NR^5C_{0-4}$alkyl$(NR^5R^6)=N$, $NOC_{0-4}$alkyl, $C_{1-4}$alkylhalo, C, O, SO, $SO_2$ and S;

Q is a 5- or 6-membered ring containing one or more atoms independently selected from the group consisting of C, N, O and S, which group may optionally be fused with a 5- or 6-membered ring containing one or more atoms independently selected from the group consisting of C, N, O and S and which fused ring may be substituted by one or more A;

$R^4$ is selected from the group consisting of hydrogen, hydroxy, $C_{0-6}$alkylcyano, oxo, $=NR^5$, $=NOR^5$, $C_{1-4}$alkylhalo, halo, $C_{1-4}$alkyl, $OC_{1-4}$alkyl, $OC_{0-6}$alkylaryl, $O(CO)C_{1-4}$alkyl, $C_{0-4}$alkyl$(S)C_{0-4}$alkyl, $C_{1-4}$alkyl$(SO)C_{0-4}$alkyl, $C_{1-4}$alkyl$(SO_2)C_{0-4}$alkyl, $(SO)C_{0-4}$alkyl, $(SO_2)C_{0-4}$alkyl, $C_{1-4}$alkyl$OR^5$, $C_{0-4}$alkyl$NR^5R^6$ and a 5- or 6-membered ring containing one or more atoms independently selected from C, N, O or S, wherein said ring may be substituted by one or more A;

$R^5$ and $R^6$ are independently selected from the group consisting of hydrogen, hydroxy, $C_{1-6}$alkyl, $C_{0-6}$alkyl$C_{3-6}$cycloalkyl, $C_{0-6}$alkylaryl, $C_{0-6}$alkylheteroaryl and a 5- or 6-membered ring containing one or more atoms independently selected from C, N, O and S, and wherein $R^5$ and $R^6$ may together form a 5- or 6-membered ring containing one or more atoms independently selected from the group consisting of C, N, O and S;

wherein any $C_{1-6}$alkyl, $C_{2-6}$alkenyl, $C_{2-6}$alkynyl, $C_{0-6}$alkyl$C_{3-6}$cycloalkyl, $C_{0-6}$alkylaryl and $C_{0-6}$alkylheteroaryl defined under $R^1$, $R^2$, $R^3$, $R^4$, $R^5$ and $R^6$ may be substituted by one or more A;

A is selected from the group consisting of hydrogen, hydroxy, oxo, halo, nitro, $C_{0-6}$alkylcyano, $C_{1-4}$alkyl, $C_{0-4}$alkyl$C_{3-6}$cycloalkyl, $C_{1-6}$alkylhalo, $OC_{1-6}$alkylhalo, $C_{2-6}$alkenyl, $OC_{1-6}$alkyl, $C_{0-3}$alkylaryl, $C_{0-6}$alkyl$OR^5$, $OC_{2-6}$alkyl$OR^5$, $C_{1-6}$alkyl$SR^5$, $OC_{2-6}$alkyl$SR^5$, $(CO)R^5$, $O(CO)R^5$, $OC_{2-6}$alkylcyano, $C_{0-6}$alkyl$CO_2R^5$, $OC_{1-6}$alkyl$CO_2R^5$, $O(CO)OR^5$, $OC_{1-6}$alkyl$(CO)R^5$, $C_{1-6}$alkyl$(CO)R^5$, $NR^5OR^6$, $C_{0-6}$alkyl$NR^5R^6$, $OC_{2-6}$alkyl$NR^5R^6$, $C_{0-6}$alkyl$(CO)NR^5R^6$, $OC_{1-6}$alkyl$(CO)NR^5R^6$, $OC_{2-6}$alkyl$NR^5(CO)R^6$, $C_{0-6}$alkyl$NR^5(CO)R^6$, $C_{0-6}$alkyl$NR^5(CO)NR^5R^6$, $O(CO)NR^5R^6$, $NR^5(CO)R^6$, $C_{0-6}$alkyl$(SO_2)NR^5R^6$, $OC_{2-6}$alkyl$(SO_2)NR^5R^6$, $C_{0-6}$alkyl$NR^5(SO_2)R^6$, $OC_{2-6}$alkyl$NR^5(SO_2)R^6$, $SO_3R^5$, $C_{1-6}$alkyl$NR^5(SO_2)NR^5R^6$, $OC_{2-6}$alkyl$(SO_2)R^5$, $C_{0-6}$alkyl$(SO_2)R^5$, $C_{0-6}$alkyl$(SO)R^5$, $OC_{2-6}$alkyl$(SO)R^5$ and a 5- or 6-membered ring containing one or more atoms independently selected from the group consisting of C, N, O and S;

m is selected from 0, 1, 2, 3 and 4; and n is selected from 0, 1, 2 and 3, or salt thereof.

The present invention provides a compound of formula I

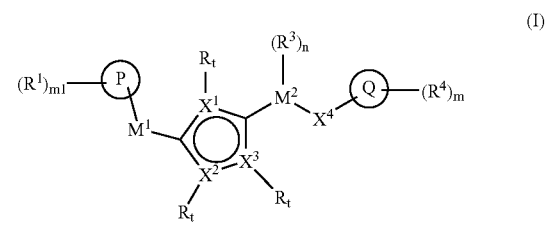

wherein:

P is selected from the group consisting of thiophene, pyridyl, thiazolyl, furyl, pyrrolyl and phenyl, whereby the phenyl ring is substituted on position 3 or disubstituted on positions 2 and 5;

$R^1$ is attached to P via a carbon atom on ring P and is selected from the group consisting of hydrogen, hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, $(CO)R^5$, $O(CO)R^5$, $O(CO)OR^5$, $O(CN)OR^5$, $C_{1-6}$alkyl$OR^5$, $OC_{2-6}$alkyl$OR^5$, $C_{1-6}$alkyl$(CO)R^5$, $OC_{1-6}$alkyl$(CO)R^5$, $C_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^6$, $OC_{2-6}$alkyl$NR^5R^6$, $C_{1-6}$alkyl$(CO)NR^5R^6$, $OC_{1-6}$alkyl$(CO)NR^5R^6$, $C_{0-6}$alkyl$NR^5(CO)R^6$, $OC_{2-6}$alkylNR$^5$(CO)R$^6$, C$_{0-6}$alkylNR$^5$(CO)NR$^5$R$^6$, C$_{0-6}$alkylSR$^5$, OC$_{2-6}$alkylSR$^5$, C$_{0-6}$alkyl(SO)R$^5$, OC$_{2-6}$alkyl(SO)R$^5$, C$_{0-6}$alkylSO$_2$R$^5$, OC$_{2-6}$alkylSO$_2$R$^5$, C$_{0-6}$alkyl(SO$_2$)NR$^5$R$^6$, OC$_{2-6}$alkyl(SO$_2$)NR$^5$R$^6$, C$_{0-6}$alkylNR$^5$(SO$_2$)R$^6$, OC$_{2-6}$alkylNR$^5$(SO$_2$)R$^6$, C$_{0-6}$alkylNR$^5$(SO$_2$)NR$^5$R$^6$, OC$_{2-6}$alkylNR$^5$ (SO$_2$)NR$^5$R$^6$, (CO)NR$^5$R$^6$, O(CO)NR$^5$R$^6$, NR$^5$OR$^6$, C$_{0-6}$alkylNR$^5$(CO)OR$^6$, OC$_{2-6}$alkylNR$^5$(CO)OR$^6$, SO$_3$R$^5$ and a 5- or 6-membered ring containing one or more atoms independently selected from the group consisting of C, N, O and S;

M$^1$ is a bond;

X$^1$ selected from the group consisting of C, CO, N, O and S;

X$^2$ is selected from the group consisting of C, N, O and S;

X$^3$ is i) selected from the group consisting of N, O and S, or ii) selected from N, O, S, and C when X$^2$ is selected from N, O, or S, and when X$^3$ is C the substituent R on X$^3$ is H;

R is selected from the group consisting of hydrogen, C$_{0-3}$alkyl, halo, C$_{0-3}$alkylOR$^5$, C$_{0-3}$alkylNR$^5$R$^6$, C$^{0-3}$alkyl(CO)OR$^5$ and C$_{0-3}$alkylaryl;

M$^2$ is selected from a group consisting of a bond, C$_{1-3}$alkyl, C$_{2-3}$alkynyl, C$_{0-4}$alkyl(CO)C$_{0-4}$alkyl, C$_{0-3}$alkylOC$_{0-3}$alkyl, C$_{0-3}$alkylNR$^5$C$_{1-3}$alkyl, C$_{0-3}$alkyl(CO)NR$^5$, C$_{0-4}$alkylNR$^5$, C$_{0-3}$alkyl(SO)C$_{0-3}$alkyl and C$_{0-3}$alkyl(SO$_2$)C$_{0-3}$alkyl;

R$^3$ is selected from a group consisting of hydroxy, C$_{0-6}$alkylcyano, oxo, =NR$^5$, =NOR$^5$, C$_{1-4}$alkylhalo, halo, C$_{1-4}$alkyl, O(CO)C$_{1-4}$alkyl, C$_{1-4}$alkyl(SO)C$_{0-4}$alkyl, C$_{1-4}$alkyl(SO$_2$)C$_{0-4}$alkyl, (SO)C$_{0-4}$alkyl, (SO$_2$)C$_{0-4}$alkyl, OC$_{1-4}$alkyl, C$_{1-4}$alkylOR$^5$ and C$_{0-4}$alkylNR$^5$R$^6$;

X$^4$ is selected from the group consisting of C$_{0-4}$alkylR$^5$R$^6$, C$_{3-7}$cycloalkyl, C$_{1-4}$alkyl(NR$^5$R$^6$), NR$^5$, C$_{0-4}$alkyl(NR$^5$R$^6$) =N, NR$^5$C$_{0-4}$alkyl(N$^5$R$^6$)=N, NOC$_{0-4}$alkyl, C$_{1-4}$alkylhalo, O, SO, SO$_2$ and S, and wherein the bond between M$^2$ and X$^4$ is a single bond;

Q is i) selected from the group consisting of triazolyl, imidazolyl, oxadiazolyl, imidazolonyl, oxazolonyl, thiazolonyl, tetrazolyl and thiadiazolyl, and wherein any substitutable nitrogen atom in the ring is substituted with R$^4$ on such nitrogen atom and any suitable carbon atom is optionally substituted with R$^4$; and R$^4$ is selected from the group consisting of C$_{0-6}$alkylcyano, =NC$_{1-4}$alkyl, =NOR$^5$, C$_{1-4}$alkylhalo, halo, C$_{1-6}$alkyl, OC$_{1-4}$alkyl, C$_{2-4}$alkenyl, C$_{0-2}$alkylC$_{3-6}$cycloalkyl, C$_{0-6}$alkylaryl, C$_{0-6}$alkylheteroaryl, OC$_{0-6}$alkylaryl, OC$_{0-6}$alkylheteroaryl, NC$_{0-6}$alkylaryl, NC$_{0-6}$alkylheteroaryl, C$_{0-6}$alkylOaryl, C$_{0-6}$alkylOheteroaryl, C$_{0-6}$alkylNaryl, C$_{0-6}$alkylNheteroaryl, OC$_{0-6}$alkylOaryl, OC$_{0-6}$alkylOheteroaryl, OC$_{0-6}$alkylNaryl, OC$_{0-6}$ alkylNheteroaryl, NC$_{0-6}$alkylOaryl, NC$_{0-6}$alkylOheteroaryl, NC$_{0-6}$alkylNaryl, NC$_{0-6}$alkylNheteroaryl, O(CO)C$_{1-4}$alkyl, C$_{0-4}$alkyl(CO)OC$_{1-4}$alkyl, C$_{1-4}$alkyl(S)C$_{0-4}$alkyl, C$_{1-4}$alkyl(SO)C$_{0-4}$alkyl, C$_{1-4}$alkyl(SO$_2$)C$_{0-4}$alkyl, (SO)C$_{0-4}$alkyl, (SO$_2$)C$_{0-4}$alkyl, C$_{1-4}$alkylOR$^5$, C$_{0-4}$alkylN(C$_{1-4}$alkyl)$_2$ and a 3- or 6-membered non-aromatic ring containing one or more atoms independently selected from C, N, O and S, which ring may optionally be fused with a 5-membered ring containing one or more atoms independently selected from the group consisting of C, N and O and wherein said ring and said fused ring may be substituted by one or two A; or ii) selected from the group consisting of benzoimidazolyl, benzooxazolyl, tetrahydrotriazolopyridyl, tetrahydrotriazolopyrimidinyl, pyridonyl, pyridazinyl, imidazopyridyl, oxazolopyridyl, thiazolopyridyl, imidazopyridazinyl, oxazolopyridazinyl, thiazolopyridazinyl and purinyl; and R$^4$ is selected from the group consisting of hydrogen, hydroxy, C$_{0-6}$alkylcyano, =NR$^5$, =NOR$^5$, C$_{1-4}$alkylhalo, halo, C$_{1-6}$alkyl, OC$_{1-4}$alkyl, OC$_{0-6}$alkylaryl, O(CO)C$_{1-4}$alkyl, C$_{0-4}$alkyl(S)C$_{0-4}$alkyl, C$_{1-4}$alkyl(SO)C$_{0-4}$alkyl, C$_{1-4}$alkyl(SO$_2$)C$_{0-4}$alkyl, (SO)C$_{0-4}$alkyl, (SO$_2$)C$_{0-4}$alkyl, C$_{1-4}$alkylOR$^5$, C$_{0-4}$alkylNR$^5$R$^6$ and a 5- or 6-membered ring containing one or more atoms independently selected from C, N, O and S, which ring may optionally be fused with a 5- or 6-membered ring containing one or more atoms independently selected from the group consisting of C, N and O and wherein said ring and said fused ring may be substituted by one or two A;

R$^5$ and R$^6$ are independently selected from the group consisting of hydrogen and C$_{1-6}$alkyl;

wherein any C$_{1-6}$alkyl defined under R$^1$, R$^2$ and R$^4$ may be substituted by one or more A;

A is selected from the group consisting of hydrogen, hydroxy, halo, nitro, oxo, C$_{0-6}$alkylcyano, C$_{0-4}$alkylC$_{3-6}$cycloalkyl, C$_{1-6}$alkyl, C$_{1-6}$alkylhalo, OC$_{1-6}$alkylhalo, C$_{2-6}$alkenyl, C$_{0-3}$alkylaryl, C$_{0-6}$alkylOR$^5$, OC$_{2-6}$alkylOR$^5$, C$_{1-6}$alkylSR$^5$, OC$_{2-6}$alkylSR$^5$, (CO)R$^5$, O(CO)R$^5$, OC$_{2-6}$alkylcyano, OC$_{1-6}$alkylCO$_2$R$^5$, O(CO)OR$^5$, OC$_{1-6}$alkyl(CO)R$^5$, C$_{1-6}$alkyl(CO)R$^5$, NR$^5$OR$^6$, OC$_{2-6}$alkylNR$^5$R$^6$, C$_{0-6}$alkyl(CO)NR$^5$R$^6$, OC$_{1-6}$alkyl(CO)NR$^5$R$^6$, OC$_{2-6}$alkylNR$^5$(CO)R$^6$, C$_{0-6}$alkylNR$^5$(CO)R$^6$, C$_{0-6}$alkylNR$^5$(CO)NR$^5$R$^6$, O(CO)NR$^5$R$^6$, C$_{0-6}$alkyl(SO$_2$)NR$^5$R$^6$, OC$_{2-6}$alkyl(SO$_2$)NR$^5$R$^6$, C$_{0-6}$alkylNR$^5$(SO$_2$)R$^6$, OC$_{2-6}$alkylNR$^5$(SO$_2$)R$^6$, SO$_3$R$^5$, C$_{1-6}$alkylNR$^5$(SO$_2$)NR$^5$R$^6$, OC$_{2-6}$alkyl(SO$_2$)R$^5$, C$_{0-6}$alkyl(SO$_2$)R$^5$, C$_{0-6}$alkyl(SO)R$^5$, OC$_{2-6}$alkyl(SO)R$^5$ and a 5-membered ring containing one or more atoms independently selected from the group consisting of C, N, O and S;

m1 is selected from 0, 1, 2, 3 and 4;

m2 is selected from 0, 1, 2 and 3;

n is selected from 0, 1 and 2; and t is 0 or 1, and salts thereof, with the proviso that the compound is not 5-(4-methyl-4H-[1,2,4]triazol-3-ylsulfanylmethyl)-3-thiophen-3-yl-[1,2,4]oxadiazole, 1,2-di{2-(3-amino-phenyl)-[1,3,4]oxadiazole-yl}ethane, 1,2-di{5-[5-(4-nitro-phenyl)furan-2-yl]-[1,3,4]oxadiazol-yl}ethane, 1,2-di{5-[5-(4-bromo-phenyl)furan-2-yl]-[1,3,4]oxadiazol-yl}ethane, 1,2-di{5-[5-(4-chloro-phenyl)furan-2-yl]-[1,3,4]oxadiazol-yl}ethane and 1,2-di{5-[5-(2,4-dibromo-phenyl)furan-2-yl]-[1,3,4]oxadiazol-yl)ethane.

The present invention provides a compound of formula Ib

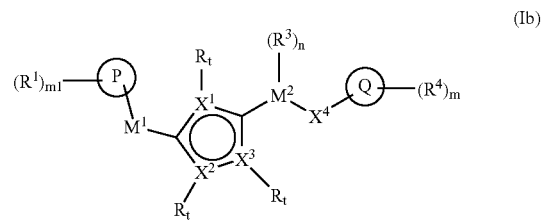

(Ib)

wherein:

P is selected from the group consisting of thiophene, pyridyl, thiazolyl, furyl, pyrrolyl and phenyl, whereby the phenyl ring is substituted on position 3 or disubstituted on positions 2 and 5;

R$^1$ is attached to P via a carbon atom on ring P and is selected from the group consisting of hydrogen, hydroxy, halo, nitro, C$_{1-6}$alkylhalo, OC$_{1-6}$alkylhalo, C$_{1-6}$alkyl, OC$_{1-6}$ alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, $(CO)R^5$, $O(CO)R^5$, $O(CO)OR^5$, $O(CN)OR^5$, $C_{1-6}$alkyl$OR^5$, $OC_{2-6}$alkyl$OR^5$, $C_{1-6}$aklyl$(CO)R^5$, $OC_{1-6}$alkyl$(CO)R^5$, $C_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^6$, $OC_{2-6}$alkyl$NR^5R^6$, $C_{1-6}$alkyl$(CO)NR^5R^6$, $OC_{1-6}$alkyl$(CO)NR^5R^6$, $C_{0-6}$alkyl$N^5(CO)R^6$, $OC_{2-6}$alkyl$NR^5(CO)R^6$, $C_{0-6}$alkyl$NR^5(CO)NR^5R^6$, $C_{0-6}$alkyl$SR^5$, $OC_{2-6}$alkyl$SR^5$, $C_{0-6}$alkyl$(SO)R^5$, $OC_{2-6}$alkyl$(SO)R^5$, $C_{0-6}$alkyl$SO_2R^5$, $OC_{2-6}$alkyl$SO_2R^5$, $C_{0-6}$alkyl$(SO_2)NR^5R^6$, $OC_{2-6}$alkyl$(SO_2)NR^5R^6$, $C_{0-6}$alkyl$NR^5(SO_2)R^6$, $OC_{2-6}$alkyl$NR^5(SO_2)R^6$, $C_{0-6}$alkyl$NR^5(SO_2)NR^5R^6$, $OC_{2-6}$alkyl$NR^5(SO_2)NR^5R^6$, $(CO)NR^5R^6$, $O(CO)NR^5R^6$, $NR^5OR^6$, $C_{0-6}$alkyl$NR^5(CO)OR^6$, $OC_{2-6}$alkyl$NR^5(CO)OR^6$, $SO_3R^5$ and a 5- or 6-membered ring containing one or more atoms independently selected from the group consisting of C, N, O and S;

$M^1$ is a bond;

$X^1$ selected from the group consisting of C, CO, N, O and S;

$X^2$ is selected from the group consisting of C, N, O and S;

$X^3$ is selected from the group consisting of N, O and S, or $X^3$ is CH when $X^2$ is N, O or S;

R is selected from the group consisting of hydrogen, $C_{0-3}$alkyl, halo, $C_{0-3}$alkyl$OR^5$, $C_{0-3}$alkyl$NR^5R^6$, $C^{0-3}$alkyl$(CO)OR^5$ and $C_{0-3}$alkylaryl;

$M^2$ is selected from a group consisting of a bond, $C_{1-3}$alkyl, $C_{2-3}$alkynyl, $C_{0-4}$alkyl$(CO)C_{0-4}$alkyl, $C_{0-3}$alkyl$OC_{0-3}$alkyl, $C_{0-3}$alkyl$NR^5C_{1-3}$alkyl, $C_{0-3}$alkyl$(CO)NR^5$, $C_{0-4}$alkyl$NR^5$, $C_{0-3}$alkyl$(SO)C_{0-3}$alkyl and $C_{0-3}$alkyl$(SO_2)C_{0-3}$alkyl;

$R^3$ is selected from a group consisting of hydroxy, $C_{0-6}$alkylcyano, oxo, $=NR^5$, $=NOR^5$, $C_{1-4}$alkylhalo, halo, $C_{1-4}$alkyl, $O(CO)C_{1-4}$alkyl, $C_{1-4}$alkyl$(SO)C_{0-4}$alkyl, $C_{1-4}$alkyl$(SO_2)C_{0-4}$alkyl, $(SO)C_{0-4}$alkyl, $(SO_2)C_{0-4}$alkyl, $OC_{1-4}$alkyl, $C_{1-4}$alkyl$OR^5$ and $C_{0-4}$alkyl$NR^5R^6$;

$X^4$ is selected from the group consisting of $C_{0-4}$alkyl$R^5R^6$, $C_{3-7}$cycloalkyl, $C_{1-4}$alkyl$(NR^5R^6)$, $NR^5$, $C_{0-4}$alkyl$(NR^5R^6)$ $=N$, $NR^5C_{0-4}$alkyl$(NR^5R^6)=N$, $NOC_{0-4}$alkyl, $C_{1-4}$alkylhalo, O, SO, $SO_2$ and S, and wherein the bond between $M^2$ and $X^4$ is a single bond;

Q is i) selected from the group consisting of triazolyl, imidazolyl, oxadiazolyl, imidazolonyl, oxazolonyl, thiazolonyl, tetrazolyl and thiadiazolyl, and wherein any substitutable nitrogen atom in the ring is substituted with $R^4$ on such nitrogen atom; and $R^4$ is selected from the group consisting of $C_{0-6}$alkylcyano, $=NC_{1-4}$alkyl, $=NOR^5$, $C_{1-4}$alkylhalo, halo, $C_{1-6}$alkyl, $OC_{1-4}$alkyl, $C_{2-4}$alkenyl, $C_{0-2}$alkyl$C_{3-6}$cycloalkyl, $C_{0-6}$alkylaryl, $C_{0-6}$alkylheteroaryl, $OC_{0-6}$alkylaryl, $OC_{0-6}$alkylheteroaryl, $NC_{0-6}$alkylaryl, $NC_{0-6}$alkylheteroaryl, $C_{0-6}$alkylOaryl, $C_{0-6}$alkylOheteroaryl, $C_{0-6}$alkylNaryl, $C_{0-6}$alkylNheteroaryl, $OC_{0-6}$alkylOaryl, $OC_{0-6}$alkylOheteroaryl, $OC_{0-6}$alkylNaryl, $OC_{0-6}$alkylNheteroaryl, $NC_{0-6}$alkylOaryl, $NC_{0-6}$alkylOheteroaryl, $NC_{0-6}$alkylNaryl, $NC_{0-6}$alkylNheteroaryl, $O(CO)C_{1-4}$alkyl, $C_{0-4}$alkyl$(CO)OC_{1-4}$alkyl, $C_{1-4}$alkyl$(S)C_{0-4}$alkyl, $C_{1-4}$alkyl$(SO)C_{0-4}$alkyl, $C_{1-4}$alkyl$(SO_2)C_{0-4}$alkyl, $(SO)C_{0-4}$alkyl, $(SO_2)C_{0-4}$alkyl, $C_{1-4}$alkyl$OR^5$, $C_{0-4}$alkyl$N(C_{1-4}$alkyl$)_2$ and a 3- or 6-membered non-aromatic ring containing one or more atoms independently selected from C, N, O and S, which ring may optionally be fused with a 5-membered ring containing one or more atoms independently selected from the group consisting of C, N and O and wherein said ring and said fused ring may be substituted by one or two A; or ii) selected from the group consisting of benzoimidazolyl, benzooxazolyl, tetrahydrotriazolopyridyl, tetrahydrotriazolopyrimidinyl, pyridonyl, pyridazinyl, imidazopyridyl, oxazolopyridyl, thiazolopyridyl, imidazopyridazinyl, oxazolopyridazinyl, thiazolopyridazinyl and purinyl; and $R^4$ is selected from the group consisting of hydrogen, hydroxy, $C_{0-6}$alkylcyano, $=NR^5$, $=NOR^5$, $C_{1-4}$alkylhalo, halo, $C_{1-6}$alkyl, $OC_{1-4}$alkyl, $OC_{0-4}$alkylaryl, $O(CO)C_{1-4}$alkyl, $C_{0-4}$alkyl$(S)C_{0-4}$alkyl, $C_{1-4}$alkyl$(SO)$ $C_{0-4}$alkyl, $C_{1-4}$alkyl$(SO_2)C_{0-4}$alkyl, $(SO)C_{0-4}$alkyl, $(SO_2)C_{0-4}$alkyl, $C_{1-4}$alkyl$OR^5$, $C_{0-4}$alkyl$NR^5R^6$ and a 5- or 6-membered ring containing one or more atoms independently selected from C, N, O and S, which ring may optionally be fused with a 5- or 6-membered ring containing one or more atoms independently selected from the group consisting of C, N and O and wherein said ring and said fused ring may be substituted by one or two A;

$R^5$ and $R^6$ are independently selected from the group consisting of hydrogen and $C_{1-6}$alkyl;

wherein any $C_{1-6}$alkyl defined under $R^1$, $R^2$ and $R^4$ may be substituted by one or more A;

A is selected from the group consisting of hydrogen, hydroxy, halo, nitro, oxo, $C_{0-6}$alkylcyano, $C_{0-4}$alkyl$C_{3-6}$cycloalkyl, $C_{1-6}$alkyl, $C_{1-6}$alkylhalo, $OC_{1-6}$alkylhalo, $C_{2-6}$alkenyl, $C_{0-3}$alkylaryl, $C_{0-6}$alkyl$OR^5$, $OC_{2-6}$alkyl$OR^5$, $C_{2-6}$alkyl$SR^5$, $OC_{2-6}$alkyl$SR^5$, $(CO)R^5$, $O(CO)R^5$, $OC_{2-6}$alkylcyano, $OC_{1-6}$alkyl$CO_2R^5$, $O(CO)OR^5$, $OC_{1-6}$alkyl$(CO)R^5$, $C_{1-6}$alkyl$(CO)R^5$, $NR^5OR^6$, $OC_{2-6}$alkyl$NR^5R^6$, $C_{0-6}$alkyl$(CO)NR^5R^6$, $OC_{1-6}$alkyl$(CO)NR^5R^6$, $OC_{2-6}$alkyl$NR^5(CO)$ $R^6$, $C_{0-6}$alkyl$NR^5(CO)R^6$, $C_{0-6}$alkyl$NR^5(CO)NR^5R^6$, $O(CO)NR^5R^6$, $C_{0-6}$alkyl$(SO_2)NR^5R^6$, $OC_{2-6}$alkyl$(SO_2)NR^5R^6$, $C_{0-6}$alkyl$NR^5(SO_2)R^6$, $OC_{2-6}$alkyl$NR^5(SO_2)R^6$, $SO_3R^5$, $C_{1-6}$alkyl$NR^5(SO_2)NR^5R^6$, $OC_{2-6}$alkyl$(SO_2)R^5$, $C_{0-6}$alkyl$(SO_2)R^5$, $C_{0-6}$alkyl$(SO)R^5$, $OC_{2-6}$alkyl$(SO)R^5$ and a 5-membered ring containing one or more atoms independently selected from the group consisting of C, N, O and S;

m1 is selected from 0, 1, 2, 3 and 4;

m2 is selected from 0, 1, 2 and 3;

n is selected from 0, 1 and 2; and t is 0 or 1, and salts thereof, with the proviso that the compound is not 5-(4-methyl-4H-[1,2,4]triazol-3-ylsulfanylmethyl)-3-thiophen-3-yl-[1,2,4]oxadiazole.

In a further aspect of the invention there is provided pharmaceutical formulations comprising a therapeutically effective amount of a compound of formula I and a pharmaceutically acceptable carrier.

In yet a further aspect of the invention there is provided a pharmaceutical formulation including a compound of formula I for use in the treatment of mGluR5 receptor-mediated disorders, and particularly neurological disorders, psychiatric disorders, acute and chronic pain.

In still a further aspect of the invention there is provided a compound of formula I for use in therapy for the treatment of mGluR5 receptor-mediated disorders, and particularly neurological disorders, psychiatric disorders, acute and chronic pain.

In another aspect of the invention there is provided a process for the preparation of compounds of formula I, and the intermediates provided therein.

These and other aspects of the present invention are described in greater detail herein below.

DETAILED DESCRIPTION OF THE INVENTION

Listed below are definitions of various terms used in the specification and claims to describe the present invention.

For the avoidance of doubt it is to be understood that where in this specification a group is qualified by 'hereinbefore defined', 'defined hereinbefore' or 'defined above' the said group encompasses the first occurring and broadest definition as well as each and all of the other definitions for that group.

For the avoidance of doubt it is to be understood that in this specification '$C_{1-6}$' means a carbon group having 1, 2, 3, 4, 5 or 6 carbon atoms.

In this specification "C" means 1 carbon atom.

In this specification, unless stated otherwise, the term "alkyl" includes both straight and branched chain alkyl groups and may be methyl, ethyl, n-propyl, i-propyl, n-butyl, i-butyl, s-butyl, t-butyl, n-pentyl, i-pentyl, t-pentyl, neo-pentyl, n-hexyl or i-hexyl, t-hexyl. The term "$C_{1-3}$alkyl" refers to an alkyl group having 1, 2 or 3 carbon atoms, and may be methyl, ethyl, n-propyl and i-propyl.

In this specification, unless stated otherwise, the term "cycloalkyl" refers to an optionally substituted, saturated cyclic hydrocarbon ring system. The term "$C_{3-7}$cycloalkyl" may be cyclopropyl, cyclobutyl, cyclopentyl, cyclohexyl and cycloheptyl.

In this specification, unless stated otherwise, the term "alkenyl" includes both straight and branched chain alkenyl groups. The term "$C_{2-6}$alkenyl" refers to an alkenyl group having 2 to 6 carbon atoms and one or two double bonds, and may be, but is not limited to vinyl, allyl, propenyl, i-propenyl, butenyl, i-butenyl, crotyl, pentenyl, i-pentenyl and hexenyl.

In this specification, unless stated otherwise, the term "alkynyl" includes both straight and branched chain alkynyl groups. The term $C_{2-6}$alkynyl having 2 to 6 carbon atoms and one or two triple bonds, and may be, but is not limited to ethynyl, propargyl, butynyl, i-butynyl, pentynyl, i-pentynyl and hexynyl.

The term "aryl" refers to an optionally substituted monocyclic or bicyclic hydrocarbon ring system containing at least one unsaturated aromatic ring. Examples and suitable values of the term "aryl" are phenyl, naphthyl, 1,2,3,4-tetrahydronaphthyl, indyl and indenyl.

In this specification, unless stated otherwise, the term "heteroaryl" refer to an optionally substituted monocyclic or bicyclic unsaturated, aromatic ring system containing at least one heteroatom selected independently from N, O or S. Examples of "heteroaryl" may be, but are not limited to thiophene, thienyl, pyridyl, thiazolyl, furyl, pyrrolyl, triazolyl, imidazolyl, oxadiazolyl, oxazolyl, isoxazolyl, pyrazolyl, imidazolonyl, oxazolonyl, thiazolonyl, tetrazolyl and thiadiazolyl, benzoimidazolyl, benzooxazolyl, tetrahydrotriazolopyridyl, tetrahydrotriazolopyrimidinyl, benzofuryl, indolyl, isoindolyl, pyridonyl, pyridazinyl, pyrimidinyl, imidazopyridyl, oxazolopyridyl, thiazolopyridyl, pyridyl, imidazopyridazinyl, oxazolopyridazinyl, thiazolopyridazinyl and purinyl.

In this specification, unless stated otherwise, the term "alkylaryl", "alkylheteroaryl" and "alkylcycloalkyl" refer to a substituent that is attached via the alkyl group to an aryl, heteroaryl and cycloalkyl group.

In this specification, unless stated otherwise, a 5- or 6-membered ring containing one or more atoms independently selected from C, N, O or S, includes aromatic and heteroaromatic rings as well as carbocyclic and heterocyclic rings which may be saturated or unsaturated. Examples of such rings may be, but are not limited to furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, triazolyl, imidazolidinyl, imidazolinyl, triazolyl, morpholinyl, piperazinyl, piperidyl, piperidonyl, pyrazolidinyl, pyrazolinyl, pyrrolidinyl, pyrrolinyl, tetrahydropyranyl, thiomorpholinyl, phenyl, cyclohexyl, cyclopentyl and cyclohexenyl.

In this specification, unless stated otherwise, a 3- to 8-membered ring containing one or more atoms independently selected from C, N, O or S, includes aromatic and heteroaromatic rings as well as carbocyclic and heterocyclic rings which may be saturated or unsaturated. Examples of such rings may be, but are not limited to imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl or thiomorpholinyl, tetrahydrothiopyranyl, furyl, pyrrolyl, isoxazolyl, isothiazolyl, oxazolyl, oxazolidinonyl, pyrazinyl, pyrazolyl, pyridazinyl, pyridyl, pyrimidyl, pyrrolyl, thiazolyl, thienyl, imidazolyl, triazolyl, phenyl, cyclopropyl, aziridinyl, cyclobutyl, azetidinyl, cyclopentyl, cyclopentenyl, cyclohexyl, cyclohexenyl, cycloheptyl, cycloheptenyl, cyclooctyl and cyclooctenyl.

In this specification, unless stated otherwise, a 3- to 8-membered ring containing one or more atoms independently selected from C, N, O or S, which group may optionally be fused with a 5- or 6-membered ring containing one or more atoms independently selected from C, N, O or S, includes aromatic and heteroaromatic rings as well as carbocyclic and heterocyclic rings which may be saturated or unsaturated. Examples of such rings may be, but are not limited to naphthyl, norcaryl, chromyl, isochromyl, indanyl, benzoimidazol or tetralinyl, benzooxazolyl, benzothiazolyl, benzofuryl, benzothienyl, benzotriazolyl, indolyl, azaindolyl, indazolyl, indolinyl, isoindolinyl, benzimidazolyl, oxadiazolyl, thiadiazolyl, quinolinyl, quinoxalinyl and benzotriazolyl.

In this specification, unless stated otherwise, the term "=$NR^5$" and "=$NOR^5$" include imino- and oximogroups carrying an $R^5$ substituent and may be, or be part of, groups including, but not limited to iminoalkyl, iminohydroxy, iminoalkoxy, amidine, hydroxyamidine and alkoxyamidine.

In the case where a subscript is the integer 0 (zero) the group to which the subscript refers, indicates that the group is absent, i.e. there is a direct bond between the groups.

In this specification, unless stated otherwise, the term "bond" is a saturated bond.

In this specification, unless stated otherwise, the term "halo" may be fluoro, chloro, bromo or iodo.

In this specification, unless stated otherwise, the term "alkylhalo" means an alkyl group as defined above, substituted with one or more halo. The term "$C_{1-6}$alkylhalo" may include, but is not limited to fluoromethyl, difluoromethyl, trifluoromethyl, fluoroethyl, difluoroethyl and bromopropyl. The term "$OC_{1-6}$alkylhalo" may include, but is not limited to fluoromethoxy, difluoromethoxy, trifluoromethoxy, fluoroethoxy and difluoroethoxy.

In one embodiments of the invention P may be hydrogen or $C_{3-7}$ alkyl or P may be a 3- to 8-membered ring containing one or more atoms selected from C, N, O or S said ring may be optionally fused with a 5- or 6-membered ring containing one or more atoms independently selected from C, N, O, or S. In a preferred embodiment of the invention P is selected from 5 and 6 membered aromatic and heteroaromatic rings.

In a further preferred embodiment P is selected from thiophene, pyridyl, thiazolyl, furyl, pyrrolyl and phenyl, whereby the phenyl ring is substituted on position 3 or disubstituted on positions 2 and 5.

In yet a further preferred embodiment of the invention P is phenyl substituted on position 3 or disubstituted on positions 2 and 5.

P is optionally substituted via a carbon atom with 0, 1, 2, 3 or 4 groups $R^1$, wherein the number of $R^1$ substituents on the P ring is designated by the term m1. In preferred embodiments of the invention m1 is 1 or 2. In further preferred embodiments of the invention m1 is 1.

In suitable embodiments of invention $R^1$ is selected from the group consisting of hydrogen, hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, $(CO)R^5$, $O(CO)R^5$, $O(CO)OR^5$, $O(CN)OR^5$, $C_{1-6}$alkyl$OR^5$, $OC_{2-6}$alkyl$OR^5$, $C_{1-6}$alkyl$(CO)R^5$, $OC_{1-6}$alkyl$(CO)R^5$, $C_{0-6}$akyl$CO_2R^5$, $OC_{1-6}$alkyl$CO_2R^5$, $C_{0-6}$alkylcyano, $OC_{2-6}$alkylcyano, $C_{0-6}$akyl$NR^5R^6$, $OC_{2-6}$alkyl$NR^5R^6$, $C_{1-6}$alkyl$(CO)NR^5R^6$, $OC_{1-6}$alkyl$(CO)NR^5R^6$, $C_{0-6}$alkyl$NR^5(CO)R^6$, $OC_{2-6}$alkyl$NR^5(CO)R^6$, $C_{0-6}$alkyl$NR^5(CO)NR^5R^6$, $C_{0-6}$alkyl$SR^5$, $OC_{2-6}$alkyl$SR^5$, $C_{0-6}$alkyl$(SO)R^5$, $OC_{2-6}$alkyl$(SO)R^5$, $C_{0-6}$alkyl$SO_2R^5$, $OC_{2-6}$alkyl$SO_2R^5$, $C_{0-6}$alkyl$(SO_2)NR^5R^6$, $OC_{2-6}$alkyl$(SO_2)NR^5R^6$, $C_{0-6}$alkyl$NR^5(SO_2)R^6$, $OC_{2-6}$alkyl$NR^5(SO_2)R^6$, $C_{0-6}$alkyl$NR^5(SO_2)NR^5R^6$, $OC_{2-6}$alkyl$NR^5(SO_2)NR^5R^6$, $NR^5OR^6$, $(CO)NR^5R^6$, $O(CO)NR^5R^6$, $NR^5OR^6$, $C_{0-6}$alkyl$NR^5(CO)OR^6$, $OC_{2-6}$alkyl$NR^5(CO)OR^6$, $SO_3R^5$ and a 5- or 6-membered ring containing one or more atoms independently selected from the group consisting of C, N, O and S.

In a more suitable embodiment of the invention $R^1$ is selected from hydrogen, hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $C_{0-6}$alkyl$C_{3-6}$cycloalkyl, $C_{1-6}$alkyl$OR^5$, $C_{1-6}$alkyl$(CO)R^5$, $C_{0-6}$alkyl$CO_2R^5$, $C_{0-6}$alkylcyano, $C_{0-6}$alkyl$NR^5R^6$, $C^{0-6}$alkyl$SR^5$ and a 5- or 6-membered ring containing one or more atoms independently selected from the group consisting of C and O.

Any $C_{1-6}$alkyl defined under $R^1$ may be substituted by one or more A. In one embodiment of the invention $R^1$ is ethyl and A is hydroxyl.

In a further suitable embodiment of the invention $R^1$ is selected from hydrogen, methyl, ethyl, cyclopropyl, hydroxy, methoxy, cyano, flouro, chloro, bromo, iodo, trifluoromethyl, difluoromethoxy, trifluoromethoxy, amino, nitro, dimethylamino, methylsulfanyl, vinyl, acetyl, formic acid methyl ester, methoxymethyl, ethanol and furyl.

In a more suitable embodiment of the invention P is selected from the group consisting of thiophene, pyridyl, thiazolyl, furyl, pyrrolyl or phenyl, whereby the phenyl ring is substituted on position 3 or disubstituted on positions 2 and 5 and $R^1$ is selected from the group consisting of hydrogen, hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $C_{0-6}$alkyl$C_{3-6}$cycloalkyl, $C_{1-6}$alkyl$OR^5$, $C_{1-6}$alkyl$(CO)R^5$, $C_{0-6}$alkyl$CO_2R^5$, $C_{0-6}$alkylcyano, $C_{0-6}$alkyl$NR^5R^6$, $C_{0-6}$alkyl$SR^5$ and a 5-membered ring containing one or more atoms independently selected from the group consisting of C and O.

In a further suitable embodiment of the invention P is phenyl substituted on position 3 or disubstituted on positions 2 and 5 and $R^1$ is selected from the group consisting of hydrogen, hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $C_{0-6}$alkyl$C_{3-6}$cycloalkyl, $C_{1-6}$alkyl$OR^5$, $C_{1-6}$alkyl$(CO)R^5$, $C_{0-6}$alkyl$CO_2R^5$, $C_{0-6}$alkylcyano, $C_{0-6}$alkyl$NR^5R^6$, $C_{0-6}$alkyl$SR^5$ and a 5-membered ring containing one or more atoms independently selected from the group consisting of C and O.

According to another aspect of the invention the ring P is connected to the core ring by $M^1$, wherein $M^1$ can be a bond directly joining P to the core ring. $M^1$ can also be a linker $C_{1-3}$alkyl.

In a preferred embodiment of the invention $M^1$ is a bond. When $M^1$ is not a direct bond $M^1$ can be further substituted with 0, 1, 2 or 3 substituents $R^2$ wherein the number of substituents $R^2$ is designated by the term n. The substituents $R^2$ may be selected from hydrogen, hydroxy, oxo, $C_{1-4}$alkylhalo, halo and $C_{1-4}$alkyl. In a preferred embodiment of the invention n is 0.

In another aspect of the invention there is provided compounds of formula I wherein $X^1$ is selected from the group consisting of C, CO, N, O and S. In a further aspect of the invention $X^2$ is selected from the group consisting of C, N, O and S. In yet a further aspect of the invention $X^3$ is selected from the group consisting of N, O and S, or $X^3$ is selected from N, O, S, and C when $X^2$ is selected from N, O, or S, and when $X^3$ is C the substituent R on $X^3$ is H.

$X^1$, $X^2$ and $X^3$ can be further substituted with 0, 1 or 2 substituents R wherein the number of substituents R is designated by the term t. The substituent R may be selected from the group consisting of hydrogen, $C_{0-3}$alkyl, halo, $C_{0-3}$alkyl$OR^5$, $C_{0-3}$alkyl$NR^5R^6$, $C_{0-3}$alkyl$(CO)OR^5$, $C_{0-3}$alkyl$NR^5R^6$ and $C_{0-3}$alkylaryl. In one embodiment of the invention R is selected from the group consisting of hydrogen, $C_{0-3}$alkyl and halo.

In a preferred embodiment of the invention $X^1$ is C, N or O and R is selected from hydrogen, $C_{0-3}$alkyl and halo. In one embodiment R is selected from hydrogen, chloro or methyl.

In another preferred embodiment of the invention $X^1$ is N.

In a suitable embodiment $x^2$ is selected from N, O and S, and R is hydrogen. In another embodiment of the invention $X^3$ is N, O or S. In a further preferred embodiment of the invention $X^1$ is O and one of $X^2$ and $X^3$ is O and the other is N. In yet a further preferred embodiment of the invention $X^1$ is N and one of $X^2$ and $X^3$ is O and the other is N. In yet another preferred embodiment of the invention $X^1$ is C or CR and one of $X^2$ and $X^3$ is O and the other is N.

In another preferred embodiment of the invention $X^2$ is O and $X^3$ is N, and in yet another preferred embodiment of the invention $X^2$ is N and $X^3$ is O.

In a further preferred embodiment of the invention $X^1$ is O and $X^2$ and $X^3$ are N.

In another suitable embodiment of the invention the ring containing $X^1$, $X^2$ and $X^3$ forms an oxadiazole, isoxazole, oxazole, chloro-isoxazole or a methyl-isoxazole.

In a preferred embodiment of the invention the ring containing $X^1$, $X^2$ and $X^3$ forms an oxadiazole. In another preferred embodiment of the invention the ring containing $X^1$, $X^2$ and $X^3$ forms an isoxazole.

The ring containing $X^1$, $X^2$ and $X^3$ should not be further annulated onto any other ring.

In a suitable embodiment of the invention $M^2$ may be a direct bond from the core ring to the variable $X^4$ or $M^2$ may be selected from the group consisting of bond, $C_{1-3}$alkyl, $C_{2-3}$alkynyl, $C_{0-4}$alkyl$(CO)C_{0-4}$alkyl, $C_{0-3}$alkyl$OC_{0-3}$alkyl, $C_{0-3}$alkyl$NR^5C_{1-3}$alkyl, $C_{0-3}$alkyl$(CO)NR^5$, $C_{0-4}$alkyl$NR^5$, $C_{0-3}$alkyl$(SO)C_{0-3}$alkyl and $C_{0-3}$alkyl$(SO_2)C_{0-3}$alkyl.

In preferred embodiments of the invention $M^2$ is a bond or $C_{1-3}$alkyl. In further preferred embodiments of the invention $M^2$ is $C_{1-3}$alkyl, preferably methyl or ethyl.

When $M_2$ is not a direct bond $M^2$ may be further substituted with 0, 1 or 2 $R^3$ groups wherein the number of substituents $R^3$ is designated by the term n. In one embodiment of the invention n is 1 or 2. In another embodiment of the invention n is 0.

In a suitable embodiment of the invention $R^3$ is selected from the group consisting of $R^3$ is selected from a group consisting of hydroxy, $C_{0-6}$alkylcyano, oxo, $=NR^5$, $=NOR^5$, $C_{1-4}$alkylhalo, halo, $C_{1-4}$alkyl, $O(CO)C_{1-4}$alkyl, $C_{1-4}$alkyl(SO)$C_{0-4}$alkyl, $C_{1-4}$alkyl(SO$_2$)$C_{0-4}$alkyl, (SO)$C_{0-4}$alkyl, (SO$_2$)$C_{0-4}$alkyl, O$C_{1-4}$alkyl, $C_{1-4}$alkylOR$^5$ and $C_{0-4}$alkylNR$^5$R$^6$.

In a preferred embodiment R$^3$ is selected from hydrogen and $C_{1-4}$alkyl, preferably methyl or dimethyl.

In another preferred embodiment M$^2$ may be selected from the group consisting of a bond, $C_{1-3}$alkyl, $C_{2-3}$alkynyl, $C_{0-4}$alkyl(CO)$C_{0-4}$alkyl, $C_{0-3}$alkylO$C_{0-3}$alkyl, $C_{0-3}$alkylNR$^5$C$_{1-3}$alkyl, $C_{0-3}$alkyl(CO)NR$^5$, $C_{0-4}$alkylNR$^5$, $C_{0-3}$alkyl(SO)$C_{0-3}$alkyl and $C_{0-3}$alkyl(SO$_2$)$C_{0-3}$alkyl and R$^3$ is selected from hydrogen and $C_{1-4}$alkyl.

In yet another preferred embodiments of the invention M$^2$ is a bond or $C_{1-3}$alkyl and R$^3$ is hydrogen, methyl or dimethyl.

In a further preferred embodiment M$^2$ may be selected from the group consisting of a bond, methyl and ethyl and R$^3$ is hydrogen, methyl or dimethyl.

In a further embodiment of the invention M$^2$ is nitrogen. In yet a further embodiment of the invention M$^2$ is oxygen.

According to another aspect of the invention X$^4$ is selected from the group consisting of $C_{0-4}$alkylR$^5$R$^6$, $C_{3-7}$cycloalkyl, $C_{1-4}$alkyl(NR$^5$R$^6$), NR$^5$, $C_{0-4}$alkyl(NR$^5$R$^6$)=N, NR$^5$C$_{0-4}$alkyl(NR$^5$R$^6$)=N, NO$C_{0-4}$alkyl, $C_{1-4}$alkylhalo, O, SO, SO$_2$ and S, and wherein the bond between M$^2$ and X$^4$ is a single bond.

In a preferred embodiment of the invention X$^4$ is selected from the group consisting of $C_{0-4}$alkylR$^5$R$^6$, $C_{3-7}$cycloalkyl, NR$^5$, O, SO, SO$^2$ and S and R$^5$ and R$^6$ are independently selected from hydrogen and $C_{1-6}$alkyl.

In a further preferred embodiment of the invention X$^4$ is selected from the group consisting of CH$_2$, CHCH$_3$, CH(CH$_3$)$_2$ and NR$^5$. In a further preferred embodiment of the invention X$^4$ is NR$^5$ and R$^5$ is selected from hydrogen and $C_{1-6}$alkyl. In a preferred embodiment of the invention R$^5$ is methyl or hydrogen and R$^6$ is hydrogen.

In still a further preferred embodiment of the invention X$^4$ is O. In yet another preferred embodiment of the invention X$^4$ is S.

It is to be understood that the bond between M$^2$ and X$^4$ is a single bond in all tautomeric forms.

Embodiments of the present invention include those wherein Q is a 5- or 6-membered ring. When Q is a 5-membered ring, Q is selected from the group consisting of the group consisting of triazolyl, imidazolyl, oxadiazolyl, imidazolonyl, oxazolonyl, thiazolonyl, tetrazolyl and thiadiazolyl, and wherein any substitutable nitrogen atom in the ring is substituted with R$^4$ on such nitrogen atom.

In one embodiment the 5 membered ring Q is selected from the group consisting of triazolyl and thiadiazolyl. In another embodiment the 5 membered ring Q is selected from the group consisting of tetrazolyl and oxadiazolyl. In a further embodiment the 5 membered ring Q is imidazolyl.

When Q is a 6-membered ring, Q is selected from the group consisting of benzoimidazolyl, benzooxazolyl, tetrahydrotriazolopyridyl, tetrahydrotriazolopyrimidinyl, pyridonyl, pyridazinyl, imidazopyridyl, oxazolopyridyl, thiazolopyridyl, imidazopyridazinyl, oxazolopyridazinyl, thiazolopyridazinyl and purinyl.

In a preferred embodiment of the invention the 6 membered ring Q is selected from the group consisting of pyridonyl, tetrahydrotriazolopyridyl and tetrahydrotriazolopyrimidinyl.

In another embodiment the 6 membered ring Q is pyridazinyl. In a further embodiment the 6 membered ring Q is selected from the group consisting of benzoimidazolyl, benzooxazolyl and imidazopyridyl.

Q can be further substituted with 0, 1, 2 or 3 substituents R$^4$, wherein the number of R$^4$ substituents is designated by the term m2. In a preferred embodiment m2 is 1 or 2.

When Q is a 5-membered ring the substituent R$^4$ is selected from the group consisting of $C_{0-6}$alkylcyano, =NC$_{1-4}$alkyl, =NOR$^5$, $C_{1-4}$alkylhalo, halo, $C_{1-6}$alkyl, O$C_{1-4}$alkyl, $C_{2-4}$alkenyl, $C_{0-2}$alkylC$_{3-6}$cycloalkyl, $C_{0-6}$alkylaryl, $C_{0-6}$alkylheteroaryl, O$C_{0-6}$alkylaryl, O$C_{0-6}$alkylheteroaryl, N$C_{0-6}$alkylaryl, N$C_{0-6}$alkylheteroaryl, $C_{0-6}$alkylOaryl, $C_{0-6}$alkylOheteroaryl, $C_{0-6}$alkylNaryl, $C_{0-6}$alkylNheteroaryl, O$C_{0-6}$alkylOaryl, O$C_{0-6}$alkylOheteroaryl, O$C_{0-6}$alkylNaryl, O$C_{0-6}$alkylNheteroaryl, N$C_{0-6}$alkylOaryl, N$C_{0-6}$alkylOheteroaryl, N$C_{0-6}$alkylNaryl, N$C_{0-6}$alkylNheteroaryl, O(CO)$C_{1-4}$alkyl, $C_{0-4}$alkyl(CO)O$C_{1-4}$alkyl, $C_{1-4}$alkyl(S)$C_{0-4}$alkyl, $C_{1-4}$alkyl(SO)$C_{0-4}$alkyl, $C_{1-4}$alkyl(SO$_2$)$C_{0-4}$alkyl, (SO)$C_{0-4}$alkyl, (SO$_2$)$C_{0-4}$alkyl, $C_{1-4}$alkylOR$^5$, $C_{0-4}$alkylN(C$_{1-4}$alkyl)$_2$ and a 3- or 6-membered non-aromatic ring containing one or more atoms independently selected from C, N, O and S, which ring may optionally be fused with a 5-membered ring containing one or more atoms independently selected from the group consisting of C, N and O and wherein said ring and said fused ring may be substituted by one or two A.

In a further embodiment of the invention R$^4$ on the 5 membered Q ring is selected from the group consisting of $C_{1-4}$alkylhalo, $C_{1-6}$alkyl, $C_{2-4}$alkenyl, $C_{0-2}$alkylC$_{3-6}$cycloalkyl, $C_{0-6}$alkylaryl, $C_{0-6}$alkylheteroaryl, O$C_{0-6}$alkylaryl, O$C_{0-6}$alkylheteroaryl, N$C_{0-6}$alkylaryl, N$C_{0-6}$alkylheteroaryl, $C_{0-6}$alkylOaryl, $C_{0-6}$alkylOheteroaryl, $C_{0-6}$alkylNaryl, $C_{0-6}$alkylNheteroaryl, O$C_{0-6}$alkylOaryl, O$C_{0-6}$alkylOheteroaryl, O$C_{0-6}$alkylNaryl, O$C_{0-6}$alkylNheteroaryl, N$C_{0-6}$alkylOaryl, N$C_{0-6}$alkylOheteroaryl, N$C_{0-6}$alkylNaryl, N$C_{0-6}$alkylNheteroaryl, $C_{0-4}$alkyl(CO)O$C_{1-4}$alkyl, $C_{1-4}$alkyl(S)$C_{0-4}$alkyl, $C_{1-4}$alkylOR$^5$ and a 3- or 6-membered non-aromatic ring containing one or more atoms independently selected from C, N, O and S, which ring may optionally be fused with a 5-membered ring containing one or more atoms independently selected from the group consisting of C, N and O and wherein said ring and said fused ring may be substituted by one or two A.

In one embodiment of the invention Q is selected from the group consisting of triazolyl, imidazolyl, oxadiazolyl, imidazolonyl, oxazolonyl, thiazolonyl, tetrazolyl and thiadiazolyl, and wherein any substitutable nitrogen atom in the ring is substituted with R$^4$ on such nitrogen atom and R$^4$ is selected from the group consisting of $C_{1-4}$alkylhalo, $C_{1-6}$alkyl, $C_{2-4}$alkenyl, $C_{0-2}$alkylC$_{3-6}$cycloalkyl, $C_{0-6}$alkylaryl, $C_{0-6}$alkylheteroaryl, O$C_{0-6}$alkylaryl, O$C_{0-6}$alkylheteroaryl, N$C_{0-6}$alkylaryl, N$C_{0-6}$alkylheteroaryl, $C_{0-6}$alkylOaryl, $C_{0-6}$alkylOheteroaryl, $C_{0-6}$alkylNaryl, $C_{0-6}$alkylNheteroaryl, O$C_{0-6}$alkylOaryl, O$C_{0-6}$alkylOheteroaryl, O$C_{0-6}$alkylNaryl, O$C_{0-6}$alkylNheteroaryl, N$C_{0-6}$alkylOaryl, N$C_{0-6}$alkylOheteroaryl, N$C_{0-6}$alkylNaryl, N$C_{0-6}$alkylNheteroaryl, $C_{0-4}$alkyl(CO)O$C_{1-4}$alkyl, $C_{1-4}$alkyl(S)$C_{0-4}$alkyl, $C_{1-4}$alkylOR$^5$ and a 3- or 6-membered non-aromatic ring containing one or more atoms independently selected from C, N, O and S, which ring may optionally be fused with a 5-membered ring containing one or more atoms independently selected from the group consisting of C, N and O and wherein said ring and said fused ring may be substituted by one or two A.

In another embodiment of the invention Q selected from the group consisting of triazolyl, imidazolyl, oxadiazolyl, tetrazolyl and thiadiazolyl, and wherein any substitutable nitrogen atom in the ring is substituted with R$^4$ on such nitrogen atom and R$^4$ is selected from the group consisting of $C_{1-4}$alkylhalo, $C_{1-6}$alkyl, $C_{2-4}$alkenyl, $C_{0-2}$alkylC$_{3-6}$cycloalkyl, $C_{0-6}$alkylaryl, $C_{0-6}$alkylheteroaryl, O$C_{0-6}$alkylaryl, O$C_{0-6}$alkylheteroaryl, N$C_{0-6}$alkylaryl, N$C_{0-6}$alkylheteroaryl, $C_{0-6}$alkylOaryl, $C_{0-6}$alkylOheteroaryl, $C_{0-6}$alkylNaryl, $C_{0-6}$alkylNheteroaryl, $OC_{0-6}$alkylOaryl, $OC_{0-6}$alkylOheteroaryl, $OC_{0-6}$alkylNaryl, $OC_{0-6}$alkylNheteroaryl, $NC_{0-6}$alkylOaryl, $NC_{0-6}$alkylOheteroaryl, $NC_{0-6}$alkylNaryl, $NC_{0-6}$alkylNheteroaryl, $C_{0-4}$alkyl(CO)$OC_{1-4}$alkyl, $C_{1-4}$alkyl(S) $C_{0-4}$ alkyl, $C_{1-4}$alkyl$OR^5$ and a 3- or 6-membered non-aromatic ring containing one or more atoms independently selected from C, N, O and S, which ring may optionally be fused with a 5-membered ring containing one or more atoms independently selected from the group consisting of C, N and O and wherein said ring and said fused ring may be substituted by one or two A.

When Q is a 6-membered ring the substituent $R^4$ is selected from the group consisting of hydrogen, hydroxy, $C_{0-6}$alkylcyano, $=NR^5$, $=NOR^5$, $C_{1-4}$alkylhalo, halo, $C_{1-6}$alkyl, $OC_{1-4}$ alkyl, $OC_{0-6}$alkylaryl, $O(CO)C_{1-4}$alkyl, $C_{0-4}$alkyl(S)$C_{0-4}$ alkyl, $C_{1-4}$alkyl(SO)$C_{0-4}$alkyl, $C_{1-4}$alkyl(SO$_2$)$C_{0-4}$alkyl, (SO)$C_{0-4}$alkyl, (SO$_2$)$C_{0-4}$alkyl, $C_{1-4}$alkyl$OR^5$, $C^{0-4}$alkyl$NR^5R^6$ and a 5- or 6-membered ring containing one or more atoms independently selected from C, N, O and S, which ring may optionally be fused with a 5- or 6-membered ring containing one or more atoms independently selected from the group consisting of C, N and O and wherein said ring and said fused ring may be substituted by one or two A.

In a suitable embodiment of the invention $R^4$ on the 6 membered Q ring is selected from hydrogen and $C_{1-6}$alkyl. In a further embodiment of the invention $R^4$ is hydrogen, methyl, ethyl, propyl, butyl or hexyl.

In a preferred embodiment of the invention Q selected from the group consisting of benzoimidazolyl, benzooxazolyl, tetrahydrotriazolopyridyl, tetrahydrotriazolopyrimidinyl, pyridonyl, pyridazinyl, imidazopyridyl, oxazolopyridyl, thiazolopyridyl, imidazopyridazinyl, oxazolopyridazinyl, thiazolopyridazinyl and purinyl and $R^4$ is hydrogen or $C_{1-6}$alkyl.

In another preferred embodiment of the invention Q selected from the group consisting of benzoimidazolyl, benzooxazolyl, tetrahydrotriazolopyridyl, tetrahydrotriazolopyrimidinyl, pyridonyl, pyridazinyl and imidazopyridyl, and $R^4$ is hydrogen or $C_{1-6}$alkyl.

In a suitable embodiment of the invention $R^4$ is selected from the group consisting of benzo[b]thiophenyl, benzodioxolyl, bromo, bromofuryl, butoxyphenyl, chloromethoxypyridyl, chlorophenyl, chlorophenylmethanol, chloropyridyl, chlorothiophene, cyanophenyl, cyclohexyl, cyclopentyl, dichloro-phenyl, dichloropyridyl, difluorophenyl, dimethylthiazolyl, ethanol, ethoxymethyl, fluoromethylphenyl, fluorophenyl, formic acid methyl ester, furyl, hydrogen, hydroxyphenoxymethyl, hydroxyphenyl, imidazolyl, methoxyethyl, methoxymethyl, methoxyphenoxymethyl, methoxyphenyl, methoxyphenylethyl, methoxypyridazinyl, pyridine-oxidyl, benzylmorpholinyl, pyridinolyl, pyridyl, pyridylmethyl, pyrimidinyl, tert-butylphenyl, tetrahydrofuryl, thiazolyl, thiophene, tolyl, trifluoromethyl, acetic acid methylester, allyl, amino, benzyl, cyclopropylmethyl, ethyl, fluorobenzyl, fluoroethyl, furylmethyl, hydroxyethyl, isobutyl, methyl, methylbenzyl, methylbutyl, methylsulfanylpropyl, n-butyl, n-hexyl, n-propyl, tetrahydrofurylmethyl, thiophenylmethyl and trifluoroethyl.

Ring Q may be substituted by one or more $R^4$ on a carbon and/or a nitrogen atom in the ring. When Q is substituted on the carbon atom, $R^4$ selected from benzo[b]thiophenyl, benzodioxolyl, bromo, bromofuryl, butoxyphenyl, chloromethoxypyridyl, chlorophenyl, chlorophenylmethanol, chloropyridyl, chlorothiophene, cyanophenyl, cyclohexyl, cyclopentyl, dichloro-phenyl, dichloropyridyl, difluorophenyl, dimethylthiazolyl, ethanol, ethoxymethyl, fluoromethylphenyl, fluorophenyl, formic acid methyl ester, furyl, hydrogen, hydroxyphenoxymethyl, hydroxyphenyl, imidazolyl, methoxyethyl, methoxymethyl, methoxyphenoxymethyl, methoxyphenyl, methoxyphenylethyl, methoxypyridazinyl, methoxypyridyl, methoxypyrimidinyl, methoxythiophene, methylimidazolyl, methylpyridyl, methylsulfanylmethyl, methylthiazolyl, methylthiophene, nitrofuryl, nitrophenyl, phenyl, p-tolyloxymethyl, pyridazinyl, pyridine-oxidyl, benzylmorpholinyl, pyridinolyl, pyridyl, pyridylmethyl, pyrimidinyl, tert-butylphenyl, tetrahydrofuryl, thiazolyl, thiophene, tolyl and trifluoromethyl.

When Q is substituted on the nitrogen atom, $R^4$ is selected from acetic acid methylester, allyl, amino, benzyl, cyclopropyl, cyclopropylmethyl, ethyl, flourobenzyl, fluoroethyl, furylmethyl, hydroxyethyl, isobutyl, methoxyethyl, methyl, methylbenzyl, methylbutyl, methylsulfanylpropyl, n-butyl, n-hexyl, n-propyl, tetrahydrofurylmethyl, thiophenylmethyl and trifluoroethyl.

When $R^4$ is a ring $R^4$ can be substituted with one or more substituents A, wherein A is selected from hydrogen, hydroxy, halo, nitro, oxo, $C_{0-6}$alkylcyano, $C_{0-4}$alkyl$C_{3-6}$cycloalkyl, $C_{1-6}$alkyl, $C_{1-6}$alkylhalo, $OC_{1-6}$alkylhalo, $C_{2-6}$alkenyl, $C_{0-3}$alkylaryl, $C_{0-6}$alkyl$OR^5$, $OC_{2-6}$alkyl$OR^5$, $C_{1-6}$alkyl$SR^5$, $OC_{2-6}$alkyl$SR^5$, (CO)$R^5$, O(CO)$R^5$, $OC_{2-6}$alkylcyano, $OC_{1-6}$alkyl$CO_2R^5$, O(CO)$OR^5$, $OC_{1-6}$alkyl(CO)$R^5$, $C_{1-6}$alkyl(CO)$R^5$, $NR^5OR^6$, $OC_{2-6}$alkyl$NR^5R^6$, $C_{0-6}$alkyl(CO)$NR^5R^6$, $OC_{1-6}$alkyl(CO)$NR^5R^6$, $OC_{2-6}$alkyl$NR^5$(CO)$R^6$, $C_{0-6}$alkyl$NR^5$(CO)$R^6$, $C_{0-6}$alkyl$NR^5$(CO)$NR^5R^6$, O(CO)$NR^5R^6$, $C_{0-6}$alkyl(SO$_2$)$NR^5R^6$, $OC_{2-6}$alkyl(SO$_2$)$NR^5R^6$, $C_{0-6}$alkyl$NR^5$(SO$_2$)$R^6$, $OC_{2-6}$alkyl$NR^5$(SO$_2$)$R^6$, $SO_3R^5$, $C_{1-6}$alkyl$NR^5$(SO$_2$)$NR^5R^6$, $OC_{2-6}$alkyl(SO$_2$)$R^5$, $C_{0-6}$alkyl(SO$_2$)$R^5$, $C_{0-6}$alkyl(SO)$R^5$, $OC_{2-6}$alkyl(SO)$R^5$ and a 5-membered ring containing one or more atoms independently selected from the group consisting of C, N, O and S.

In a preferred embodiment A is selected from hydroxy, halo, nitro, oxo, $C_{0-6}$alkylcyano, $C_{1-6}$alkyl, $C_{2-6}$alkenyl, $C_{0-3}$alkylaryl, $C_{0-6}$alkyl$OR^5$ and a 5-membered ring containing one or more atoms independently selected from the group consisting of C and O.

Specific embodiments of the invention include,

2-[5-(3-Methoxy-phenyl)-[1,2,4]oxadiazol-3-ylmethylsulfanyl]-1H-benzoimidazole, 5-(3-Methoxy-phenyl)-3-(4-Methyl-5-thiophen-2-yl-4H-[1,2,4]triazol-3-ylsulfanylmethyl)-[1,2,4]oxadiazole, 3-[5-(1-Methyl-5-thiophen-2-yl-1H-imidazol-2-ylsulfanylmethyl)-[1,2,4]oxadiazol-3-yl]-benzonitrile, 3-(4-Methyl-5-thiophen-2-yl-4H-[1,2,4]traiazol-3-ylsulfanylmethyl)-5-phenyl-[1,2,4]oxadiazole, 2-[5-(3-Methoxy-phenyl)-[1,2,4]oxadiazol-3-ylmethylsulfanyl]-5-methyl-1H-benzoimidazole, 3-(4-Methyl-5-thiophen-2-yl-4H-[1,2,4]triazol-3-ylsulfanylmethyl)-5-m-tolyl-[1,2,4]oxadiazole, 3-(4-Methyl-5-thiophen-2-yl-4H-[1,2,4]triazol-3-ylsulfanylmethyl)-5-(3-trifluoromethyl-phenyl)-[1,2,4]oxadiazole, 3-(3-Methoxy-phenyl)-5-(4-methyl-5-thiophen-2-yl-4H-[1,2,4]triazol-3-ylsulfanylmethyl)-[1,2,4]oxadiazole, 5-(4-Methyl-5-thiophen-2-yl-4H-[1,2,4]triazol-3-ylsulfanylmethyl)-3-phenyl-[1,2,4]oxadiazole, 5-(4-Methyl-5-thiophen-2-yl-4H-[1,2,4]triazol-3-ylsulfanylmethyl)-3-m-tolyl-[1,2,4]oxadiazole, 3-[3-(4-Methyl-5-thiophen-2-yl-4H-[1,2,4]triazol-3-ylsulfanylmethyl)-[1,2,4]oxadiazol-5-yl]-benzonitrile, 3-[4-Methyl-5-(2-methyl-thiazol-4-yl)-4H-[1,2,4]triazol-3-ylsulfanylmethyl]-5-5-m-tolyl-[1,2,4]oxadiazole, 3-[5-(2-Methyl-thiazol-4-yl)-[1,3,4]oxadiazol-2-ylsulfanylmethyl]-5-m-tolyl-[1,2,4]oxadiazole, 3-(4Methyl-5-thiophen-2-yl-4H-[1,2,4]triazol-3-ylsulfanylmethyl)-5-thiophen-2-yl-[1,2,4]oxadiazole, 3-[5-(2,4-Dimethyl-thiazol-5-yl)-4-methyl-4H-[1,2,4]triazol-3-ylsulfanylmethyl]-5-m-tolyl-[1,2,4]oxadiazole, 3-[4-Methyl-5-(5-nitro-furan-2-yl)-4H-[1,2,4]triazol-3-ylsulfanylmethyl]-5-m-tolyl-[1,2,4]oxadiazole, 4-[4-Methyl-5-(5-m-tolyl-[1,2,4]oxadiazol-3-ylmethylsulfanyl)-4H-[1,2,4]triazol-3-yl]-pyridine, 3-[5-(4-tert-Butyl-phenyl)-4-methyl-4H-[1,2,4]triazol-3-ylsulfanylmethyl]-5-m-tolyl-[1,2,4]-oxadiazole, 2-Chloro-5-[4-methyl-5-(5-m-tolyl-[1,2,4]oxadiazol-3-ylmethylsulfanyl)-4H-[1,2,4]triazol-3-yl]-pyridine, 2-[5-(3-Methoxy-phenyl)-[1,2,4]oxadiazol-3-ylmethylsulfanyl]-benzooxazole, 3-(4-Methyl-5-thiophen-2-yl-4H-[1,2,4]triazol-3-ylsulfanylmethyl)-5-thiophen-3-yl-[1,2,4]oxadiazole, 3-(5-Furan-2-yl-4-methyl-4H-[1,2,4]triazol-3-ylsulfanylmethyl)-5-m-tolyl-[1,2,4]oxadiazole, 5-(3-Fluoro-phenyl)-3-(4-methyl-5-thiophen-2-yl-4H-[1,2,4]triazol-3-ylsulfanylmethyl)-[1,2,4]oxadiazole, 2-(5-m-Tolyl-[1,2,4]oxadiazol-3-ylmethylsulfanyl)-pyridine, 2-[5-(3-Methoxy-phenyl)-[1,2,4]oxadiazol-3-ylmethylsulfanyl]-1H-imidazo[4,5-b]pyridine, 5-(3-Fluoro-5-methyl-phenyl)-3-(4-methyl-5-thiophen-2-yl-4H-[1,2,4]triazol-3-ylsulfanylmethyl)-[1,2,4]oxadiazole, 3-Methyl-5-[3-(4-methyl-5-thiophen-2-yl-4H-[1,2,4]triazol-3-ylsulfanylmethyl)-[1,2,4]oxadiazol-5-yl]-pyridine, 3-(4-Methyl-5-phenyl-4H-[1,2,4]triazol-3-ylsulfanylmethyl)-5-m-tolyl-[1,2,4]oxadiazole, 2-[4-Methyl-5-(5-m-tolyl-[1,2,4]oxadiazol-3-ylmethylsulfanyl)-4H-[1,2,4]triazol-3-yl]-pyridine, 4-Benzyl-2-[4-methyl-5-(5-m-tolyl-[1,2,4]oxadiazol-3-ylmethylsulfanyl)-4H-[1,2,4]triazol-3-yl]-morpholine, 4-[4-Methyl-5-(5-thiophen-3-yl-[1,2,4]oxadiazol-3-ylmethylsulfanyl)-4H-[1,2,4]triazol-3-yl]-pyridine, 3-(4-Methyl-5-thiophen-2-yl-4H-[1,2,4]triazol-3-ylsulfanylmethyl)-5-thiazol-4-yl-[1,2,4]oxadiazole, 3-(4-Methyl-5-thiophen-2-yl-4H-[1,2,4]triazol-3-ylsulfanylmethyl)-5-(3-nitro-phenyl)-[1,2,4]oxadiazole, 2-Methyl-4-[3-(4-methyl-5-thiophen-2-yl-4H-[1,2,4]triazol-3-ylsulfanylmethyl)-[1,2,4]oxadiazol-5-yl]-pyridine, 3-[4-Methyl-5-(5-m-tolyl-[1,2,4]oxadiazol-3-ylmethylsulfanyl)-4H-[1,2,4]triazol-3-yl]-pyridine, 3-(4-Methyl-5-thiophene-3-yl-4H-[1,2,4]triazol-3-ylsulfanylmethyl)-5-m-tolyl-[1,2,4]oxadiazole, 3-(4-Methyl-5-thiazol-4-yl-4H-[1,2,4]triazol-3-ylsulfanylmethyl)-5-m-tolyl-[1,2,4]oxadiazole, 5-(3-Iodo-phenyl)-3-(4-methyl-5-thiophen-2-yl-4H-[1,2,4]triazol-3-ylsulfanylmethyl)-[1,2,4]oxadiazole, 5-(3-Ethyl-phenyl)-3-(4-methyl-5-thiophen-2-yl-4H-[1,2,4]triazol-3-ylsulfanylmethyl)-[1,2,4]oxadiazole, 2-[5-(2-Methyl-pyridin-4-yl)-[1,2,4]oxadiazol-3-ylmethylsulfanyl]-1H-benzoimidazole, 2-[5-(3-Iodo-phenyl)-[1,2,4]oxadiazol-3-ylmethylsulfanyl]-1H-benzoimidazole, 3-(4-Methyl-5-trifluoromethyl-4H-[1,2,4]triazol-3-ylsulfanylmethyl)-5-m-tolyl-[1,2,4]oxadiazole, 2,6-Dichloro-4-[4-methyl-5-(5-m-tolyl-[1,2,4]oxadiazol-3-ylmethylsulfanyl)-4H-[1,2,4]triazol-3-yl]-pyridine, 3-(4-Methyl-5-p-tolyl-4H-[1,2,4]triazol-3-ylsulfanylmethyl)-5-m-tolyl-[1,2,4]oxadiazole, Dimethyl-{3-[3-(4-methyl-5-thiophen-2-yl-4H-[1,2,4]triazol-3-ylsulfanylmethyl)-[1,2,4]oxadiazol-5-yl]phenyl}-amine, 5-(3-Chloro-phenyl)-3-(4-methyl-5-thiophen-2-yl-4H-[1,2,4]triazol-3-ylsulfanylmethyl)-[1,2,4]oxadiazole, 3-(4-Methyl-5-thiophen-2-yl-4H-[1,2,4]triazol-3-ylsulfanylmethyl)-5-(3-trifluoromethoxy-phenyl)[1,2,4]oxadiazole, 3-(5-Cyclohexyl-4-methyl-4H-[1,2,4]triazol-3-ylsulfanylmethyl)-5-m-tolyl-[1,2,4]oxadiazole, 3-(5-tert-Butyl-4-methyl-4H-[1,2,4]triazol-3-ylsulfanylmethyl)-5-m-tolyl-[1,2,4]oxadiazole, 5-(3-Bromo-phenyl)-3-(4-methyl-5-thiophen-2-yl-4H-[1,2,4]triazol-3-ylsulfanylmethyl)-[1,2,4]oxadiazole, 2-[5-(3-Bromo-phenyl)-[1,2,4]oxadiazol-3-ylmethylsulfanyl]-1H-benzoimidazole, 5-(3-Methoxymethyl-phenyl)-3-(4-methyl-5-thiophen-2-yl-4H-[1,2,4]triazol-3-ylsulfanylmethyl)-[1,2,4)oxadiazole, 2-(5-(3-Methoxymethyl-phenyl)-[1,2,4]oxadiazol-3-ylmethylsulfanyl]-1H-benzoimidazole, 4-[5-(4-Methyl-5-thiophen-2-yl-4H-[1,2,4]triazol-3-ylsulfanylmethyl)-[1,2,4]oxadiazol-3-yl]-pyridine, 2-{1-[5-(3-Methoxy-phenyl)-[1,2,4]oxadiazol-3-yl]-ethylsulfanyl}-1-methyl-1H-imidazo[4,5-b]pyridine, 2-[5-(3-Methoxy-phenyl)-[1,2,4]oxadiazol-3-ylmethylsulfanyl]-1-methyl-1H-imidazo[4,5-b], 3-[1-Methyl-1-(4-methyl-5-thiophen-2-yl-4H-[1,2,4]triazol-3-ylsulfanyl)-ethyl]-5-m-tolyl-[1,2,4]oxadiazole, 3-[1-(4-Methyl-5-thiophen-2-yl-4H-[1,2,4]triazol-3-ylsulfanyl)-ethyl]-5-m-tolyl-[1,2,4]oxadiazole, 3-(4-Methyl-5-thiophen-2-yl-4H-[1,2,4]triazole-3-sulfonylmethyl)-5-m-tolyl-[1,2,4]oxadiazole, 3-(4-Methyl-5-thiophen-2-yl-4H-[1,2,4]triazole-3-sulfinylmethyl)-5-m-tolyl-[1,2,4]oxadiazole, or 5-(3-Furan-3-yl-phenyl)-3-(4-methyl-5-thiophen-2-yl-4H-[1,2,4]triazol-3-ylsulfanylmethyl)-[1,2,4]oxadiazole, or salt thereof.

Further specific embodiments of the invention include, 4-(4-Cyclopropyl-5-{1-[5-(2,5-difluoro-phenyl)-[1,2,4]oxadiazol-3-yl]-ethylsulfanyl}-4H-[1,2,4]triazol-3-yl)-pyridine, 4-(5-{1-[5-(3-Methoxy-phenyl)-[1,2,4]oxadiazol-3-yl]-ethylsulfanyl}-4-methyl-4H-[1,2,4]triazol-3-yl)-pyridine, 4-{4-Methyl-5-[1-(5-m-tolyl-[1,2,4]oxadiazol-3-yl)-ethylsulfanyl]-4H-[1,2,4]triazol-3-yl}-pyridine, 5-(4-Methyl-5-thiophen-2-yl-4H-[1,2,4]triazol-3-ylsulfanylmethyl)-3-o-tolyl-[1,2,4]oxadiazole, 5-(3-Chloro-phenyl)-3-(4-cyclopropyl-5-thiophen-2yl-4H-[1,2,4]triazol-3-ylsulfanylmethyl)-[1,2,4]oxadiazole, 2-{3-[5-(2-Fluoro-5-methyl-phenyl)-[1,2,4]oxadiazol-3-ylmethylsulfanyl]-5-thiophen-2-yl-[1,2,4]triazol-4-yl}-ethanol, 4-{4-Ethyl-5-[5-(2-fluoro-5-methyl-phenyl)-[1,2,4]oxadiazol-3-ylmethylsulfanyl]-4H-[1,2,4]triazol-3-yl}-pyrimidine, 3-(4-Ethyl-5-furan-3-yl-4H-[1,2,4]triazol-3-ylsulfanylmethyl)-5-(2-fluoro-5-methyl-phenyl)-[1,2,4]oxadiazole, {3-[5-(2-Fluoro-5-methyl-phenyl)-[1,2,4]oxadiazol-3-ylmethylsulfanyl]-5-thiophen-2-yl-[1,2,4]triazol-4-yl}-acetic acid methyl ester, 5-(2-Fluoro-5-methyl-phenyl)-3-[5-furan-2-yl-4-(2-methoxy-ethyl)-4H-[1,2,4]triazol-3-ylsulfanylmethyl]-[1,2,4]oxadiazole, 3-(4-Cyclopropyl-5-furan-2-yl-4H-[1,2,4]triazol-3-ylsulfanylmethyl)-5-(2-fluoro-5-methyl-phenyl)-[1,2,4]oxadiazole, 3-(5-Chloro-2-fluoro-phenyl)-5-(4-cyclopropylmethyl-5-thiophen-2-yl-4H-[1,2,4]triazol-3-ylsulfanylmethyl)-[1,2,4]oxadiazole, 4-{5-[3-(5-Chloro-2-fluoro-phenyl)-[1,2,4]oxadiazol-5-ylmethylsulfanyl]-4-ethyl-4H-[1,2,4]triazol-3-yl}-pyrimidine, 3-(5-Cyclopentyl-4-ethyl-4H-[1,2,4]triazol-3-ylsulfanylmethyl)-5-m-tolyl-[1,2,4]oxadiazole, 3-(3-Chloro-phenyl)-5-{4-ethyl-5-[2-(4-methoxy-phenyl)-ethyl]-4H-[1,2,4]triazol-3-ylsulfanylmethyl}-[1,2,4]oxadiazole, 5-(3-Chloro-phenyl)-3-(4-ethyl-5-p-tolyloxymethyl-4H-[1,2,4]triazol-3-ylsulfanylmethyl)-[1,2,4]oxadiazole, 5-(3-Chloro-phenyl)-3-[4-(2-methoxy-ethyl)-5-thiophen-2-yl-4H-[1,2,4]triazol-3-ylsulfanylmethyl]-[1,2,4]oxadiazole, 3-(5-Chloro-2-fluoro-phenyl)-5-(4-ethyl-5-methoxymethyl-4H-[1,2,4]triazol-3-ylsulfanylmethyl)-[1,2,4]oxadiazole, 5-(5-Chloro-2-fluoro-phenyl)-3-(4-ethyl-5-methoxymethyl-4H-[1,2,4]triazol-3-ylsulfanylmethyl)-[1,2,4]oxadiazole, 5-(3-Chloro-phenyl)-3-(4-ethyl-5-methoxymethyl-4H-[1,2,4]triazol-3-ylsulfanylmethyl)-[1,2,4]oxadiazole, 3-(3-Chloro-phenyl)-5-(4-ethyl-5-methoxymethyl-4H-[1,2,4]triazol-3-ylsulfanylmethyl)-[1,2,4]oxadiazole, 4-(5-{1-[3-(3-Chloro-phenyl)-isoxazol-5-yl]-ethylsulfanyl}-4-methyl-4H-[1,2,4]triazol-3-yl)-pyridine, 3-(4-Allyl-5-furan-2-yl-4H-[1,2,4]triazol-3-ylsulfanylmethyl)-5-(3-chloro-phenyl)-[1,2,4]oxadiazole, 3-(4-Allyl-5-furan-2-yl-4H-[1,2,4]triazol-3-ylsulfanylmethyl)-5-thiophen-3-yl-[1,2,4]oxadiazole, 5-(4-Allyl-5-furan-2-yl-4H-[1,2,4]triazol-3-ylsulfanylmethyl)-3-furan-2-yl-[1,2,4]oxadiazole, 5-(3-Chloro-phenyl)-3-[4-ethyl-5-(4-methoxy-phenoxymethyl)-4H-[1,2,4]triazol-3-ylsulfanylmethyl]-[1,2,4]oxadiazole, 3-(3-Chloro-phenyl)-5-[4-ethyl-5-(4-methoxy-phenoxymethyl)-4H-[1,2,4]triazol-3-ylsulfanylmethyl]-[1,2,4]oxadiazole, {5-[3-(3-Chloro-phenyl)-[1,2,4]oxadiazol-5-ylmethylsulfanyl]-4-ethyl-4H-[1,2,4]triazol-3-yl}-methanol, 3-(3-Chloro-phenyl)-5-[4-ethyl-5-(2-methoxy-ethyl)-4H-[1,2,4]triazol-3-ylsulfanylmethyl]-[1,2,4]oxadiazole, 3-(3-Chloro-phenyl)-5-(4-ethyl-5-methylsulfanylmethyl-4H-[1,2,4]triazol-3-ylsulfanylmethyl)-[1,2,4]oxadiazole, 3-(3-Chloro-phenyl)-5-(5-ethoxymethyl-4-ethyl-4H-[1,2,4]triazol-3-ylsulfanylmethyl)-[1,2,4]oxadiazole, 5-[3-(3-Chloro-phenyl)-[1,2,4]oxadiazol-5-ylmethylsulfanyl]-4-ethyl-4H-[1,2,4]triazole-3-carboxylic acid methyl ester, 2-(5-Chloro-2-fluoro-phenyl)-5-(4-ethyl-5-furan-2-yl-4H-[1,2,4]triazol-3-ylsulfanylmethyl)-[1,3,4]oxadiazole, 2-(3-Chloro-phenyl)-5-(4-cyclopropyl-5-furan-2-yl-4H-[1,2,4]triazol-3-ylsulfanylmethyl)-[1,3,4]oxadiazole, 5-(3-Chloro-phenyl)-3-{1-[4-ethyl-5-(tetrahydro-furan-2-yl)-4H-[1,2,4]triazol-3-ylsulfanyl]-ethyl}-[1,2,4]oxadiazole, 4-(5-{1-[5-(3-Chloro-phenyl)-[1,2,4]oxadiazol-3-yl]-ethylsulfanyl}-4-ethyl-4H-[1,2,4]triazol-3-yl)-pyridazine, 4-(5-{1-[5-(3-Chloro-phenyl)-[1,2,4]oxadiazol-3-yl]-ethylsulfanyl}-4-ethyl-4H-[1,2,4]triazol-3-ylmethyl)-pyridine, 5-(5-{1-[5-(3-Chloro-phenyl)-[1,2,4]oxadiazol-3-yl]-ethylsulfanyl}-4-ethyl-4H-[1,2,4]triazol-3-yl)-pyridin-2-ol, 4-(5-{1-[5-(3-Chloro-phenyl)-[1,2,4]oxadiazol-3-yl]-ethylsulfanyl}-4-ethyl-4H-[1,2,4]triazol-3-yl)-phenol, 5-(3-Chloro-phenyl)-3-[5-(4-methoxy-phenoxymethyl)-4-(tetrahydro-furan-2-ylmethyl)-4H-[1,2,4]triazol-3-ylsulfanylmethyl]-[1,2,4]oxadiazole, 5-(3-Chloro-phenyl)-3-[4-cyclopropyl-5-(4-methoxy-phenoxymethyl)-4H-[1,2,4]triazol-3-ylsulfanylmethyl]-[1,2,4]oxadiazole, 5-(5-Chloro-2-fluoro-phenyl)-3-(4-ethyl-5-furan-2-yl-4H-[1,2,4]triazol-3-ylsulfanylmethyl)-[1,2,4]oxadiazole, 3-(4-Ethyl-5-methoxymethyl-4H-[1,2,4]triazol-3-ylsulfanylmethyl)-5-m-tolyl-[1,2,4]oxadiazole, 3-[4-Ethyl-5-(tetrahydro-furan-2-yl)-4H-[1,2,4]triazol-3-ylsulfanylmethyl]-5-m-tolyl-[1,2,4]oxadiazole, 2-(3-Chloro-phenyl)-5-{1-[4-ethyl-5-(4-methoxy-phenyl)-4H-[1,2,4]triazol-3-ylsulfanyl]-ethyl}-[1,3,4]oxadiazole, 4-{5-[3-(2,5-Difluoro-phenyl)-[1,2,4]oxadiazol-5-ylmethylsulfanyl]-4-ethyl-4H-[1,2,4]triazol-3-yl}-pyrimidine, 4-{5-[5-(5-Chloro-2-fluoro-phenyl)-[1,2,4]oxadiazol-3-ylmethylsulfanyl]-4-methyl-4H-[1,2,4]triazol-3-yl}-pyrimidine, 3-(3-Chloro-phenyl)-5-(4-methyl-5-thiophen-2-yl-4H-[1,2,4]triazol-3-ylsulfanylmethyl)-[1,2,4]oxadiazole, 5-(3-Methylsulfanyl-phenyl)-3-(4-methyl-5-thiophen-2-yl-4H-[1,2,4]triazol-3-ylsulfanylmethyl)-[1,2,4]oxadiazole, 2-[5-(3-Methylsulfanyl-phenyl)-[1,2,4]oxadiazol-3-ylmethylsulfanyl]-1H-benzoimidazole, 5-(2,5-Dimethyl-phenyl)-3-(4-methyl-5-thiophen-2-yl-4H-[1,2,4]triazol-3-ylsulfanylmethyl)-[1,2,4]oxadiazole, 5-(2-Fluoro-5-methyl-phenyl)-3-(4-methyl-5-thiophen-2-yl-4H-[1,2,4]triazol-3-ylsulfanylmethyl)-[1,2,4]oxadiazole, 5-(3-Cyclopropyl-phenyl)-3-(4-methyl-5-thiophen-2-yl-4H-[1,2,4]triazol-3-ylsulfanylmethyl)-[1,2,4]oxadiazole, 4-{5-[2-(3-Chloro-phenyl)-oxazol-4-ylmethylsulfanyl]-4-methyl-4H-[1,2,4]triazol-3-yl}-pyridine, 4-[4-Methyl-5-(5-thiophen-2-yl-[1,2,4]oxadiazol-3-ylmethylsulfanyl)-4H-[1,2,4]triazol-3-yl]-pyridine, 4-{4-Methyl-5-[5-(3-methylsulfanyl-phenyl)-[1,2,4]oxadiazol-3-ylmethylsulfanyl]-4H-[1,2,4]triazol-3-yl}-pyridine, 4-{5-[5-(3-Chloro-phenyl)-[1,2,4]oxadiazol-3-ylmethylsulfanyl]-4-methyl-4H-[1,2,4]triazol-3-yl}-pyridine, 2-Methyl-4-[3-(4-methyl-5-pyridin-4-yl-4H-[1,2,4]triazol-3-ylsulfanylmethyl)-[1,2,4]oxadiazol-5-yl]-pyridine, 1-{3-[3-(4-Methyl-5-thiophen-2-yl-4H-[1,2,4]triazol-3-ylsulfanylmethyl)-[1,2,4]oxadiazol-5-yl]-phenyl}-ethanone, 4-{5-[5-(2-Fluoro-5-methyl-phenyl)-[1,2,4]oxadiazol-3-ylmethylsulfanyl]-4-methyl-4H-[1,2,4]triazol-3-yl}-pyridine, 2-Methyl-4-[4-methyl-5-(5-m-tolyl-[1,2,4]oxadiazol-3-ylmethylsulfanyl)-4H-[1,2,4]triazol-3-yl]-pyridine, 3-[5-(3-Chloro-phenyl)-isoxazol-3-ylmethylsulfanyl]-4-methyl-5-thiophen-2-yl-4H-[1,2,4]triazole, 4-{5-[5-(3-Chloro-phenyl)-isoxazol-3-ylmethylsulfanyl]-4-methyl-4H-[1,2,4]triazol-3-yl}-pyridine, 3-(4-Butyl-5-thiophen-2-yl-4H-[1,2,4]triazol-3-ylsulfanylmethyl)-5-(3-chloro-phenyl)-[1,2,4]oxadiazole, 5-(3-Chloro-phenyl)-3-[4-(3-methoxy-propyl)-5-thiophen-2-yl-4H-[1,2,4]triazol-3-ylsulfanylmethyl]-[1,2,4]oxadiazole, 3-(4-Benzyl-5-thiophen-2-yl-4H-[1,2,4]triazol-3-ylsulfanylmethyl)-5-(3-chloro-phenyl)-[1,2,4]oxadiazole, 5-(3-Chloro-phenyl)-3-(4-furan-2-ylmethyl-5-thiophen-2-yl-4H-[1,2,4]triazol-3-ylsulfanylmethyl)-[1,2,4]oxadiazole, 3-{5-[5-(3-Chloro-phenyl)-[1,2,4]oxadiazol-3-ylmethylsulfanyl]-4-methyl-4H-[1,2,4]triazol-3-yl}-pyridine, 5-(3-Chloro-phenyl)-3-(4-methyl-5-thiophen-3-yl-4H-[1,2,4]triazol-3-ylsulfanylmethyl)-[1,2,4]oxadiazole,
4-{5-[5-(3-Chloro-phenyl)-[1,2,4]oxadiazol-3-ylmethylsulfanyl]-4-methyl-4H-[1,2,4]triazol-3-yl}-2-methyl-pyridine,
5-(5-Chloro-2-fluoro-phenyl)-3-(4-methyl-5-thiophen-2-yl-4H-[1,2,4]triazol-3-ylsulfanylmethyl)-[1,2,4]oxadiazole,
4-{5-[5-(5-Chloro-2-fluoro-phenyl)-[1,2,4]oxadiazol-3-ylmethylsulfanyl]-4-methyl-4H-[1,2,4]triazol-3-yl}-pyridine,
3-{5-[5-(2-Fluoro-5-methyl-phenyl)-[1,2,4]oxadiazol-3-ylmethylsulfanyl]-4-methyl-4H-[1,2,4]triazol-3-yl}-pyridine,
5-(3-Chloro-phenyl)-3-(5-thiophen-2-yl-4-thiophen-2-ylmethyl-4H-[1,2,4]triazol-3-ylsulfanylmethyl)-[1,2,4]oxadiazole,
5-(3-Chloro-phenyl)-3-(4-ethyl-5-thiophen-2-yl-4H-[1,2,4]triazol-3-ylsulfanylmethyl)-[1,2,4]oxadiazole,
3-{5-[3-(2-Fluoro-5-methyl-phenyl)-[1,2,4]oxadiazol-5-ylmethylsulfanyl]-4-methyl-4H-[1,2,4]triazol-3-yl}-pyridine,
4-{5-[3-(2-Fluoro-5-methyl-phenyl)-[1,2,4]oxadiazol-5-ylmethylsulfanyl]-4-methyl-4H-[1,2,4]triazol-3-yl}-pyridine,
4-{5-[5-(5-Bromo-2-fluoro-phenyl)-[1,2,4]oxadiazol-3-ylmethylsulfanyl]-4-methyl-4H-[1,2,4]triazol-3-yl}-pyridine,
3-{5-[5-(5-Bromo-2-fluoro-phenyl)-[1,2,4]oxadiazol-3-ylmethylsulfanyl]-4-methyl-4H-[1,2,4]triazol-3-yl}-pyridine,
5-(5-Bromo-2-fluoro-phenyl)-3-(4-methyl-5-thiophen-2-yl-4H-[1,2,4]triazol-3-ylsulfanylmethyl)-[1,2,4]oxadiazole,
5-(4-Methyl-5-thiophen-3-yl-4H-[1,2,4]triazol-3-ylsulfanylmethyl)-3-phenyl-[1,2,4]oxadiazole,
3-{5-[5-(3-Fluoro-phenyl)-[1,2,4]oxadiazol-3-ylmethylsulfanyl]-4-methyl-4H-[1,2,4]triazol-3-yl}-pyridine,
4-{5-[5-(3-Fluoro-phenyl)-[1,2,4]oxadiazol-3-ylmethylsulfanyl]-4-methyl-4H-[1,2,4]triazol-3-yl}-pyridine,
5-(3-Fluoro-phenyl)-3-(4-methyl-5-thiophen-3-yl-4H-[1,2,4]triazol-3-ylsulfanylmethyl)-[1,2,4]oxadiazole,
3-[4-Methyl-5-(5-thiophen-3-yl-[1,2,4]oxadiazol-3-ylmethylsulfanyl)-4H-[1,2,4]triazol-3-yl]-pyridine,
3-(4-Methyl-5-thiophen-3-yl-4H-[1,2,4]triazol-3-ylsulfanylmethyl)-5-thiophen-3-yl-[1,2,4]oxadiazole,
2-Chloro-4-[3-(4-methyl-5-pyridin-3-yl-4H-[1,2,4]triazol-3-ylsulfanylmethyl)-[1,2,4]oxadiazol-5-yl]-pyridine,
2-Chloro-4-[3-(4-methyl-5-pyridin-4-yl-4H-[1,2,4]triazol-3-ylsulfanylmethyl)-[1,2,4]oxadiazol-5-yl]-pyridine,
2-Chloro-4-[3-(4-methyl-5-thiophen-2-yl-4H-[1,2,4]triazol-3-ylsulfanylmethyl)-[1,2,4]oxadiazol-5-yl]-pyridine,
4-[4-Methyl-5-(5-phenyl-[1,2,4]oxadiazol-3-ylmethylsulfanyl)-4H-[1,2,4]triazol-3-yl]-pyridine,
3-(4-Methyl-5-thiophen-3-yl-4H-[1,2,4]triazol-3-ylsulfanylmethyl)-5-phenyl-[1,2,4]oxadiazole,
5-(5-Bromo-2-fluoro-phenyl)-3-(4-methyl-5-thiophen-3-yl-4H-[1,2,4]triazol-3-ylsulfanylmethyl)-[1,2,4]oxadiazole,
3-[5-(3-Chloro-phenyl)-isoxazol-3-ylmethylsulfanyl]-4-ethyl-5-thiophen-2-yl-4H-[1,2,4]triazole,
2-Chloro-4-[3-(4-methyl-5-thiophen-2-yl-4H-[1,2,4]triazol-3-ylsulfanylmethyl)-[1,2,4]oxadiazol-5-yl]-pyridine,
4-{5-[3-(3-Fluoro-phenyl)-[1,2,4]oxadiazol-5-ylmethylsulfanyl]-4-methyl-4H-[1,2,4]triazol-3-yl}-pyridine,
3-(3-Fluoro-phenyl)-5-(4-methyl-5-thiophen-2-yl-4H-[1,2,4]triazol-3-ylsulfanylmethyl)-[1,2,4]oxadiazole,
3-(4-Ethyl-5-thiophen-2-yl-4H-[1,2,4]triazol-3-ylsulfanylmethyl)-5-m-tolyl-[1,2,4]oxadiazole,
3-(4-Ethyl-5-thiophen-2-yl-4H-[1,2,4]triazol-3-ylsulfanylmethyl)-5-(2-fluoro-5-methyl-phenyl)-[1,2,4]oxadiazole,
4-{5-[5-(3-Chloro-phenyl)-[1,2,4]oxadiazol-3-ylmethylsulfanyl]-4-furan-2-ylmethyl-4H-[1,2,4]triazol-3-yl}-pyridine,
4-{5-[5-(3-Chloro-phenyl)-[1,2,4]oxadiazol-3-ylmethylsulfanyl]-4-ethyl-4H-[1,2,4,]triazol-3-yl}-pyridine,
3-{5-[5-(3-Chloro-phenyl)-[1,2,4]oxadiazol-3-ylmethylsulfanyl]-4-ethyl-4H-[1,2,4]triazol-3-yl}-pyridine,
5-(3-Chloro-phenyl)-3-(4-ethyl-5-thiophen-3-yl-4H-[1,2,4]triazol-3-ylsulfanylmethyl)-[1,2,4]oxadiazole,
3-{5-[5-(3-Chloro-phenyl)-[1,2,4]oxadiazol-3-ylmethylsulfanyl]-4-furan-2-ylmethyl-4H-[1,2,4]triazol-3-yl}-pyridine,
3-(4-Furan-2-ylmethyl-5-thiophen-2-yl-4H-[1,2,4]triazol-3-ylsulfanylmethyl)-5-m-tolyl-[1,2,4]oxadiazole,
5-(5-Fluoro-2-methyl-phenyl)-3-(4-furan-2-ylmethyl-5-thiophen-2-yl-4H-[1,2,4]triazol-3-ylsulfanylmethyl)-[1,2,4]oxadiazole,
5-(3-Chloro-phenyl)-3-(4-furan-2-ylmethyl-4H-[1,2,4]triazol-3-ylsulfanylmethyl)-[1,2,4]oxadiazole,
3-[3-(4-Methyl-5-pyridin-3-yl-4H-[1,2,4]triazol-3-ylsulfanylmethyl)-[1,2,4]oxadiazol-5-yl]-benzonitrile,
3-[3-(4-Methyl-5-pyridin-4-yl-4H-[1,2,4]triazol-3-ylsulfanylmethyl)-[1,2,4]oxadiazol-5-yl]-benzonitrile,
3-[3-(4-Methyl-5-thiophen-3-yl-4H-[1,2,4]triazol-3-ylsulfanylmethyl)-[1,2,4]oxadiazol-5-yl]-benzonitrile,
5-(5-Chloro-2-fluoro-phenyl)-3-(4-ethyl-5-thiophen-2-yl-4H-[1,2,4]triazol-3-ylsulfanylmethyl)-[1,2,4]oxadiazole,
2-Chloro-4-[3-(4-ethyl-5-thiophen-2-yl-4H-[1,2,4]triazol-3-ylsulfanylmethyl)-[1,2,4]oxadiazol-5-yl]-pyridine,
3-(4-Ethyl-5-thiophen-2-yl-4H-[1,2,4]triazol-3-ylsulfanylmethyl)-5-thiophen-3-yl-[1,2,4]oxadiazole,
3-(4-Ethyl-5-thiophen-3-yl-4H-[1,2,4]triazol-3-ylsulfanylmethyl)-5-m-tolyl-[1,2,4]oxadiazole,
4-[4-Ethyl-5-(5-m-tolyl-[1,2,4]oxadiazol-3-ylmethylsulfanyl)-4H-[1,2,4]triazol-3-yl]-pyridine,
3-[4-Ethyl-5-(5-m-tolyl-[1,2,4]oxadiazol-3-ylmethylsulfanyl)-4H-[1,2,4]triazol-3-yl]-pyridine,
3-(4-Ethyl-5-thiophen-3-yl-4H-[1,2,4]triazol-3-ylsulfanylmethyl)-5-(2-fluoro-5-methyl-phenyl)-[1,2,4]oxadiazole,
4-{4-Ethyl-5-[5-(2-fluoro-5-methyl-phenyl)-[1,2,4]oxadiazol-3-ylmethylsulfanyl]-4H-[1,2,4]triazol-3-yl}-pyridine,
3-{4-Ethyl-5-[5-(2-fluoro-5-methyl-phenyl)-[1,2,4]oxadiazol-3-ylmethylsulfanyl]-4H-[1,2,4]triazol-3-yl}-pyridine,
3-[5-(3-Chloro-phenyl)-[1,2,4]oxadiazol-3-ylmethylsulfanyl]-5-pyridin-4yl-[1,2,4]triazol-4-ylamine,
4-{5-[5-(5-Bromo-2-fluoro-phenyl)-[1,2,4]oxadiazol-3-ylmethylsulfanyl]-4-ethyl-4H-[1,2,4]triazol-3-yl}-pyridine,
5-(4-Methyl-5-thiophen-3-yl-4H-[1,2,4]triazol-3-ylsulfanylmethyl)-3-thiophen-2-yl-[1,2,4]oxadiazole,
3-[3-(4-Ethyl-5-thiophen-2-yl-4H-[1,2,4]triazol-3-ylsulfanylmethyl)-[1,2,4oxadiazol-5-yl]-benzonitrile,
3-(4-Ethyl-5-thiophen-2-yl-4H-[1,2,4]triazol-3-ylsulfanylmethyl)-5-phenyl-[1,2,4]oxadiazole,
4-[3-(4-Ethyl-5-thiophen-2-yl-4H-[1,2,4]triazol-3-ylsulfanylmethyl)-[1,2,4]oxadiazol-5-yl]-2-methoxy-pyridine,
3-(3-Chloro-phenyl)-5-(4-ethyl-5-thiophen-2-yl-4H-[1,2,4]triazol-3-ylsulfanylmethyl)-[1,2,4]oxadiazole,
4-{5-[5-(3-Chloro-phenyl)-isoxazol-3-ylmethylsulfanyl]-4-ethyl-4H-[1,2,4]triazol-3-yl}-pyridine,
2-Methyl-4-[3-(4-methyl-5-thiophen-3-yl-4H-[1,2,4]triazol-3-ylsulfanylmethyl)-[1,2,4]oxadiazol-5-yl]-pyridine,
4-[3-(4-Ethyl-5-thiophen-2-yl-4H-[1,2,4]triazol-3-ylsulfanylmethyl)-[1,2,4]oxadiazol-5-yl]-2-methyl-pyridine, 5-(4-Ethyl-5-thiophen-2-yl-4H-[1,2,4]triazol-3-ylsulfanylmnethyl)-3-thiophen-2-yl-[1,2,4]oxadiazole,
4-{5-[5-(5-Chloro-2-fluoro-phenyl)-[1,2,4]oxadiazol-3-ylmethylsulfanyl]-4-ethyl-4H-[1,2,4]triazol-3-yl}-pyridine,
4-[3-(4-Ethyl-5-pyridin-yl-4H-[1,2,4]triazol-3-ylsulfanylmnethyl)-[1,2,4]oxadiazol-5-yl]-2-methyl-pyridine,
3-{5-[5-(3-Chloro-phenyl)-[1,2,4]oxadiazol-3-ylmethylsulfanyl]-4-methyl-4H-[1,2,4]triazol-3-yl}-benzonitrile,
5-(3-Chloro-phenyl)-3-[5-(3-chloro-phenyl)-4-methyl-4H-[1,2,4]triazol-3-ylsulfanylmethyl]-[1,2,4]oxadiazole,
5-(3-Chloro-phenyl)-3-[5-(4-chloro-phenyl)-4-methyl-4H-[1,2,4]triazol-3-ylsulfanylmethyl]-[1,2,4]oxadiazole,
4-{5-[5-(2,5-Dichloro-phenyl)-[1,2,4]oxadiazol-3-ylmethylsulfanyl]-4-ethyl-4H-[1,2,4]triazol-3-yl}-pyridine,
5-(2,5-Dichloro-phenyl)-3-(4-ethyl-5-thiophen-2-yl-4H-[1,2,4]triazol-3-ylsulfanylmethyl)-[1,2,4]oxadiazole,
5-(2,5-Difluoro-phenyl)-3-(4-ethyl-5-thiophen-2-yl-4H-[1,2,4]triazol-3-ylsulfanylmethyl)-[1,2,4]oxadiazole,
4-{5-[5-(2,5-Difluoro-phenyl)-[1,2,4]oxadiazol-3-ylmethylsulfanyl]-4-ethyl-4H-[1,2,4]triazol-3-yl}-pyridine,
5-(2,5-Dichloro-phenyl)-3-(4-ethyl-5-thiophen-3-yl-4H-[1,2,4]triazol-3-ylsulfanylmethyl)-[1,2,4]oxadiazole,
5-(2,5-Difluoro-phenyl)-3-(4-ethyl-5-thiophen-3-yl-4H-[1,2,4]triazol-3-ylsulfanylmethyl)-[1,2,4]oxadiazole,
4-{5-[5-(3-Chloro-phenyl)-[1,2,4]oxadiazol-3-ylmethylsulfanyl]-4-propyl-4H-[1,2,4]triazol-3-yl}-pyridine,
4-{5-[5-(2-Fluoro-5-methyl-phenyl)-[1,2,4]oxadiazol-3-ylmethylsulfanyl]-4-propyl-4H-[1,2,4]triazol-3-yl}-pyridine,
3-(4-Ethyl-5-thiophen-2-yl-4H-[1,2,4]triazol-3-ylsulfanylmethyl)-5-thiophen-2-yl-[1,2,4]oxadiazole,
3-(4-Methyl-5-thiophen-3-yl-4H-[1,2,4]triazol-3-ylsulfanylmethyl)-5-thiophen-2-yl-[1,2,4]oxadiazole,
4-[4-Methyl-5-(3-thiophen-3-yl-[1,2,4]oxadiazol-5-ylmethylsulfanyl)-4H-[1,2,4]triazol-3-yl]-pyridine,
5-(4-Methyl-5-thiophen-3-yl-4H-[1,2,4]triazol-3-ylsulfanylmethyl)-3-thiophen-3-yl-[1,2,4]oxadiazole,
5-(4-Ethyl-5-thiophen-2-yl-4H-[1,2,4]triazol-3-ylsulfanylmethyl)-3-thiophen-3-yl-[1,2,4]oxadiazole,
5-[3-(4-Ethyl-5-thiophen-2-yl-4H-[1,2,4]triazol-3-ylsulfanylmethyl)-[1,2,4]oxadiazol-5-yl]-thiophene-3-carbonitrile,
5-(3-Chloro-phenyl)-3-[5-(2-fluoro-phenyl)-4-methyl-4H-[1,2,4]triazol-3-ylsulfanylmethyl]-[1,2,4]oxadiazole,
5-(3-Chloro-phenyl)-3-[5-(3-fluoro-phenyl)-4-methyl-4H-[1,2,4]triazol-3-ylsulfanylmethyl]-[1,2,4]oxadiazole,
5-(3-Chloro-phenyl)-3-[5-(4-fluoro-phenyl)-4-methyl-4H-[1,2,4]triazol-3-ylsulfanylmethyl]-[1,2,4]oxadiazole,
3-(5-Benzo[b]thiophen-2-yl-4-methyl-4H-[1,2,4]triazol-3-ylsulfanylmethyl)-5-(3-chloro-phenyl)-[1,2,4]oxadiazole,
5-(3-Chloro-phenyl)-3-[5-(3-methoxy-phenyl)-4-methyl-4H-[1,2,4]triazol-3-ylsulfanylmethyl]-[1,2,4]oxadiazole,
5-(3-Chloro-phenyl)-3-[5-(4-methoxy-phenyl)-4-methyl-4H-[1,2,4]triazol-3-ylsulfanylmethyl]-[1,2,4]oxadiazole,
3-(4-Ethyl-5-furan-2-yl-4H-[1,2,4]triazol-3-ylsulfanylmethyl)-5-(2-fluoro-5-methyl-phenyl)-[1,2,4]oxadiazole,
3-(4-Ethyl-5-furan-2-yl-4H-[1,2,4]triazol-3-ylsulfanylmethyl)-5-m-tolyl-[1,2,4]oxadiazole,
3-(4-Ethyl-5-trifluoromethyl-4H-[1,2,4]triazol-3-ylsulfanylmethyl)-5-(2-fluoro-5-(2-fluoro-5-methyl-phenyl)-[1,2,4]oxadiazole,
3-[5-(2-Fluoro-5-methyl-phenyl)-[1,2,4]oxadiazol-3-ylmethylsulfanyl]-5-pyridin-4-yl-[1,2,4]triazol-4-ylamine,
3-[5-(2-Fluoro-5-methyl-phenyl)-[1,2,4]oxadiazol-3-ylmethylsulfanyl]-5-thiophen-2-yl-[1,2,4]triazol-4-ylamine,
3-Pyridin-4-yl-5-(5-m-tolyl-[1,2,4]oxadiazol-3-ylmethylsulfanyl)-[1,2,4]triazol-4-ylamine,
3-Thiophen-2-yl-5-(5-m-tolyl-[1,2,4]oxadiazol-3-ylmethylsulfanyl)-[1,2,4]triazol-4-ylamine,
3-(4-Ethyl-5-furan-2-yl-4H-[1,2,4]triazol-3-ylsulfanylmethyl)-5-thiophen-3-yl-[1,2,4]oxadiazole,
5-(3-Chloro-phenyl)-3-(4-ethyl-5-furan-2-yl-4H-[1,2,4]triazol-3-ylsulfanylmethyl)-[1,2,4]oxadiazole,
4-[3-(4-Ethyl-5-furan-2-yl-4H-[1,2,4]triazol-3-ylsulfanylmethyl)-[1,2,4]oxadiazol-5-yl]-2-methyl-pyridine,
5-(2,5-Difluoro-phenyl)-3-(4-ethyl-5-furan-2-yl-4H-[1,2,4]triazol-3-ylsulfanylmethyl)-[1,2,4]oxadiazole,
4-[4-Ethyl-5-(5-thiophen-3-yl-isoxazol-3-ylmethylsulfanyl)-4H-[1,2,4]triazol-3-yl]-pyridine,
4-Ethyl-3-furan-2-yl-5-(5-thiophen-3-yl-isoxazol-3-ylmethylsulfanyl)-4H-[1,2,4]triazole,
5-(3-Chloro-phenyl)-3-[5-(3,5-dichloro-phenyl)-4-ethyl-4H-[1,2,4]triazol-3-ylsulfanylmethyl]-[1,2,4]oxadiazole,
5-(3-Chloro-phenyl)-3-(4-ethyl-5-p-tolyl-4H-[1,2,4]triazol-3-ylsulfanylmethyl)-[1,2,4]oxadiazole,
5-(3-Chloro-phenyl)-3-(4-ethyl-5-m-tolyl-4H-[1,2,4]triazol-3-ylsulfanylmethyl)-[1,2,4]oxadiazole,
5-(3-Chloro-phenyl)-3-[4-ethyl-5-(3-nitro-phenyl)-4H-[1,2,4]triazol-3-ylsulfanylmethyl]-[1,2,4]oxadiazole,
4-{5-[3-(3-Chloro-phenyl)-isoxazol-5-ylmethylsulfanyl]-4-methyl-4H-[1,2,4]triazol-3-yl}-pyridine,
5-(3-Chloro-phenyl)-3-[5-(2,5-difluoro-phenyl)-4-ethyl-4H-[1,2,4]triazol-3-ylsulfanylmethyl]-[1,2,4]oxadiazole,
5-(3-Chloro-phenyl)-3-[5-(3-chloro-phenyl)-4-ethyl-4H-[1,2,4]triazol-3-ylsulfanylmethyl]-[1,2,4]oxadiazole,
5-(3-Chloro-phenyl)-3-[5-(4-chloro-phenyl)-4-ethyl-4H-[1,2,4]triazol-3-ylsulfanylmethyl]-[1,2,4]oxadiazole,
4-{5-[5-(3-Chloro-phenyl)-oxazol-2-ylmethylsulfanyl]-4ethyl-4H-[1,2,4]triazol-3-yl}-pyridine,
3-[5-(3-Chloro-phenyl)-oxazol-2-ylmethylsulfanyl]-4-ethyl-5-thiophen-2-yl-4H-[1,2,4]triazole,
3-[5-(3-Chloro-phenyl)-oxazol-2-ylmethylsulfanyl]-4-ethyl-5-furan-2-yl-4H-[1,2,4]triazole,
5-(2-Chloro-5-methyl-phenyl)-3-(4-ethyl-5-thiophen-2-yl-4H-[1,2,4]triazol-3-ylsulfanylmethyl)-[1,2,4]oxadiazole,
4-{5-[3-(3-Chloro-phenyl)-isoxazol-5-ylmethylsulfanyl]-4ethyl-4H-[1,2,4]triazol-3-yl}-pyridine,
3-[3-(3-Chloro-phenyl)-isoxazol-5-ylmethylsulfanyl]-4-ethyl-5-thiophen-2-yl-4H-[1,2,4]triazole,
3-[3-(3-Chloro-phenyl)-isoxazol-5-ylmethylsulfanyl]-4-ethyl-5-furan-2-yl-4H-[1,2,4]triazole,
4-{5-[5-(2-Fluoro-5-methyl-phenyl)-isoxazol-3-ylmethylsulfanyl]-4-methyl-4H-[1,2,4]triazol-3-yl}-pyridine,
5-(2,5-Dichloro-thiophen-3-yl)-3-(4-ethyl-5-thiophen-2-yl-4H-[1,2,4]triazol-3-ylsulfanylmethyl)-[1,2,4]oxadiazole,
4-{5-[5-(2,5-Dichloro-thiophen-3-yl)-[1,2,4]oxadiazol-3-ylmethylsulfanyl]-4-ethyl-4H-[1,2,4]triazol-3-yl}-pyridine,
4-{4-Ethyl-5-[5-(2-fluoro-5-methyl-phenyl)-isoxazol-3-ylmethylsulfanyl]-4H-[1,2,4]triazol-3-yl}-pyridine,
4-Ethyl-3-[5-(2-fluoro-5-methyl-phenyl)-isoxazol-3-ylmethylsulfanyl]-5-thiophen-2-yl-4H-[1,2,4]triazole,
4-Ethyl-3-[5-(2-fluoro-5-methyl-phenyl)-isoxazol-3-ylmethylsulfanyl]-5-furan-2-yl-4H-[1,2,4]triazole,
5-(3-Chloro-phenyl)-3-(4-ethyl-5-trifluoromethyl-4H-[1,2,4]triazol-3-ylsulfanylmethyl)-[1,2,4]oxadiazole,
3-(3-Chloro-phenyl)-5-(4-ethyl-5-trifluoromethyl-4H-[1,2,4]triazol-3-ylsulfanylmethyl)-[1,2,4]oxadiazole,
3-(4-Ethyl-5-trifluoromethyl-4H-[1,2,4]triazol-3-ylsulfanylmethyl)-5-thiophen-3-yl-[1,2,4]oxadiazole,
5-(4-Ethyl-5-trifluoromethyl-4H-[1,2,4]triazol-3-ylsulfanylmethyl)-3-thiophen-3-yl-[1,2,4]oxadiazole,
5-(3-Chloro-phenyl)-3-[4-ethyl-5-(3-fluoro-phenyl)-4H-[1,2,4]triazol-3-ylsulfanylmethyl]-[1,2,4]oxadiazole, 5-(3-Chloro-phenyl)-3-[4-ethyl-5-(4-fluoro-phenyl)-4H-[1,2,4]triazol-3-ylsulfanylmethyl]-[1,2,4]oxadiazole, 3-(4-Ethyl-5-trifluoromethyl-4H-[1,2,4]triazol-3-ylsulfanylmethyl)-5-thiophen-2-yl-[1,2,4]oxadiazole, 3-{3-[5-(3-Chloro-thiophen-2-yl)-4-ethyl-4H-[1,2,4]triazol-3-ylsulfanylmethyl]-[1,2,4]oxadiazol-5-yl}-benzonitrile, 4-{5-[5-(3-Chloro-phenyl)-[1,3,4]oxadiazol-2-ylmethylsulfanyl]-4-ethyl-4H-[1,2,4]triazol-3-yl}-pyridine, 2-(3-Chloro-phenyl)-5-(4-ethyl-5-furan-2-yl-4H-[1,2,4]triazol-3-ylsulfanylmethyl)-[1,3,4]oxadiazole, 5-(3-Chloro-phenyl)-3-[4-ethyl-5-(4-methoxy-phenyl)-4H-[1,2,4]triazol-3-ylsulfanylmethyl]-[1,2,4]oxadiazole, 5-(3-Chloro-phenyl)-3-[5-(2-fluoro-5-methyl-phenyl)-4-furan-2-ylmethyl-4H-[1,2,4]triazol-3-ylsulfanylmethyl]-[1,2,4]oxadiazole, 4-[3-(4-Ethyl-5-trifluoromethyl-4H-[1,2,4]triazol-3-ylsulfanylmethyl)-[1,2,4]oxadiazol-5-yl]-2-methyl-pyridine, 3-(4-Ethyl-5-trifluoromethyl-4H-[1,2,4]triazol-3-ylsulfanylmethyl)-5-(3-methoxy-phenyl)-[1,2,4]oxadiazole, 5-(4-Ethyl-5-trifluoromethyl-4H-[1,2,4]triazol-3-ylsulfanylmethyl)-3-(3-methoxy-phenyl)-[1,2,4]oxadiazole, 5-(4-Ethyl-5-trifluoromethyl-4H-[1,2,4]triazol-3-ylsulfanylmethyl)-3-thiophen-2-yl-[1,2,4]oxadiazole, 5-(5-Chloro-2-fluoro-phenyl)-3-(4-ethyl-5-trifluoromethyl-4H-[1,2,4]triazol-3-ylsulfanylmethyl)-[1,2,4]oxadiazole, 3-[3-(4-Ethyl-5-trifluoromethyl-4H-[1,2,4]triazol-3-ylsulfanylmethyl)-[1,2,4oxadiazol-5-yl]-benzonitrile, 3-[5-(3-Chloro-phenyl)-isoxazol-3-ylmethylsulfanyl]-4-ethyl-5-trifluoromethyl-4H-[1,2,4]triazole, 3-[5-(3-Chloro-phenyl)-oxazol-2-ylmethylsulfanyl]-4-ethyl-5-trifluoromethyl-4H-[1,2,4]triazole, 4-Ethyl-3-(5-thiophen-3-yl-isoxazol-3-ylmethylsulfanyl)-5-trifluoromethyl-4H-[1,2,4]triazole, 4-{3-[5-(3-Fluoro-phenyl)-4-methyl-4H-[1,2,4]triazol-3-ylsulfanylmethyl]-[1,2,4]oxadiazol-5-yl}-2-methyl-pyridine, 4-{3-[5-(3-Chloro-phenyl)-4-methyl-4H-[1,2,4]triazol-3-ylsulfanylmethyl]-[1,2,4]oxadiazol-5-yl}-2-methyl-pyridine, 4-{3-[5-(4-Chloro-phenyl)-4-methyl-4H-[1,2,4]triazol-3-ylsulfanylmethyl]-[1,2,4]oxadiazol-5-yl}-2-methyl-pyridine, 4-{3-[5-(4-Methoxy-phenyl)-4-methyl-4H-[1,2,4]triazol-3-ylsulfanylmethyl]-[1,2,4]oxadiazol-5-yl}-2-methyl-pyridine, 4-[3-(4-Ethyl-5-p-tolyl-4H-[1,2,4]triazol-3-ylsulfanylmethyl)-[1,2,4]oxadiazol-5-yl]-2-methyl-pyridine, 3-(4-Ethyl-5-thiophen-2-yl-4H-[1,2,4]triazol-3-ylsulfanylmethyl)-5-(3-fluoro-phenyl)-[1,2,4]oxadiazole, 4-{4-Ethyl-5-[5-(3-fluoro-phenyl)-[1,2,4]oxadiazol-3-ylmethylsulfanyl]-4H-[1,2,4]triaazol-3-yl}-pyridine, 5-(3-Chloro-phenyl)-3-[5-(3,5-difluoro-phenyl)-4-ethyl-4H-[1,2,4]triazol-3-ylsulfanylmethyl]-[1,2,4]oxadiazole, 5-(3-Chloro-phenyl)-3-[5-(2,6-difluoro-phenyl)-4-ethyl-4H-[1,2,4]triazol-3-ylsulfanylmethyl]-[1,2,4]oxadiazole, 2-[3-(4-Ethyl-5-thiophen-2-yl-4H-[1,2,4]triazol-3-ylsulfanylmethyl)-[1,2,4]oxadiazol-5-yl]-4-methyl-phenol, 3-{1-[5-(3-Chloro-phenyl)-isoxazol-3-yl]-ethylsulfanyl}-4-ethyl-5-furan-2-yl-4H-[1,2,4]triazole, 4-(5-{1-[5-(3-Chloro-phenyl)-isoxazol-3-yl]-ethylsulfanyl}-4-ethyl-4H-[1,2,4]triazol-3-yl)-pyridine, 3-(5-(4-Butoxy-phenyl)-4-ethyl-4H-[1,2,4]triazol-3-ylsulfanylmethyl]-5-(3-chloro-phenyl)-[1,2,4]oxadiazole, 3-(5-Benzo[1,3]dioxol-5-yl-4-ethyl-4H-[1,2,4]triazol-3-ylsulfanylmethyl)-5-(3-chloro-phenyl)-[1,2,4]oxadiazole, 3-(4-Ethyl-5-thiophen-2-yl-4H-[1,2,4]triazol-3-ylsulfanylmethyl)-5-(2-methyl-thiazol-4-yl)-[1,2,4]oxadiazole, 3-(4-Ethyl-5-thiophen-2-yl-4H-[1,2,4]triazol-3-ylsulfanylmethyl)-5-(4-fluoro-phenyl)-[1,2,4]oxadiazole, 4-Ethyl-3-{1-[5-(2-fluoro-5-methyl-phenyl)-isoxazol-3-yl]-ethylsulfanyl}-5-furan-2-yl-4H-[1,2,4]triazole, 4-(4-Ethyl-5-{1-[5-(2-fluoro-5-methyl-phenyl)-isoxazol-3-yl]-ethylsulfanyl}-4H-[1,2,4]triazol-3-yl)-pyridine, 5-(3-Chloro-phenyl)-3-[4-ethyl-5-(3-methyl-3H-imidazol-4-yl)-4H-[1,2,4]triazol-3-ylsulfanylmethyl]-[1,2,4]oxadiazole, 5-(3-Chloro-phenyl)-3-[4-ethyl-5-(1-methyl-1H-imidazol-2-yl)-4H-[1,2,4]triazol-3-ylsulfanylmethyl]-[1,2,4]oxadiazole, 5-(3-Chloro-phenyl)-3-[4-ethyl-5-(1-methyl-1H-imidazol-4-yl)-4H-[1,2,4]triazol-3-ylsulfanylmethyl]-[1,2,4]oxadiazole, 4-{5-[5-(3-Chloro-phenyl)-4-methyl-isoxazol-3-ylmethylsulfanyl]-4-ethyl-4H-[1,2,4]triazol-3-yl}-pyridine, 3-[5-(3-Chloro-phenyl)-4-methyl-isoxazol-3-ylmethylsulfanyl]-4-ethyl-5-furan-2-yl-4H-[1,2,4]triazole, 3-(4-Ethyl-5-thiophen-2-yl-4H-[1,2,4]triazol-3-ylsulfanylmethyl)-5-(4-methyl-thiophen-2-yl)-[1,2,4]oxadiazole, 5-(3-Chloro-phenyl)-3-[4-ethyl-5-(3-methyl-thiophen-2-yl)-4H-[1,2,4]triazol-3-ylsulfanylmethyl]-[1,2,4]oxadiazole, 5-(3-Chloro-phenyl)-3-[4-ethyl-5-(5-methyl-thiophen-2-yl)-4H-[1,2,4]triazol-3-ylsulfanylmethyl]-[1,2,4]oxadiazole, 4-{5-[4-Chloro-5-(3-chloro-phenyl)-isoxazol-3-ylmethylsulfanyl]-4-ethyl-4H-[1,2,4]triazol-3-yl}-pyridine, 3-[4-Chloro-5-(3-chloro-phenyl)-isoxazol-3-ylmethylsulfanyl]-4-ethyl-5-furan-2-yl-4H-[1,2,4]triazole, 2-Chloro-4-{5-[5-(3-chloro-phenyl)-[1,2,4]oxadiazol-3-ylmethylsulfanyl]-4-ethyl-4H-[1,2,4]triazol-3-yl}-6-methyl-pyridine, 3-[5-(5-Bromo-furan-2-yl)-4-ethyl-4H-[1,2,4]triazol-3-ylsulfanylmethyl]-5-(3-chloro-phenyl)-[1,2,4]oxadiazole, 2-Chloro-4-{5-[5-(3-chloro-phenyl)-[1,2,4]oxadiazol-3-ylmethylsulfanyl]-4-ethyl-4H-[1,2,4]triazol-3-yl}-pyridine, 2-Chloro-4-{5-[5-(3-chloro-phenyl)-[1,2,4]oxadiazol-3-ylmethylsulfanyl]-4-ethyl-4H-[1,2,4]triazol-3-yl}-6-methoxy-pyridine, 2-[3-(4-Ethyl-5-thiophen-2-yl-4H-[1,2,4]triazol-3-ylsulfanylmethyl)-[1,2,4]oxadiazol-5-yl]-4-methyl-benzonitrile, 5-(3-Chloro-phenyl)-3-[4-ethyl-5-(3-methoxy-thiophen-2-yl)-4H-[1,2,4]triazol-3-ylsulfanylmethyl]-[1,2,4]oxadiazole, 3-[5-(5-Chloro-thiophen-3-yl)-isoxazol-3-ylmethylsulfanyl]-4-ethyl-5-furan-2-yl-4H-[1,2,4]triazole, 3-[3-(4-Ethyl-5-furan-2-yl-4H-[1,2,4]triazol-3-ylsulfanylmethyl)-[1,2,4oxadiazol-5-yl]-5-fluoro-benzonitrile, 4-Ethyl-3-(5-phenyl-isoxazol-3-ylmethylsulfanyl)-5-thiophen-2-yl-4H-[1,2,4]triazole, 4-Methyl-3-(5-phenyl-isoxazol-3-ylmethylsulfanyl)-5-thiophen-3-yl-4H-[1,2,4]triazole, 4-Ethyl-3-furan-2-yl-5-(5-phenyl-isoxazol-3-ylmethylsulfanyl)-4H-[1,2,4]triazole, 4-[4-Ethyl-5-(5-phenyl-isoxazol-3-ylmethylsulfanyl)-4H-[1,2,4]triazol-3-yl]-pyridine, 4-[4-Methyl-5-(5-phenyl-isoxazol-3-ylmethylsulfanyl)-4H-[1,2,4]triazol-3-yl]-pyridine, 2-(4-Ethyl-5-furan-2-yl-4H-[1,2,4]triazol-3-ylsulfanylmethyl)-5-m-tolyl-[1,3,4oxadiazole, 4-[4-Methyl-5-(5-m-tolyl-[1,3,4]oxadiazol-2-ylmethylsulfanyl)-4H-[1,2,4]triazol-3-yl]-pyridine, 4-[4-Ethyl-5-(5-m-tolyl-[1,3,4]oxadiazol-2-ylmethylsulfanyl)-4H-[1,2,4]triazol-3-yl]-pyridine, 4-{5-[5-(5-Chloro-thiophen-3-yl)-[1,3,4]oxadiazol-3-ylmethylsulfanyl]-4-ethyl-4H-[1,2,4]triazol-3-yl}-pyridine, 3-[3-(4-Ethyl-5-pyridin-4-yl-4H-[1,2,4]triazol-3-ylsulfanylmethyl)-[1,2,4]oxadiazol-5-yl]-4-fluoro-benzonitrile, 3-[3-(4-Ethyl-5-furan-2-yl-4H-[1,2,4]triazol-3-ylsulfanylmethyl)-[1,2,4]oxadiazol-5-yl]-4-fluoro-benzonitrile, 3-[3-(4-Ethyl-5-thiophen-2-yl-4H-[1,2,4]triazol-3-ylsulfanylmethyl)-[1,2,4]oxadiazol-5-yl]-4-fluoro-benzonitrile, 3-[3-(4-Ethyl-5-furan-2-yl-4H-[1,2,4]triazol-3-ylsulfanylmethyl)-[1,2,4]oxadiazol-5-yl]-benzonitrile, 3-(5-(4-Ethyl-5-furan-2-yl-4H-[1,2,4]triazol-3-ylsulfanylmethyl)-[1,2,4]oxadiazol-3-yl]-benzonitrile, 3-[3-(4-Methyl-5-trifluoromethyl-4H-[1,2,4]triazol-3-ylsulfanylmethyl)-[1,2,4]oxadiazol-5-yl]-benzonitrile, 5-(5-Chloro-2-fluoro-phenyl)-3-(4-methyl-5-trifluoromethyl-4H-[1,2,4]triazol-3-ylsulfanylmethyl)-[1,2,4]oxadiazole, 2-Chloro-4-[3-(4-ethyl-5-furan-2-yl-4H-[1,2,4]triazol-3-ylsulfanylmethyl)-[1,2,4]oxadiazol-5-yl]-pyridine, 2-Chloro-4-[3-(5-furan-2-yl-4-methyl-4H-[1,2,4]triazol-3-ylsulfanylmethyl)-[1,2,4]oxadiazol-5-yl]-pyridine, 2-(3-Chloro-phenyl)-5-[4-methyl-5-(2-methyl-thiazol-4-yl)-4H-[1,2,4]triazol-3-ylsulfanylmethyl]-[1,3,4]oxadiazole, 2-(3-Chloro-phenyl)-5-(4-methyl-5-thiazol-4-yl-4H-[1,2,4]triazol-3-ylsulfanylmethyl)-[1,3,4]oxadiazole, 2-(3-Chloro-phenyl)-5-(5-furan-2-yl-4-methyl-4H-[1,2,4]triazol-3-ylsulfanylmethyl)-[1,3,4]oxadiazole, 2-(3-Chloro-phenyl)-5-(4-ethyl-5-trifluoromethyl-4H-[1,2,4]triazol-3-ylsulfanylmethyl)-[1,3,4]oxadiazole, 4-{4-Ethyl-5-[5-(4-methyl-thiophen-2-yl)-[1,2,4]oxadiazol-3-ylmethylsulfanyl]-4H-[1,2,4]triazol-3-yl}-pyridine, 3-(4-Ethyl-5-furan-2-yl-4H-[1,2,4]triazol-3-ylsulfanylmethyl)-5-(4-methyl-thiophen-2-yl)-[1,2,4]oxadiazole, 3-(3-Chloro-phenyl)-5-(4-ethyl-5-furan-2-yl-4H-[1,2,4]triazol-3-ylsulfanylmethyl)-[1,2,4]oxadiazole, 4-{5-[3-(3-Chloro-phenyl)-[1,2,4]oxadiazol-5-ylmethylsulfanyl]-4-ethyl-4H-[1,2,4]triazol-3-yl}-pyridine, 4-{4-Ethyl-5-[5-(3-nitro-phenyl)-[1,3,4]oxadiazol-2-ylmethylsulfanyl]-4H-[1,2,4]triazol-3-yl}-pyridine, 2-(4-Ethyl-5-furan-2-yl-4H-[1,2,4]triazol-3-ylsulfanylmethyl)-5-(3-nitro-phenyl)-[1,3,4]oxadiazole, 4-{5-[5-(3-Chloro-phenyl)-isoxazol-3-ylmethylsulfanyl]-4-cyclopropyl-4H-[1,2,4]triazol-3-yl}-pyridine, 3-[5-(3-Chloro-phenyl)-isoxazol-3-ylmethylsulfanyl]-4-ethyl-5-(4-methoxy-phenyl)-4H-[1,2,4]triazole, 5-(3-Chloro-phenyl)-3-[1-(4-methyl-5-thiophen-2-yl-4H-[1,2,4]triazol-3-ylsulfanyl)-ethyl]-[1,2,4]oxadiazole, 5-(3-Chloro-phenyl)-3-[1-(4-ethyl-5-thiophen-2-yl-4H-[1,2,4]triazol-3-ylsulfanyl)-ethyl]-[1,2,4]oxadiazole, 4-(5-{1-[5-(3-Chloro-phenyl)-[1,2,4]oxadiazol-3-yl]-ethylsulfanyl}-4-methyl-4H-[1,2,4]triazol-3-yl)-pyridine, 4-(5-{1-[5-(3-Chloro-phenyl)-[1,2,4]oxadiazol-3-yl]-ethylsulfanyl}-4-ethyl-4H-[1,2,4]triazol-3-yl)-pyridine, 3-[5-(4-Ethyl-5-pyridin-4-yl-4H-[1,2,4]triazol-3-ylsulfanylmethyl)-[1,3,4]oxadiazol-2-yl]-benzonitrile, 3-[5-(4-Ethyl-5-furan-2-yl-4H-[1,2,4]triazol-3-ylsulfanylmethyl)-[1,3,4]oxadiazol-2-yl]-benzonitrile, 3-[5-(4-Methyl-5-pyridin-4-yl-4H-[1,2,4]triazol-3-ylsulfanylmethyl)-[1,3,4]oxadiazol-2-yl]-benzonitrile, 3-[5-(4-Cyclopropyl-5-pyridin-4-yl-4H-[1,2,4]triazol-3-ylsulfanylmethyl)-[1,3,4]oxadiazol-2-yl]-benzonitrile, 4-{5-[5-(3-Chloro-phenyl)-[1,3,4]oxadiazol-2-ylmethylsulfanyl]-4-methyl-4H-[1,2,4]triazol-3-yl}-pyridine, 4-{5-[5-(3-Chloro-phenyl)-[1,3,4]oxadiazol-2-ylmethylsulfanyl]-4-cyclopropyl-4H-[1,2,4]triazol-3-yl}-pyridine, 4-{5-[5-(5-Chloro-2-fluoro-phenyl)-[1,3,4]oxadiazol-2-ylmethylsulfanyl]-4-cyclopropyl-4H-[1,2,4]triazol-3-yl}-pyridine, 2-(5-Chloro-2-fluoro-phenyl)-5-[4-ethyl-5-(4-methoxy-phenyl)-4H-[1,2,4]triazol-3-ylsulfanylmethyl]-[1,3,4]oxadiazole, 4-{5-[5-(5-Chloro-2-fluoro-phenyl)-[1,3,4]oxadiazol-2-ylmethylsulfanyl]-4-methyl-4H-[1,2,4]triazol-3-yl}-pyridine, 4-{5-[5-(5-Chloro-2-fluoro-phenyl)-[1,3,4]oxadiazol-2-ylmethylsulfanyl]-4-ethyl-4H-[1,2,4]triazol-3-yl}-pyridine, 2-(3-Chloro-phenyl)-5-[4-ethyl-5-(4-methoxy-phenyl)-4H-[1,2,4]triazol-3-ylsulfanylmethyl]-[1,3,4]oxadiazole, 2-(3-Chloro-phenyl)-5-[1-(4-ethyl-5-furan-2-yl-4H-[1,2,4]triazol-3-ylsulfanyl)-ethyl]-[1,3,4]oxadiazole, 5-(5-Chloro-2-fluoro-phenyl)-3-[1-(4-methyl-5-thiophen-2-yl-4H-[1,2,4]triazol-3-ylsulfanyl)-ethyl]-[1,2,4]oxadiazole, 4-(5-{1-[5-(5-Chloro-2-fluoro-phenyl)-[1,2,4]oxadiazol-3-yl]-ethylsulfanyl}-4-methyl-4H-[1,2,4]triazol-3-yl)-pyridine, 4-(5-{1-[5-(5-Chloro-2-fluoro-phenyl)-[1,2,4]oxadiazol-3-yl]-ethylsulfanyl}-4-ethyl-4H[1,2,4]triazol-3-yl)-pyridine, 2-Chloro-4-[3-(4-cyclopropyl-5-pyridin-4-yl-4H-[1,2,4]triazol-3-ylsulfanylmethyl)-[1,2,4]oxadiazol-5-yl]-pyridine, 4-{5-[5-(2-Fluoro-5-methyl-phenyl)-[1,3,4]oxadiazol-2-ylmethylsulfanyl]-4-methyl-4H-[1,2,4]triazol-3-yl}-pyridine, 4-{4-Ethyl-5-[5-(2-fluoro-5-methyl-phenyl)-[1,3,4]oxadiazol-2-ylmethylsulfanyl]-4H-[1,2,4]triazol-3-yl}-pyridine, 4-{4-Cyclopropyl-5-[5-(2-fluoro-5-methyl-phenyl)-[1,3,4]oxadiazol-2-ylmethylsulfanyl]-4H-[1,2,4]triazol-3-yl}-pyridine, 2-(4-Ethyl-5-furan-2-yl-4H-[1,2,4]triazol-3-ylsulfanylmethyl)-5-(2-fluoro-5-methyl-phenyl)-[1,3,4]oxadiazole, 2-[4-Ethyl-5-(4-methoxy-phenyl)-4H-[1,2,4]triazol-3-ylsulfanylmethyl]-5-(2-fluoro-5-methyl-phenyl)-[1,3,4]oxadiazole, 4-{5-[5-(5-Chloro-2-fluoro-phenyl)-isoxazol-3-ylmethylsulfanyl]-4-ethyl-4H-[1,2,4]triazol-3-yl}-pyridine, 4-(5-{1-[5-(5-Chloro-2-fluoro-phenyl)-isoxazol-3-yl]-ethylsulfanyl}-4-ethyl-4H-[1,2,4]triazol-3-yl)-pyridine, 4-{5-[5-(5-Chloro-2-fluoro-phenyl)-isoxazol-3-ylmethylsulfanyl]-4-methyl-4H-[1,2,4]triazol-3-yl}-pyridine, 4-(5-{1-[5-(5-Chloro-2-fluoro-phenyl)-isoxazol-3-yl]-ethylsulfanyl}-4-methyl-4H-[1,2,4]triazol-3-yl)-pyridine, 4-{5-[5-(5-Chloro-2-fluoro-phenyl)-isoxazol-3-ylmethylsulfanyl]-4-cyclopropyl-4H-[1,2,4]triazol-3-yl}-pyridine, 4-(5-{1-[5-(5-Chloro-2-fluoro-phenyl)-isoxazol-3-yl]-ethylsulfanyl}-4-cyclopropyl-4H-[1,2,4]triazol-3-yl)-pyridine, 3-[5-(5-Chloro-2-fluoro-phenyl)-isoxazol-3-ylmethylsulfanyl]-4-ethyl-5-furan-2-yl-4H-[1,2,4]triazole, 3-{1-[5-(5-Chloro-2-fluoro-phenyl)-isoxazol-3-yl]-ethylsulfanyl}-4-ethyl-5-furan-2-yl-4-H-[1,2,4]triazole, 4-(5-{1-[5-(3-Chloro-phenyl)-[1,3,4]oxadiazol-2-yl]-ethylsulfanyl}-4-methyl-4H-[1,2,4]triazol-3-yl)-pyridine, 4-(5-{1-[5-(3-Chloro-phenyl)-[1,3,4]oxadiazol-2-yl]-ethylsulfanyl}-4-ethyl-4H-[1,2,4]triazol-3-yl)-pyridine, 4-(5-{1-[5-(3-Chloro-phenyl)-[1,3,4]oxadiazol-2-yl]-ethylsulfanyl}-4-cyclopropyl-4H-[1,2,4]triazol-3-yl)-pyridine, 5-(5-Chloro-2-fluoro-phenyl)-3-(5-furan-2-yl-4-methyl-4H-[1,2,4]triazol-3-ylsulfanylmethyl)-[1,2,4]oxadiazole, 5-(5-Chloro-2-fluoro-phenyl)-3-(5-furan-3-yl-4-methyl-4H-[1,2,4]triazol-3-ylsulfanylmethyl)-[1,2,4]oxadiazole, 4-Chloro-2-[3-(4-ethyl-5-thiophen-2-yl-4H-[1,2,4]triazol-3-ylsulfanylmethyl)-[1,2,4]oxadiazol-5-yl]-phenol, 2-Chloro-4-[5-(4-methyl-5-pyridin-4-yl-4H-[1,2,4]triazol-3-ylsulfanylmethyl)-[1,3,4]oxadiazol-2-yl]-pyridine, 2-Chloro-4-[5-(4-ethyl-5-pyridin-4-yl-4H-[1,2,4]triazol-3-ylsulfanylmethyl)-[1,3,4]oxadiazol-2-yl]-pyridine, 2-Chloro-4-[5-(4-cyclopropyl-5-pyridin-4-yl-4H-[1,2,4]triazol-3-ylsulfanylmethyl)-[1,3,4]oxadiazol-2-yl]-pyridine, 2-Chloro-4-[5-(4-ethyl-5-furan-2-yl-4H-[1,2,4]triazol-3-ylsulfanylmethyl)-[1,3,4]oxadiazol-2-yl]-pyridine, 2-Chloro-4-{5-[4-ethyl-5-(4-methoxy-phenyl)-4H-[1,2,4]triazol-3-ylsulfanylmethyl]-[1,3,4]oxadiazol-2-yl}-pyridine, 2-(3-Chloro-phenyl)-5-{1-[5-(4-methoxy-phenyl)-4-methyl-4H-[1,2,4]triazol-3-ylsulfanyl]-ethyl}-[1,3,4]oxadiazole, 4-(5-{1-[5-(5-Chloro-2-fluoro-phenyl)-[1,3,4]oxadiazol-2-yl]-ethylsulfanyl}-4-methyl-4H-[1,2,4]triazol-3-yl)-pyridine, 5-(5-Bromo-2-fluoro-phenyl)-3-(4-ethyl-5-furan-2-yl-4H-[1,2,4]triazol-3-ylsulfanylmethyl)-[1,2,4]oxadiazole, 2-(3-Chloro-phenyl)-5-[5-(4-methoxy-phenyl)-4-methyl-4H-[1,2,4]triazol-3-ylsulfanylmethyl]-[1,3,4]oxadiazole, 4-{5-[3-(3-Chloro-phenyl)-[1,2,4]oxadiazol-5-ylmethylsulfanyl]-4-cyclopropyl-4H-[1,2,4]triazol-3-yl}-pyridine, 4-{5-(5-(3-Chloro-phenyl)-[1,2,4]oxadiazol-3-ylmethylsulfanyl]-4-cyclopropyl-4H-[1,2,4]triazol-3-yl}-pyridine, 4-(5-{1-[5-(2-Fluoro-5-methyl-phenyl)-[1,3,4]oxadiazol-2-yl]-ethylsulfanyl}-4-methyl-4H-[1,2,4]triazol-3-yl)-pyridine, 4-(4-Ethyl-5-{1-[5-(2-fluoro-5-methyl-phenyl)-[1,3,4]oxadiazol-2-yl]-ethylsulfanyl}-4H-[1,2,4]triazol-3-yl)-pyridine, 4-(4-Cyclopropyl-5-{1-[5-(2-fluoro-5-methyl-phenyl)-[1,3,4]oxadiazol-2-yl]-ethylsulfanyl}-4H-[1,2,4]triazol-3-yl)-pyridine, 4-(4-Cyclopropylmethyl-5-{1-[5-(2-fluoro-5-methyl-phenyl)-[1,3,4]oxadiazol-2-yl]-ethylsulfanyl}-4H-[1,2,4]triazol-3-yl)-pyridine, 2-(2-Fluoro-5-methyl-phenyl)-5-{1-[4-methyl-5-(2-methyl-thiazol-4-yl)-4H-[1,2,4triazol-3-ylsulfanyl]-ethyl}-[1,3,4]oxadiazole, 4-(5-{1-[5-(5-Chloro-2-fluoro-phenyl)-[1,3,4]oxadiazol-2-yl]-ethylsulfanyl}-4-ethyl-4H-[1,2,4]triazol-3-yl)-pyridine, 4-(5-{1-[5-(5-Chloro-2-fluoro-phenyl)-[1,3,4]oxadiazol-2-yl]-ethylsulfanyl}-4-cyclopropyl-4H-[1,2,4]triazol-3-yl)-pyridine, 2-(5-Chloro-2-fluoro-phenyl)-5-[1-(4-ethyl-5-furan-2-yl-4H-[1,2,4]triazol-3-ylsulfanyl)-ethyl]-[1,3,4]oxadiazole, 2-(5-Chloro-2-fluoro-phenyl)-5-{1-[4-methyl-5-(2-methyl-thiazol-4-yl)-4H-[1,2,4]triazol-3-ylsulfanyl]-ethyl}-[1,3,4]oxadiazole, 4-(4-Cyclopropylmethyl-5-{1-[5-(2-fluoro-5-methyl-phenyl)-isoxazol-3-yl]-ethylsulfanyl}-4H-[1,2,4]triazol-3-yl)-pyridine, 4-(5-{1-[5-(3-Fluoro-phenyl)-[1,2,4]oxadiazol-3-yl]-ethylsulfanyl}-4-methyl-4H-[1,2,4]triazol-3-yl)-pyridine, 4-(4-Cyclopropyl-5-{1-[5-(3-fluoro-phenyl)-[1,2,4]oxadiazol-3-yl]-ethylsufanyl}-4H-[1,2,4]triazol-3-yl)-pyridine, 4-(5-{1-[5-(4-Methoxy-phenyl)-4-methyl-4H-[1,2,4]triazol-3-ylsulfanyl]-ethyl}-[1,3,4]oxadiazol-2-yl)-2-methyl-pyridine, 4-(5-{1-[4-Ethyl-5-(4-methoxy-phenyl)-4H-[1,2,4]triazol-3-ylsulfanyl]-ethyl}-[1,3,4]oxadiazol-2-yl)-2-methyl-pyridine, 4-{5-[1-(4-Ethyl-5-pyridin-4-yl-4H-[1,2,4]triazol-3-ylsulfanyl)-ethyl]-[1,3,4]oxadiazol-2-yl}-2-methyl-pyridine, 4-{5-[1-(4-Cyclopropyl-5-pyridinyl-4H-[1,2,4]triazol-3-ylsulfanyl)-ethyl]-[1,3,4]oxadiazol-2-yl}-2-methyl-pyridine, 4-{5-[1-(5-Furan-2-yl-4-methyl-4H-[1,2,4]triazol-3-ylsulfanyl)-ethyl]-[1,3,4oxadiazol-2-yl}-2-methyl-pyridine, 2-(3-Chloro-phenyl)-5-{1-[4-methyl-5-(2-methyl-thiazol-4-yl)-4H-[1,2,4]triazol-3-ylsulfanyl]-ethyl}-[1,3,4]oxadiazole, 3-(5-{1-[5-(3-Chloro-phenyl)-[1,3,4]oxadiazol-2-yl]-ethylsulfanyl}-4-methyl-4H-[1,2,4]triazol-3-yl)-pyridine, 4-(5-{1-[5-(3-Chloro-phenyl)-[1,3,4]oxadiazol-2-yl]-ethylsulfanyl}-4-methyl-4H-[1,2,4]triazol-3-yl)-2-methyl-pyridine, 4-(5-{1-[5-(3-Chloro-phenyl)-[1,2,4]oxadiazol-3-yl]-ethylsulfanyl}-4-4-cyclopropyl-4H-[1,2,4]triazol-3-yl)-pyridine, 5-(3-Chloro-phenyl)-3-{1-[5-(4-methoxy-phenyl)-4-methyl-4H-[1,2,4]triazol-3-ylsulfanyl]-ethyl}-[1,2,4]oxadiazole, 4-(5-{1-[5-(5-Chloro-2-fluoro-phenyl)-[1,2,4]oxadiazol-3-yl]-ethylsulfanyl}-4-cyclopropyl-4H-[1,2,4]triazol-3-yl)-pyridine, 5-(5-Chloro-2-fluoro-phenyl)-3-{1-[5-(4-methoxy-phenyl)-4-methyl-4H-[1,2,4]triazol-3-ylsulfanyl]-ethyl}-[1,2,4]oxadiazole, 4-[5-(4-Ethyl-5-pyridin-4-yl-4H-[1,2,4]triazol-3-ylsulfanylmethyl)-[1,3,4]oxadiazol-2-yl]-2-methyl-pyridine, 4-[5-(4-Cyclopropyl-5-pyridin-4-yl-4H-[1,2,4]triazol-3-ylsulfanylmethyl)-[1,3,4]oxadiazol-2-yl]-2-methyl-pyridine, 4-{5-[5-(5-Chloro-2-fluoro-phenyl)-[1,2,4]oxadiazol-3-ylmethylsulfanyl]-4-cyclopropyl-4H-[1,2,4]triazol-3-yl}-pyridine, 4-[5-(5-Furan-2-yl-4-methyl-4H-[1,2,4]triazol-3-ylsulfanylmethyl)-[1,3,4]oxadiazol-2-yl]-2-methyl-pyridine, 4-(5-{1-[5-(3-Chloro-phenyl)-[1,3,4]oxadiazol-2-yl]-ethylsulfanyl}-4-cyclopropylmethyl-4H-[1,2,4]triazol-3-yl)-pyridine, 4-(5-{1-[5-(4-Fluoro-phenyl)-4-methyl-4H-[1,2,4]triazol-3-ylsulfanyl]-ethyl}-[1,3,4]oxadiazol-2-yl)-2-methyl-pyridine, 4-(5-{1-[5-(3-Fluoro-phenyl)-4-methyl-4H-[1,2,4]triazol-3-ylsulfanyl]-ethyl}-[1,3,4]oxadiazol-2-yl)-2-methyl-pyridine, 3-[3-(4-Cyclopropyl-5-pyridin-4-yl-4H-[1,2,4]triazol-3-ylsulfanylmethyl)-[1,2,4]oxadiazol-5-yl]-4-fluoro-benzonitrile, 4-Chloro-2-[3-(4-cyclopropyl-5-pyridin-4-yl-4H-[1,2,4]triazol-3-ylsulfanylmethyl)-[1,2,4]oxadiazol-5-yl]-phenol, 4-{4-Cyclopropyl-5-[5-(3-methoxy-phenyl)-[1,2,4]oxadiazol-3-ylmethylsulfanyl]-4H-[1,2,4]triazol-3-yl}-pyridine, 4-{4-Cyclopropyl-5-[5-(2-fluoro-5-methyl-phenyl)-[1,2,4]oxadiazol-3-ylmethylsulfanyl]-4H-[1,2,4]triazol-3-yl}-pyridine, 4-{4-Cyclopropyl-5-[5-(3-fluoro-phenyl)-[1,2,4]oxadiazol-3-ylmethylsulfanyl]-4H-[1,2,4]triazol-3-yl}-pyridine, 4-[4-Cyclopropyl-5-(5-m-tolyl-(1,2,4]oxadiazol-3-ylmethylsulfanyl)-4H-[1,2,4]triazol-3-yl]-pyridine, 3-[3-(4-Cyclopropyl-5-pyridin-4-yl-4H-[1,2,4]triazol-3-ylsulfanylmethyl)-[1,2,4]oxadiazol-5-yl]-benzonitrile, 4-{4-Cyclopropyl-5-[5-(2,5-difluoro-phenyl)-[1,2,4]oxadiazol-3-ylmethylsulfanyl]-4H-[1,2,4]triazol-3-yl}-pyridine, 4-{4-Cyclopropyl-5-[1-(5-m-tolyl-[1,2,4]oxadiazol-3-yl)-ethylsulfanyl]-4H-[1,2,4]triazol-3-yl}-pyridine, 4-(4-Cyclopropyl-5-{1-[5-(3-methoxy-phenyl)-[1,2,4]oxadiazol-3-yl]-ethylsulfanyl}-4H-[1,2,4]triazol-3-yl)-pyridine, 4-{5-[5-(2-Chloro-5-methyl-phenyl)-[1,2,4]oxadiazol-3-ylmethylsulfanyl]-4-cyclopropyl-4H-[1,2,4]triazol-3-yl}-pyridine, 2-[3-(4-Cyclopropyl-5-pyridin-4-yl-4H-[1,2,4]triazol-3-ylsulfanylmethyl)-[1,2,4]oxadiazol-5-yl]-4-methyl-phenol, 4-(5-{1-[5-(2-Chloro-5-methyl-phenyl)-[1,2,4]oxadiazol-3-yl]-ethylsulfanyl}-4-cyclopropyl-4H-[1,2,4]triazol-3-yl)-pyridine, {3-[3-(4-Methyl-5-thiophen-2-yl-4H-[1,2,4]triazol-3-ylsulfanylmethyl)-[1,2,4]oxadiazol-5-yl]-phenyl}-methanol, 3-[5-(4-Methyl-5-thiophen-2-yl-4H-[1,2,4]triazol-3-ylsulfanylmethyl)-[1,2,4]oxadiazol-3-yl]-phenol, 5-(3-Chloro-phenyl)-3-[4-(tetrahydro-furan-2-ylmethyl)-5-thiophen-2-yl-4H-[1,2,4]triazol-3-ylsulfanylmethyl]-[1,2,4]oxadiazole, (2-Chloro-phenyl)-{5-[5-(3-chlorophenyl)-[1,2,4]oxadiazol-3-ylmethylsulfanyl]-4-isobutyl-4H-[1,2,4]triazol-3-yl}-methanol, 5-(2-Fluoro-5-methyl-phenyl)-3-[5-thiophen-2-yl-4-(2,2,2-trifluoro-ethyl)-4H-[1,2,4]triazol-3-ylsulfanylmethyl]-[1,2,4]oxadiazole, 3-(2,5-Difluoro-phenyl)-5-(4-ethyl-5-thiophen-2-yl-4H-[1,2,4]triazol-3-ylsulfanylmethyl)-[1,2,4]oxadiazole, 5-Furan-3-yl-3-(4-methyl-5-thiophen-2-yl-4H-[1,2,4]triazol-3-ylsulfanylmethyl)-[1,2,4]oxadiazole, 3-(3-Chloro-phenyl)-5-(5-furan-2-yl-4-methyl-4H-[1,2,4]triazol-3-ylsulfanylmethyl)-[1,2,4]oxadiazole, 3-(3-Chloro-phenyl)-5-(5-furan-3-yl-4-methyl-4H-[1,2,4]triazol-3-ylsulfanylmethyl)-[1,2,4]oxadiazole, 5-(3-Chloro-phenyl)-3-(5-furan-2-yl-4-methyl-4H-[1,2,4]triazol-3-ylsulfanylmethyl)-[1,2,4]oxadiazole, 5-(3-Chloro-phenyl)-3-(5-furan-3-yl-4-methyl-4H-[1,2,4]triazol-3-ylsulfanylmethyl)-[1,2,4]oxadiazole, 4-{5-[5-(3-Chloro-phenyl)-[1,2,4]oxadiazol-3-ylmethylsulfanyl]-4-methyl-4H-[1,2,4]triazol-3-yl}-pyrimidine, 4-{5-[3-(3-Chloro-phenyl)-[1,2,4]oxadiazol-5-ylmethylsulfanyl]-4-methyl-4H-[1,2,4]triazol-3-yl}-pyrimidine, 3-(5-Chloro-2-fluoro-phenyl)-5-(4-ethyl-5-thiophen-2-yl-4H-[1,2,4]triazol-3-ylsulfanylmethyl)-[1,2,4]oxadiazole, 3-(5-Chloro-2-fluoro-phenyl)-5-(4-ethyl-5-furan-2-yl-4H-[1,2,4]triazol-3-ylsulfanylmethyl)-[1,2,4]oxadiazole, 5-(5-Chloro-thiophen-2-yl)-3-(4-ethyl-5-thiophen-2-yl-4H-[1,2,4]triazol-3-ylsulfanylmethyl)-[1,2,4]oxadiazole, 5-(5-Chloro-thiophen-2-yl)-3-(4-ethyl-5-furan-2-yl-4H-[1,2,4]triazol-3-ylsufanylmethtl)-[1,2,4]oxadiazole, 5-(5-Chloro-thiophen-3-yl)-3-(4-ethyl-5-thiophen-2-yl-4H-[1,2,4]triazol-3-ylsulfanylmethyl)-[1,2,4]oxadiazole, 4-{5-[5-(3-Chloro-phenyl)-[1,2,4]oxadiazol-3-ylmethylsulfanyl]-4-ethyl-4H-[1,2,4]triazol-3-ylmethoxy}-phenol, 4-{5-[5-(5-Chloro-2-fluoro-phenyl)-[1,3,4]oxadiazol-2-ylmethylsulfanyl]-4-ethyl-4H-[1,2,4]triazol-3-ylmethoxy}-phenol, 3-(2,5-Difluoro-phenyl)-5-(4-ethyl-5-furan-2-yl-4H-[1,2,4]triazol-3-ylsulfanylmethyl)-[1,2,4]oxadiazole, 3-(2,5-Difluoro-phenyl)-5-(5-furan-2-yl-4methyl-4H-[1,2,4]triazol-3-ylsulfanylmethyl)-[1,2,4]oxadiazole, 4-(5-{1-[3-(3-Chloro-phenyl)-[1,2,4]oxadiazol-5-yl]-ethylsulfanyl}-4-methyl-4H-[1,2,4]triazol-3-yl)-pyridine, 4-{5-[5-(5-Chloro-2-fluoro-phenyl)-[1,2,4]oxadiazol-3-ylmethylsulfanyl]-4-cyclopropyl-4H-[1,2,4]triazol-3-yl}-pyrimidine, 2-(5-{1-[5-(3-Chloro-phenyl)-[1,2,4]oxadiazol-3-yl]-ethylsulfanyl}-4-ethyl-4H-[1,2,4]triazol-3-yl)-5-methoxy-pyrimidine, 2-(5-{1-[5-(3-Chloro-phenyl)-[1,2,4]oxadiazol-3-yl]-ethylsulfanyl}-4-ethyl-4H-[1,2,4]triazol-3-yl)-pyrimidine, 4-(5-{1-[5-(3-Chloro-phenyl)-[1,2,4]oxadiazol-3-yl]-ethylsulfanyl}-4-ethyl-4H-[1,2,4]triazol-3-yl)-2-methoxy-pyridine, 5-(5-{1-[5-(3-Chloro-phenyl)-[1,2,4]oxadiazol-3-yl]-ethylsulfanyl}-4-ethyl-4H-[1,2,4]triazol-3-yl)-2-methoxy-pyridine, 2-(5-{1-[5-(3-Chloro-phenyl)-[1,2,4]oxadiazol-3-yl]-ethylsulfanyl}-4-ethyl-4H-[1,2,4]triazol-3-yl)-5-methoxy-pyridine, 3-(5-{1-[5-(3-Chloro-phenyl)-[1,2,4]oxadiazol-3-yl]-ethylsulfanyl}-4-ethyl-4H-[1,2,4]triazol-3-yl)-6-methoxy-pyridazine, 3-(5-{1-[5-(3-Chloro-phenyl)-[1,2,4]oxadiazol-3-yl]-ethylsulfanyl}-4-cyclopropyl-4H-[1,2,4]triazol-3-yl)-pyridine, 4-{5-[3-(3-Chloro-phenyl)-[1,2,4]oxadiazol-5-ylmethylsulfanyl]-4-methyl-4H-[1,2,4]triazol-3-yl}-pyridine, 5-(3-Chloro-phenyl)-3-(5-furan-2-yl-4-isobutyl-4H-[1,2,4]triazol-3-ylsulfanylmethyl)-[1,2,4]oxadiazole, 5-(3-Chloro-phenyl)-3-[4-(3-methylsulfany-propyl)-5-thiophen-2-yl-4H-[1,2,4]triazol-3-ylsulfanylmethyl]-[1,2,4]oxadiazole, 5-(3-Chloro-phenyl)-3-(4-hexyl-5-thiophen-2-yl-4H-[1,2,4]triazol-3-ylsulfanylmethyl)-[1,2,4]oxadiazole, 5-(3-Chloro-phenyl)-3-(4-cyclopropylmethyl-5-thiophen-2-yl-4H-[1,2,4]triazol-3-ylsulfanylmethyl)-[1,2,4]oxadiazole, 5-(3-Chloro-phenyl)-3-[4-(3-fluoro-benzyl)-5-thiophen-2-yl-4H-[1,2,4]triazol-3-ylsulfanylmethyl]-[1,2,4]oxadiazole, 5-(3-Chloro-phenyl)-3-[4-(3-methyl-benzyl)-5-thiophen-2-yl-4H-[1,2,4]triazol-3-ylsulfanylmethyl]-[1,2,4]oxadiazole, 5-(3-Chloro-phenyl)-3-[4-(2-methyl-butyl)-5-thiophen-2-yl-4H-[1,2,4]triazol-3-ylsulfanylmethyl]-[1,2,4]oxadiazole, 5-(3-Chloro-phenyl)-3-[4-(3-methyl-butyl)-5-thiophen-2-yl-4H-[1,2,4]triazol-3-ylsulfanylmethyl]-[1,2,4]oxadiazole, 5-(3-Chloro-phenyl)-3-[4-(2-fluoro-benzyl)-5-thiophen-2-yl-4H-[1,2,4]triazol-3-ylsulfanylmethyl]-[1,2,4]oxadiazole, 5-(3-Chloro-phenyl)-3-(4-ethyl-5-thiophen-2-yl-4H-[1,2,4]triazol-3-yloxymethyl)-[1,2,4]oxadiazole, 4-{5-[5-(5-Chloro-2-fluoro-phenyl)-[1,2,4]oxadiazol-3-ylmethoxy]-4-methyl-4H-[1,2,4]triazol-3-yl}-pyridine, 4-(5-{1-[5-(3-Chloro-phenyl)-[1,3,4]oxadiazol-2-yl]-ethoxy}-4-methyl-4H-[1,2,4]triazol-3-yl)-pyridine, 4-(5-{1-[3-(3-Chloro-phenyl)-isoxazol-5-yl]-ethoxy}-4-methyl-4H-[1,2,4]triazol-3-yl)-pyridine, 5-(2-Methoxy-phenyl)-3-(4-methyl-5-thiophen-2-yl-4H-[1,2,4]triazol-3-ylsulfanylmethyl)-[1,2,4]oxadiazole, 5-Furan-2-yl-3-(4-methyl-5-thiophen-2-yl-4H-[1,2,4]triazol-3-ylsulfanylmethyl)-[1,2,4]oxadiazole, 3-[3-(4-Methyl-5-thiophen-2-yl-4H-[1,2,4]triazol-3-ylsulfanylmethyl)-[1,2,4]oxadiazol-5-yl]-benzoic acid methyl ester, 5-(2-Fluoro-phenyl)-3-(4-methyl-5-thiophen-2-yl-4H-[1,2,4]triazol-3-ylsulfanylmethyl)-[1,2,4]oxadiazole, 5-(2,5-Difluoro-phenyl)-3-(4-methyl-5-thiophen-2-yl-4H-[1,2,4]triazol-3-ylsulfanylmethyl)-[1,2,4]oxadiazole, 3-(4-Methyl-5-thiophen-2-yl-4H-[1,2,4]triazol-3-ylsulfanylmethyl)-5-(3-vinyl-phenyl)-[1,2,4]oxadiazole, 5-(3-Difluoromethoxy-phenyl)-3-(4-methyl-5-thiophen-2-yl-4H-[1,2,4]triazol-3-ylsulfanylmethyl)-[1,2,4]oxadiazole, 5-(4-Methoxy-thiophen-3-yl)-3-(4-methyl-5-thiophen-2-yl-4H-[1,2,4]triazol-3-ylsulfanylmethyl)-[1,2,4]oxadiazole, 5-(2-Chloro-phenyl)-3-(4-methyl-5-thiophen-2-yl-4H-[1,2,4]triazol-3-ylsulfanylmethyl)-[1,2,4]oxadiazole, 5-(4-Fluoro-phenyl)-3-(4-methyl-5-thiophen-2-yl-4H-[1,2,4]triazol-3-ylsulfanylmethyl)-[1,2,4]oxadiazole, 3-(3-Chloro-phenyl)-5-[1-(4-methyl-5-thiophen-2-yl-4H-[1,2,4]triazol-3-ylsulfanyl)-ethyl]-[1,2,4]oxadiazole, -(5-{1-[3-(3-Chloro-phenyl)-[1,2,4]oxadiazol-5-yl]-ethylsulfanyl}-4-methyl-4H-[1,2,4]triazol-3-yl)-pyridine, 3-(3-Chloro-phenyl)-5-[2-(4-ethyl-5-thiophen-2-yl-4H-[1,2,4]triazol-3-yl)-ethyl]-[1,2,4]oxadiazole, 5-(3-Chloro-phenyl)-3-(5-furan-2-yl-4-methyl-4H-[1,2,4]triazol-3-ylmethyl)-[1,2,4]oxadiazole, 2-(3-Chloro-phenyl)-5-[2-(5-furan-2-yl-4-methyl-4H-[1,2,4]triazol-3-yl)-ethyl]-[1,3,4]oxadiazole, 2-(3-Chloro-phenyl)-5-[2-(4-ethyl-5-furan-2-yl-4H-[1,2,4]triazol-3-yl)-ethyl]-[1,3,4]oxadiazole, 2-(3-Chloro-phenyl)-5-[2-(4-cyclopropyl-5-furan-2-yl-4H-[1,2,4]triazol-3-yl)-ethyl]-[1,3,4]oxadiazole, 4-(5-{2-[3-(3-Chloro-phenyl)-[1,2,4]oxadiazol-5-yl]-ethyl}-4-methyl-4H-[1,2,4]triazol-3-yl)-pyridine, 4-(5-{2-[3-(3-Chloro-phenyl)-[1,2,4]oxadiazol-5-yl]-ethyl}-4-ethyl-4H-[1,2,4]triazol-3-yl)-pyridine, 4-(5-{2-[3-(3-Chloro-phenyl)-[1,2,4]oxadiazol-5-yl]-ethyl}-4-cyclopropyl-4H-[1,2,4]triazol-3-yl)-pyridine, 4-(5-{2-[3-(3-Chloro-phenyl)-[1,2,4]oxadiazol-5-yl]-propyl}-4-cyclopropyl-4H-[1,2,4]triazol-3-yl)-pyridine, 4-(5-{2-[3-(3-Chloro-phenyl)-[1,2,4]oxadiazol-5-yl]-2-methyl-propyl}-4-cyclopropy-4H-[1,2,4]triazol-3-yl)-pyridine, 4-(5-{2-[5-(3-Chloro-phenyl)-[1,3,4]oxadiazol-2-yl]-propyl}-4-cyclopropyl-4H-[1,2,4]triazol-3-yl)-pyridine, 8-[5-(3-Chloro-phenyl)-[1,2,4]oxadiazol-3-ylmethyl]-3-pyridin-4-yl-5,6,7,8-tetrahydro-[1,2,4]triazolo[4,3-a]pyridine, 8-[5-(3-Chloro-phenyl)-[1,2,4]oxadiazol-3-ylmethyl]-3-thiophen-2-yl-5,6,7,8-tetiahydro-[1,2,4]triazolo[4,3-a]pyridine, 8-[5-(5-Chloro-2-fluoro-phenyl)-1,2,4]oxadiazol-3-ylmethyl]-3-pyridin-4-yl-5,6,7,8-tetrahydro-[1,2,4]triazolo[4,3-a]pyridine, 5-(5-Bromo-4-methyl-4H-[1,2,4]triazol-3-ylsulfanylmethyl)-3-(3-chloro-phenyl)-[1,2,4]oxadiazole, 3-[3-(4-Methyl-5-thiophen-2-yl-4H-[1,2,4]triazol-3-ylsulfanylmethyl)-[1,2,4]oxadiazol-5-yl]-phenylamine, 5-(3-Chloro-phenyl)-3-(4-methyl-5-thiophen-2-yl-4H-[1,2,4]triazole-3-sulfonylmethyl)-[1,2,4]oxadiazole, 5-(3-Chloro-phenyl)-3-(4-methyl-5-thiophen-2-yl-4H-[1,2,4]triazole-3-sulfinylmethyl)-[1,2,4]oxadiazole, 2-Methyl-6-[3-(4-methyl-5-thiophen-2-yl-4H-[1,2,4]triazol-3-ylsulfanylmethyl)-[1,2,4]oxadiazol-5-yl]-pyridine, 4-(5-{1-[5-(3-Chloro-phenyl)-[1,2,4]oxadiazol-3-yl]-ethylsulfanyl}-4-ethyl-4H-[1,2,4]triazol-3-yl)-pyridin-2-ol, 4-(5-{2-[5-(3-Chloro-phenyl)-[1,2,4]oxadiazol-3-yl]-propyl}-4-methyl-4H-[1,2,4]triazol-3-yl)-pyridine,

[5-(3-Chloro-phenyl)-[1,2,4]oxadiazol-3-ylmethyl]-methyl-(4-methyl-5-pyridin-4-yl-4H-[1,2,4]triazol-3-yl)-amine, 8-[5-(3-Chloro-phenyl)-[1,2,4]oxadiazol-3-ylmethyl]-3-pyridin-4-yl-5,6,7,8-tetrahydro-[1,2,4]tnazolo[4,3-a]pyrimidine, 8-[5-(5-Chloro-2-fluoro-phenyl)-[1,2,4]oxadiazol-3-ylmethyl]-3-pyridin-4-yl-5,6,7,8-tetrahydro-[1,2,4]triazolo[4,3-a]pyrimidine, 8-[5-(3-Chloro-phenyl)-[1,3,4]oxadiazol-2-ylmethyl]-3-pyridin-4-yl-5,6,7,8-tetrahydro-[1,2,4]triazolo[4,3-a]pyrimidine, 8-{1-[5-(3-Chloro-phenyl)-[1,3,4]oxadiazol-2-yl]-ethyl}-3-pyridin-4-yl-5,6,7,8-tetrahydro-[1,2,4]triazolo[4,3-a]pyrimidine, 8-[5-(5-Chloro-2-fluoro-phenyl)-[1,2,4]oxadiazol-3-ylmethyl]-3-furan-2-yl-5,6,7,8-tetrahydro-[1,2,4]triazolo[4,3-a]pyrimidine, 8-{1-[5-(3-Chloro-phenyl)-[1,2,4]oxadiazol-3-yl]-ethyl}-3-pyridin-4-yl-5,6,7,8-tetrahydro-[1,2,4]triazolo[4,3-a]pyrimidine, 3-(4-Ethyl-5-thiophen-2-yl-4H-[1,2,4]triazol-3-ylsulfanylmethyl)-5-(1H-pyrrol-3-yl)-[1,2,4]oxadiazole, 4-{5-[5-(3-Chloro-phenyl)-[1,2,4]oxadiazol-3-ylmethylsulfanyl]-4-methyl-4H-[1,2,4]triazol-3-yl}-pyridine 1-oxide, 5-(3-Chloro-phenyl)-3-(2-furan-2-yl-3-methyl-3H-imidazol-4-ylsulfanylmethyl)-[1,2,4]oxadiazole, 5-(5-Chloro-2-fluoro-phenyl)-3-[4-(2-fluoro-ethyl)-5-thiophen-2-yl-4H-[1,2,4]triazol-3-ylsulfanylmethyl]-[1,2,4]oxadiazole, 5-(5-Chloro-thiophen-3-yl)-3-(4-ethyl-5-furan-2-yl-4H-[1,2,4]triazol-3-ylsulfanylmethyl)-[1,2,4]oxadiazole, 3-[3-(4-Ethyl-5-furan-2-yl-4H-[1,2,4]triazol-3-ylsulfanylmethyl)-[1,2,4]oxadiazol-5-yl]-4-hydroxy-benzonitrile, 3-(3-Chloro-phenyl)-5-[2-(4-methyl-5-thiophen-2-yl-4H-[1,2,4]triazol-3-yl)-ethyl]-[1,2,4]oxadiazole, 4-(5-{2-[3-(3-Chloro-phenyl)-[1,2,4]oxadiazol-5-yl]-propyl}-[1,3,4]oxadiazol-2-yl)-pyridine, 4-(5-{2-[3-(3-Chloro-phenyl)-[1,2,4]oxadiazol-5-yl]-1-methyl-ethyl}-4-cyclopropyl-4H-[1,2,4]triazol-3-yl)-pyridine, 4-(5-{2-[3-(3-Chloro-phenyl)-[1,2,4]oxadiazol-5-yl]-cyclopropyl}-4-cyclopropyl-4H-[1,2,4]triazol-3-yl)-pyridine, or 4-(5-{2-[3-(3-Chloro-phenyl)-[1,2,4]oxadiazol-5-yl]-1,1-dimethyl-ethyl}-[1,3,4]oxadiazol-2-yl)-pyridine, 3-(5-{1-[5-(3-Chloro-phenyl)-[1,2,4]oxadiazol-3-yl]-ethoxy}-4-cyclopropyl-4H-[1,2,4]triazol-3-yl)-pyridine, 4-(5-{1-[5-(2-Chloro-5-methyl-phenyl)-[1,2,4]oxadiazol-3-yl]-ethylsulfanyl}-4-methyl-4H-[1,2,4]triazol-3-yl)-pyridine, 4-(5-{-[5-(2,5-Difluoro-phenyl)-[1,2,4]oxadiazol-3-yl]-ethylsulfanyl}-4-methyl-4H-[1,2,4]triazol-3-yl)-pyridine, 4-(5-{1-[5-(2-Fluoro-5-methyl-phenyl)-[1,2,4]oxadiazol-3-yl]-ethylsulfanyl}-4-methyl-4H-[1,2,4]triazol-3-yl)-pyridine, 4-(4-Cyclopropyl-5-{1-[5-(2-fluoro-5-methyl-phenyl)-[1,2,4]oxadiazol-3-yl]-ethylsulfanyl}-4H-[1,2,4]triazol-3-yl)-pyridine, 3-{3-[1-(4-Methyl-5-pyridin-4-yl-4H-[1,2,4]triazol-3-ylsulfanyl)-ethyl]-[1,2,4]oxadiazol-5-yl}-benzonitrile, 3-{3-[1-(4-Cyclopropyl-5-pyridin-4-yl-4H-[1,2,4]triazol-3-ylsulfanyl)-ethyl]-[1,2,4]oxadiazol-5-yl}-benzonitrile, 3-{1-[5-(3-Chloro-phenyl)-[1,3,4]oxadiazol-2-yl]-ethylsulfanyl}-5-pyridin-4-yl-[1,2,4]triazol-4-ylamine, 3-(3-Chloro-phenyl)-5-[2-(4-methyl-5-thiophen-2-yl-4H-[1,2,4]triazol-3-yl)ethyl]-[1,2,4]oxadiazole, 4-(5-{2-[3-(3-Chloro-phenyl)-[1,2,4]oxadiazol-5-yl]-1-methyl-ethyl}-4-cyclopropyl-4H-[1,2,4]triazol-3-yl)-pyridine, cis-4-(5-{2-[3-(3-Chloro-phenyl)-[1,2,4]oxadiazol-5-yl]-cyclopropyl}-4-cyclopropyl-4H-[1,2,4]triazol-3-yl)-pyridine, 4-(5-{2-[3-(3-Chloro-phenyl)-[1,2,4]oxadiazol-5-yl]-1,1-dimethyl-ethyl}-[1,3,4]oxadiazol-2-yl)-pyridine, 4-(5-{2-[3-(3-Chloro-phenyl)-[1,2,4]oxadiazol-5-yl]-2-methyl-propyl}-[1,3,4]oxadiazol-2-yl)-pyridine, 4-(5-{2-[3-(3-Chloro-phenyl)-[1,2,4]oxadiazol-5-yl]-1-methyl-ethyl}-[1,3,4]oxadiazol-2-yl)-pyridine, 4-(5-{2-[3-(3-Chloro-phenyl)-[1,2,4]oxadiazol-5-yl]-cyclopropyl}-[1,3,4]oxadiazol-2-yl)-pyridine, 4-(5-{2-[3-(3-Chloro-phenyl)-[1,2,4]oxadiazol-5-yl]-cyclopropyl}-4-methyl-4H-[1,2,4]triazol-3-yl)-pyridine, 4-(5-{2-[5-(3-Chloro-phenyl)-[1,3,4]oxadiazol-2-yl]-propyl}-4-methyl-4H-[1,2,4]triazol-3-yl)-pyridine, 4-(5-{2-[3-(3-Chloro-phenyl)-[1,2,4]oxadiazol-5-yl]-propyl}-[1,3,4]oxadiazol-2-yl)-pyridine, 4-(5-{2-[3-(3-Chloro-phenyl)-[1,2,4]oxadiazol-5-yl]-propyl}-4-methyl-4H-[1,2,4]triazol-3-yl)-pyridine, 4-(5-{2-[3-(3-Chloro-phenyl)-[1,2,4]oxadiazol-5-yl]-propyl}-4-cyclopropyl-4H-[1,2,4]triazol-3-yl)-pyridine, (S)-[1-[3-(3-Chloro-phenyl)-[1,2,4]oxadiazol-5-yl]-2-(4-cyclopropyl-5-pyridin-4-yl-4H-[1,2,4]triazol-3-yl)-ethyl]-carbamic acid tert-butyl ester, (S)-1-[3-(3-Chloro-phenyl)-[1,2,4]oxadiazol-5-yl]-2-(4-cyclopropyl-5-pyridin-4-yl-4H-[1,2,4]triazol-3-yl)-ethylamine, (S)-[1-[3-(3-Chloro-phenyl)-[1,2,4]oxadiazol-5-yl]-2-(4-cyclopropyl-5-pyridin-4-yl-4H-[1,2,4]triazol-3-yl)-ethyl]-dimethyl-amine, or salt thereof.

Further feasible examples of compounds of formula I are provided by compounds of formula Ia $$(Ia)$$

$(R^1)_m$—P—$M^1$—$X^1$—$M^2$—Q—$(R^4)_m$
  |           $X^2$—$X^3$
$(R^2)_n$                    $(R^3)_n$ wherein:

P is selected from the group consisting of hydrogen, $C_{3-7}$alkyl and a 3- to 8-membered ring containing one or more atoms independently selected from the group consisting of C, N, O and S, which ring may optionally be fused with a 5- or 6-membered ring containing one or more atoms independently selected from the group consisting of C, N, O and S;

$R^1$ is selected from the group consisting of hydrogen, hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, $(CO)R^5$, $O(CO)R^5$, $O(CO)OR^5$, $O(CN)OR^5$, $C_{1-6}$alkyl$OR^5$, $OC_{2-6}$alkyl$OR^5$, $C_{1-6}$alkyl$(CO)R^5$, $OC_{1-6}$alkyl$(CO)R^5$, $C_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^6$, $OC_{2-6}$alkyl$NR^5R^6$, $C_{1-6}$alkyl$(CO)NR^5R^6$, $OC_{1-6}$alkyl$(CO)NR^5R^6$, $C_{0-6}$alkyl$NR^5(CO)R^6$, $OC_{2-6}$alkyl$NR^5(CO)R^6$, $C_{0-6}$alkyl$NR^5(CO)NR^5R^6$, $C_{0-6}$alkyl$SR^5$, $OC_{2-6}$alkyl$SR^5$, $C_{0-6}$alkyl$(SO)R^5$, $OC_{2-6}$alkyl$(SO)R^5$, $OC_{2-6}$alkyl$SO_2R^5$, $OC_{2-6}$alkyl$SO_2R^5$, $C_{0-6}$alkyl$(SO_2)NR^5R^6$, $OC_{2-6}$alkyl$(SO_2)NR^5R^6$, $C_{0-6}$alkyl$NR^5(SO_2)R^6$, $OC_{2-6}$alkyl$NR^5(SO_2)R^6$, $C_{0-6}$alkyl$NR^5(SO_2)NR^5R^6$, $OC_{2-6}$alkyl$NR^5(SO_2)NR^5R^6$, $(CO)NR^5R^6$, $O(CO)NR^5R^6$, $NR^5OR^6$, $C_{0-6}$alkyl$NR^5(CO)OR^6$, $OC_{2-6}$alkyl$NR^5(CO)OR^6$, $SO_3R^5$ and a 5- or 6-membered ring containing one or more atoms independently selected from the group consisting of C, N, O and S, wherein said ring may be substituted by one or more A;

$M^1$ is selected from the group consisting of a bond, $C_{1-3}$alkyl, $C_{2-3}$alkenyl, $C_{2-3}$alkynyl, $C_{0-4}$alkyl$(CO)C_{0-4}$alkyl, $C_{0-3}$alkyl$OC_{0-3}$alkyl, $C_{0-3}$alkyl$(CO)NR^5$, $C_{0-3}$alkyl$(CO)NR^5C_{0-3}$alkyl, $C_{0-4}$alkyl$NR^5$, $C_{0-3}$alkyl$SC_{0-3}$alkyl, $C_{0-3}$alkyl$(SO)C_{0-3}$alkyl and $C_{0-3}$alkyl$(SO_2)C_{0-3}$alkyl;

$R^2$ is selected from the group consisting of hydrogen, hydroxy, $C_{0-6}$alkylcyano, oxo, =$NR^5$, =$NOR^5$, $C_{1-4}$alkylhalo, halo, $C_{1-4}$alkyl, $O(CO)C_{1-4}$alkyl, $C_{1-4}$alkyl$(SO)C_{0-4}$alkyl, $C_{1-4}$alkyl$(SO_2)C_{0-4}$alkyl, $(SO)C_{0-4}$alkyl, $(SO_2)C_{0-4}$alkyl, $OC_{1-4}$alkyl, $C_{1-4}$alkyl$OR^5$ and $C_{0-4}$alkyl$NR^5R^6$;

$X^1$, $X^2$ and $X^3$ are independently selected from the group consisting of CR, CO, N, NR, O and S;

R is selected from the group consisting of hydrogen, $C_{0-3}$alkyl, halo, $C_{0-3}$alkyl$OR^5$, $C_{0-3}$alkyl$NR^5R^6$, $C_{0-3}$alkyl$(CO)OR^5$, $C_{0-3}$alkyl$NR^5R^6$ and $C_{0-3}$alkylaryl;

$M^2$ is selected from the group consisting of a bond, $C_{1-3}$alkyl, $C_{3-7}$cycloalkyl, $C_{2-3}$alkenyl, $C_{2-3}$alkynyl, $C_{0-4}$alkyl$(CO)C_{0-4}$alkyl, $C_{0-3}$alkyl$OC_{0-3}$alkyl, $C_{0-3}$alkyl$NR^5C_{1-3}$alkyl, $C_{0-3}$alkyl$(CO)NR^5$, $C_{0-4}$aklyl$NR^5$, $C_{0-3}$alkyl$SC_{0-3}$alkyl, $C_{0-3}$alkyl$(SO)C_{0-3}$alkyl and $C_{0-3}$alkyl$(SO_2)C_{0-3}$alkyl;

$R^3$ is selected from the group consisting of hydrogen, hydroxy, $C_{0-6}$alkylcyano, oxo, =$NR^5$, =$NOR^5$, $C_{1-4}$alkylhalo, halo, $C_{1-4}$alkyl, $O(CO)C_{1-4}$alkyl, $C_{1-4}$alkyl$(SO)C_{0-4}$alkyl, $C_{1-4}$alkyl$(SO_2)C_{0-4}$alkyl, $(SO)C_{0-4}$alkyl, $(SO_2)C_{0-4}$alkyl, $OC_{1-4}$alkyl, $C_{1-4}$alkyl$OR^5$ and $C_{0-4}$alkyl$NR^5R^6$;

$X^4$ is selected from the group consisting of $C_{0-4}$alkyl$R^5$, $C_{0-4}$alkyl$(NR^5R^6)$, $C_{0-4}$alkyl$(NR^5R^6)$=N, $NR^5C_{0-4}$alkyl $(N^5R^6)$=N, $NOC_{0-4}$alkyl, $C_{1-4}$alkylhalo, C, O, SO, $SO_2$ and S;

Q is a 5- or 6-membered ring containing one or more atoms independently selected from C, N, O and S, which group may optionally be fused with a 5- or 6-membered ring containing one or more atoms independently selected from C, N, O and S and which fused ring may be substituted by one or more A;

$R^4$ is selected from the group consisting of hydrogen, hydroxy, $C_{0-6}$alkylcyano, oxo, =$NR^5$, =$NOR^5$, $C_{1-4}$alkylhalo, halo, $C_{1-4}$alkyl, $OC_{1-4}$alkyl, $OC_{1-6}$alkylaryl, $O(CO)C_{1-4}$alkyl, $C_{0-4}$alkyl$(S)C_{0-4}$alkyl, $C_{1-4}$alkyl$(SO)C_{0-4}$alkyl, $C_{1-4}$alkyl$(SO_2)C_{0-4}$alkyl, $(SO)C_{0-4}$alkyl, $(SO_2)C_{0-4}$alkyl, $C_{1-4}$alkyl$OR^5$, $C_{0-4}$alkyl$NR^5R^6$ and a 5- or 6-membered ring containing one or more atoms independently selected from C, N, O and S, wherein said ring may be substituted by one or more A;

$R^5$ and $R^6$ are independently selected from the group consisting of hydrogen, hydroxy, $C_{1-6}$alkyl, $C_{0-6}$alkyl$C_{3-6}$cycloalkyl, $C_{0-6}$alkylaryl, $C_{0-6}$alkylheteroaryl and a 5- or 6-membered ring containing one or more atoms independently selected from C, N, O and S, and wherein $R^5$ and $R^6$ may together form a 5- or 6-membered ring containing one or more atoms independently selected from C, N, O and S;

wherein any $C_{1-6}$alkyl, $C_{2-6}$alkenyl, $C_{2-6}$alkynyl, $C_{0-6}$alkyl$C_{3-6}$cycloalkyl, $C_{0-6}$alkylaryl and $C_{0-6}$alkylheteroaryl defined under $R^1$, $R^2$, $R^3$, $R^4$, $R^5$ and $R^6$ may be substituted by one or more A; and A is selected from the group consisting of hydrogen, hydroxy, oxo, halo, nitro, $C_{0-6}$alkylcyano, $C_{1-4}$alkyl, $C_{0-4}$alkyl$C_{3-6}$cycloalkyl, $C_{1-6}$alkylhalo, $OC_{1-6}$alkylhalo, $C_{2-6}$alkenyl, $OC_{1-6}$alkyl, $C_{0-3}$alkylaryl, $C_{0-6}$alkyl$OR^5$, $OC_{2-6}$alkyl$OR^5$, $C_{1-6}$alkyl$SR^5$, $OC_{2-6}$alkyl$SR^5$, $(CO)R^5$, $O(CO)R^5$, $OC_{2-6}$alkylcyano, $C_{0-6}$alkyl$CO_2R^5$, $OC_{1-6}$alkyl$CO_2R^5$, O(CO)OR$^5$, OC$_{1-6}$alkyl(CO)R$^5$, C$_{1-6}$alkyl(CO)R$^5$, NR$^5$OR$^6$, C$_{0-6}$alkylNR$^5$R$^6$, OC$_{2-6}$alkylNR$^5$R$^6$, C$_{0-6}$alkyl(CO)NR$^5$R$^6$, OC$_{1-6}$alkyl(CO)NR$^5$R$^6$, OC$_{2-6}$alkylNR$^5$(CO)R$^6$, C$_{0-6}$alkylNR$^5$(CO)R$^6$, C$_{0-6}$alkylNR$^5$(CO)NR$^5$R$^6$, O(CO)NR$^5$R$^6$, NR$^5$(CO)OR$^6$, C$_{0-6}$alkyl(SO$_2$)NR$^5$R$^6$, OC$_{2-6}$alkyl(SO$_2$)NR$^5$R$^6$, C$_{0-6}$alkylNR$^5$(SO$_2$)R$^6$, OC$_{2-6}$alkylNR$^5$(SO$_2$)R$^6$, SO$_3$R$^5$, C$_{1-6}$alkylNR$^5$(SO$_2$)NR$^5$R$^6$, OC$_{2-6}$alkyl(SO$_2$)R$^5$, C$_{0-6}$alkyl(SO$_2$)R$^5$, C$_{0-6}$alkyl(SO)R$^5$, OC$_{2-6}$alkyl(SO)R$^5$ and a 5- or 6-membered ring containing one or more atoms independently selected from C, N, O and S;

m is selected from 0, 1, 2, 3 and 4; and
n is selected from 0, 1, 2 and 3,
or salt thereof.

The present invention relates to the use of compounds of formula I and IA as hereinbefore defined as well as to the salts thereof. Salts for use in pharmaceutical formulations will be pharmaceutically acceptable salts, but other salts may be useful in the production of the compounds of formula I and Ia.

Examples of pharmaceutically acceptable salts may be, but are not limited to hydrochloride, 4-aminobenzoate, anthranilate, 4-aminosalicylate, 4-hydroxybenzoate, 3,4-dihydroxybenzoate, 3-hydroxy-2-naphthoate, nitrate and trifluoroacetate. Other pharmaceutically acceptable salts and methods of preparing these salts may be found in, for example, Remington's Pharmaceutical Sciences (18$^{th}$ Edition, Mack Publishing Co.).

Some compounds of formula I may have chiral centres and/or geometric isomeric centres (E- and Z-isomers), and it is to be understood that the invention encompasses all such optical, diastereoisomers and geometric isomers.

The invention relates to any and all tautomeric forms of the compounds of formula I.

The invention relates to the following compounds, which may be used as intermediates in the preparation of a compound of formula I;
6-Methylpyridine-4-carboxylic acid,
1-Cyano-3-ethylbenzene,
3-Ethylbenzoic acid,
3-Fluoro-5-methyl-benzoic acid,
3-Methoxymethyl-benzoic acid,
N-Hydroxy-3-methoxy-benzamidine,
N-Hydroxy-benzamidine,
N-Hydroxy-3-methyl-benzamidine,
5-Chloromethyl-3-(3-methoxy-phenyl)-[1,2,4]oxadiazole,
5-Chloromethyl-3-phenyl-[1,2,4]oxadiazole,
5-Chloromethyl-3-m-tolyl-[1,2,4]oxadiazole,
3-(3-Chloromethyl-[1,2,4]oxadiazol-5-yl)-benzonitrile,
3-(5-Chloromethyl-[1,2,4]oxadiazol-3-yl)-benzonitrile,
3-Chloromethyl-5-m-tolyl-[1,2,4]oxadiazole,
3-Chloromethyl-5-(3-fluoro-phenyl)-[1,2,4]oxadiazole,
3-Chloromethyl-5-thiophen-3-yl-[1,2,4]oxadiazole,
3-(3-Chloromethyl-[1,2,4]oxadiazol-5-yl)-5-methyl-pyridine,
3-Chloromethyl-5-(3-nitro-phenyl)-[1,2,4]oxadiazole,
4-(3-Chloromethyl-[1,2,4]oxadiazol-5-yl)-2-methyl-pyridine,
3-Chloromethyl-5-(3-ethyl-phenyl)-[1,2,4]oxadiazole,
3-(3-Chloromethyl-[1,2,4]oxadiazol-5-yl)-phenyl]-dimethyl-amine,
3-Chloromethyl-5-(3-chloro-phenyl)-[1,2,4]oxadiazole,
3-Chloromethyl-5-(3-trifluoromethoxy-phenyl)-[1,2,4]oxadiazole,
5-(3-Bromo-phenyl)-3-chloromethyl-[1,2,4]oxadiazole,
3-Chloromethyl-5-thiophen-2-yl-[1,2,4]oxadiazole,
3-Chloromethyl-5-(3-fluoro-5-methyl-phenyl)-[1,2,4]oxadiazole,
3-Chloromethyl-5-thiazol-4-yl-[1,2,4]oxadiazole,
3-Chloromethyl-5-(3-iodo-phenyl)-[1,2,4]oxadiazole,
3-Chloromethyl-5-(3-methoxymethyl-phenyl)-[1,2,4]oxadiazole,
5-Furan-2-yl-4-methyl-4H-[1,2,4]triazole-3-thiol,
4-Methyl-5-phenyl-4H-[1,2,4]triazole-3-thiol,
4-Methyl-5-pyridin-2-yl-4H-[1,2,4]triazole-3-thiol,
5-(4-Benzyl-morpholin-2-yl)-4-methyl-4H-[1,2,4]triazole-3-thiol,
5-tert-Butyl-4-methyl-4H-[1,2,4]triazole-3-thiol,
4-Methyl-5-pyridin-3-yl-4H-[1,2,4]triazole-3-thiol,
4-Methyl-5-thiophene-3-yl-4H-[1,2,4]triazole-3-thiol,
4-Methyl-5-thiazol-4-yl-4H-[1,2,4]triazole-3-thiol,
5-Cyclohexyl-4-methyl-4H-[1,2,4]triazole-3-thiol,
5-Chloro-thiophene-3-carboxylic acid,
3-Methylsulfanyl-benzoic acid,
3-Cyclopropyl-benzoic acid,
3-tert-Butoxycarbonylamino-benzoic acid,
3-Acetyl-benzoic acid,
2-Methyl-isonicotinic acid hydrazide,
5-Chloro-2-fluoro-benzoic acid hydrazide,
3-Cyano-benzoic acid hydrazide,
2-Chloro-isonicotinic acid hydrazide,
2-Fluoro-5-methyl-benzoic acid hydrazide,
Pyrimidine-4-carboxylic acid hydrazide,
3-Fluoro-N-hydroxy-benzamidine,
N-Hydroxy-thiophene-3-carboxamidine,
2-Chloro-N-hydroxy-propionamidine,
3,N-Dihydroxy-benzamidine,
N-Hydroxy-2-methyl-benzamidine,
N-Hydroxy-2-(4-methyl-5-thiophen-2-yl-4H-[1,2,4]triazol-3-ylsulfanyl)-acetamidine,
3-Chloro-N-hydroxy-benzamidine,
N-Hydroxy-2-(4-methyl-5-thiophen-2-yl-4H-[1,2,4]triazol-3-ylsulfanyl)-acetamidine,
2,5-Difluoro-N-hydroxy-benzamidine,
4-Methyl-5-pyridin-3-yl-4H-[1,2,4]triazole-3-thiol,
4-Butyl-5-thiophen-2-yl-4H-[1,2,4]triazole-3-thiol,
4-(3-Methoxy-propyl)-5-thiophen-2-yl-4H-[1,2,4]triazole-3-thiol,
4-Benzyl-5-thiophen-2-yl-4H-[1,2,4]triazole-3-thiol,
4-Furan-2-ylmethyl-5-thiophen-2-yl-4H-[1,2,4]triazole-3-thiol,
5-Thiophen-2-yl-4-thiophen-2-ylmethyl-4H-[1,2,4]triazole-3-thiol,
4-Ethyl-5-thiophen-2-yl-4H-[1,2,4]triazole-3-thiol,
4-Furan-2-ylmethyl-5-pyridin-4-yl-4H-[1,2,4]triazole-3-thiol,
4-Ethyl-5-pyridin-4-yl-4H-[1,2,4]triazole-3-thiol,
4-Ethyl-5-pyridin-3-yl-4H-[1,2,4]triazole-3-thiol,
4-Ethyl-5-thiophen-2-yl-4H-[1,2,4]triazole-3-thiol,
4-Furan-2-ylmethyl-5-pyridin-3-yl-4H-[1,2,4]triazole-3-thiol,
4-Ethyl-5-furan-2-yl-4H-[1,2,4]triazole-3-thiol,
4-Ethyl-5-(3-fluoro-phenyl)-4H-[1,2,4]triazole-3-thiol,
4-Ethyl-5-(4-fluoro-phenyl)-4H-[1,2,4]triazole-3-thiol,
5-(2-Fluoro-5-methyl-phenyl)-4-furan-2-ylmethyl-4H-[1,2,4]triazole-3-thiol,
4-Ethyl-5-(3-methyl-thiophen-2-yl)-4H-[1,2,4]triazole-3-thiol,
4-Ethyl-5-(5-methyl-thiophen-2-yl)-4H-[1,2,4]triazole-3-thiol,
5-(2-Chloro-6-methyl-pyridin-4-yl)-4-ethyl-4H-[1,2,4]triazole-3-thiol,
5-(5-Bromo-furan-2-yl)-4-ethyl-4H-[1,2,4]triazole-3-thiol,
4-Ethyl-5-(3-methoxy-thiophen-2-yl)-4H-[1,2,4]triazole-3-thiol, 4-Ethyl-5-(tetrahydro-furan-2-yl)-2,4-dihydro-[1,2,4]triazole-3-thione,
4-Ethyl-5-thioxo-4,5-dihydro-1H-[1,2,4]triazole-3-carboxylic acid methyl ester,
5-(2-Chloro-pyridin-4-yl)-4-ethyl-4H-[1,2,4]triazole-3-thiol,
5-(2-Chloro-6-methoxy-pyridin-4-yl)-4-ethyl-4H-[1,2,4]triazole-3-thiol,
4-Ethyl-5-(3-methyl-3H-imidazol-4-yl)-4H-[1,2,4]triazole-3-thiol,
4-Propyl-5-pyridin-4-yl-4H-[1,2,4]triazole-3-thiol,
4-Ethyl-5-(1-methyl-1H-imidazol-2-yl)-4H-[1,2,4]triazole-3-thiol,
4-Ethyl-5-(1-methyl-1H-imidazol-4-yl)-4H-[1,2,4]triazole-3-thiol,
3-(5-Mercapto-4-methyl-4H-[1,2,4]triazol-3-yl)-benzonitrile,
5-(3-Chloro-phenyl)-4-methyl-4H-[1,2,4]triazole-3-thiol,
5-(4-Chloro-phenyl)-4-methyl-4H-[1,2,4]triazole-3-thiol,
5-(2-fluoro-phenyl)-4-methyl-4H-[1,2,4]triazole-3-thiol,
5-(3-fluoro-phenyl)-4-methyl-4H-[1,2,4]triazole-3-thiol,
5-(4-fluoro-phenyl)-4-methyl-4H-[1,2,4]triazole-3-thiol,
5-Benzo[b]thiophen-2-yl-4-methyl-4H-[1,2,4]triazole-3-thiol,
5-(3-methoxy-phenyl)-4-methyl-4H-[1,2,4]triazole-3-thiol,
5-(4-methoxy-phenyl)-4-methyl-4H-[1,2,4]triazole-3-thiol,
4-Ethyl-5-(4-methoxy-phenyl)-4H-[1,2,4]triazole-3-thiol,
5-(3,5-Difluoro-phenyl)-4-ethyl-4H-[1,2,4]triazole-3-thiol,
5-(2,6-Difluoro-phenyl)-4-ethyl-4H-[1,2,4]triazole-3-thiol,
5-(4-Butoxy-phenyl)-4-ethyl-4H-[1,2,4]triazole-3-thiol,
5-Benzo[1,3]dioxol-5-yl-4-ethyl-4H-[1,2,4]triazole-3-thiol,
4-Ethyl-5-pyrimidin-5-yl-2,4-dihydro-[1,2,4]triazole-3-thione,
4-Ethyl-5-furan-3-yl-2,4-dihydro-[1,2,4]triazole-3-thione,
4-(Tetrahydrofuran-2-ylmethyl)-5-thiophene-2-yl-2,4-dihydro-[1,2,4]triazole-3-thione,
5-Cyclopentyl-4-ethyl-2,4-dihydro-[1,2,4]triazole-3-thione,
4-Ethyl-5-[2-(4-methoxy-phenyl)-ethyl]-2,4-dihydro-[1,2,4]triazole-3-thione,
5-(3,5-Dichloro-phenyl)-4-ethyl-4H-[1,2,4]triazole-3-thiol,
5-(3-Methylphenyl)-4-ethyl-4H-[1,2,4]triazole-3-thiol,
5-(4-Methylphenyl)-4-ethyl-4H-[1,2,4]triazole-3-thiol,
4-Ethyl-5-(3-nitrophenyl)-4H-[1,2,4]triazole-3-thiol,
5-(2,5-Difluorophenyl)-4-ethyl-4H-[1,2,4]triazole-3-thiol,
5-(3-Chlorophenyl)-4ethyl-4H-[1,2,4]triazole-3-thiol,
5-(4-Chlorophenyl)-4-ethyl-4H-[1,2,4]triazole-3-thiol,
4-Ethyl-5-methoxymethyl-2,4-dihydro-[1,2,4]triazole-3-thione,
4-Methyl-5-pyridin-4-yl-2,4-dihydro-[1,2,4]triazole-3-thione,
4-Allyl-5-furan-2-yl-2,4-dihydro-[1,2,4]triazole-3-thione,
4-Ethyl-5-(4-methoxy-phenoxymethyl)-2,4-dihydro-[1,2,4]triazole-3-thione,
4-Ethyl-5-phenoxymethyl-2,4-dihydro-[1,2,4]triazole-3-thione,
4-Ethyl-5-hydroxymethyl-2,4-dihydro-[1,2,4]triazole-3-thione,
4-Ethyl-5-(2-methoxy-ethyl)-2,4-dihydro-[1,2,4]triazole-3-thione,
4-Ethyl-5-methylsulfanylmethyl-2,4-dihydro-[1,2,4]triazole-3-thione,
5-Ethoxymethyl-4-ethyl-2,4-dihydro-[1,2,4]triazole-3-thione,
5-Furan-3-yl-4-methyl-2,4-dihydro-[1,2,4]triazole-3-thione,
4-Methyl-5-pyrimidin-4-yl-2,4-dihydro-[1,2,4]triazole-3-thione,
4-Ethyl-5-pyridazin-4-yl-2,4-dihydro-[1,2,4]triazole-3-thione,
4-Ethyl-5-pyridin-4-ylmethyl-2,4-dihydro-[1,2,4]triazole-3-thione,
4-Ethyl-5-(6-hydroxy-pyridin-3-yl)-2,4-dihydro-[1,2,4]triazole-3-thione,
4-Ethyl-5-(4-hydroxy-phenyl)-2,4-dihydro-[1,2,4]triazole-3-thione,
4-Ethyl-5-p-tolyloxymethyl-2,4-dihydro-[1,2,4]triazole-3-thione,
4-Ethyl-5-(6-methoxy-pyridin-3-yl)-2,4-dihydro-[1,2,4]triazole-3-thione,
4-Ethyl-5-(2-methoxy-pyridin-4-yl)-2,4-dihydro-[1,2,4]triazole-3-thione,
4-Ethyl-5-pyrimidin-2-yl-2,4-dihydro-[1,2,4]triazole-3-thione,
4-Ethyl-5-(5-methoxy-pyrimidin-2-yl)-2,4-dihydro-[1,2,4]triazole-3-thione,
4-Furan-2-ylmethyl-4H-[1,2,4]triazole-3-thiol,
4-Cyclopropyl-5-pyridin-4-yl-4H-[1,2,4]triazole-3-thiol,
4-Cyclopropylmethyl-5-pyridin-4-yl-4H-[1,2,4]triazole-3-thiol,
4-Cyclopropyl-5-thiophen-2-yl-2,4-dihydro-[1,2,4]triazole-3-thione,
5-Furan-2-yl-4-(2-methoxy-ethyl)-2,4-dihydro-[1,2,4]triazole-3-thione,
4-Cyclopropyl-5-furan-2-yl-2,4-dihydro-[1,2,4]triazole-3-thione,
(3-Thiophen-2-yl-5-thioxo-1,5-dihydro-[1,2,4]triazol-4-yl)-acetic acid methyl ester,
4-Cyclopropylmethyl-5-thiophene-2-yl-2,4-dihydro-[1,2,4]triazole-3-thione,
4-(2-Methoxy-ethyl)-5-thiophen-2-yl-2,4-dihydro-[1,2,4]triazole-3-thione,
Thiophen-2-yl-4-(2,2,2-trifluoroethyl)-2,4-dihydro-[1,2,4]triazole-3-thione,
4-Cyclopropyl-5-pyrimidin-4-yl-2,4-dihydro-[1,2,4]triazole-3-thione,
4-Cyclopropyl-5-pyridin-3-yl-2,4-dihydro-[1,2,4]triazole-3-thione,
4-Ethyl-5-trifluoromethyl-4H-[1,2,4]triazole-3-thiol,
4-Ethyl-3-methanesulfonyl-5-thiophen-2-yl-4H-[1,2,4]triazole,
4-(5-Methanesulfonyl-4-methyl-4H-[1,2,4]triazol-3-yl)-pyridine,
4-(2-Hydroxy-ethyl)-5-thiophen-2-yl-2,4-dihydro-[1,2,4]triazole-3-thione,
4-(4,5-Dimethyl-4H-[1,2,4]triazol-3-yl)-pyridine,
Methyl-(4-methyl-5-pyridin-4-yl-4H-[1,2,4]triazol-3-yl)-amine,
3-Pyridin-4-yl-5,6,7,8-tetrahydro-[1,2,4]triazolo[4,3-a]pyrimidine,
3-Furan-2-yl-5,6,7,8-tetrahydro-[1,2,4]triazolo[4,3-a]pyrimidine,
4-Ethyl-5-(6-methoxy-pyridazin-3-yl)-2,4-dihydro-[1,2,4]triazole-3-thione,
4-Ethyl-5-(5-methoxy-pyridin-2-yl)-2,4-dihydro-[1,2,4]triazole-3-thione,
5-Chloromethyl-3-phenyl-[1,2,4]oxadiazole,
5-Chloromethyl-3-(3-fluoro-phenyl)-[1,2,4]oxadiazole,
5-Chloromethyl-3-(2-fluoro-5-methyl-phenyl)-[1,2,4]oxadiazole,
5-Chloromethyl-3-thiophen-2-yl-[1,2,4]oxadiazole,
5-Chloromethyl-3-thiophen-3-yl-[1,2,4]oxadiazole,
3-(5-Chloromethyl-[1,2,4]oxadiazol-3-yl)-phenol,
5-Chloromethyl-3-o-tolyl-[1,2,4]oxadiazole,
5-Chloromethyl-3-(3-chloro-phenyl)-[1,2,4]oxadiazole, 5-Chloromethyl-3-(2,5-difluoro-phenyl)-[1,2,4]oxadiazole,
3-(3-Chloromethyl-[1,2,4]oxadiazol-5-yl)-benzonitrile,
2-Chloro-4-(3-chloromethyl-[1,2,4]oxadiazol-5-yl)-pyridine,
3-Chloromethyl-5-(2,5-dimethyl-phenyl)-[1,2,4]oxadiazole,
3-Chloromethyl-5-(2-fluoro-5-methyl-phenyl)-[1,2,4]oxadiazole,
3-Chloromethyl-5-(2,5-dichloro-phenyl)-[1,2,4]oxadiazole,
3-Chloromethyl-5-(2-fluoro-5-bromo-phenyl)-[1,2,4]oxadiazole,
3-Chloromethyl-5-(3-methyl-phenyl)-[1,2,4]oxadiazole,
3-Chloromethyl-5-(2,5-difluoro-phenyl)-[1,2,4]oxadiazole,
3-Chloromethyl-5-(3-methylsulfanyl-phenyl)-[1,2,4]oxadiazole,
3-Chloromethyl-5-(3-cyclopropyl-phenyl)-[1,2,4]oxadiazole,
3-(3-Chloromethyl-[1,2,4]oxadiazol-5-yl)-phenyl]-carbamic acid tert-butyl ester,
1-[3-(3-Chloromethyl-[1,2,4]oxadiazol-5-yl)-phenyl]-ethanone,
5-(5-Chloro-2-fluoro-phenyl)-3-chloromethyl-[1,2,4]oxadiazole,
2-(3-Chloromethyl-[1,2,4]oxadiazol-5-yl)-4-methyl-phenol,
3-Chloromethyl-5-(2-chloro-5-methyl-phenyl)-[1,2,4]oxadiazole,
3-Chloromethyl-5-(2,5-dichloro-thiophen-3-yl)-[1,2,4]oxadiazole,
3-(3-Chloromethyl-[1,2,4]oxadiazol-5-yl)-benzonitrile,
3-Chloromethyl-5-(3-fluoro-phenyl)-[1,2,4]oxadiazole,
3-Chloromethyl-5-(2-methyl-thiazol-4-yl)-[1,2,4]oxadiazole,
3-Chloromethyl-5-(4-fluoro-phenyl)-[1,2,4]oxadiazole,
5-(5-Bromo-2-fluoro-phenyl)-3-chloromethyl-[1,2,4]oxadiazole,
3-Chloromethyl-5-(4-methyl-thiophen-2-yl)-[1,2,4]oxadiazole,
5-(3-chloromethyl-[1,2,4]oxadiazol-5-yl)-thiophene-3-carbonitrile,
2-(3-Chloromethyl-[1,2,4]oxadiazol-5-yl)-4-methyl-benzonitrile,
3-(3-Chloromethyl-[1,2,4]oxadiazol-5-yl)-5-fluoro-benzonitrile,
3-(3-Chloromethyl-[1,2,4]oxadiazol-5-yl)-4-fluoro-benzonitrile,
4-Chloro-2-(3-chloromethyl-[1,2,4]oxadiazol-5-yl)-phenol,
3-(1-Chloro-ethyl)-5-(3-chloro-phenyl)-[1,2,4]oxadiazole,
3-(1-Chloro-ethyl)-5-(3-fluoro-phenyl)-[1,2,4]oxadiazole,
3-(1-Chloro-ethyl)-5-(5-chloro-2-fluoro-phenyl)-[1,2,4]oxadiazole,
[3-(3-Chloromethyl-[1,2,4]oxadiazol-5-yl)-phenyl-3-methanol,
3-Chloromethyl-5-[1-(toluene-4-sulfonyl)-1H-pyrrol-3-yl]-[1,2,4]oxadiazole,
3-Chloromethyl-5-furan-3-yl-[1,2,4]oxadiazole,
3-Chloromethyl-5-(5-chloro-thiophen-2-yl)-[1,2,4]oxadiazole,
1-[5-(3-Chloro-phenyl)-[1,3,4]oxadiazol-2-yl]-ethanol,
[5-(5-Chloro-2-fluoro-phenyl)-[1,2,4]oxadiazol-3-yl]-methanol,
1-[5-(3-Chloro-phenyl)-[1,2,4]oxadiazol-3-yl]-ethanol,
[5-(3-Chloro-phenyl)-[1,2,4]oxadiazol-3-yl]-methanol,
2-Chloromethyl-5-(2-fluoro-5-methyl-phenyl)-[1,3,4]oxadiazole,
2-Chloromethyl-5-(3-chloro-phenyl)-[1,3,4]oxadiazole,
4-(5-Chloromethyl-[1,3,4]oxadiazol-2-yl)-2-methyl-pyridine,
2-Chloromethyl-5-m-tolyl-[1,3,4]oxadiazole,
3-(5-Chloromethyl-[1,3,4]oxadiazol-2-yl)-benzonitrile,
2-Chloro-4-(5-chloromethyl-[1,3,4]oxadiazol-2-yl)-pyridine,
2-(5-Chloro-2-fluoro-phenyl)-5-chloromethyl-[1,3,4]oxadiazole,
2-(1-Bromo-ethyl)-5-(3-chloro-phenyl)-[1,3,4]oxadiazole,
2-(1-Bromo-ethyl)-5-(5-chloro-2-fluoro-phenyl)-[1,3,4]oxadiazole,
4-[5-(1-Bromo-ethyl)-[1,3,4]oxadiazol-2-yl]-2-methyl-pyridine,
2-(1-Bromo-ethyl)-5-(2-fluoro-5-methyl-phenyl)-[1,3,4]oxadiazole,
2-(1-Bromo-ethyl)-5-(3-chloro-phenyl)-[1,3,4]oxadiazole,
3-(1-Bromo-ethyl)-5-(3-chloro-phenyl)-[1,2,4]oxadiazole,
1-[5-(3-Chloro-phenyl)-isoxazol-3-yl]-ethanol,
1-[5-(2-Fluoro-5-methyl-phenyl)-isoxazol-3-yl]-ethanol,
5-(2-Fluoro-5-methyl-phenyl)-isoxazole-3-carboxylic acid methyl ester,
5-Thiophen-3-yl-isoxazole-3-carboxylic acid methyl ester,
5-Phenyl-isoxazole-3-carboxylic acid methyl ester,
5-(3-Chloro-phenyl)-4-methyl-isoxazole-3-carboxylic acid ethyl ester,
5-(5-Chloro-thiophen-3-yl)-isoxazole-3-carboxylic acid methyl ester,
[5-(3-Chlorophenyl)-isoxazol-3-yl]-methanol,
[2-(3-Chloro-phenyl)-oxazol-4-yl]-methanol,
[3-(3-Chloro-phenyl)-isoxazol-5-yl]-methanol,
5-(Thiophen-3-yl-isoxazol-3-yl)methanol,
[5-(2-Fluoro-5-methyl-phenyl)-isoxazol-3-yl]-methanol,
(5-Phenyl-isoxazol-3-yl)-methanol,
[5-(3-Chloro-phenyl)-4-methyl-isoxazol-3-yl]-methanol,
[5-(5-Chloro-thiophen-3-yl)-isoxazol-3-yl)]-methanol,
Methanesulfonic acid 1-[5-(3-Chloro-phenyl)-isoxazol-3-yl]-ethyl ester,
Methanesulfonic acid 2-(3-chloro-phenyl)-oxazol-4-ylmethyl ester,
Methanesulfonic acid 3-(3-chloro-phenyl)-isoazol-5-ylmethyl ester,
Methanesulfonic acid 5-(2-fluoro-5-methyl-phenyl)-isoxazol-3-ylmethyl ester,
Methanesulfonic acid-phenyl)-isoxazol-5-yl]-ethyl ester,
Methanesulfonic acid 5-(5-chloro-2-fluoro-phenyl)-isoxazol-3-ylmethyl ester,
Methanesulfonic acid 5-(3-chloro-phenyl)-isoxazol-3-ylmethyl ester,
Methanesulfonic acid 5-thiophen-3-yl-isoxazol-3-ylmethyl ester,
Methanesulfonic acid 5-(2-fluoro-5-methyl-phenyl)-isoxazol-3-ylmethyl ester,
Methanesulfonic acid 5-phenyl-isoxazol-3-ylmethyl ester,
Methanesulfonic acid 5-(3-chloro-phenyl)-4-methyl-isoxazol-3-ylmethyl ester,
Methanesulfonic acid 5-(5-chloro-thiophen-3-yl)-isoxazol-3-ylmethyl ester,
Methanesulfonic acid 1-[5-(2-fluoro-5-methyl-phenyl)-isoxazol-3-yl]-ethyl ester,
Methanesulfonic acid 1-[5-(5-chloro-2-fluoro-phenyl)-isoxazol-3-yl]-ethyl ester,
Methanesulfonic acid 4-chloro-5-(3-chloro-phenyl)-isoxazol-3-ylmethyl ester,
Pyrimidine-4-carboxylic acid,
3-(3-Chloro-phenyl)-isoxazole-5-carboxylic acid methyl ester,
2-Bromomethyl-5-(3-chloro-phenyl)-oxazole,
2-(3-Chloro-phenyl)-oxazole-4-carboxylic acid methyl ester,
2-(3-Chloro-phenyl)-oxazole-4-carboxylic acid methyl ester, 1-[5-(5-Chloro-2-fluoro-phenyl)-isoxazol-3-yl]-ethanol,
1-[3-(3-Chloro-phenyl)-isoxazol-5-yl]-ethanol,
[5-(5-Chloro-2-fluoro-phenyl)-isoxazol-3-yl]-methanol,
3-[5-(3-Chloro-phenyl)-[1,3,4]oxadiazol-2-yl]-propionic acid hydrazide,
3-[5-(3-Chloro-phenyl)-[1,3,4]oxadiazol-2-yl]-butyric acid hydrazide,
3-[3-(3-Chloro-phenyl)-[1,2,4]oxadiazol-5-yl]-propionimidic acid ethyl ester hydrochloride,
3-[3-(3-Chloro-phenyl)-[1,2,4]oxadiazol-5-yl]-propionic acid hydrazide,
[5-(3-Chloro-phenyl)-[1,2,4]oxadiazol-3-yl]-acetic acid hydrazide,
(R)-3-[3-(3-Chloro-phenyl)-[1,2,4]oxadiazol-5-yl]-butyric acid hydrazide,
3-[3-(3-Chloro-phenyl)-[1,2,4]oxadiazol-5-yl]-3-methyl-butyric acid hydrazide,
3-[5-(3-Chloro-phenyl)-[1,2,4]oxadiazol-3-ylmethyl]-piperidin-2-one,
3-[5-(5-Chloro-2-fluoro-phenyl)-[1,2,4]oxadiazol-3-ylmethyl]-piperidin-2-one,
3-Chloromethyl-5-(5-chloro-thiophen-3-yl)-[1,2,4]oxadiazole,
1-[5-(5-Chloro-thiophen-3-yl)-[1,2,4]oxadiazol-3-yl-methoxy]-1H-benzotriazole,
(4-Methyl-5-thiophen-2-yl-4H-[1,2,4]triazol-3-ylsulfanyl)-acetonitrile,
2-(4-Methyl-5-thiophen-2-yl-4H-[1,2,4]triazol-3-ylsulfanyl)-propionic acid,
2-(4-Methyl-5-pyridin-3-yl-4H-[1,2,4]triazol-3-ylsulfanyl)-propionic acid,
3-(3-Chloro-phenyl)-5-(4-methyl-4H-[1,2,4]triazol-3-ylsulfanylmethyl)-[1,2,4]oxadiazole or,
{3-[3-(4-Methyl-5-thiophen-2-yl-4H-[1,2,4]triazol-3-ylsulfanylmethyl)-[1,2,4]oxadiazol-5-yl-phenyl}-carbamic acid tert-butyl ester.

Pharmaceutical Formulations

According to one aspect of the present invention there is provided a pharmaceutical formulation comprising a compound of formula I, or salt thereof, for use in the prevention and/or treatment of metabotropic glutamate receptor subtype 5 receptor (mGluR5) mediated disorders and any disorder listed below.

The composition may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration as an ointment, patch or cream or for rectal administration as a suppository.

In general the above compositions may be prepared in a conventional manner using one or more conventional excipients, pharmaceutical diluents and/or inert carriers.

According to another aspect of the invention thee is provided a pharmaceutical formulation comprising as active ingredient a therapeutically effective amount of a compound of formula I in association with one or more pharmaceutically acceptable diluent, excipients and/or inert carrier.

Suitable daily doses of the compounds of formula I in the treatment of a mammal, including man are approximately 0.01 to 250 mg/kg bodyweight at peroral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

Medical Use

It has been found that the compounds according to the present invention, or salts thereof, exhibit a high degree of potency and selectivity for individual metabotropic glutamate receptor (mGluR) subtypes. In particular there are compounds according to the present invention that are potent and selective for the mGluR Group I receptor and more particularly for mGluR5. Accordingly, the compounds of the present invention are expected to be useful in the prevention and/or treatment of conditions associated with excitatory activation of an mGluR Group I receptor and for inhibiting neuronal damage caused by excitatory activation of an mGluR Group I receptor, specifically when the mGluR Group I receptor is mGluR5. The compounds may be used to produce an inhibitory effect of mGluR Group I, especially mGluR5, in mammals, including man. mGluR5 is highly expressed in the central and peripheral nervous system and in other tissues. Thus, it is expected that the compounds of the invention are well suited for the prevention and/or treatment of mGluR5 receptor-mediated disorders such as acute and chronic neurological and psychiatric disorders and chronic and acute pain disorders.

Further disorders are Alzheimer's disease senile dementia, AIDS-induced dementia, Parkinson's disease, amyotrophic lateral sclerosis, Huntington's Chorea, migraine, epilepsy, schizophrenia, depression, anxiety, acute anxiety, obsessive compulsive disorder, ophthalmological disorders such as retinopathies, diabetic retinopathies, glaucoma, auditory neuropathic disorders such as tinnitus, chemotherapy induced neuropathies, post-herpetic neuralgia and trigeminal neuralgia, tolerance, dependency, addiction and craving disorders, neurodevelopmental disorders including Fragile X, autism, mental retardation, schizophrenia and Down's Syndrome.

The compounds are also well suited for the prevention and/or treatment of pain related to migraine, inflammatory pain, neuropathic pain disorders such as diabetic neuropathies, arthritis and rheumatitiod diseases, low back pain, post-operative pain and pain associated with various conditions including angina, renal or billiary colic, menstruation, migraine and gout.

Other disorders are stroke, head trauma, anoxic and ischemic injuries, hypoglycemia, cardiovascular diseases and epilepsy.

The dose required for the therapeutic or preventive treatment of a particular disorder will necessarily be varied depending on the host treated, the route of administration and the severity of the illness being treated.

The invention relates to compounds of formula I as defined hereinbefore, for use in therapy.

The invention relates to compounds of formula I as defined hereinbefore, for use in prevention and/or treatment of neurological disorders.

The invention relates to compounds of formula I as defined hereinbefore, for use in prevention and/or treatment of psychiatric disorders.

The invention relates to compounds of formula I as defined hereinbefore, , for use in prevention and/or treatment of chronic and acute pain disorders.

The invention relates to compounds of formula I as defined hereinbefore, for use in prevention and/or treatment of mGluR5 receptor-mediated disorders.

The invention relates to compounds of formula I as defined hereinbefore, for use in prevention and/or treatment of Alzheimer's disease senile dementia, AIDS-induced dementia, Parkinson's disease, amylotropic lateral sclerosis, Huntington's Chorea, migraine, epilepsy, schizophrenia, depression, anxiety, acute anxiety, ophthalmological disorders such as retinopathies, diabetic retinopathies, glaucoma, auditory neuropathic disorders such as tinnitus, chemotherapy induced neuropathies, post-herpetic neuralgia and trigeminal neuralgia, tolerance, dependency, Fragile X, autism, mental retardation, schizophrenia and Down's Syndrome.

The invention relates to compounds of formula I as defined hereinbefore, for use in prevention and/or treatment of pain related to migraine, inflammatory pain, neuropathic pain disorders such as diabetic neuropathies, arthritis and rheumatitiod diseases, low back pain, post-operative pain and pain associated with various conditions including angina, renal or billiary colic, menstruation, migraine and gout.

The invention relates to compounds of formula I as defined hereinbefore, for use in prevention and/or treatment of stroke, head trauma, anoxic and ischemic injuries, hypoglycemia, cardiovascular diseases and epilepsy.

The present invention relates also to the use of a compound of formula I as defined hereinbefore, in the manufacture of a medicament for the prevention and/or treatment of mGluR5 receptor-mediated disorders and any disorder listed above.

The invention also provides a method of treatment and/or prevention of mGluR5 receptor-mediated disorders and any disorder listed above, in a patient suffering from, or at risk of, said condition, which comprises administering to the patient an effective amount of a compound of formula I, as hereinbefore defined.

In the context of the present specification, the term "therapy" includes treatment as well as prevention, unless there are specific indications to the contrary. The terms "therapeutic" and "therapeutically" should be construed accordingly.

In this specification, unless stated otherwise, the term 'antagonist' means a compound that by any means, partly or completely, blocks the transduction pathway leading to the production of a response by the ligand.

The term "disorder", unless stated otherwise, means any condition and disease associated with metabotropic glutamate receptor activity.

Non-Medical Use

In addition to their use in therapeutic medicine, the compounds of formula I or salt thereof, are also useful as pharmacological tools in the development and standardisation of in vitro and in vivo test systems for the evaluation of the effects of inhibitors of mGluR related activity in laboratory animals such as cats, dogs, rabbits, monkeys, rats and mice, as part of the search for new therapeutics agents.

Pharmacology

The pharmacological properties of the compounds of the invention can be analyzed using standard assays for functional activity. Examples of glutamate receptor assays are well known in the art as described in for example Aramori et al., Neuron 8:757 (1992), Tanabe et al., Neuron 8:169 (1992), Miller et al., J. Neuroscience 15: 6103 (1995), Balazs, et al., J. Neurochemistry 69:151 (1997). The methodology described in these publications is incorporated herein by reference. Conveniently, the compounds of the invention can be studied by means of an assay that measures the mobilization of intracellular calcium, $[Ca^{2+}]_i$ in cells expressing mGluR5.

Intracellular calcium mobilization was measured by detecting changes in fluorescence of cells loaded with the fluorescent indicator fluo-3. Fluorescent signals were measured using the FLIPR system (Molecular Devices). A two addition experiment was used that could detect compounds that either activate or antagonize the receptor.

For FLIPR analysis, cells expressing human mGluR5d were seeded on collagen coated clear bottom 96-well plates with black sides and analysis of $[Ca^{2+}]_i$ mobilization was done 24 hours after seeding.

FLIPR experiments were done using a laser setting of 0.800 W and a 0.4 second CCD camera shutter speed. Each FLIPR experiment was initiated with 160 µL of buffer present in each well of the cell plate. After each addition of the compound, the fluorescence signal was sampled 50 times at 1 second intervals followed by 3 samples at 5 second intervals. Responses were measured as the peak height of the response within the sample period. $EC_{50}$ and $IC_{50}$ determinations were made from data obtained from 8-point concentration response curves (CRC) performed in duplicate. Agonist CRC were generated by scaling all responses to the maximal response observed for the plate. Antagonist block of the agonist challenge was normalized to the average response of the agonist challenge in 14 control wells on the same plate.

We have validated a secondary functional assay for mGluR5d based on Inositol Phosphate ($IP_3$) turnover. $IP_3$ accumulation is measured as an index of receptor mediated phospholipase C turnover. GHEK cells stably expressing the human mGluR5d receptors were incubated with [3H] myo-inositol overnight, washed three times in HEPES buffered saline and pre-incubated for 10 minutes with 10 mM LiCl. Compounds (agonists) were added and incubated for 30 minutes at 37° C. Antagonist activity was determined by pre-incubating test compounds for 15 minutes, then incubating in the presence of glutamate (80 µM) or DHPG (30 µM) for 30 minutes. Reactions were terminated by the addition of perchloric acid (5%). Samples were collected and neutralized, and inositol phosphates were separated using Gravity-Fed Ion-Exchange Columns.

A detailed protocol for testing the compounds of the invention is provided below in Pharmaceutical Examples.

| Abbreviations | |
|---|---|
| FLIPR | Fluorometric Imaging Plate reader |
| CCD | Charge Coupled Device |
| CRC | Concentration Response Curve |
| GHEK | Human Embrionic Kidney expressing Glutamate Transporter |
| HEPES | 4-(2-hydroxyethyl)-1-piperazineethanesulfonic acid (buffer) |
| $IP_3$ | inositol triphosphate |
| DHPG | 3,5-dihydroxyphenylglycine; |
| BSA | Bovine Serum Albumin |
| EDTA | Ethylene Diamine Tetraacetic Acid |

Methods of Preparation

Another aspect of the present invention provides a process for preparing a compound of formula I, or salt thereof.

Throughout the following description of such processes it is understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis" T. W. Green, P. G. M. Wuts, Wiley-Interscience, New York, 1999.

Unless specified otherwise, are P, Q, $X^1$, $X^2$, $X^3$, $X^4$, R, $R^1$, $R^2$, $R^3$, $R^4$, $R^5$, $R^6$, $M^1$, $M^2$, m and n, defined as in formula I.

All starting materials are commercially available or earlier described in the literature. The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, d: doublet, t: triplet, q: quartet, m: multiplet).

Analytical in line liquid chromatography separations followed by mass spectra detections, were recorded on a Waters LCMS consisting of an Alliance 2795 (LC) and a ZQ single quadropole mass spectrometer. The mass spectrometer was equipped with an electrospray ion source operated in a positive or negative ion mode. The ion spray voltage was ±3 kV and the mass spectrometer was scanned from m/z 100-700 at a scan time of 0.8 s. To the column, X-Terra MS, Waters, C8, 2.1×50 mm, 3.5 μm, was applied a linear gradient from 5% to 100% acetonitrile in 10 mM ammonium acetate (aq.), or in 0.1% TFA (aq.). Preparative reversed phase chromatography was run on a Gilson autopreparative HPLC with a diode array detector using an XTerra MS C8, 19×300 mm, 7 μm as column. MS-triggered preparative reversed phase chromatograpy was run on a Waters autopurification LC-MS system with a diode array detector and a ZQ mass detector using an XTerra MS C8, 19×100 mm, 5 μm as column.

Purification by a chromatotron was performed on rotating silica gel/gypsum (Merck, 60 PF-254 with calcium sulphate) coated glass sheets, with coating layer of 1, 2, or 4 mm using a TC Research 7924T chromatotron.

Purification of products were also done using Chem Elut Extraction Columns (Varian, cat #1219-8002), Mega BE-SI (Bond Elut Silica) SPE Columns (Varian, cat # 12256018; 12256026; 12256034), or by flash chromatography in silica-filled glass columns. Microwave heating was performed in a Smith Synthesizer Single-mode microwave cavity producing continuous irradiation at 2450 MHz (Personal Chemistry AB, Uppsala, Sweden).

| Abbreviations: | |
|---|---|
| DMF | N,N-dimethylformamide |
| BOPA | Benzoyl Peroxide |
| P-BEMP | Polystyrene bound 2-tert-Butylimino-2-diethylamino-1,3-dimethyl-perhydro-1,3,2-diazaphosporine Deoxofluor[Bis(2-methoxyethyl)amino]sulfur trifluoride |
| DAST | (Diethylamino)sulfur trifluoride |
| EDGI | 1-(3-dimethylaminopropyl)-3-ethylcarbodiimide hydrochloride |
| HOBt | 1-hydroxybenzotriazole hydrate |
| THF | tetrahydrofuran |
| TFA | trifluoroacetic acid |
| Et | ethyl |
| Ac | acetyl |
| DIBAL | diisobutylaluminum hydride |
| M, N | molar and normal |
| HBTU | O-Benzotriazol-1-yl-N,N,N',N'-tetramethyluronium hexafluorophosphate |
| Boc | tert-butoxycarbonyloxy |
| LDA | Lithium diisopropylamine |
| LHA | Lithium aluminium hydride |
| MCPBA | meta-chloroperoxybenzoic acid |
| SPE | solid phase extraction |
| Lawesson's Reagent | [2,4-bis(4-methoxyphenyl)-1,3-dithia-2,4-diphosphetane-2,4-disulfide |

General syntheses of compounds of formula V.

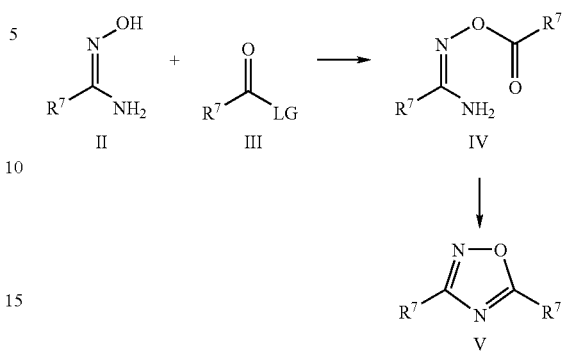

A compound of formula V, wherein $R^7$ is independently selected from a group consisting of $M^1$-$(R^2)_n$—P—$(R^1)_{m1}$, $M^2$-$(R^3)_n$—$X^4$-Q-$(R^4)_{m2}$, and $M^2$-$(R^3)_n$-G wherein G is a leaving group or a group which may subsequently be transformed into a leaving group, may be prepared through cyclization of a compound of formula IV formed from a suitably activated compound of formula III, wherein LG is a leaving group, with a compound of formula II. The compound of formula II may be prepared from a suitable nitrile by addition of hydroxylamine in a suitable solvent such as, methanol, ethanol, water or mixture thereof, using an appropriate base such as hydroxide, carbonate or acetate.

The compound of formula III may be activated as follows; i) as the acid chloride formed from the acid using a suitable reagent such as oxalyl chloride or thionyl chloride; ii) as an anhydride or mixed anhydride formed from treatment with a reagent such as alkyl chloroformate; iii) using traditional methods to activate acids in amide coupling reactions such as EDCI with HOBt or uronium salts like HBTU; iv) as an alkyl ester when the hydroxyamidine is deprotonated using a strong base like tert-butoxide; v) by any other suitable method of activation for the desired substrate.

The ester formation may be accomplished using an appropriate aprotic solvent such as dichloromethane, tetrahydrofuran, N,N-dimethylformamide or toluene, with optionally an appropriate organic base such as triethylamine, diisopropylethylamine and the like or an inorganic base such sodium bicarbonate or potassium carbonate.

The cyclization of the ester to form an oxadiazole may be carried out on the crude ester, with evaporation and replacement of the solvent with a higher boiling solvent such as DMF, or with aqueous extraction to provide a semi-purified material or with material purified by standard chromatographic methods. The cyclization may be accomplished by heating conventionally or by microwave irradiation (100-180° C.), in a suitable solvent such as pyridine or N,N-dimethylformamide or using a lower temperature method employing reagents like tetrabutylammonium fluoride in tetrahydrofuran or by any other suitable known literature method.

Other compatible non-reacting functional groups suitably protected may also be present in the substrates.

Further examples of the above described reactions can be found in Poulain et al., Tetrahedron Lett., (2001), 42, 1495-98, Ganglott et al., Tetrahedron Lett., (2001), 42, 1441-43, which are hereby included as references.

Synthesis of Nitriles and Acids for Use in Preparation of Compounds of Formula II and III Aryl nitrites are available by a variety of methods including cyanation of an aryl halide or triflate under palladium or nickel catalysis using an appropriate cyanide source such as zinc cyanide in an appropriate solvent such as N,N-dimethylformamide. The corresponding acid is available from the nitrile by hydrolysis under either acidic or basic conditions in an appropriate solvent such as aqueous alcohols. Aryl acids are also available from a variety of other sources, including iodo- or bromo-lithium exchange followed by trapping with $CO_2$ to give directly the acid.

The acid may be converted to the primary amide using any compatible method to activate the acid, including via the acid chloride or mixed anhydride, followed by trapping with any source of ammonia, including ammonium chloride in the presence of a suitable base, ammonium hydroxide, methanolic ammonia or ammonia in an aprotic solvent such as dioxane. This amide intermediate may be converted to the nitrile using a variety of dehydration reagents such as oxalyl chloride or thionyl chloride. This reaction sequence to convert an acid into a nitrile may also be applied to non-aromatic acids, including suitably protected amino acid derivatives. A suitable protecting group for an amine, in an amino acid or in a remote position of any other acid starting material, may be any group which removes the basicity and nucleophilicity of the amine functionality, including such carbamate protecting group as Boc.

Some acids are more easily prepared taking advantage of commercially available analogs. For example, 6-methylpyridine-4-carboxylic acid is prepared by dechlorination of 2-chloro-6-methylpyridine-4-carboxylic acid. Certain types of substituted fluoro-benzonitriles and benzoic acids are available from bromo-difluoro-benzene via displacement of one fluoro group with a suitable nucleophile such as imidazole in the presence of a base such as potassium carbonate in a compatible solvent such as N,N-dimethylformamide at elevated temperatures (80-120° C.) for extended periods of time. The bromo group may subsequently be elaborated into the acid or nitrile as above. 1,3-Disubsituted and 1,3,5-trisubstituted benzoic acids and benzonitriles may be prepared by taking advantage of readily available substituted isophthalic acid derivatives. Monohydrolysis of the diester allows selective reaction of the acid with a variety of reagents, most typically activating agents such as thionyl chloride, oxalyl chloride or isobutyl chloroformate and the like. From the activated acid, a number of products are available. In addition to the primary amide used to form the nitrile by dehydration as mentioned above, reduction to the hydroxymethyl analog may be carried out on the mixed anhydride or acid chloride using a variety of reducing agents such as sodium borohydride in a compatible solvent such as tetrahydrofuran. The hydroxymethyl derivative may be further reduced to the methyl analog using catalytic hydrogenation with an appropriate source of catalyst such as palladium on carbon in an appropriate solvent such as ethanol. The hydroxymethyl group may also be used in any reaction suitable for benzylic alcohols such as acylation, alkylation, transformation to halogen and the like. Halomethylbenzoic acids of this type may also be obtained from bromination of the methyl derivative when not commercially available. Ethers obtained by alkylation of the hydroxymethyl derivatives may also be obtained from the halomethylaryl benzoate derivatives by reaction with the appropriate alcohol using an appropriate base such as potassium carbonate or sodium hydroxide in an appropriate solvent such as tetrahydrofuran or the alcohol. When other substituents are present, these may also be employed in standard transformation reactions. Treatment of an aniline with acid and sodium nitrite may yield a diazonium salt, which may be transformed into a halide such as fluoride using tetrafluoroboric acid. Phenols react in the presence of a suitable base such as potassium carbonate with alkylating agents to form aromatic ethers.

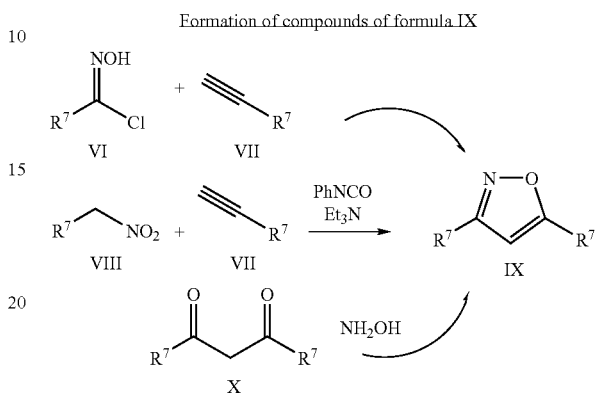

Formation of compounds of formula IX

A compound of formula IX, wherein $R^7$ is independently selected from a group consisting of $M^1$-$(R^2)_n$—P—$(R^1)_{m1}$, $M^2$-$(R^3)_n$—$X^4$-Q-$(R^4)_{m2}$, and $M^2$-$(R^3)_n$-G wherein G is a leaving group or a group which may subsequently be transformed into a leaving group, may be prepared by a 1,3-dipolar cycloaddition between compounds of formula VI and VII under basic conditions using a suitable base such as sodium bicarbonate or triethylamine at suitable temperatures (0° C.-100° C.) in solvents such as toluene. Synthesis of compounds of type VI has previously been described in the literature, e.g. Kim, Jae Nyoung; Ryu, Eung K; J. Org. Chem. (1992), 57, 6649-50. 1,3-Dipolar cycloaddition with acetylenes of type VII can also be effected using substituted nitromethanes of type VIII via activation with an electrophilic reagent such as PhNCO in the presence of a base such as triethylamine at elevated temperatures (50-100° C.). Li, C-S.; Lacasse, E.; Tetrahedron Lett. (2002) 43; 3565-3568. Several compounds of type VII are commercially available, or may be synthesized by standard methods as known by one skilled in the art.

Alternativley, compounds of formula X, which are available from a Claisen condensation of a methyl keone and an ester using basic conditions using such bases as sodium hydride or potassium tert-butoxide, may yield compounds of formula IX via condensation and subsequent cyclization using hydroxylamine, for example in the form of the hydrochloric acid salt, at elevated temperatures (60-120° C.).

It is understood that for both methods subsequent functional group transformations may be necessary. In the case of an ester group, these transformations may include, but is not limited to either of following three procedures: a) Complete reduction using a suitable reducing agent such as LAH in solvents such as THF. b) Partial reduction using a suitable selective reducing agent such as DIBAL followed by alkylation with an alkylhalide. c) Alkylation using an alkylmetal reagent such as an alkyl magnesium halide in solvents such as toluene or THF, followed by reduction with for example sodium borohydride in methanol.

Formation of compounds of formula XIV

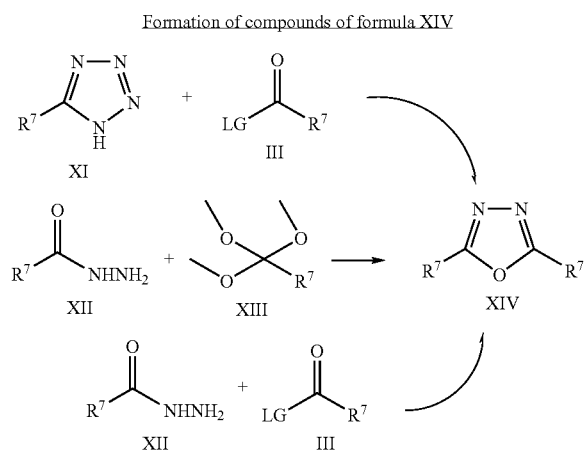

A compound of formula XIV, wherein $R^7$ is independently selected from a group consisting of $M^1\text{-}(R^2)_n\text{—}P\text{—}(R^1)_{m1}$, $M^2\text{-}(R^3)_n\text{—}X^4\text{-}Q\text{-}(R^4)_{m2}$, and $M^2\text{-}(R^3)_n\text{-}G$ wherein G is a leaving group or a group which may subsequently be transformed into a leaving group, may be prepared from tetrazole compounds of type XI via acylation using an isolable compound of type III such as an acid chloride or anhydride, or a compound of type III wherein the LG may be formed in situ, for example from activation of an acid using a reagent such as DCC or EDCI, followed by rearrangement to the 1,3,4-oxadizaole. Jursic, B. S.; Zdravkovski, Z.; Synth. Commun.; (1994) 24; 1575-1582.

Alternatively, compounds of formula XIV may also be prepared from acyl hydrazide of type XII via heating in the presence of compounds of formula XIII or III, wherein LG is a leaving group such as chloride or alkoxide, at elevated temperatures (60-130° C.) in one step. The reaction of compounds of Formula XIII may be carried out neat or using a suitable aprotic solvent such as benzene or xylene, or a protic solvent such as ethanol or n-butanol, and may be facilitated by the presence of abase such as KOtBu or a acid such as p-toluene sulfonic acid or acetic acid. Se references: Saunders, J.; Cassidy, M.; Freedman, S. B.; Harley, E. A.; Iversen, L. L. J. Med. Chem.; (1990) 33; 1128-1138; Peet, N. P.; Sunder, S. J. Heterocycl. Chem.; (1984) 21; 1807-1816. For compounds of formula III a dehydrating agent such as phosphorous pentoxide may be used to increase cyclization of the formed reaction intermediate as has been previously been decribed for example by Kakefuda, Akio; et al.; Bioorg. Med. Chem. (2002), 10; 1905-1912.

Formation of compounds of formula XVI

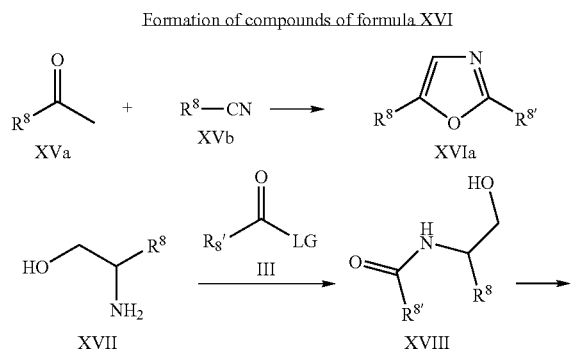

-continued

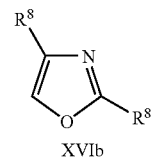
XVIb

A compound of formula XVI, wherein $R^8$ as defined above is independently selected from a group consisting of $M^1\text{-}(R^2)_n\text{—}P\text{—}(R^1)_{m1}$, $M^2\text{-}(R^3)_n\text{—}X^4\text{-}Q\text{-}(R^4)_{m2}$, and $M^2\text{-}(R^3)_n\text{-}G$ wherein G is a leaving group or a group which may subsequently be transformed into a leaving group, may be prepared by the reaction of compounds of formula XVa and XVb in the presence of in situ generated Tl(OTf)3 under acidic conditions according to the procedure of Lee and Hong; Tetrahedron Lett., (1997), 38, 8959-60.

Alternatively compounds of formula III and XVII are reacted as described above for formula V to give an intermediate of formula XVIII. Such an intermediate may give the required oxazole by cyclodehydration with to generate the oxazoline followed by dehydrogenation using $BrCCl_3$ in the same reaction pot. Phillips, A. J.; Uto, Y.; Wipf, P.; Reno, M. J. and Williams, D. R., Organic Letters, (2000) 2, 1165-8.

Formation of the bond between $X^4$ and $M^2$ or Q and $M^2$ through nucleophilic displacement of a leaving group:

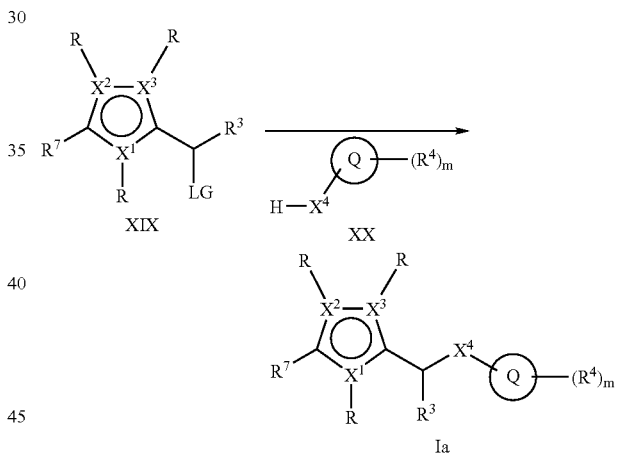

A compound of formula XX, may be used to displace the leaving group LG in compounds of formula XIX ($R^7$ is $M^1\text{-}(R^2)_n\text{—}P\text{—}(R^1)_{m1}$). When $X^4$ is represented by a heteroatom such as N and S, the reaction is carried out in the presence of an appropriate base such as potassium carbonate, cesium carbonate, sodium hydride, triethylamine or the like, which may facilitate the reaction by deprotonation of the $X^4$ residue and prevent the formation of any excess acid that would be generated by the reaction in the absence of a base. The reaction may be accomplished using any appropriate solvent such as acetonitrile or DMF, and may be carried out at room temperature or at elevated temperature (35-100° C.) to accelerate the reaction.

Such conditions may be used with appropriate modifications of employed equipment for parallel synthesis, using standard techniques known to the one skilled in the art. Similarly these reaction conditions may be carried out for compounds of formula XX when $X^4$=bond and ring Q is a fused bicycle containing a heteroatom such as N as defined aboved.

In either the latter or the above described case with $X^4=N$, NaH in DMF is preferred as desribed in literature precedences, for example Murdoch, Robert; Tully, W. Roger; Westwood, Robert; J. Heterocycl. Chem.; (1986), 23; 833-841.

For compounds of formula XX containing $X^4=C$ a stronger base needs to be employed to achieve deprotonation, such as for example LDA, n-butyllithium or any other alkyl metal base in apropriate aprotic solvents such as THF, hexane or toluene at temperatures generally below ambient temperatures, e.g. at −78° C. or 0° C.

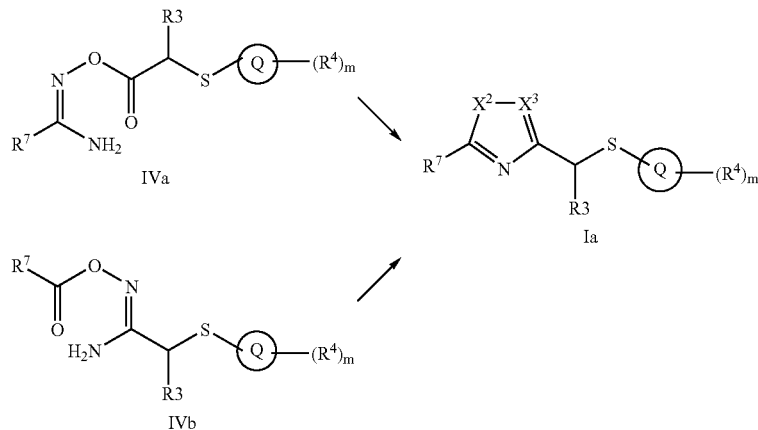

An alternative procedure for the synthesis of above described type of thiomethyl oxadiazole is to form an acyclic ester IVa and IVb from the combination of a suitably substituted hydroxyamidine and activated acid coupling partner also suitably substituted. Displacement of the chloride using the thiol nucleophile may occur immediately prior to cyclization using one of the methods of oxadiazole formation described above. The displacement can also be carried out on the chloromethyl hydroxyamidine or chloromethyl acid starting materials followed by the two step esterification and cyclization as above. The conditions described may be used with appropriate modifications of employed equipment for parallel synthesis using standard techniques known to the one skilled in the art.

Formation of 4-alkyl-triazoles thiols/thiones:

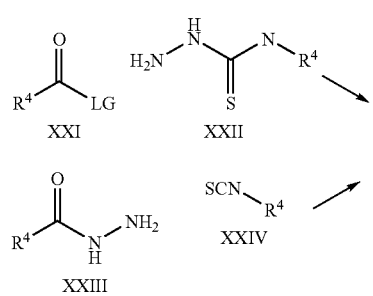

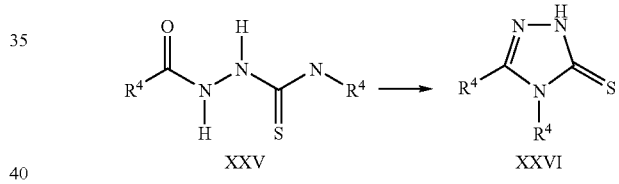

Any suitable acylating agent such as an acid chloride or an activated acid or the corresponding acid under amide coupling conditions as mentioned above, is reacted with a suitable 4-alkyl-3-thiosemicarbazide in the presence of a base such as pyridine or non-nucleophilic amines to form the acyclic intermediate compound of formula XXV, wherein $R^4$ is as defined above. The same intermediate is also available through reaction of an acyl hydrazide with an alkyl isothiocyanate. Cyclization to give a compound of formula XXVI is easily effected by treatment with an appropriate inorganic base such as hydroxide or bicarbonate at elevated temperature in an appropriate solvent such as water, water-dioxane, an aqueous alcohol or mixture thereof.

Such conditions may be used with appropriate modifications of employed equipment when using a solid phase base instead of above-mentioned ones, such as for example P-BEMP for parallel synthesis using standard techniques known to the one skilled in the art.

The compound of formula XXV reacts through its tautomeric form under the conditions described above with compounds of formula XIX to yield the S-alkylation compounds of the formula Ia.

The triazole thiones XXIX and XXXI alkylated on the other nitrogen atoms of the ring (1 and 2) are available through similar procedures. The 2-alkyl triazole thione XXVIII may be obtained by treatment of an aroyl isothiocyanate with an alkyl hydrazine in toluene at elevated temperatures, e.g. 85° C., followed by heating with aqueous bicarbonate. The same product may also be obtained through treatment of the analogous 2-alkyl-3-thiosemicarbazide with an activated acid in the presence of a suitable base such as pyridine or triethylamine followed by alkaline ring closure in a manner similar to the alkaline ring closure yielding product XXVI above.

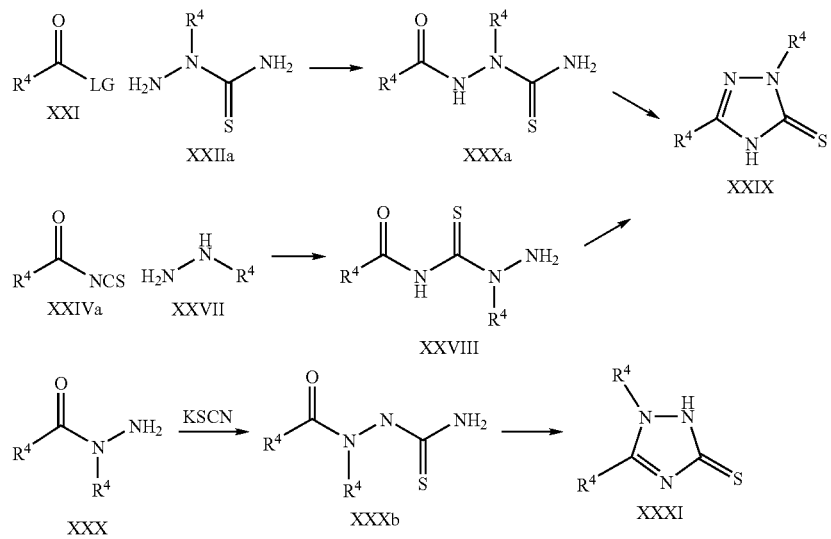

The 1-alkyl triazole thiones XXXI may be prepared by the reaction of a suitable N-alkyl-N-acylhydrazide with potassium thiocyanate in the presence of an acid such as HCl or other compatible strong acid via the 1-acyl-1-alkyl-3-thiosemicarbazide intermediate which undergoes alkaline ring closure in a manner similar to the alkaline ring closure yielding compounds of formula XXVI above.

Formation of compounds of formula XXXIII

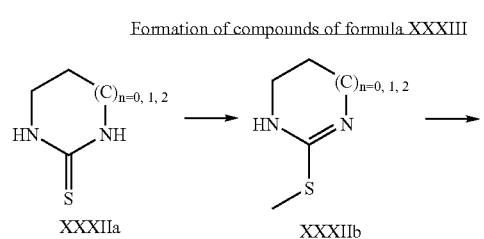

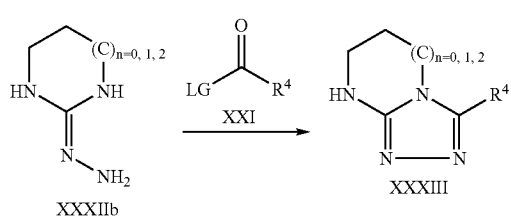

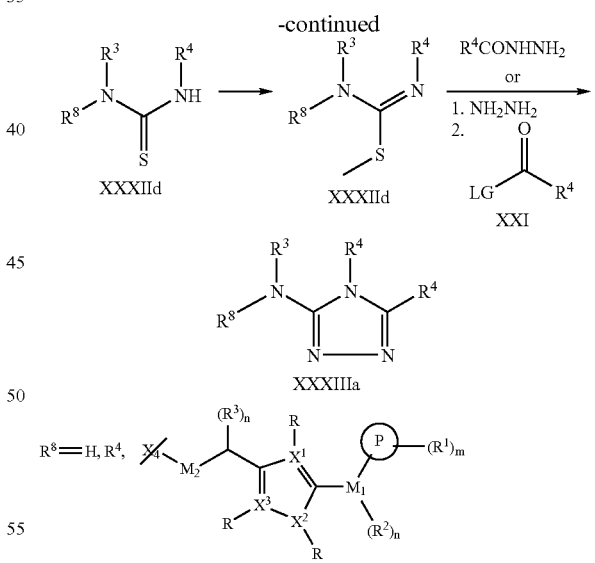

A compound of formula XXXIII may be prepared by alkylation of cyclic thioureas of formula XXXIIa, wherein n is defined as 0,1 or 2, resulting in compound of formula XXXIIb, e.g. 2-methylthio-1,4,5,6-tetrahydropyrimidine in case of n=1. The alkylation with for example methyliodide as alkylating agent can be done in several solvents (DMF, acetone, $CH_2Cl_2$ etc.) at room temperature or elevated temperatures and will give the product as its hydroiodide salt as has been previously described by Kennedy, Kevin J.; Simandan, Tiberiu L.; Dix, Thomas A.; Synth. Commun.; (1998); 24; 741-746. Cyclic thioureas are readily available either through synthesis as known by the one skilled in the art, or commercial sources. Compounds of formula XXXIIc result from the hydrazinolysis of the corresponding compounds of type XXXIIb. The hydrazinolysis is preferably done in refluxing EtOH with hydrazine hydrate as described previously by Krezel, Izabella; Pharmazie; (1994); 94, 27-31. Finally, fused triazoles of formula XXXIII may be formed through the thermal acylation and condensation reaction between compounds of formula XXI wherein LG is a leaving group as for example a halide, and compounds of formula XXXIIc. Such reactions may be conducted in pyridine or in EtOH or toluene in the presence of base. Normal heating or microwave irradiation may be used. Similarly, XXXIII may be prepared in the presence of a base, such as sodium methoxide in a suitable solvent such as methanol or ethanol at elevated temperatures where XXI may also be an ester or carboxylic acid.

Acyclic thioureas of formula XXXIId, wherein $R^8$ is defined as in the scheme and $R^3$ and $R^4$ are as defined in Formula I, may also be employed using a similar method to obtain compounds of formula XXXIIIa, wherein the introduction of the hydrazine portion may be carried out using either hydrazine followed by acylation, or by using a preformed acyl hydrazine.

Compounds of formula XXXIVb may be prepared by using similar methods as above, e.g. by activation of XXXIVa to give the corresponding imidoyl chloride by using oxalyl chloride or pentachlorophosphine in the optional presence of a base such as triethylamine. The intermediate may be used in-situ or may be isolated prior to trapping by a compound of formula XXII as has been used above. The subsequent product may be cyclized under acidic or basic conditions in a suitable solvent such as DMF to give compounds of formula XXXV. XXXV may be an intermediate used in the formation of compounds of Formula I, or may be the final bioactive compound of Formula I.

A compound of formula XXXV, wherein $R^8$ is selected independently from a group as depicted above may also be prepared through reaction of compounds of formula XXXVIa (ethyl imidoate is depicted as example) and XXXVIb followed by cyclization at elevated temperatures (40-80° C.) in the presence of an amine, whereas the amine preferably should have, but is not limited to, a low boiling point such as that it can be used in excess and simplify the work-up procedure. Examples for such amines may be, but are not limited to methylamine or ethylamine which may be used as solutions in for example methanol, THF or dichloromethane.

Formation of compounds of formula XXXV

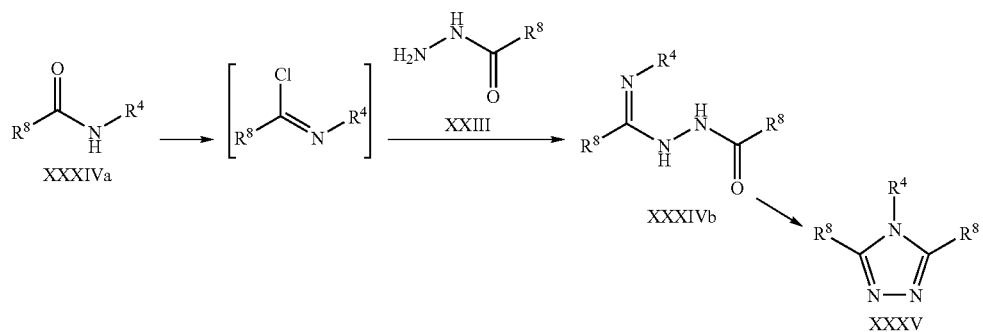

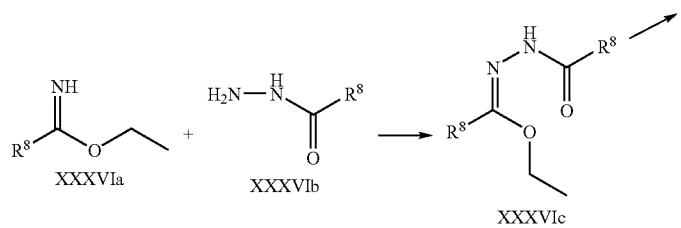

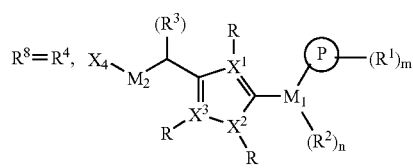

Formation of compounds of formula XXXVIa and XXXVIb

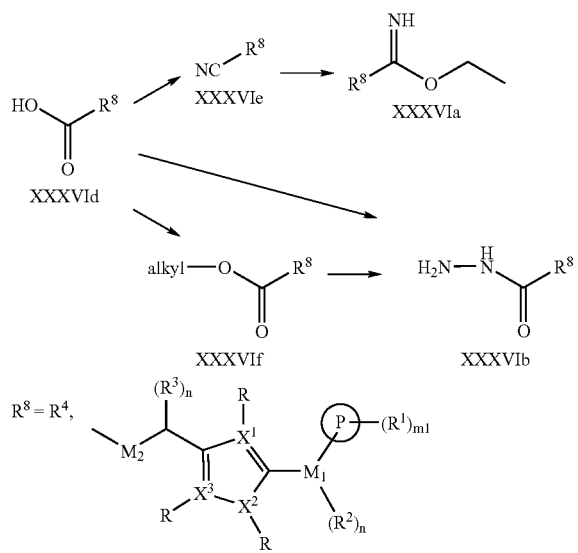

A compound of formula XXXVIa, wherein $R^8$ is selected independently from a group as depicted above may be prepared through reaction of a nitrile of formula XXXVIe in an alcohol such as ethanol in the presence of a protic acid, for example hydrochloric acid. The nitrile may be obtained from an acid XXXVId as described above. Compounds of formula XXXVId may also be used to prepare acyl hydrazides of formula XXXVIb, wherein $R^8$ is selected independently from a group as depicted above. This type of substance XXXVIb may also be formed directly from an acid. There may be advantages to react an intermediate ester of type XXXVIf with either neat hydrazine, hydrazine salt in the presence of a base or hydrazine hydrate in facilitating a simpler workup. However, the direct route via the acid using in situ activation may be advantageous in substrates sensitive to nucleophilic attack and also give the product in a shorter sequence of steps.

Formation of compounds of formula XXXVId and XXXVIf

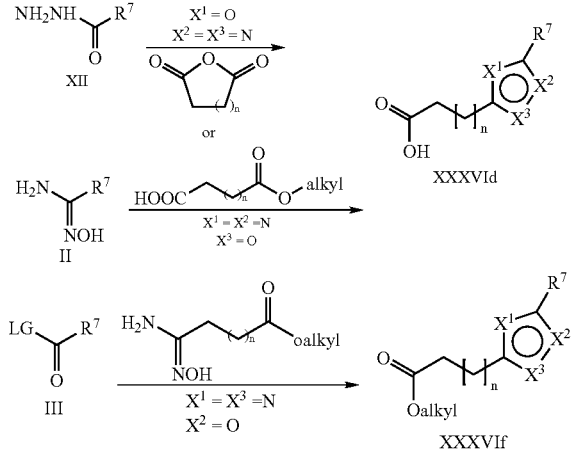

Compound of formula XXXVId & XXXVIf, wherein $R^7$ is a group consisting of $M^1$-$(R^2)_n$—P—$(R^1)_m$, may be prepared by either of the non-limiting methods: a) reaction of acyl hydrazide compounds of formula XII with a cyclic anhydride or monoesterified diacid followed by the cyclization of the formed intermediate would lead to 1,3,4-oxadiazoles of type XXXVId and XXXVIf respectively ($X^1$=O, $X^2$ and $X^3$=N); b) reaction and cyclization of an hydroxyamidine of Formula II with a cyclic anhydride or with the monoesterified diacid may be used to provide the 1,2,4-oxaziazole analogs XXXVId and XXXVIf wherein $X^1$ and $X^2$=N, $X^3$=O; c) reaction of a compound of type III with an hydroxamidine type compound, with the exception of the succinyl derivative, may be used to provide the 1,2,4-oxaziazole analogs XXXVIf wherein $X^1$ and $X^3$=N, $X^2$=O.

Compounds XXXVId and XXXVIf may be interconverted independent of the nature of $X^1$, $X^2$ or $X^3$ as described above.

Formation of compounds of formula Ib

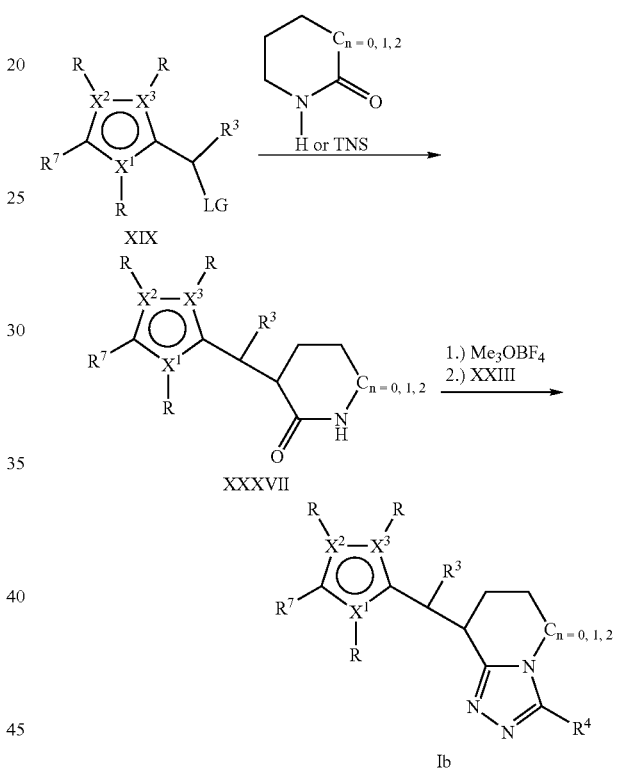

A compound of formula Ib, wherein $R^7$ is selected from a group $M^1$-$(R^2)_n$—P—$(R^1)_{m1}$ may be prepared from compounds of formula XXXVII, generated from XIV as described below, through selective O alkylation using $Me_3OBF_4$ or dimethyl sulfate (as described in literature precedences, for example: a) Sheu, Jennline; Smith, Michael B.; Oeschger, Thomas R.; Satchell, Jacqueline; Org. Prep. Proced. Int.; (1992); 24, 147-158; or b) Hutchinson, Ian S.; Matlin, Stephen A.; Mete, Antonio, Tetrahedron Lett.; (2001); 42; 1773-1776). The methoxy group may then be displaced by an acyl hydrazide of type XXIII, followed by a ring closing condensation to form the triazole heterocycle. This may be done in ethanol, toluene, DMF or pyridine under thermal conditions with regular heating or microwave irradiation, as has been previously described by for example Lawson, Edward C.; Hoekstra, William J.; Addo, Michael F.; Andrade-Gordon, Patricia; Damiano, Bruce P.; Kauffman, Jack A.; Mitchell, John A.; Maryanoff, Bruce E.; Bioorg. Med. Chem. Lett.; (2001); 11; 2619-2622.

Compounds of type XXXVII may be prepared by the reaction of cyclic amides, lactams, which are readily alkylated in the α-position to the carbonyl by successive treatment with 2 equivalents of a strong base e.g n-Buli to generate the dianion followed by addition of 1 equivalent of compounds of formula XIX, in an aprotic solvent such as THF, as has been previously described by for example Grieco, Paul A.; Kaufman, Michael D.; J. Org. Chem.; (1999); 64; 6041-6048). Alternatively, a N-protected lactam may be used in which only 1 equivalent base e.g. LDA is needed to generate the anion for the alkylation as has been previously described by for example Padwa, Albert; Beall, L. Scott; Heidelbaugh, Todd M.; Liu, Bing; Sheehan, Scott M.; J. Org. Chem.; (2000); 65; 2684-2695.

General synthesis of compounds of formula Ic

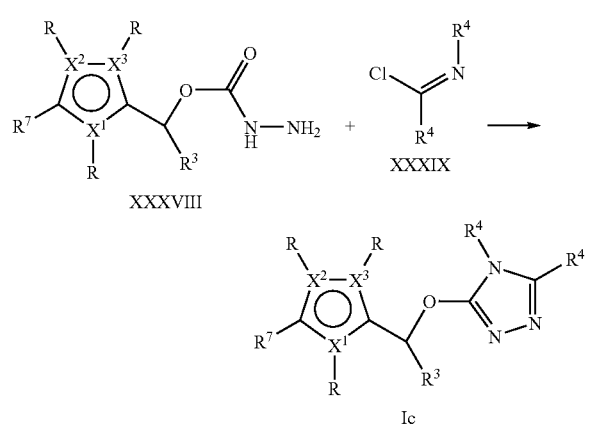

A compound of formula Ic, wherein $R^7$ is consisting of $M^1\text{-}(R^2)_n\text{---}P\text{---}(R^1)_{m1}$, may be prepared through reaction with subsequent cyclization of compounds of formula XXXVIII, with a compound of formula XXXIX. The compound of formula XXXIX may be prepared from a suitable secondary amide using oxalyl chloride or pentachlorophosphine in the optional presence of a base such as triethylamine and used either in-situ or as isolated material as described above from XXXIVa.

Compounds of formula XXXVIII, may be prepared from the corresponding alcohol by reacting it with phosgene or preferably a phosgene analog such as carbonyldiimidazole followed by coupling to hydrazine.

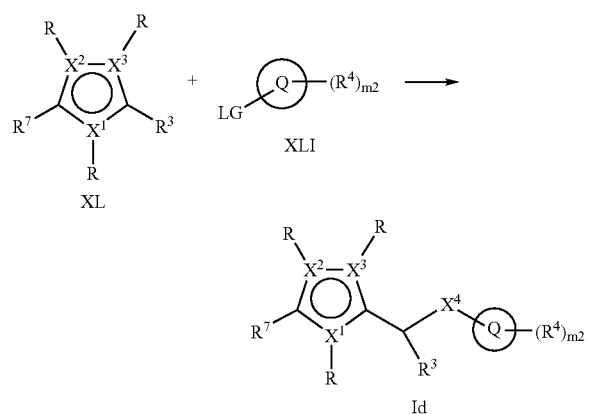

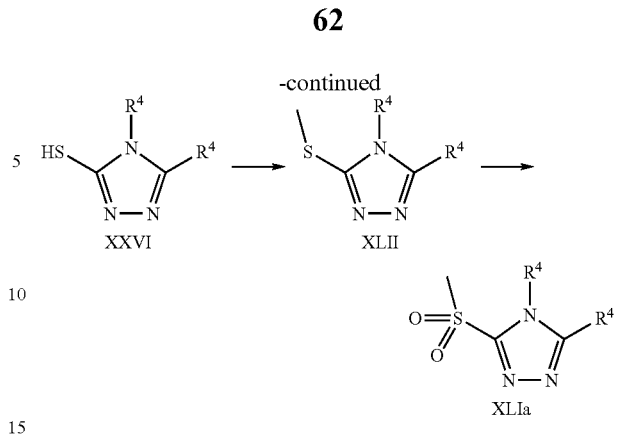

Other means of synthesizing a compound of formula Ic or Id, wherein $X^4$=O and wherein $R^7$ is $M^1\text{-}(R^2)_n\text{---}P\text{---}(R^1)_{m1}$, may be by the O-alkylation of compounds of type XL with compounds of type XLI wherein the leaving group may consist of a tosyl-, mesyl-, halo- or any other appropriate group, in the a suitable base such as cesium or potassium carbonate, sodium hydride in solvents such as for example DMF or DMSO.

Compounds of type XLI may be synthesized as exemplified with triazole XXVI by alkylation or arylation of the sulfur group using an apropriate alkylating or arylating reagent followed by double oxidation of the thiogroup to the corresponding sulfone using oxidants such as MCPBA, hydrogen peroxide in acetic acid or potassium permanganate. Such a sequence has previously been described for example by Åkerblom et al. J. Med. Chem. 16, 312 (1973). Alternatively, triazole halides may be synthesized as previously described in the literature by for example Ashton, W. T. et al. J. Med. Chem. 36, 591 (1993).

The alcohols may be prepared either directly upon synthesis of the oxadiazole or isoxazole part as described above under general synthesis of compounds of formula V. Alternatively they may be prepared from an oxadiazole or isoxazole unit with an appropriate leaving group such as a halide, e.g. chloride, using a three step sequence as described by Palazzo et al. J. Heterocycl. Chem. (1979) 16:1469, followed by a standard reduction protocol of the resulting aldehyde (or hydrate thereof) using for example sodium borohydride in methanol.

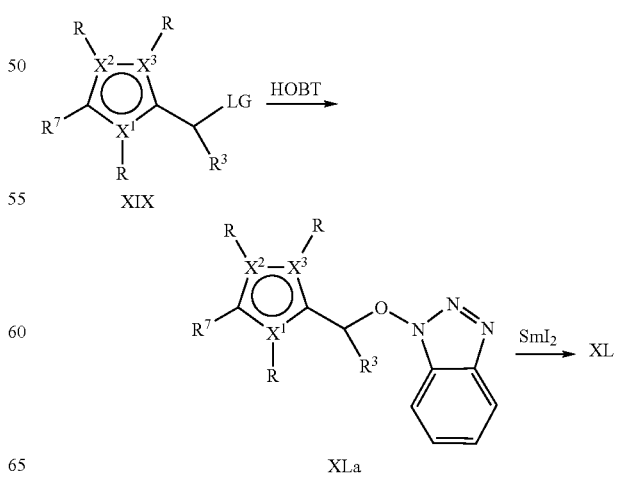

Yet another method may involve the reaction of a compound of structure XIV unit containing an appropriate leaving group such as a halide, e.g. chloride with hydroxybenzotriazole in the presence of a suitable base such as potassium carbonate or triethylamine in a suitable solvent such as DMSO, acetonitrile, acetone, DMF to give compounds of type XLa. Alternatively XLa may be obtained if hydroxybenzotriazole is present during cyclization to the oxadiazole, either as a co-activator with EDCI or as a result of a byproduct from a coupling reagent such as HBTU as described above under the reaction of compounds of formula I-V. XLa may be converted to the alcohol by the addition of samarium diiode, preferably over an elongated period of time (5-360 minutes) in a suitable solvent such as tetrahydrofuran, methanol, water or mixtures thereof, with THF being a preferred solvent, at an appropriate temperature (−75° C.-+75° C.). The cleavage of the N—O bond can alternatively be done using commonly used hydrogenation methods in the presence of a suitable catalyst such as raney-nickel as known by the one skilled in the art. In compounds of formula XLa the oxobenzotriazole functionality may also serve as a leaving group. Thus compounds XLa may react with compounds XX as described above.

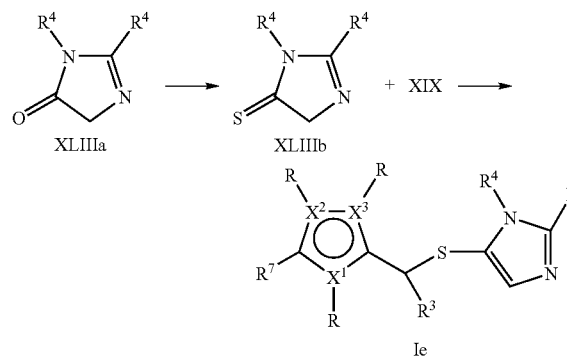

Formation of compounds of type Ie

A compound of formula Ie, wherein $R^7$ is $M^1$-$(R^2)_n$—P—$(R^1)_{m1}$, may be prepared through nucleophilic substitution of compounds of type XLIIIb with compounds of type XIX as described above. Compounds of type XLIIIb may be prepared by reaction of their oxo-analogues XLIIIa using $P_2S_{10}$ or Lawesson's reagent under thermal conditions. Synthesis of compounds of type XLIIIa has been described by Takeuchi, H., Hagiwara, S., Eguchi, S., Tetrahedron (1989); 45; 6375-6386.

Introduction of Substitution in the Q Ring:

If substitution on the Q ring is desired, one may choose an appropriately substituted aryl or heteroaryl thiol to use for the displacement reaction. The same is valid for other nucleophilic reagents other than substituted or non-substituted aryl or heteroaryl thiols serving to substitute the same in the final compounds. If the aryl or heteroaryl residue has an amenable reactive moiety, either directly introduced or as a result of a deprotection reaction, including but not limited to a free NH site as in aniline, imidazole, benzimidazole, indole and the like, a compound of formula If ($R^7$ is $M^1$-$(R^2)_n$—P—$(R^1)_{m1}$) may be substituted with $R^4$ using a suitable base such as an alkyllithium or alkali-metal hydride or hydroxide to deprotonate the NH residue, followed by the addition of a suitable electrophilic reagent such as an alkyl halides, acid chlorides or anhydrides, chloroformates, carbamoyl chlorides, sulfonyl chlorides, isocyanates, isothiocyanates and the like to provide the substituted product of Formula Ia.

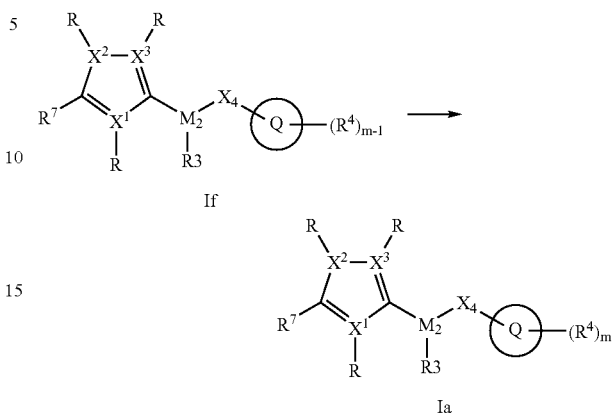

Introduction of the $M^2$ Substituent(s) and of the $X^4$ Substituent(s):

When the most acidic protons are positioned on the atom adjacent to $X^4$, or on $X^4$ itself, substitution may be achieved by deprotonation of compound of Formual Ia with a strong base such as an alkyllithium or an alkali-metal hydride in a suitable aprotic non-acidic solvent like THF or diethylether followed by trapping of the resulting anion with a suitable electrophile such as alkyl halides, acid chlorides or anhydrides, chloroformates, carbamoyl chlorides, sulfonyl chlorides, isocyanates, isothiocyanates and the like. When an excess of base and electrophile are employed and the reaction is left for sufficient time, two hydrogens may be replaced by the electrophile as illustrated below for the introduction of two $R^3$-substituents ($M^2$ exemplified as carbon). Two or more, different or same substituents, might also be introduced accordingly by subsequent deprotonations and reactions with appropriate electrophiles to yield compounds of Formula Ig.

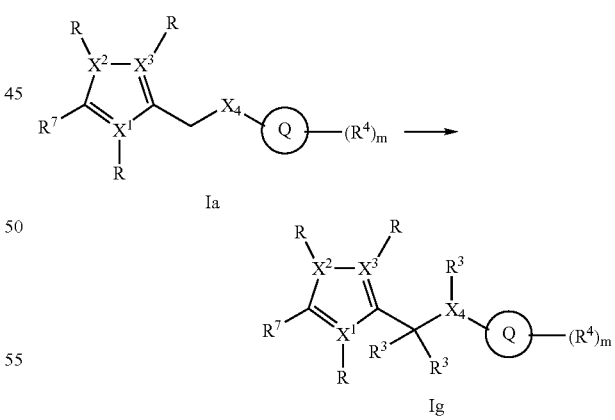

Oxidation of S Atom of Chain (when $X^4$ is S) or N Atoms on Substituents:

Oxidation of the sulfur atom to give sulfones (Y=O) and sulfoxides (Y=":", i.e. a lone pair) may be achieved by direct oxidation using any suitable oxidizing agent including peroxyacids such as MCPBA. In the case of MCPBA oxidation, it is possible to obtain a mixture of products from a single reaction and separate them by standard column chromatog-

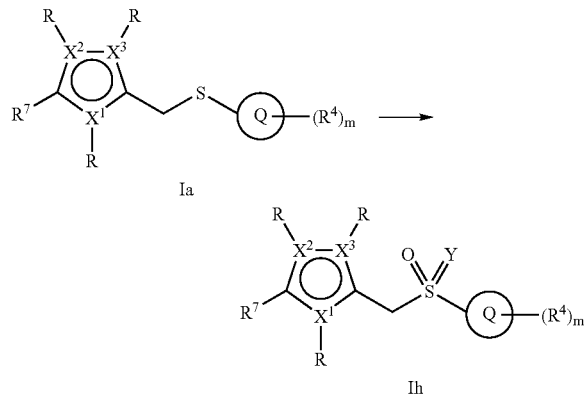

Ia

Ih

If one of the subsitutents, e.g. $R^4$ contains one or more nitrogen atoms as for example a pyridine moiety or any other susbtituent as defined above, then oxidation of this nitrogen may occur in the above reaction of Ia with an oxidant such as MCPBA to give the corresponding N-oxide. It is understood to the one skilled in the art that such products may be obtained by separation via standard column chromatography or any other standard purifcation protocol even in the case of mixtures containing for example Ih and N-oxide. It is also understood to the skilled in the art that the formation of N-oxides may be reduced by choice of suitable reaction conditions such as using acidic media to protect the nasic amine.

Other Miscellaneous Reactions:

When the intermediate compounds contain a suitable reactive functionality such as an aryl halide or triflate, the functionality may be employed to further elaborate the product. For example, when 3-halo-phenyl is present in P—$(R^1)_{m1}$, it is possible to use standard Suzuki conditions to couple an aryl boronic acid to yield a diaryl coupling product. Miyaura, N., Yanagi, T., Suzuki, A., Synth. Commun., (1981),11; 7, 513-520.

Other functionalities such as an aliphatic alcohol may for example be converted to a fluoro group by the use of a fluorinating agent such as DAST, or other halide groups by the use of for example triphenylphosphine and either iodine, N-bromosuccinimide or N-chlorosuccinimide These halides may serve as leaving groups for further elaboration or may remain as substituent in active compounds of formula Ia.

In a similar fashion alcohols may be transformed to leaving grous such as the non-limiting examples mesyl or tosyl by employing the appropriate sulfonyl halide or sulfonyl anhydride in the presence of a non-nucleophilic base together with the alcohol to obtain the sulfonic ester derivative.

Other funtionalities which may be further elaborated are depicted in the following, non-limiting example (R7 is $M^1$-$(R^2)_n$—P—$(R^1)_{m1}$), where halogenation may be undergone on a carbon-atom of an oxazole unit employing a chlorinating agent such as sulfuryl chloride.

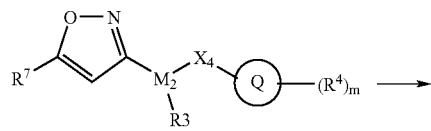

-continued

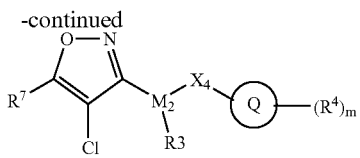

EXAMPLES

Suitable embodiments of the invention will now be illustrated by the following non-limiting examples.

NMR measurements were made on the delta scale (δ).

The compounds prepared according to Examples 1 to 39 and 100 to 328 are intermediates.

The compounds prepared according to Examples 40 to 99 and 329 to 794 are end products.

Intermediates

Example 1

6-Methylpyridine-4-carboxylic acid

A hydrogen filled balloon was attached to a flask containing 2-chloro-6-methylpyridine-4-carboxylic acid (2 g, 12.0 mmol), palladium 10 wt. % on activated carbon (0.5 g), triethyl amine (4.8 ml) and ethanol (24 ml) and then stirred overnight at room temperature. The is reaction mixture was filtered through celite, washed with methanol and concentrated. The residue was titurated with dichloromethane and then filtered to afford 6-methylpyridine-4-carboxylic acid as a white solid; 1.05 g (66%). $^1$H NMR (MeOD) δ (ppm): 8.62 (d, 1H), 7.68 (s, 1H), 7.60 (d, 1H), 2.55 (s, 3H).

Example 2

1-Cyano-3-ethylbenzene

Argon was bubbled into a solution of 1-bromo-3-ethylbenzene (2.5 g, 13.5 mmol) in DMF (37 ml) for 10 min. and then zinc cyanide (1.75 g, 14.9 mmol) and tetrakis(triphenylphosphine)palladium(0) (1.56 g, 1.35 mmol) were added. After stirring at 80° C. overnight the reaction mixture was diluted with ethyl acetate (35 ml) then filtered through celite to remove the precipitate. The filtrate was washed with water (3×), saturated brine, dried over anhydrous sodium sulfate, filtered and concentrated. The product was purified by flash column chromatography using 2% ethyl acetate in hexane affording a colorless liquid (1.42 g). GC-MS (M+): 131.18.

Example 3

3-Ethylbenzoic acid

6 M Sodium hydroxide (25 ml) was added to 1-cyano-3-ethylbenzene (1 g, 7.62 mmol) in methanol (25 ml) and then heated at 100° C. overnight. After concentrating the reaction mixture, the aqueous layer was washed with dichloromethane (2×), then acidified pH about 3 with 12 M HCl. The precipitate was extracted with ethyl acetate then washed with water and saturated brine, dried over anhydrous sodium sulfate, filtered and concentrated to afford 3-ethylbenzoic acid as a colorless oil; 0.770 g (28% yield over 2 steps). $^1$H NMR (CDCl$_3$), δ (ppm): 7.76 (d, 2H), 7.43 (m, 2H), 2.67 (m, 2H), 1.19 (t, 3H).

Example 4

3-Fluoro-5-methyl-benzoic acid

Concentrated HCl (30 ml) was added to a cooled (−5° C.) suspension of dimethyl 5-amino isophthalate (20 g, 95.6 mmol) in water (75 ml), followed by portionwise addition of $NaNO_2$ (7.5 g, 109 mmol). The reaction mixture was then stirred for 15 min., after which $HBF_4$ (18 ml, 100 mmol, 48% aqueous solution) was added. The resulting mixture was stirred at 0° C. for 30 min. and the precipitate formed was collected by filtration and washed with cold methanol (60 ml) and ether (60 ml). The residue was then decomposed by heating in an oil bath (~110° C.). The cooled mixture was then diluted with ether, concentrated onto silica gel and purified by flash chromatography with 5% ethyl acetate hexane as eluant giving 9.0 g (44%) of product as a white fluffy solid. $^1$H NMR ($CDCl_3$), δ (ppm): 8.57 (s, 1H), 7.95 (d, 2H), 3.97 (s, 6H).

A suspension of 5-fluoro-isophthalic acid dimethyl ester (1.7 g, 8.0 mmol) in methanol (41 ml) was treated with 1.0 N sodium hydroxide (7.2 ml, 7.2 mmol). The reaction was left stirring overnight at room temperature. After the solution was concentrated, the residue was dissolved in water and transferred to a separatory funnel. The aqueous layer was washed with dichloromethane (3 times) and then acidified with 1.0 N HCl to pH 2. Ethyl acetate was used to extract the precipitate, which was then washed with brine and dried over anhydrous sodium sulphate. After removal of solvent in vacuo, a total of 1.3 g (83%) of 5-fluoro-isophthalic acid monomethyl ester was isolated as a white solid. $^1$H NMR (DMSO), δ (ppm): 8.31 (t, 1H), 7.96 (m, 2H), 3.91 (s, 3H).

Triethylamine (2.2 ml, 16.0 mmol) and isobutyl chloroformate (1.0 ml, 8.0 mmol) were added to an ice-cooled solution of 5-fluoro-isophthalic acid monomethyl ester (1.3 g, 6.7 mmol) in dichloromethane (20 ml) and then warmed to room temperature. After stirring for 2 h, the reaction mixture was filtered and concentrated. The residue was re-dissolved tetrahydrofuran (10 ml) and then sodium borohydride (1.1 g, 29.02 mmol) in water (3 ml) was added drop-wise. After 1 h, the reaction was quenched with methanol and then diluted with ethyl acetate, washed with water and brine, dried over anhydrous sodium sulfate, filtered and concentrated. Flash column chromatography on silica gel using 30% ethyl acetate in hexanes afforded 667 mg (54%) of 3-fluoro-5-hydroxymethyl-benzoic acid methyl ester as a colorless oil. $^1$H NMR ($CDCl_3$), δ (ppm): 7.82 (s, 1H), 7.63 (d, 1H), 7.32 (d, 1H), 4.76 (s, 2H), 3.93 (s, 3H).

Ethanol (2 ml) was added to round bottom flask containing 3-fluoro-5-hydroxymethyl-benzoic acid methyl ester (667 mg, 3.6 mmol) and palladium (10 wt. % on activated carbon, 300 mg) under argon. The flask was evacuated using a water aspirator and then filled with hydrogen from a balloon. After stirring for 2 h, the palladium on carbon was removed by filtration through celite. The filtrate was then concentrated to afford 520 mg (87%) of 3-fluoro-5-methyl-benzoic acid methyl ester. $^1$H NMR ($CDCl_3$), δ (ppm): 7.65 (s, 1H), 7.51 (d, 1H), 7.08 (d, 1H), 3.91 (s, 3H), 2.40 (s, 3H).

0.5 N Lithium hydroxide (7.4 ml, 3.7 mmol) was added to a solution 3-fluoro-5-methyl-benzoic acid methyl ester (520 mg, 3.1 mmol) in tetrahydrofuran (7.4 ml). The reaction was stirred at 75° C. for 2 h and then the solvent was removed in vacuo. The residue was dissolved in a small amount of water and then acidified (pH about 2) by the addition of 10% HCl (aq.). Following extraction of the aqueous layer with ethyl acetate, the organic layer was then washed with water and saturated brine, dried over anhydrous sodium sulfate, filtered, and concentrated to afford 469 mg (98%) of 3-fluoro-5-methyl-benzoic acid as a white solid. 1H NMR (DMSO), d (ppm): 7.62 (s, 1H), 7.45 (d, 1H), 7.32 (d, 1H), 2.38 (s, 3H).

Example 5

3-Methoxymethyl-benzoic acid

A mixture of 3-bromomethyl-benzoic acid methyl ester (556 mg, 2.4 mmol) and potassium carbonate (670 mg, 4.9 mmol) in methanol (10 ml) and tetrahydrofuran (10 ml) was heated at 55° C. for 2 h. After cooling, the reaction mixture was diluted with water and then extracted with ethyl acetate. The organic layer was washed with water and saturated brine, dried over anhydrous sodium sulfate, filtered and concentrated. After drying in vacuo, 3-methoxymethyl-benzoic acid methyl ester (436 mg, quantitative) was isolated as a white solid. $^1$H NMR ($CDCl_3$), δ (ppm): 8.01 (s, 1H), 7.98 (d, 1H), 7.55 (d, 1H), 7.43 (t, 1H), 4.50 (s, 2H), 3.92 (s, 3H), 3.41 (s, 3H).

1 N Sodium hydroxide (3.6 ml, 3.6 mmol) was added to a 3-methoxymethyl-benzoic acid methyl ester (436 mg, 2.4 mmol) in methanol (5 ml) and tetrahydrofuran (5 ml). The reaction was stirred at 70° C. for 30 min. and then the solvent was removed in vacuo. The residue was dissolved in a small amount of water and then acidified (pH about 2) by the addition of 1 N HCl (aq.). Following extraction of the aqueous layer with ethyl acetate, the organic layer was then washed with water and saturated brine, dried over anhydrous sodium sulfate, filtered, and concentrated to afford 395 mg (98%) of 3-methoxymethyl-benzoic acid as a white solid. $^1$H NMR (DMSO), δ (ppm): 7.90 (s, 1H), 7.87 (d, 1H), 7.56 (d, 1H), 7.48 (t, 1H), 4.48 (s, 2H), 3.31 (s, 3H).

Example 6

N-Hydroxy-3-methoxy-benzamidine

Using the general procedure of Shine et al., J. Heterocyclic Chem. (1989) 26:125-128, hydroxylamine hydrochloride (22 ml, 5 M, 110 mmol) and sodium hydroxide (11 ml, 10 M, 110 mmol) were added to a solution of 3-methoxybenzonitrile (11.5 ml. 94 mmol) in ethanol (130 ml). The reaction mixture was then heated at reflux (80° C.) for 12 h. After the mixture was cooled, most of the solvent was removed in vacuo. The crude product was partitioned between ethyl acetate and water, washed with saturated brine, dried over anhydrous sodium sulfate and the solvent was removed in vacuo. Flash chromatography on silica gel using 35-50% ethyl acetate in hexane yielded the title compound (8.05 g, 52%). Examples 7-9 were prepared in an analogous method to the procedure given in Example 6.

Example 7

N-Hydroxy-benzamidine

N-hydroxy-benzamidine (4.83 g, 91%, white solid) was obtained from benzonitrile (4 g, 38.9 mmol), hydroxylamine hydrochloride (8.89 ml, 44.0 mmol) and sodium hydroxide (4.49 ml, 45.0 mmol) in ethanol (30 ml). $^1$H NMR ($CDCl_3$), δ (ppm): 8.81 (broad peak, 1H), 7.63 (m, 2H), 7.39 (m, 3H), 4.91 (s, 2H).

Example 8

N-Hydroxy-3-methyl-benzamidine

N-Hydroxy-3-methyl-benzamidine (3.65 g, 94%, white solid) was obtained from m-tolunitrile (3 g, 26.0 mmol), hydroxylamine hydrochloride (5.9 ml, 29.6 mmol), and sodium hydroxide (3.0 ml, 29.9 mmol) in ethanol (20 ml). $^1$H NMR (CDCl$_3$), δ (ppm): 8.25 (broad peak, 1H), 7.36 (m, 2H), 7.25 (m, 2H), 4.88 (s, 2H), 2.38 (s, 3H).

Example 9

3-Cyano-N-hydroxy-benzamidine

3-Cyano-N-hydroxy-benzamidine (1.32 g, 52%, white solid) was obtained from isophthalonitrile (2 g, 15.6 mmol), hydroxylamine hydrochloride (3.12 ml, 5 M, 15.6 mmol) and sodium hydroxide (15.6 ml, 1 M, 15.6 mmol) in ethanol (20 ml). Purification was performed by flash column chromatography using 20-50% ethyl acetate in hexanes. $^1$H NMR (DMSO), δ (ppm): 9.91 (s, 1H), 8.06 (s, 1H), 8.01 (d, 1H), 7.85 (d, 1H), 7.59 (t, 1H), 6.01 (bs, 2H).

Example 10

5-Chloromethyl-3-(3-methoxy-phenyl)-[1,2,4]oxadiazole

Chloroacetyl chloride (0.72 ml, 9.03 mmol) and triethylamine (1.50 ml, 10.23 mmol) were added to N-hydroxy-3-methoxy-benzamidine (1 g, 6.02 mmol) in dichloromethane (12.0 ml) at 0° C. and the resulting mixture was stirred for 20 min. To effect cyclization to oxadiazole, the solution was concentrated and DMF (20 ml) was added to the residue and heated at 120° C. for 5 h. The product was purified by flash chromatography using 10-20% ethyl acetate in hexane affording 0.90 g (66% yield over 2 steps) of the title compound (yellow oil). $^1$H NMR (CDCl$_3$), δ (ppm): 7.68 (m, 1H), 7.60 (d, 1H), 7.40 (t, 1H), 7.07 (m, 1H), 4.76 (s, 2H), 3.88 (s, 3H).

Examples 11-14 were prepared in an analogous method to the procedure given in Example 10.

Example 11

5-Chloromethyl-3-phenyl-[1,2,4]oxadiazole

5-Chloromethyl-3-phenyl-[1,2,4]oxadiazole (1.62 g, 57% yield over 2 steps, yellow oil) was obtained from chloroacetyl chloride (1.76 ml, 22.05 mmol) and triethylamine (3.32 ml, 24.99 mmol) with N-hydroxy-benzamidine (2 g, 14.7 mmol) in dichloromethane (29.3 ml). Purification was performed by flash chromatography using 10% ethyl acetate in hexane. $^1$H NMR (CDCl$_3$), δ (ppm): 8.08 (m, 2H), 7.51 (m, 3H), 4.76 (s, 2H).

Example 12

5-Chloromethyl-3-m-tolyl-[1,2,4]oxadiazole

5-Chloromethyl-3-m-tolyl-[1,2,4]oxadiazole (1.75 g, 62% yield over 2 steps, yellow oil) was obtained from chloroacetyl chloride (1.59 ml, 20.0 mmol) and triethylamine (3.00 ml, 22.7 mmol) with N-hydroxy-3-methyl-benzamidine (2 g, 13.3 mmol) in dichloromethane (26.6 ml). Purification was performed by flash chromatography using 10% ethyl acetate in hexane. $^1$H NMR (CDCl$_3$), δ (ppm): 7.90 (s, 1H), 7.87 (s, 1H), 7.36 (m, 2H), 4.75 (s, 2H), 2.34 (s, 3H)

Example 13

3-(3-Chloromethyl-[1,2,4]oxadiazol-5-yl)-benzonitrile 3-(3-Chloromethyl-[1,2,4]oxadiazol-5-yl)-benzonitrile (3.57 g, 43%) was obtained from 2-chloro-N-hydroxy-acetamidine (4.05 g, 37.4 mmol) and 3-cyanobenzoyl-chloride (6.2 g, 37.4 mmol) in dichloromethane (60 ml) with triethylamine (6.5 ml, 46.7 mmol).

Purification was performed by silica gel chromatography. $^1$H NMR (CDCl$_3$), δ (ppm): 8.47 (bs, 1H), 8.41 (dd, 1H), 7.91 (dd, 1H), 7.72 (t, 1H), 4.70 (s, 2H); GC-MS (M+): 219.

Example 14

3-(5-Chloromethyl-[1,2,4]oxadiazol-3-yl)-benzonitrile 3-(5-Chloromethyl-[1,2,4]oxadiazol-3-yl)-benzonitrile (1.2 g, 87%, light brown solid): 3-cyano-N-hydroxy-benzamidine (1.0 g, 6.2 mmol), triethylamine (1.5 ml, 10.6 mmol) and chloroacetyl chloride (0.74 ml, 9.3 mmol) in dichloromethane (12 ml). Purification was performed by decolorizing with silica gel. 1H NMR (CDCl3), d (ppm): 8.40 (s, 1H), 8.32 (d, 1H), 7.82 (d, 1H), 7.64 (t, 1H), 4.77 (s, 2H).

Example 15

3-Chloromethyl-5-m-tolyl-[1,2,4]oxadiazole

3-Methyl-benzoyl chloride (0.80 ml, 6.1 mmol) was added to a solution of 2-chloro-N-hydroxy-acetamidine (440 mg, 4.1 mmol) in dichloromethane (10 ml) at room temperature and the resulting mixture was stirred for 30 min. Then triethylamine (0.62 ml, 4.5 mmol) was added and the resulting mixture was stirred for 30 min. The product was partitioned into dichloromethane and the organic layer was washed with water and brine and dried over sodium sulfate. Evaporation of the solvent and flash chromatography on silica (10-20% ethyl acetate in hexanes) yielded the acyclic ester intermediate (814 mg). A solution of this intermediate in DMF (10 ml) was heated at 135° C. for 4 h. The product was partitioned into ethyl acetate and the organic layer was washed with water and brine and dried over sodium sulfate. Evaporation of the solvent and flash chromatography on silica (5% ethyl acetate in hexanes) yielded 3-chloromethyl-5-m-tolyl-[1,2,4]oxadiazole (469 mg, 54% over 2 steps, white solid). $^1$H NMR (CDCl$_3$), δ (ppm): 7.99 (s, 1H), 7.97 (m, 1H), 7.43 (d, 2H), 4.68 (s, 2H), 2.45 (s, 3H).

Example 16

3-Chloromethyl-5-(3-fluoro-phenyl)-[1,2,4]oxadiazole

DMF (10 ml) was added to a mixture of 3-fluorobenzoic acid (710 mg, 5.07 mmol), 1-(3-dimethylaminopropyl)-3-ethylcarbodiimide hydrochloride (EDCI) (972 mg, 5.07 mmol), 1-hydroxybenzotriazole hydrate (HOBt) (685 mg, 5.07 mmol) and 2-chloro-N-hydroxy-acetamidine (500 mg, 4.61 mmol) at room temperature and then stirred overnight. The reaction mixture was diluted with ethyl acetate, washed with water (3 times) and brine, dried over anhydrous sodium sulfate, filtered and concentrated. DMF (14 ml) was added to the residue and the resulting solution was heated at 135° C. for 3.5 h to effect cyclization to oxadiazole. After cooling the reaction mixture was washed with water (3 times) and brine, dried over anhydrous sodium sulfate, filtered and concentrated. 3-Chloromethyl-5-(3-fluoro-phenyl)-[1,2,4]oxadiazole (383 mg, 35% yield over 2 steps, yellow oil) was obtained by flash chromatography on silica gel, using 5% ethyl acetate in hexane. $^1$H NMR (CDCl$_3$), δ (ppm): 7.96 (d, 1H), 7.86 (m, 1H), 7.54 (m, 1H), 7.33 (m, 1H), 4.68 (s, 2H).

Examples 17-30 were prepared in an analogous method to the procedure given in Example 16.

Example 17

3-Chloromethyl-5-thiophen-3-yl-[1,2,4]oxadiazole

3-Chloromethyl-5-thiophen-3-yl-[1,2,4]oxadiazole (197 mg, 20% yield over 2 steps, white solid) was obtained from 3-thiophenecarboxylic acid (700 mg, 4.96 mmol), EDCI (950 mg, 4.96 mmol), HOBt (670 mg, 4.96 mmol) and 2-chloro-N-hydroxy-acetamidine (538 mg, 5.46 mmol) in DMF (10 ml). The acyclic product was purified by flash column chromatography eluting with 2:1.2:0.8 dichloromethane:hexane: ethyl acetate. The title compound was purified by flash column chromatography using 5% ethyl acetate in hexane. $^1$H NMR (CDCl$_3$), δ (ppm): 8.28 (s, 1H), 7.70 (d, 1H), 7.48 (m, 1H).

Example 18

3-(3-Chloromethyl-[1,2,4]oxadiazol-5-yl)-5-methylpyridine 3-(3-Chloromethyl-[1,2,4]oxadiazol-5-yl)-5-methyl-pyridine (25 mg, 4% yield over 2 steps) was obtained from 5-methynicotinic acid (472 mg, 3.44 mmol), EDCI (652 mg, 3.44 mmol), HOBt (465 mg, 3.44 mmol) and 2-chloro-N-hydroxy-acetamidine (340 mg, 3.13 mmol) in DMF (10 ml). The acyclic intermediate was purified by flash column chromatography using 100% ethyl acetate; 200 mg (30%) of the acyclic ester was also isolated as side product.

Example 19

3-Chloromethyl-5-(3-nitro-phenyl)-[1,2,4]oxadiazole

3-Chloromethyl-5-(3-nitro-phenyl)-[1,2,4]oxadiazole (335 mg, 30% yield over 2 steps, yellow solid) was obtained from 3-nitrobenzoic acid (847 mg, 5.07 mmol), EDCI (972 mg, 5.07 mmol), HOBt (685 mg, 5.07 mmol) and 2-chloro-N-hydroxy-acetamidine (500 mg, 4.61 mmol) in DMF (10 ml). The acyclic intermediate was purified by flash column chromatography using 100% ethyl acetate. Purification was performed by flash column chromatography using 15% ethyl acetate in hexane. $^1$H NMR (CDCl$_3$), δ (ppm): 9.03 (t, 1H), 8.50 (t, 2H), 7.79 (t, 1H), 4.71 (s, 2H)

Example 20

4-(3-Chloromethyl-[1,2,4]oxadiazol-5-yl)-2-methylpyridine 4-(3-Chloromethyl-[1,2,4]oxadiazol-5-yl)-2-methyl-pyridine (316 mg, 28% yield over 2 steps, yellow oil) was obtained from 6-methylpyridine-4-carboxylic acid (800 mg, 5.8 mmol), EDCI (1.12 g, 5.8 mmol), HOBt (788 mg, 5.8 mmol) and 2-chloro-N-hydroxy-acetamidine (575 mg, 5.3 mmol) in DMF (10 ml) plus triethylamine (536 mg, 5.3 mmol). Purification was performed by flash column chromatography using 30% ethyl acetate in hexane. $^1$H NMR (CDCl$_3$), δ (ppm): 8.75 (d, 1H), 7.88 (s, 1H), 7.79 (d, 1H), 4.70 (s, 2H), 2.70 (s, 3H)

Example 21

3-Chloromethyl-5-(3-ethyl-phenyl)-[1,2,4]oxadiazole

3-Chloromethyl-5-(3-ethyl-phenyl)-[1,2,4]oxadiazole (446 mg, 52% yield over 2 steps, yellow oil) was obtained from 3-ethylbenzoic acid (770 mg, 3.81 mmol), EDCI (803 mg, 4.19 mmol), HOBt (566 mg, 4.19 mmol) and 2-chloro-N-hydroxy-acetamidine (454 mg, 4.19 mmol) in DMF (10 ml). Purification was performed by flash column chromatography using 5% ethyl acetate in hexane. $^1$H NMR (CDCl$_3$), δ (ppm): 7.96 (t, 2H), 7.42 (m, 2H), 4.68 (s, 2H), 2.74 (m, 2H), 1.28 (m, 3H).

Example 22

3-(3-Chloromethyl-[1,2,4]oxadiazol-5-yl)-phenyl]-dimethyl-amine 3-(3-Chloromethyl-[1,2,4]oxadiazol-5-yl)-phenyl]-dimethyl-amine (40 mg, 4% yield over 2 steps, yellow solid) was obtained from 3-(dimethylamino)benzoic acid (656 mg, 3.97 mmol), EDCI (761 mg, 3.97 mmol), HOBt (536 mg, 3.97 mmol) and 2-chloro-N-hydroxy-acetamidine (500 mg, 3.6 mmol) in DMF (10 ml). Purification was performed by flash column chromatography using 5% ethyl acetate in hexane. $^1$H NMR (CDCl$_3$), δ (ppm): 7.46 (t, 2H), 7.37 (t, 1H), 6.94 (d, 1H), 4.68 (s, 2H), 3.04 (s, 6H).

Example 23

3-Chloromethyl-5-(3-chloro-phenyl)-[1,2,4]oxadiazole

3-Chloromethyl-5-(3-chloro-phenyl)-[1,2,4]oxadiazole (406 mg, 43% yield over 2 steps, white solid) was obtained from 3-chlorobenzoic acid (708 mg, 4.52 mmol), EDCI (866 mg, 4.52 mmol), HOBt (611 mg, 4.52 mmol) and 2-chloro-N-hydroxy-acetamidine (446 mg, 4.11 mmol) in DMF (10 ml). Purification was performed by flash column chromatography using 5% ethyl acetate in hexane. $^1$H NMR (CDCl$_3$), δ (ppm): 8.17 (t, 1H), 8.05 (d, 1H), 7.59 (t, 1H), 7.50 (t, 1H), 4.68 (s, 2H).

Example 24

3-Chloromethyl-5-(3-trifluoromethoxy-phenyl)-[1,2,4]oxadiazole

3-Chloromethyl-5-(3-trifluoromethoxy-phenyl)-[1,2,4] oxadiazole (707 mg, 55% yield over 2 steps, light yellow oil) was obtained from 3-trifluoromethoxybenzoic acid (1.05 g, 5.07 mmol), EDCI (972 mg, 5.07 mmol), HOBt (685 mg, 5.07 mmol) and 2-chloro-N-hydroxy-acetamidine (500 mg, 4.61 mmol) in DMF (10 ml). Purification was performed by flash column chromatography using 5% ethyl acetate in hexane. $^1$H NMR (CDCl$_3$), δ (ppm): 8.10 (m, 1H), 8.03 (s, 1H), 7.61 (t, 1H), 7.48 (d, 1H), 4.69 (s, 2H).

Example 25

5-(3-Bromo-phenyl)-3-chloromethyl-[1,2,4]oxadiazole 5-(3-Bromo-phenyl)-3-chloromethyl-[1,2,4]oxadiazole (707 mg, 55% yield over 2 steps, white solid) was obtained from 3-bromobenzoic acid (1.05 g, 5.07 mmol), EDCI (972 mg, 5.07 mmol), HOBt (685 mg, 5.07 mmol) and 2-chloro-N-hydroxy-acetamidine (500 mg, 4.61 mmol) in DMF (10 ml). Purification was performed by flash column chromatography using 5% ethyl acetate in hexane. 1H NMR (CDCl3) d (ppm): 8.10 (m, 1H), 8.03 (s, 1H), 7.61 (t, 1H), 7.48 (d, 1H), 4.69 (s, 2H).

Example 26

3-Chloromethyl-5-thiophen-2-yl-[1,2,4]oxadiazole

3-Chloromethyl-5-thiophen-2-yl-[1,2,4]oxadiazole (202 mg, 20%, off-white solid) was obtained from thiophene-2-carboxylic acid (649 mg, 5.1 mmol), 2-chloro-N-hydroxy-acetamidine (500 mg, 4.6 mmol), EDCI (972 mg, 5.1 mmol) and HOBt (684 mg, 5.1 mmol) in DMF (5 ml). Purification was performed by SPE (flash) chromatography using 5% ethyl acetate in hexanes. $^1$H NMR (CDCl$_3$), δ (ppm): 8.00 (s, 1H), 7.83 (d, 1H), 7.19 (t, 1H), 4.13 (s, 2H).

Example 27

3-Chloromethyl-5-(3-fluoro-5-methyl-phenyl)-[1,2,4]oxadiazole

3-Chloromethyl-5-(3-fluoro-5-methyl-phenyl)-[1,2,4]oxadiazole (312 mg, 46%, colorless oil) was obtained from 3-fluoro-5-methyl-benzoic acid (469 mg, 3.0 mmol), 2-chloro-N-hydroxy-acetamidine (363 mg, 3.3 mmol), EDCI (641 mg, 3.3 mmol) and HOBt (452 mg, 3.3 mmol) in DMF (5 ml). Purification was performed by SPE (flash) chromatography using 5% ethyl acetate in hexanes. $^1$H NMR (CDCl$_3$), δ (ppm): 7.79 (s, 1H), 7.65 (d, 1H), 7.15 (d, 1H), 4.67 (s, 2H), 2.46 (s, 3H).

Example 28

3-Chloromethyl-5-thiazol-4-yl-[1,2,4]oxadiazole

3-Chloromethyl-5-thiazol-4-yl-[1,2,4]oxadiazole (37 mg, 5%, yellow solid) was obtained from thiazole-4-carboxylic acid (500 mg, 3.9 mmol), 2-chloro-N-hydroxy-acetamidine (462 mg, 4.3 mmol), EDCI (817 mg, 4.3 mmol) and HOBt (575 mg, 4.3 mmol) in DMF (5 ml). Purification was performed by SPE (flash) chromatography using 30% ethyl acetate in hexanes. $^1$H NMR (CDCl$_3$), δ (ppm): 9.02 (d, 1H), 8.42 (d, 1H), 4.70 (s, 2H).

Example 29

3-Chloromethyl-5-(3-iodo-phenyl)-[1,2,4]oxadiazole

3-Chloromethyl-5-(3-iodo-phenyl)-[1,2,4]oxadiazole (2.9 g, 44%, white solid) was obtained from 3-iodo-benzoic acid (5.0 g, 20.2 mmol), 2-chloro-N-hydroxy-acetamidine (2.4 g, 22.2 mmol), EDCI (4.3 g, 22.2 mmol) and HOBt (3.0 g, 22.2 mmol) in DMF (10 ml). The acyclic ester intermediate was purified by flash column chromatography using 50-80% ethyl acetate in hexanes. The title compound was purified by SPE (flash) chromatography using 5% ethyl acetate in hexanes. $^1$H NMR (CDCl$_3$), δ (ppm): 8.52 (s, 1H), 8.13 (d, 1H), 7.96 (d, 1H), 7.29 (t, 1H), 4.68 (s, 2H).

Example 30

3-Chloromethyl-5-(3-methoxymethyl-phenyl)-[1,2,4]oxadiazole

3-Chloromethyl-5-(3-methoxymethyl-phenyl)-[1,2,4]oxadiazole (193 mg, 34%, light yellow oil) was obtained from 3-methoxymethyl-benzoic acid (395 mg, 2.4 mmol), 2-chloro-N-hydroxy-acetamidine (284 mg, 2.6 mmol), EDCI (501 mg, 2.6 mmol) and HOBt (353 mg, 2.6 mmol) in DMF (5 ml). Purification was performed by SPE (flash) chromatography using 5% ethyl acetate in hexanes. $^1$H NMR (CDCl$_3$), δ (ppm): 8.14 (s, 1H), 8.08 (d, 1H), 7.61 (d, 1H), 7.53 (t, 1H), 4.68 (s, 2H), 4.54 (s, 2H), 3.44 (s, 3H).

Example 31

5-Furan-2-yl-4-methyl-4H-[1,2,4]triazole-3-thiol

2-Furoyl chloride (0.76 ml, 7.66 mmol) was added in a dropwise manner to a solution of 4-methyl-3-thiosemicarbazide (732 mg, 6.96 mmol) and pyridine (7 ml) and the resulting solution was stirred at room temperature for 4 h. The reaction mixture was diluted with ethyl acetate (100 ml), successively washed with water (3×100 ml) and brine (100 ml). The organic phase was dried (sodium sulfate), filtered and concentrated in-vacuo. The residue was suspended in sodium bicarbonate (70 ml, 69.6 mmol, 1 M water) and left stirring at 100° C. overnight. The reaction mixture was cooled to 0° C., then brought to pH about 6 using hydrochloric acid (70 ml, 1 N water). The title compound (298 mg) was collected by filtration as a white solid. $^1$H NMR (CDCl$_3$), δ (ppm): 11.4 (bs, 1H), 7.63 (d, 1H), 7.02 (d, 1H), 6.60 (dd, 1H), 3.83 (s, 3H).

Examples 32-35 were prepared in an analogous method to the procedure given in Example 31.

Example 32

4-Methyl-5-phenyl-4H-[1,2,4]triazole-3-thiol

4-Methyl-5-phenyl-4H-[1,2,4]triazole-3-thiol (478 mg, off-white solid) was obtained from 4-methyl-3-thiosemicarbazide (732 mg, 6.96 mmol) and pyridine (7 ml) with benzoyl chloride (0.89 ml, 7.66 mmol). Then sodium bicarbonate (70 ml, 69.6 mmol, 1 M water) was added at 100° C. overnight and the title compound was collected by filtration. $^1$H NMR (CDCl$_3$), δ (ppm): 12.3(bs, 1H), 7.55 (m, 5H), 3.65 (s, 3H).

Example 33

4-Methyl-5-pyridin-2-yl-4H-[1,2,4]triazole-3-thiol

4-Methyl-5-pyridin-2-yl-4H-[1,2,4]triazole-3-thiol (44 mg, greenish solid) was obtained from 4-methyl-3-thiosemicarbazide (537 mg, 5.11 mmol) and pyridine (7 ml) with 2-pyridinecarbonyl chloride hydrochloride (1.00 g, 5.62 mmol). Then sodium bicarbonate (51 ml, 1 M water) was added at 100° C. overnight and the title compound was collected using extraction and evaporation. $^1$H NMR (CDCl$_3$), δ (ppm): 11.1 (bs, 1H), 8.70 (d, 1H), 8.02 (d, 1H), 7.84 (m, 1H), 7.41 (dd, 1H), 4.05 (s, 3H).

Example 34

5-(4-Benzyl-morpholin-2-yl)-4-methyl-4H-[1,2,4]triazole-3-thiol (83.3 mg, dirty yellow solid) was obtained from 4-methyl-3-thiosemicarbazide (346 mg, 3.29 mmol) and pyridine (7 ml) with 4-benzyl-2-morpholinecarbonyl chloride hydrochloride (1.00 g, 3.62 mmol). Then sodium bicarbonate (33 ml, 1 M water) was added at 100° C. overnight and the title compound was collected using extraction and evaporation. $^1$H NMR (CDCl$_3$), δ (ppm): 9.48 (bs, 1H), 7.25 (m, 5H), 4.68 (dd, 1H), 3.86 (dAb, 1H), 3.68 (tAB, 1H), 3.59-3.64 (m, 5H), 3.07 (d, 1H), 2.88 (d, 1H), 2.61 (t, 1H), 2.37 (dt, 1H).

Example 35

5-tert-Butyl-4-methyl-4H-[1,2,4]triazole-3-thiol 5-tert-Butyl-4-methyl-4H-[1,2,4]triazole-3-thiol (2.21 g, 83%, off-white solid) was obtained from 4-methyl-3-thiosemicarbazide (1.80 g, 17.2 mmol) and pyridine (20 ml) with trimethylacetyl chloride (1.92 ml, 15.6 mmol). Then sodium hydroxide (200 ml, 5% water) was added and left stirring at 60° C. overnight and the title compound was collected extraction and evaporation $^1$H NMR (CDCl$_3$), δ (ppm): 11.7 (bs, 1H), 3.72 (s, 3H) 1.40 (s, 9H).

Example 36

4-Methyl-5-pyridin-3-yl-4H-[1,2,4]triazole-3-thiol

A solution of 4-methyl-3-thiosemicarbazide (902 mg, 8.58 mmol), nicotinic acid (960 mg, 7.80), EDCI (1.64 g, 8.58 mmol), HOBt (1.16 g, 8.58 mmol) in DMF (10 ml) was stirred at room temperature overnight. The reaction mixture was diluted with ethyl acetate (100 ml), successively washed with hydrochloric acid (50 ml, 10% aqueous), water (50 ml), saturated sodium carbonate (50 ml, aqueous), water (50 ml) and brine (50 ml). The organic phase was dried (sodium sulfate), filtered and concentrated in-vacuo. The residue was stirred in sodium hydroxide (53.4 ml, 66.7 mmol, 5% aqueous) at 60° C. overnight. The reaction mixture was cooled to room temperature, then carefully brought to pH about 6 using hydrochloric acid (1 N water). The aqueous phase was saturated with solid sodium chloride, then extracted with ethyl acetate (4×50 ml). The combined organic phase was washed with brine (100 ml), dried (sodium sulfate), filtered and concentrated in-vacuo (180 mg, off-white solid). $^1$H NMR (CDCl$_3$), δ (ppm): 11.6 (bs, 1H), 8.94 (s, 1H), 8.83 (dd, 1H), 7.98 (m, 1H), 7.51 (dd, 1H), 3.69 (s, 3H).

Examples 37-39 were prepared in an analogous method to the procedure given in Example 36.

Example 37

4-Methyl-5-thiophene-3-yl-4H-[1,2,4]triazole-3-thiol

4-Methyl-5-thiophene-3-yl-4H-[1,2,4]triazole-3-thiol (693 mg, white solid) was obtained from 4-methyl-3-thiosemicarbazide (902 mg, 8.58 mmol), 3-thiophenecarboxylic acid (1 g, 7.80 mmol), EDCI (1.64 g, 8.58 mmol), HOBt (1.16 g, 8.58 mmol) in DMF (10 ml). Then sodium hydroxide (88 ml, 110 mmol, 5% aqueous) at 60° C. overnight and the title compound was product collected extraction and evaporation. $^1$H NMR (CDCl$_3$), δ (ppm): 11.4 (bs, 1H), 7.77 (dd, 1H), 7.51 (dd, 1H), 7.42 (dd, 1H), 3.61 (s, 3H).

Example 38

4-Methyl-5-thiazol-4-yl-4H-[1,2,4]triazole-3-thiol

4-Methyl-5-thiazol-4-yl-4H-[1,2,4]triazole-3-thiol (71.2 mg, sticky yellow oil) was obtained from 4-methyl-3-thiosemicarbazide (902 mg, 8.58 mmol), 4-carboxythiazole (1.01 g, 7.80), EDCI (1.64 g, 8.58 mmol), HOBt (1.16 g, 8.58 mmol) in DMF (10 ml). Then sodium hydroxide (43 ml, 54 mmol, 5% aqueous) at 60° C. overnight and the title compound was collected extraction and evaporation.

Example 39

5-Cyclohexyl-4-methyl-4H-[1,2,4]triazole-3-thiol

5-Cyclohexyl-4-methyl-4H-[1,2,4]triazole-3-thiol (403 mg, beige solid) was obtained from 4-methyl-3-thiosemicarbazide (1.80 g, 17.2 mmol), cyclohexane carboxylic acid (2 g, 15.6 mmol), EDCI (2.99 g, 17.2 mmol) and HOBt (2.10 g, 17.2 mmol) in DMF(20 ml); then sodium hydroxide (195 ml, 244 mmol, 5% aqueous) at 60° C. overnight.

Example 40

2-[5-(3-Methoxy-phenyl)-[1,2,4]oxadiazol-3-ylmethylsulfanyl]-1H-benzoimidazole 1H-Benzoimidazole-2-thiol (150 mg, 1 mmol) was added to a solution of the 3-chloromethyl-5-(3-methoxy-phenyl)-[1,2,4]oxadiazole (30 mg, 0.13 mmol) and potassium carbonate (50 mg, 0.36 mmol) in DMF (2 ml) at room temperature. The solvent was removed in vacuo and the product obtained by flash chromatography using 20-100% ethyl acetate in hexane. $^1$H NMR (CDCl$_3$), δ (ppm): 7.71 (d, 1H), 7.62 (d, 1H), 7.53 (m, 2H), 7.42 (t, 1H), 7.18 (overlapping, m, 3H), 4.52 (s, 2H), 3.87 (s, 3H).

Examples 41-92 were prepared in an analogous method to the procedure given in Example 40.

Example 41

5-(3-Methoxy-phenyl)-3-(4-Methyl-5-thiophen-2-yl-4H-[1,2,4]triazol-3-ylsulfanylmethyl)-[1,2,4]oxadiazole The title compound was prepared from 3-chloromethyl-5-(3-methoxy-phenyl)-[1,2,4]oxadiazole (50 mg, 0.22 mmol), potassium carbonate (92.4 mg, 0.67 mmol), 4-methyl-5-thiophen-2-yl-4H-[1,2,4]triazole-3-thiol (52.8 mg, 0.27 mmol) in acetonitrile (1 ml) at room temperature. Purification was performed by SPE (flash) chromatography using 30-40% ethyl acetate in hexanes afforded 76 mg (90%) of the title compound as a white solid. $^1$H NMR (CDCl$_3$), δ (ppm): 7.68 (d, 1H), 7.57 (t, 1H), 7.49 (m, 2H), 7.41 (t, 1H), 7.15 (m, 2H), 4.53 (s, 2H), 3.85 (s, 3H), 3.72 (s, 3H). LC-MS (M+1)$^+$ 386.3.

Example 42

3-[5-(1-Methyl-5-thiophen-2-yl-1H-imidazol-2-ylsulfanylmethyl)-[1,2,4]oxadiazol-3-yl]-benzonitrile 3-[5-(1-Methyl-5-thiophen-2-yl-1H-imidazol-2-ylsulfanylmethyl)-[1,2,4]oxadiazol-3-yl]-benzonitrile (39 mg, 47%, white solid) was obtained from 3-chloromethyl-3-(5-chloromethyl-[1,2,4]oxadiazol-3-yl)-benzonitrile (50 mg, 0.22 mmol), potassium carbonate (92.4 mg, 0.67 mmol), 4-methyl-5-thiophen-2-yl-4H-[1,2,4]triazole-3-thiol (52.8 mg, 0.27 mmol) in acetonitrile (1 ml) at room temperature. Purification was performed by SPE (flash) chromatography using 50-70% ethyl acetate in hexanes. $^1$H NMR (CDCl$_3$), δ (ppm): 8.34 (s, 1H), 8.28 (d, 1H), 7.79 (d, 1H), 7.60 (t, 1H), 7.53 (d, 1H), 7.49 (d, 1H), 7.19 (m, 1H), 4.70 (s, 2H), 3.74 (s, 3H). LS-MS (ES+full scan, C$_{17}$H$_{12}$N$_6$OS$_2$) M$^+$ calc. 380.05, found (M+1)$^+$ 381.04.

Example 43

3-(4-Methyl-5-thiophen-2-yl-4H-[1,2,4]traiazol-3-ylsulfanylmethyl)-5-phenyl-[1,2,4]oxadiazole 3-(4-Methyl-5-thiophen-2-yl-4H-[1,2,4]traiazol-3-ylsulfanylmethyl)-5-phenyl-[1,2,4]oxadiazole (41.2 mg, 44%, off-white solid) was obtained from 3-chloromethyl-5-phenyl-[1,2,4]oxadiazole (50 mg, 0.26 mmol), potassium carbonate (106 mg, 0.77 mmol), 4-methyl-5-thiophen-2-yl-4H-[1,2,4]triazole-3-thiol (60.8 mg, 0.31 mmol) in acetonitrile (2 ml) at 60° C. overnight. Purification was performed on silica gel using 50% ethyl acetate in hexanes. $^1$H NMR (CDCl$_3$), δ (ppm): 8.09 (m, 2H), 7.57 (m, 5H), 7.17 (dd, 1H), 4.53 (s, 2H), 3.72 (s, 3H).

Example 44

2-[5-(3-Methoxy-phenyl)-[1,2,4]oxadiazol-3-ylmethylsulfanyl]-5-methyl-1H-benzoimidazole 2-[5-(3-Methoxy-phenyl)-[1,2,4]oxadiazol-3-ylmethylsulfanyl]-5-methyl-1H-benzoimidazole (75.5 mg, 70.5%, white foam) was obtained from 3-chloromethyl-5-(3-methoxy-phenyl)-[1,2,4]oxadiazole (82 mg, 0.365 mmol), potassium carbonate (210 mg, 1.520 mmol), 2-thiol-5-methyl-1H-benzoimidazole (50 mg, 0.305 mmol) in acetonitrile (3 ml) at room temperature. Purification was performed by SPE flash chromatography using 50% ethyl acetate in hexanes followed by trituration with ethyl acetate. $^1$H NMR (CDCl$_3$), δ (ppm): 11.95 (bs, 1H), 7.80 (d, 1H), 7.70 (s, 1H), 7.52 (m, 2H), 7.21 (dd, 2H), 7.17 (d, 1H), 4.40 (s, 2H), 3.95 (s, 3H), 2.50 (s, 3H).

Example 45

3-(4-Methyl-5-thiophen-2-yl-4H-[1,2,4]triazol-3-ylsulfanylmethyl)-5-m-tolyl-[1,2,4]oxadiazole 3-(4-Methyl-5-thiophen-2-yl-4H-[1,2,4]triazol-3-ylsulfanylmethyl)-5-m-tolyl-[1,2,4]oxadiazole (76 mg, 85%, white solid) was obtained from 3-chloromethyl-5-m-tolyl-[1,2,4]oxadiazole (50 mg, 0.24 mmol), potassium carbonate (99.4 mg, 0.72 mmol), 4-methyl-5-thiophen-2-yl-4H-[1,2,4]triazole-3-thiol (56.7 mg, 0.27 mmol) in acetonitrile (1 ml) at room temperature. Purification was performed by SPE (flash) chromatography using 50-70% ethyl acetate in hexanes. $^1$H NMR (CDCl$_3$), δ (ppm): 7.89 (m, 2H), 7.50 (m, 2H), 7.40 (m, 2H), 7.18 (t, 1H), 4.52 (s, 2H), 3.71 (s, 3H), 2.41 (s, 3H).

Example 46

3-(4-Methyl-5-thiophen-2-yl-4H-[1,2,4]triazol-3-ylsulfanylmethyl)-5-(3-trifluoromethyl-phenyl)-[1,2,4]oxadiazole 3-(4-Methyl-5-thiophen-2-yl-4H-[1,2,4]triazol-3-ylsulfanylmethyl)-5-(3-trifluoromethyl-phenyl)-[1,2,4]oxadiazole (84 mg, 86%, white solid) was obtained from 3-chloromethyl-5-(3-trifluoromethyl-phenyl)-[1,2,4]oxadiazole (60 mg, 0.23 mmol), potassium carbonate (95 mg, 0.69 mmol), 4-methyl-5-thiophen-2-yl-4H-[1,2,4]triazole-3-thiol (54 mg, 0.27 mmol) in acetonitrile (1 ml) at room temperature. Purification was performed by SPE (flash) chromatography using 40-60% ethyl acetate in hexanes. $^1$H NMR (CDCl$_3$), δ (ppm): 8.38 (s, 1H), 7.29 (d, 1H), 7.86 (d, 1H), 7.68 (t, 1H), 7.50 (t, 2H), 7.19 (m, 1H), 4.57 (s, 2H), 3.75 (s, 3H).

Example 47

3-(3-Methoxy-phenyl)-5-(4-methyl-5-thiophen-2-yl-4H-[1,2,4]triazol-3-ylsulfanylmethyl)-[1,2,4]oxadiazole 3-(3-Methoxy-phenyl)-5-(4-methyl-5-thiophen-2-yl-4H-[1,2,4]triazol-3-ylsulfanylmethyl)-[1,2,4]oxadiazole (74.3 mg, 88%, white solid) was obtained from 4-methyl-5-thiophen-2-yl-4H-[1,2,4]triazole-3-thiol (53.3 mg, 0.27 mmol), 5-chloromethyl-3-(3-methoxy-phenyl)-[1,2,4]oxadiazole (50 mg, 0.22) mmol), and potassium carbonate (92.6 mg, 0.67 mmol) in acetonitrile (1 ml) at room temperature. Purification was performed by SPE (flash) chromatography using 40-70% ethyl acetate in hexane. $^1$H NMR (CDCl$_3$), δ (ppm): 7.62 (d, 1H), 7.52 (d, 2H), 7.48 (d, 1H), 7.37 (t, 1H), 7.18 (t, 1H), 7.06 (m, 1H), 4.64 (s, 2H), 3.84 (s, 3H), 3.71 (s, 3H). LC-MS (MH+): 386.06.

Example 48

5-(4-Methyl-5-thiophen-2-yl-4H-[1,2,4]triazol-3-ylsulfanylmethyl)-3-phenyl-[1,2,4]oxadiazole 5-(4-Methyl-5-thiophen-2-yl-4H-[1,2,4]triazol-3-ylsulfanylmethyl)-3-phenyl-[1,2,4]oxadiazole (79.9 mg, 87%, white solid) was obtained from 4-methyl-5-thiophen-2-yl-4H-[1,2,4]triazole-3-thiol (86.8 mg, 0.44 mmol), 5-chloromethyl-3-phenyl-[1,2,4]oxadiazole (50 mg, 0.26 mmol), and potassium carbonate (152.0 mg, 1.1 mmol) in acetonitrile (1 ml) at room temperature. Purification was performed by SPE (flash) chromatography using 40-70% ethyl acetate in hexane. $^1$H NMR (CDCl$_3$), δ (ppm): 8.02 (d, 2H), 7.47 (m, 5H), 7.18 (t, 1H).

Example 49

5-(4-Methyl-5-thiophen-2-yl-4H-[1,2,4]triazol-3-ylsulfanylmethyl)-3-m-tolyl-[1,2,4]oxadiazole 5-(4-Methyl-5-thiophen-2-yl-4H-[1,2,4]triazol-3-ylsulfanylmethyl)-3-m-tolyl-[1,2,4]oxadiazole (71.8 mg, 91%, white solid) was obtained from 4-methyl-5-thiophen-2-yl-4H-[1,2,4]triazole-3-thiol (78.9 mg, 0.40 mmol), 5-chloromethyl-3-m-tolyl-[1,2,4]oxadiazole (50 mg, 0.24 mmol) and potassium carbonate (138.2 mg, 1.0 mmol) in acetonitrile (1 ml) at room temperature. Purification was performed by SPE (flash) chromatography using 45-65% ethyl acetate in hexane. $^1$H NMR (CDCl$_3$), δ (ppm): 7.82 (d, 2H), 7.52 (d, 1H), 7.47 (d, 1H), 7.31 (m, 2H), 7.18 (m, 1H), 4.64 (s, 2H), 3.70 (s, 3H), 2.39 (s, 3H). LC-MS (MH$^{+i}$): 370.06.

Example 50

3-[3-(4-Methyl-5-thiophen-2-yl-4H-[1,2,4]triazol-3-ylsulfanylmethyl)-[1,2,4]oxadiazol-5-yl]-benzonitrile 3-[3-(4-Methyl-5-thiophen-2-yl-4H-[1,2,4]triazol-3-ylsulfanylmethyl)-[1,2,4]oxadiazol-5-yl]-benzonitrile (130 mg, 75%) was obtained from 3-(3-chloromethyl-[1,2,4]oxadiazol-5-yl)-benzonitrile (100 mg, 0.45 mmol) with K$_2$CO$_3$ (189 mg, 1.36 mmol) and 4-methyl-5-(2-thienyl)1,2,4-triazole-3-thiol (110 mg, 0.54 mmol) in acetonitrile at room temperature. Purification was performed by flash chromatography using 50% ethyl acetate in dichloromethane. $^1$H NMR (CDCl$_3$), δ (ppm): 8.38 (bs, 1H), 8.32 (d, 1H), 7.88 (d, 1H), 7.68 (t, 1H), 7.51 (dd, 2H), 7.18 (dd, 1H), 4.56 (s, 2H), 3.75 (s, 3H); LC-MS (M+H)$^+$: 381.

Example 51

3-[4-Methyl-5-(2-methyl-thiazol-4-yl)-4H-[1,2,4]triazol-3-ylsulfanylmethyl]-5-m-tolyl-[1,2,4]oxadiazole 3-[4-Methyl-5-(2-methyl-thiazol-4-yl)-4H-[1,2,4]triazol-3-ylsulfanylmethyl]-5-m-tolyl-[1,2,4]oxadiazole (82.8 mg, 90%, white solid) was obtained from 3-chloromethyl-5-m-tolyl-[1,2,4]oxadiazole (50 mg, 0.24 mmol), potassium carbonate (99 mg, 0.72 mmol), 4-methyl-5-(2-methyl-thiazol-4-yl)-4H-[1,2,4]triazole-3-thiol (61 mg, 0.29 mmol) in acetonitrile (2 ml) at 60° C. overnight. Purification was performed on silica gel using 80% ethyl acetate in hexanes. $^1$H NMR (CDCl$_3$), δ (ppm): 7.96 (s, 1H), 7.88 (m, 2H), 7.38 (m, 2H), 4.53 (s, 2H), 3.91 (s, 3H), 2.75 (s, 3H), 2.41 (s, 3H).

Example 52

3-[5-(2-Methyl-thiazol-4-yl)-[1,3,4]oxadiazol-2-ylsulfanylmethyl]-5-m-tolyl-[1,2,4]oxadiazole 3-[5-(2-Methyl-thiazol-4-yl)-[1,3,4]oxadiazol-2-ylsulfanylmethyl]-5-m-tolyl-[1,2,4]oxadiazole (89 mg, 99%, off-white solid) was obtained from 3-chloromethyl-5-m-tolyl-[1,2,4]oxadiazole (50 mg, 0.24 mmol), potassium carbonate (99 mg, 0.72 mmol), 5-(2-methyl-thiazol-4-yl)-[1,3,4]oxadiazole-2-thiol (57.3 mg, 0.29 mmol) in acetonitrile (2 ml) at 60° C. overnight. Purification was performed on silica gel using 80% ethyl acetate in hexanes. $^1$H NMR (CDCl$_3$), δ (ppm): 7.97 (s, 1H), 7.90 (m, 2H), 7.40 (m, 2H), 4.66 (s, 2H), 2.80 (s, 3H), 2.42 (s, 3H).

Example 53

3-(4-Methyl-5-thiophen-2-yl-4H-[1,2,4]triazol-3-ylsulfanylmethyl)-5-thiophen-2-yl-[1,2,4]oxadiazole 3-(4-Methyl-5-thiophen-2-yl-4H-[1,2,4]triazol-3-ylsulfanylmethyl)-5-thiophen-2-yl-[1,2,4]oxadiazole (80 mg, 88%, white solid) was obtained from 3-chloromethyl-5-thiophen-2-yl-[1,2,4]oxadiazole (50 mg, 0.25 mmol), potassium carbonate (103 mg, 0.75 mmol), 4-methyl-5-thiophen-2-yl-4H-[1,2,4]triazole-3-thiol (59 mg, 0.30 mmol) in acetonitrile (1 ml) at room temperature. Purification was performed by SPE (flash) chromatography using 50-70% ethyl acetate in hexanes. $^1$H NMR (CDCl$_3$), δ (ppm): 7.89 (d, 1H), 7.65 (m, 1H), 7.51 (m, 2H), 7.19 (m, 2H), 4.50 (t, 2H), 3.74 (s, 3H).

Example 54

3-[5-(2,4-Dimethyl-thiazol-5-yl)-4-methyl-4H-[1,2,4]triazol-3-ylsulfanylmethyl]-5-m-tolyl-[1,2,4]oxadiazole 3-[5-(2,4-Dimethyl-thiazol-5-yl)-4-methyl-4H-[1,2,4]triazol-3-ylsulfanylmethyl]-5-m-tolyl-[1,2,4]oxadiazole (54.2 mg, 57%, off-white solid) was obtained from 3-chloromethyl-5-m-tolyl-[1,2,4]oxadiazole (50 mg, 0.24 mmol), potassium carbonate (99 mg, 0.72 mmol), 5-(2,4-dimethyl-thiazol-5-yl)-4-methyl-4H-[1,2,4]triazole-3-thiol (65.1 mg, 0.29 mmol) in acetonitrile (2 ml) at 60° C. overnight. Purification was performed on silica gel using 80% ethyl acetate in hexanes. $^1$H NMR (CDCl$_3$), δ (ppm): 7.88 (m, 2H), 7.39 (m, 2H), 4.57 (s, 2H), 3.49 (s, 3H), 2.73 (s, 3H), 2.43 (d, 6H).

Example 55

3-[4-Methyl-5-(5-nitro-furan-2-yl)-4H-[1,2,4]triazol-3-ylsulfanylmethyl]-5-m-tolyl-[1,2,4]oxadiazole 3-[4-Methyl-5-(5-nitro-furan-2-yl)-4H-[1,2,4]triazol-3-ylsulfanylmethyl]-5-m-tolyl-[1,2,4]oxadiazole (77.9 mg, 81%, yellow solid) was obtained from 3-chloromethyl-5-m-tolyl-[1,2,4]oxadiazole (50 mg, 0.24 mmol), potassium carbonate (99 mg, 0.72 mmol), 4-methyl-5-(5-nitro-furan-2-yl)-4H-[1,2,4]triazole-3-thiol (65.1 mg, 0.29 mmol) in acetonitrile (2 ml) at 60° C. overnight. Purification was performed on silica gel using 80% ethyl acetate in. $^1$H NMR (CDCl$_3$), δ (ppm): 7.90 (m, 2H), 7.46 (d, 1H), 7.40 (m, 2H), 7.33 (d, 1H), 4.59 (s, 2H), 3.91 (s, 3H), 2.42 (s, 3H).

Example 56

4-[4-Methyl-5-(5-m-tolyl-[1,2,4]oxadiazol-3-ylmethylsulfanyl)-4H-[1,2,4]triazol-3-yl-pyridine 4-[4-Methyl-5-(5-m-tolyl-[1,2,4]oxadiazol-3-ylmethylsulfanyl)-4H-[1,2,4]triazol-3-yl]-pyridine (66 mg, 75%, white solid) was obtained from 3-chloromethyl-5-m-tolyl-[1,2,4]oxadiazole (50 mg, 0.24 mmol), potassium carbonate (99 mg, 0.72 mmol), 4-methyl-5-pyridin-4-yl-4H-[1,2,4]triazole-3-thiol (55.3 mg, 0.29 mmol) in acetonitrile (2 ml) at 60° C. overnight. Purification was performed on silica gel using 80% ethyl acetate in hexanes. $^1$H NMR (CDCl$_3$), δ (ppm): 8.79 (dd, 2H), 7.89 (m, 2H), 7.63 (dd, 2H), 7.40 (m, 2H), 4.59 (s, 2H), 3.69 (s, 3H), 2.41 (s, 3H).

Example 57

3-[5-(4-tert-Butyl-phenyl)-4-methyl-4H-[1,2,4]triazol-3-ylsulfanylmethyl]-5-m-tolyl-[1,2,4]-oxadiazole 3-[5-(4-tert-Butyl-phenyl)-4-methyl-4H-[1,2,4]triazol-3-ylsulfanylmethyl]-5-m-tolyl-[1,2,4]-oxadiazole (100 mg, 99%, white waxy solid) was obtained from 3-chloromethyl-5-m-tolyl-[1,2,4]oxadiazole (50 mg, 0.24 mmol), potassium carbonate (99 mg, 0.72 mmol), 5-(4-tert-butyl-phenyl)-4-methyl-4H-[1,2,4]triazole-3-thiol (71.1 mg, 0.29 mmol) in acetonitrile (2 ml) at 60° C. overnight. Purification was performed on silica gel using 80% ethyl acetate in hexanes. $^1$H NMR (CDCl$_3$), δ (ppm): 7.89 (m, 2H), 7.57 (m, 4H), 7.39 (d, 2H), 4.55 (s, 2H), 3.61 (s, 3H), 2.40 (s, 3H), 1.35 (s, 9H).

Example 58

2-Chloro-5-[4-methyl-5-(5-m-tolyl-[1,2,4]oxadiazol-3-ylmethylsulfanyl)-4H-[1,2,4]triazol-3-yl]-pyridine 2-Chloro-5-[4-methyl-5-(5-m-tolyl-[1,2,4]oxadiazol-3-ylmethylsulfanyl)-4H-[1,2,4]triazol-3-yl]-pyridine (53.8 mg, 56%, white solid) was obtained from 3-chloromethyl-5-m-tolyl-[1,2,4]oxadiazole (50 mg, 0.24 mmol), potassium carbonate (99 mg, 0.72 mmol), 5-(6-chloro-pyridin-3-yl)-4-methyl-4H-[1,2,4]triazole-3-thiol (65.2 mg, 0.29 mmol) in acetonitrile (2 ml) at 60° C. overnight. Purification was performed on silica gel using 80% ethyl acetate in hexanes. $^1$H NMR (CDCl$_3$), δ (ppm): 8.67 (d, 1H), 8.02 (dd, 1H), 7.88 (m, 2H), 7.49 (d, 1H), 7.40 (m, 2H), 4.58 (s, 2H), 3.65 (s, 3H), 2.42 (s, 3H).

Example 59

2-[5-(3-Methoxy-phenyl)-[1,2,4]oxadiazol-3-ylmethylsulfanyl]-benzooxazole

2-[5-(3-Methoxy-phenyl)-[1,2,4]oxadiazol-3-ylmethylsulfanyl]-benzooxazole (138 mg, 62%) was obtained from 3-chloromethyl-5-(3-methoxy-phenyl)-[1,2,4]oxadiazole (225.9 mg, 1.11 mmol), benzooxazole-2-thiol (167 mg, 1.00 mmol), potassium carbonate (180 mg, 1.3 mmol) in DMF (4.5 ml) at room temperature overnight. Purification was performed on silica gel using 10-20% ethyl acetate in hexanes. $^1$H NMR (CDCl$_3$), δ (ppm): 7.67 (d, 1H), 7.57 (m, 3H), 7.43 (t, 1H), 7.21 (m, 2H), 7.14 (m, 1H), 4.50 (s, 2H), 3.86 (s, 3H).

Example 60

3-(4-Methyl-5-thiophen-2-yl-4H-[1,2,4]triazol-3-ylsulfanylmethyl)-5-thiophen-3-yl-[1,2,4]oxadiazole 3-(4-Methyl-5-thiophen-2-yl-4H-[1,2,4]triazol-3-ylsulfanylmethyl)-5-thiophen-3-yl-[1,2,4]oxadiazole (73.6 mg, 73%, white solid) was obtained from 4-methyl-5-thiophen-2-yl-4H-[1,2,4]triazole-3-thiol (61 mg, 0.31 mmol), 3-chloromethyl-5-thiophen-3-yl-[1,2,4]oxadiazole (50 mg, 0.28 mmol), and potassium carbonate (115 mg, 0.83 mmol) in acetonitrile (1 ml) at room temperature. Purification was performed by SPE (flash) chromatography using 50-70% ethyl acetate in hexane. $^1$H NMR (CDCl$_3$), δ (ppm): 8.20 (d, 1H), 7.64 (d, 1H), 7.48 (m, 3H), 7.18 (m, 1H), 4.52 (s, 2H), 3.72 (s, 3H)

Example 61

3-(5-Furan-2-yl-4-methyl-4H-[1,2,4]triazol-3-ylsulfanylmethyl)-5-m-tolyl-[1,2,4]oxadiazole 3-(5-Furan-2-yl-4-methyl-4H-[1,2,4]triazol-3-ylsulfanylmethyl)-5-m-tolyl-[1,2,4]oxadiazole (51.0 mg, 76%, white solid) was obtained from 3-chloromethyl-5-m-tolyl-[1,2,4]oxadiazole (40.0 mg, 0.19 mmol), potassium carbonate (79 mg, 0.58 mmol), 5-furan-2-yl-4-methyl-4H-[1,2,4]triazole-3-thiol (41.7 mg, 0.23 mmol) in acetonitrile (2 ml) at 60° C. overnight. Purification was performed on silica gel using 80% ethyl acetate in hexanes. $^1$H NMR (CDCl$_3$), δ (ppm): 7.88 (m, 2H), 7.58 (s, 1H), 7.40 (m, 2H), 7.10 (d, 1H), 6.58 (dd, 1H), 4.51 (s, 2H), 3.77 (s, 3H), 2.41 (s, 3H).

Example 62

5-(3-Fluoro-phenyl)-3-(4-methyl-5-thiophen-2-yl-4H-(1,2,4]triazol-3-ylsulfanylmethyl)-[1,2,4]oxadiazole 5-(3-Fluoro-phenyl)-3-(4-methyl-5-thiophen-2-yl-4H-[1,2,4]triazol-3-ylsulfanylmethyl)-[1,2,4]oxadiazole (75;4 mg, 83%, white solid) was obtained from 4-methyl-5-thiophen-2-yl-4H-[1,2,4]triazole-3-thiol (51 mg, 0.26 mmol), 3-chloromethyl-5-(3-fluoro-phenyl)-[1,2,4]oxadiazole (50 mg, 0.24 mmol) and potassium carbonate (98 mg, 0.71 mmol) in acetonitrile (1 ml) at room temperature. Purification was performed by SPE (flash) chromatography using 55-60% ethyl acetate in hexane. $^1$H NMR (CDCl$_3$), δ (ppm): 7.89 (d, 1H), 7.78 (m, 1H), 7.51 (m, 3H), 7.32 (m, 1H), 7.18 (m, 1H), 4.55 (s, 2H), 3.74 (s, 3H)

Example 63

2-(5-m-Tolyl-[1,2,4]oxadiazol-3-ylmethylsulfanyl)-pyridine 2-(5-m-Tolyl-[1,2,4]oxadiazol-3-ylmethylsulfanyl)-pyridine (27.3 mg, 96.5%) was obtained from 3-chloromethyl-5-m-tolyl-[1,2,4]oxadiazole (20.8 mg, 0.1 mmol) with pyridine-2-thiol (12.2 mg, 0.11 mmol) and potassium carbonate in DMF (0.8 ml) at room temperature for 15 h. Purification was performed by flash chromatography on silica gel using 20% ethyl acetate in hexane. $^1$H NMR (CDCl$_3$), δ (ppm): 8.47 (dd, 1H), 7.94 (s, 1H), 7.90 (t, 1H), 7.51 (dt, 1H), 7.38 (d, 2H), 7.26 (dd, 1H), 7.02 (dd, 1H), 4.61 (s, 2H), 2.42 (s, 3H).

Example 64

2-[5-(3-Methoxy-phenyl)-[1,2,4]oxadiazol-3-ylmethylsulfanyl]-1H-imidazo[4,5-b]pyridine 2-[5-(3-Methoxy-phenyl)-[1,2,4]oxadiazol-3-ylmethylsulfanyl]-1H-imidazo[4,5-b]pyridine (74.5 mg, 96%) was obtained from 3-chloromethyl-5-(3-methoxy-phenyl)-[1,2,4]oxadiazole (51.2 mg, 0.25 mmol), 1H-imidazo[4,5-b]pyridine-2-thiol (37.5 mg, 0.23 mmol) and potassium carbonate (80 mg, 0.58 mmol) in DMF (1.5 ml) at room temperature overnight. Purification was performed on silica gel using 25-50% ethyl acetate in dichloromethane. $^1$H-NMR (DMSO-d$_6$), δ (ppm): 8.24 (br s, 1H), 7.88 br s, 1H), 7.66 (d, 1H), 7.55 (m, 3H), 7.29 (d, 1H), 7.19 (m, 1H), 4.82 (s, 2H), 3.85 (s, 3H).

Example 65

5-(3-Fluoro-5-methyl-phenyl)-3-(4-methyl-5-thiophen-2-yl-4H-[1,2,4]triazol-3-ylsulfanylmethyl)-[1,2,4]oxadiazole 5-(3-Fluoro-5-methyl-phenyl)-3-(4-methyl-5-thiophen-2-yl-4H-[1,2,4]triazol-3-ylsulfanylmethyl)-[1,2,4]oxadiazole (58 mg, 68%, white solid) was obtained from 3-chloromethyl-5-(3-fluoro-5-methyl-phenyl)-[1,2,4]oxadiazole (50 mg, 0.22 mmol), potassium carbonate (91.5 mg, 0.66 mmol), 4-methyl-5-thiophen-2-yl-4H-[1,2,4]triazole-3-thiol (52.2 mg, 0.26 mmol) in acetonitrile (1 ml) at room temperature. Purification was performed by SPE (flash) chromatography using 40-100% ethyl acetate in hexanes. $^1$H NMR (CDCl$_3$), δ (ppm): 7.70 (s, 1H), 7.58 (d, 1H), 7.52 (m, 1H), 7.49 (m, 1H), 7.18 (m, 1H), 7.12 (d, 1H), 4.53 (s, 2H), 3.73 (s, 3H), 2.42 (s, 3H).

Example 66

3-Methyl-5-[3-(4-methyl-5-thiophen-2-yl-4H-[1,2,4]triazol-3-ylsulfanylmethyl)-[1,2,4]oxadiazol-5-yl]-pyridine 3-Methyl-5-[3-(4-methyl-5-thiophen-2-yl-4H-[1,2,4]triazol-3-ylsulfanylmethyl)-[1,2,4]oxadiazol-5-yl]-pyridine (19.0 mg, 43%, light yellow solid) was obtained from 4-methyl-5-thiophen-2-yl-4H-[1,2,4]triazole-3-thiol (26 mg, 0.13 mmol), 3-(3-chloromethyl-[1,2,4]oxadiazol-5-yl)-5-methyl-pyridine (25 mg, 0.12 mmol) and potassium carbonate (50 mg, 0.36 mmol) in acetonitrile (1 ml) at room temperature.

Purification was performed by SPE (flash) chromatography using 100% ethyl acetate. ¹H NMR (CDCl₃), δ (ppm): 9.13 (s, 1H), 8.65 (s, 1H), 8.16 (s, 1H), 7.50 (m, 2H), 7.19 (t, 1H) 4.57 (s, 2H), 3.74 (s, 3H), 2.43 (s, 3H)

Example 67

3-(4-Methyl-5-phenyl-4H-[1,2,4]triazol-3-ylsulfanylmethyl)-5-m-tolyl-[1,2,4]oxadiazole 3-(4-Methyl-5-phenyl-4H-[1,2,4]triazol-3-ylsulfanylmethyl)-5-m-tolyl-[1,2,4]oxadiazole (55.8 mg, 67%, white solid) was obtained from 3-chloromethyl-5-m-tolyl-[1,2,4]oxadiazole (48.4 mg, 0.23 mmol), potassium carbonate (96 mg, 0.70 mmol), 4-methyl-5-phenyl-4H-[1,2,4]triazole-3-thiol (44.4 mg, 0.23 mmol) in acetonitrile (2 ml) at 60° C. overnight. Purification was performed on silica gel using 50% ethyl acetate in hexanes. ¹H NMR (CDCl₃), δ (ppm): 7.89 (m, 2H), 7.64 (m, 2H), 7.50 (m, 3H), 7.39 (m, 2H), 4.56 (s, 2H), 3.61 (s, 3H), 2.41 (s, 3H).

Example 68

2-[4-Methyl-5-(-m-tolyl-[1,2,4]oxadiazol-3-ylmethylsulfanyl)-4H-[1,2,4]triazo1-3-yl]-pyridine 2-[4-Methyl-5-(5-m-tolyl-[1,2,4]oxadiazol-3-ylmethylsulfanyl)4H-[1,2,4]triazol-3-yl]-pyridine (42.8 mg, 51%, off-white solid) was obtained from 3-chloromethyl-5-m-tolyl-[1,2,4]oxadiazole (48.4 mg, 0.23 mmol), potassium carbonate (96 mg, 0.70 mmol), 4-methyl-5-pyridin-2-yl-4H-[1,2,4]triazole-3-thiol (44.6 mg, 0.23 mmol) in acetonitrile (2 ml) at 60° C. overnight. Purification was performed on silica gel using 50% ethyl acetate in hexanes. ¹H NMR (CDCl₃), δ (ppm): 8.62 (d, 1H), 8.30 (d, 1H), 7.85 (m, 3H), 7.36 (m, 3H), 4.59 (s, 2H), 4.02 (s, 3H), 2.40 (s, 3H).

Example 69

4-Benzyl-2-[4-methyl-5-(5-m-tolyl-[1,2,4]oxadiazol-3-ylmethylsulfanyl)-4H-[1,2,4]triazol-3-yl]-morpholine 4-Benzyl-2-[4-methyl-5-(5-m-tolyl-[1,2,4]oxadiazol-3-ylmethylsulfanyl)-4H-[1,2,4]triazol-3-yl]-morpholine (95.8 mg, 83%, clear oil) was obtained from 3-chloromethyl-5-m-tolyl-[1,2,4]oxadiazole (59.9 mg, 0.29 mmol), potassium carbonate (119 mg, 0.86 mmol), 5-(4-benzyl-morpholin-2-yl)-4-methyl-4H-[1,2,4]triazole-3-thiol (83.3 mg, 0.29 mmol) in acetonitrile (2 ml) at 60° C. overnight. Purification was performed on silica gel using 10% methanol in ethyl acetate. ¹H NMR (CDCl₃), δ (ppm): 7.88 (m, 2H), 7.31 (m, 7H), 4.75 (dd, 1H), 4.47 (dd, 2H), 3.84 (m, 2H), 3.59 (bs, 5H), 3.20 (d, 1H), 2.72 (m, 2H), 2.43 (s, 3H), 2.30 (dt, 1H).

Example 70

4-[4-Methyl-5-(5-thiophen-3-yl-[1,2,4]oxadiazol-3-ylmethylsulfanyl)-4H-[1,2,4]triazol-3-yl]-pyridine 4-[4-Methyl-5-(5-thiophen-3-yl-[1,2,4]oxadiazol-3-ylmethylsulfanyl)-4H-[1,2,4]triazol-3-yl]-pyridine (24 mg, 34%, white solid) was obtained from 3-chloromethyl-5-thiophen-3-yl-[1,2,4]oxadiazole (40 mg, 0.20 mmol), potassium carbonate (82.5 mg, 0.60 mmol), 4-methyl-5-pyridin-4-yl-4H-[1,2,4]triazole-3-thiol (38.3 mg, 0.20 mmol) in acetonitrile (2 ml) at 60° C. overnight. Purification was performed on silica gel using 10% methanol in ethyl acetate. ¹H NMR (CDCl₃), δ (ppm): 8.80 (bs, 2H), 8.20 (dd, 1H), 7.62 (m, 3H), 7.45 (dd, 1H), 4.59 (s, 2H), 3.70 (s, 3H).

Example 71

3-(4-Methyl-5-thiophen-2-yl-4H-[1,2,4]triazol-3-ylsulfanylmethyl)-5-thiazol-4-yl-1,2,4]oxadiazole 3-(4-Methyl-5-thiophen-2-yl-4H-[1,2,4]triazol-3-ylsulfanylmethyl)-5-thiazol-4-yl-[1,2,4]oxadiazole (44 mg, 67%, white solid) was obtained from 3-chloromethyl-5-thiophen-2-yl-[1,2,4]oxadiazole (37 mg, 0.18 mmol), potassium carbonate (75.3 mg, 0.54 mmol), 4-methyl-5-thiophen-2-yl-4H-[1,2,4]triazole-3-thiol (43 mg, 0.22 mmol) in acetonitrile (1 ml) at room temperature. Purification was performed by SPE (flash) chromatography using 50-100% ethyl acetate in hexanes. ¹H NMR (DMSO), δ (ppm): 9.37 (d, 1H), 8.86 (d, 1H), 7.80 (d, 1H), 7.65 (d, 1H), 7.26 (t, 1H), 4.54 (s, 2H), 3.75 (s, 3H).

Example 72

3-(4-Methyl-5-thiophen-2-yl-4H-[1,2,4]triazol-3-ylsulfanylmethyl)-5-(3-nitro-phenyl)-[1,2,4]oxadiazole 3-(4-Methyl-5-thiophen-2-yl-4H-[1,2,4]triazol-3-ylsulfanylmethyl)-5-(3-nitro-phenyl)-[1,2,4]oxadiazole (21.1 mg, 13%, white solid) was obtained from 4-methyl-5-thiophen-2-yl-4H-[1,2,4]triazole-3-thiol (91 mg, 0.46 mmol), 3-chloromethyl-5-(3-nitro-phenyl)-[1,2,4]oxadiazole (100 mg, 0.42 mmol) and and potassium carbonate (173 mg, 1.25 mmol) in acetonitrile (2 ml) at room temperature. Purification was performed by SPE (flash) chromatography using 60% ethyl acetate in hexane. ¹H NMR (CDCl₃), δ (ppm): 8.96 (s, 1H), 8.44 (t, 2H), 7.75 (t, 1H), 7.51 (m, 2H), 7.19 (t, 1H), 4.59 (s, 2H), 3.76 (s, 3H)

Example 73

2-Methyl-4-[3-(4-methyl-5-thiophen-2-yl-4H-[1,2,4]triazol-3-ylsulfanylmethyl)-[1,2,4]oxadiazol-5-yl]-pyridine 2-Methyl-4-[3-(4-methyl-5-thiophen-2-yl-4H-[1,2,4]triazol-3-ylsulfanylmethyl)-[1,2,4]oxadiazol-5-yl]-pyridine (59.2 mg, 66%, white solid) was obtained from 4-methyl-5-thiophen-2-yl-4H-[1,2,4]triazole-3-thiol (51 mg, 0.26 mmol), 4-(3-chloromethyl-[1,2,4]oxadiazol-5-yl)-2-methyl-pyridine (50 mg, 0.24 mmol), and potassium carbonate (100 mg, 0.72 mmol) in acetonitrile (1 ml) at room temperature. Purification was performed by SPE (flash) chromatography using 100% ethyl acetate. ¹H NMR (CDCl₃), δ (ppm): 8.71 (d, 1H), 7.79 (s, 1H), 7.73 (d, 1H), 7.49 (m, 2H), 7.19 (t, 1H), 4.58 (s, 2H), 3.73 (s, 3H), 2.65 (s, 3H)

Example 74

3-[4-Methyl-5-(5-m-tolyl-[1,2,4]oxadiazol-3-ylmethylsulfanyl)-4H-[1,2,4]triazol-3-yl]-pyridine 3-[4-Methyl-5-(5-m-tolyl-[1,2,4]oxadiazol-3-ylmethylsulfanyl)-4H-[1,2,4]triazol-3-yl]-pyridine (30 mg, off-white solid) was obtained from 3-chloromethyl-5-m-tolyl-[1,2,4]oxadiazole (50 mg, 0.24 mmol), potassium carbonate (100 mg, 0.72 mmol), 4-methyl-5-pyridin-3-yl-4H-[1,2,4]triazole-3-thiol (46.1 mg, 0.24 mmol) in acetonitrile (2 ml) at 60° C. overnight. Purification was performed on silica gel using 5% methanol in ethyl acetate. $^1$H NMR (CDCl$_3$), δ (ppm): 8.90 (bs, 1H), 8.76 (bs, 1H), 8.03 (m, 1H), 7.88 (m, 2H), 7.46 (dd, 1H), 7.40 (m, 2H), 4.58 (s, 2H), 3.66 (s, 3H), 2.42 (s, 3H).

Example 75

3-(4-Methyl-5-thiophene-3-yl-4H-[1,2,4]triazol-3-ylsulfanylmethyl)-5-m-tolyl-[1,2,4]oxadiazole 3-(4-Methyl-5-thiophene-3-yl-4H-[1,2,4]triazol-3-ylsulfanylmethyl)-5-m-tolyl-[1,2,4]oxadiazole (60 mg, white solid) was obtained from 3-chloromethyl-5-m-tolyl-[1,2,4]oxadiazole (50 mg, 0.24 mmol), potassium carbonate (100 mg, 0.72 mmol), 4-methyl-5-thiophene-3-yl-4H-[1,2,4]triazole-3-thiol (47.3 mg, 0.24 mmol) in acetonitrile (2 ml) at 60° C. overnight. Purification was performed on silica gel using 40% ethyl acetate in dichloromethane. $^1$H NMR (CDCl$_3$), δ (ppm): 7.87 (m, 2H), 7.71 (dd, 1H), 7.48 (m, 2H), 7.38 (m, 2H), 4.52 (s, 2H), 3.67 (s, 3H), 2.41 (s, 3H).

Example 76

3-(4-Methyl-5-thiazol-4-yl-4H-[1,2,4]triazol-3-ylsulfanylmethyl)-5-m-tolyl-[1,2,4]oxadiazole 3-(4-Methyl-5-thiazol-4-yl-4H-[1,2,4]triazol-3-ylsulfanylmethyl)-5-m-tolyl-[1,2,4]oxadiazole (30 mg, off-white solid) was obtained from 3-chloromethyl-5-m-tolyl-[1,2,4]oxadiazole (50 mg, 0.24 mmol), potassium carbonate (100 mg, 0.72 mmol), 4-methyl-5-thiazol-yl-4H-[1,2,4]triazole-3-thiol (47.5 mg, 0.24 mmol) in acetonitrile (2 ml) at 60° C. overnight. Purification was performed on silica gel using 60% ethyl acetate in dichloromethane. $^1$H NMR (CDCl$_3$), δ (ppm): 8.89 (d, 1H), 8.22 (d, 1H), 7.88 (m, 2H), 7.38 (m, 2H), 4.55 (s, 2H), 3.94 (s, 3H), 2.41 (s, 3H).

Example 77

5-(3-Iodo-phenyl)-3-(4-methyl-5-thiophen-2-yl-4H-[1,2,4]triazol-3-ylsulfanylmethyl)-[1,2,4]oxadiazole 5-(3-Iodo-phenyl)-3-(4-methyl-5-thiophen-2-yl-4H-[1,2,4]triazol-3-ylsulfanylmethyl)-[1,2,4]oxadiazole (725 mg, 97%, white solid) was obtained from 3-chloromethyl-5-(3-iodo-phenyl)-[1,2,4]oxadiazole (500 mg, 1.56 mmol), potassium carbonate (647 mg, 4.68 mmol), 4-methyl-5-thiophen-2-yl-4H-[1,2,4]triazole-3-thiol (369 mg, 1.87 mmol) in acetonitrile (10 ml) at room temperature. Purification was performed by flash column chromatography on silica gel using 40% ethyl acetate in hexanes. $^1$H NMR (CDCl$_3$), δ (ppm): 8.44 (d, 1H), 8.06 (d, 1H), 7.93 (d, 1H), 7.51 (m, 2H), 7.26 (t, 1H), 7.19 (m, 1H), 4.54 (s, 2H), 3.73 (s, 3H).

Example 78

5-(3-Ethyl-phenyl)-3-(4-methyl-5-thiophen-2-yl-4H-[1,2,4]triazol-3-ylsulfanylmethyl)-[1,2,4]oxadiazole 5-(3-Ethyl-phenyl)-3-(4-methyl-5-thiophen-2-yl-4H-[1,2,4]triazol-3-ylsulfanylmethyl)-[1,2,4]oxadiazole (28.1 mg, 27%, white solid) was obtained from 4-methyl-5-thiophen-2-yl-4H-[1,2,4]triazole-3-thiol (59 mg, 0.30 mmol), 3-chloromethyl-5-(3-ethyl-phenyl)-[1,2,4]oxadiazole (60 mg, 0.27 mmol) and potassium carbonate (111 mg, 0.80 mmol) in acetonitrile (1 ml) at room temperature. Purification was performed by SPE (flash) chromatography using 50% ethyl acetate in hexane. $^1$H NMR (CDCl$_3$), δ (ppm): 7.90 (t, 2H), 7.51 (m, 2H), 7.42 (t, 2H)7.18 (m, 1H), 4.52 (s, 2H), 3.72 (s, 3H), 2.70 (m, 2H), 1.26 (t, 3H)

Example 79

2-[5-(2-Methyl-pyridin-4-yl)-[1,2,4]oxadiazol-3-ylmethylsulfanyl]-1H-benzoimidazole 2-[5-(2-Methyl-pyridin-4-yl)-[1,2,4]oxadiazol-3-ylmethylsulfanyl]-1H-benzoimidazole (46.0 mg, 59%, white solid) was obtained from 2-mercaptobenzimidazole (41 mg, 0.27 mmol), 4-(3-chloromethyl-[1,2,4]oxadiazol-5-yl)-2-methylpyridine (50 mg, 0.24 mmol), and potassium carbonate (100 mg, 0.72 mmol) in DMF (1 ml) at room temperature. Purification was performed by SPE (flash) chromatography using 100% ethyl acetate and titurated with ether. $^1$H NMR (DMSO-d$_6$), δ (ppm): 8.72 (d, 1H), 7.87 (s, 1H), 7.78 (d, 1H), 7.47 (t, 2H), 7.14 (m, 2H), 4.81 (s, 2H), 2.59 (s, 3H)

Example 80

2-[5-(3-Iodo-phenyl)-[1,2,4]oxadiazol-3-ylmethylsulfanyl]-1H-benzoimidazole

2-[5-(3-Iodo-phenyl)-[1,2,4]oxadiazol-3-ylmethylsulfanyl]-1H-benzoimidazole (36 mg, 51%, white solid) was obtained from 3-chloromethyl-5-(3-iodo-phenyl)-[1,2,4]oxadiazole (50 mg, 0.16 mmol), potassium carbonate (65 mg, 0.47 mmol), 1H-benzoimidazole-2-thiol (23 mg, 0.16 mmol) in DMF (1 ml) at room temperature. Purification was performed by SPE (flash) chromatography using 50-100% ethyl acetate in hexanes followed by trituration with ethyl acetate. $^1$H NMR (DMSO), δ (ppm): 12.73 (bs, 1H), 8.30 (s, 1H), 8.09 (d, 2H), 7.45 (m, 3H), 7.18 (m, 2H), 4.78 (s, 2H).

Example 81

3-(4-Methyl-5-trifluoromethyl-4H-[1,2,4]triazol-3-ylsulfanylmethyl)-5-m-tolyl-[1,2,4]oxadiazole 3-(4-Methyl-5-trifluoromethyl-4H-[1,2,4]triazol-3-ylsulfanylmethyl)-5-m-tolyl-[1,2,4]oxadiazole (54.3 mg, 80%, clear oil) was obtained from 3-chloromethyl-5-m-tolyl-[1,2,4]oxadiazole (40 mg, 0.19 mmol), potassium carbonate (79 mg, 0.58 mmol), 4-methyl-5-trifluromethyl-4H-[1,2,4]triazole-3-thiol (35.1 mg, 0.19 mmol) in acetonitrile (2 ml) at 60° C. overnight. Purification was performed on silica gel using 50% ethyl acetate in hexanes. $^1$H NMR (CDCl$_3$), δ (ppm): 7.87 (m, 2H), 7.41 (m, 2H), 4.59 (s, 2H), 3.69 (s, 3H), 2.43 (s, 3H).

Example 82

2,6-Dichloro-4-[4-methyl-5-(5-m-tolyl-[1,2,4]oxadiazol-3-ylmethylsulfanyl)-4H-[1,2,4]triazol-3-yl]-pyridine 2,6-Dichloro-4-[4-methyl-5-(5-m-tolyl-[1,2,4]oxadiazol-3-ylmethylsulfanyl)-4H-[1,2,4]triazol-3-yl]-pyridine (51.4 mg, 62%, off-white solid) was obtained from 3-chloromethyl-5-m-tolyl-[1,2,4]oxadiazole (40 mg, 0.19 mmol), potassium carbonate (79 mg, 0.58 mmol), 5-(2,6-dichloropyridin-4-yl)-4-methyl-4H-[1,2,4]triazole-3-thiol (50.1 mg, 0.19 mmol) in acetonitrile (2 ml) at 60° C. overnight. Purification was performed on silica gel using 80% ethyl acetate in hexanes. ¹H NMR (CDCl₃), δ (ppm): 7.87 (m, 2H), 7.61 (s, 2H), 7.40 (m, 2H), 4.60 (s, 2H), 3.71 (s, 3H), 2.42 (s, 3H).

Example 83

3-(4-Methyl-5-p-tolyl-4H-[1,2,4]triazol-3-ylsulfanylmethyl)-5-m-tolyl-[1,2,4]oxadiazole 3-(4-Methyl-5-p-tolyl-4H-[1,2,4]triazol-3-ylsulfanylmethyl)-5-m-tolyl-[1,2,4]oxadiazole (57.8 mg, 81%, off-white solid) was obtained from 3-chloromethyl-5-m-tolyl-[1,2,4]oxadiazole (40 mg, 0.19 mmol), potassium carbonate (79 mg, 0.58 mmol), 4-methyl-5-p-tolyl-4H-[1,2,4]triazole-3-thiol (39.4 mg, 0.19 mmol) in acetonitrile (2 ml) at 60° C. overnight. Purification was performed on silica gel using 80% ethyl acetate in hexanes. ¹H NMR (CDCl₃), δ (ppm): 7.88 (m, 2H), 7.53 (d, 2H), 7.39 (m, 2H), 7.30 (d, 2H), 4.55 (s, 2H), 3.59 (s, 3H), 2.42 (d, 6H).

Example 84

Dimethyl-{3-[3-(4-methyl-5-thiophen-2-yl-4H-[1,2,4]triazol-3-ylsulfanylmethyl)-[1,2,4]oxadiazol-5-yl]phenyl}-amine Dimethyl-{3-[3-(4-methyl-5-thiophen-2-yl-4H-[1,2,4]triazol-3-ylsulfanylmethyl)-[1,2,4]oxadiazol-5-yl]phenyl}-amine (28.0 mg, 85%, white solid) was obtained from 4-methyl-5-thiophen-2-yl-4H-[1,2,4]triazole-3-thiol (18 mg, 0.093 mmol), 3-(3-chloromethyl-[1,2,4]oxadiazol-5-yl)-phenyl]-dimethyl-amine (20 mg, 0.084 mmol), and potassium carbonate (35 mg, 0.25 mmol) in acetonitrile (1 ml) at room temperature. Purification was performed by SPE (flash) chromatography using 70% ethyl acetate in hexane. ¹H NMR (CDCl₃), δ (ppm): 7.49 (m, 2H), 7.36 (m, 3H), 7.17 (t, 1H), 6.91 (d, 1H), 4.51 (s, 2H), 3.72 (s, 3H), 3.00 (s, 6H)

Example 85

5-(3-Chloro-phenyl)-3-(4-methyl-5-thiophen-2-yl-4H-[1,2,4]triazol-3-ylsulfanylmethyl)-[1,2,4]oxadiazole 5-(3-Chloro-phenyl)-3-(4-methyl-5-thiophen-2-yl-4H-[1,2,4]triazol-3-ylsulfanylmethyl)-[1,2,4]oxadiazole (76.8 mg, 90%, white solid) was obtained from 4-methyl-5-thiophen-2-yl-4H-[1,2,4]triazole-3-thiol (47 mg, 0.24 mmol), 3-chloromethyl-5-(3-chloro-phenyl)-[1,2,4]oxadiazole (50 mg, 0.22 mmol), and potassium carbonate (91 mg, 0.66 mmol) in acetonitrile (1 ml) at room temperature. Purification was performed by SPE (flash) chromatography using 70% ethyl acetate in hexane. ¹H NMR (CDCl₃), δ (ppm): 8.09 (s, 1H), 7.98 (d, 1H), 7.49 (m, 4H), 7.18 (m, 1H), 4.55 (s, 2H), 3.73 (s, 3H)

Example 86

3-(4-Methyl-5-thiophen-2-yl-4H-[1,2,4]triazol-3-ylsulfanylmethyl)-5-(3-trifluoromethoxy-phenyl)[1,2,4]oxadiazole 3-(4-Methyl-5-thiophen-2-yl-4H-[1,2,4]triazol-3-ylsulfanylmethyl)-5-(3-trifluoromethoxy-phenyl)[1,2,4]oxadiazole (144.0 mg, 91%, white solid) was obtained from 4-methyl-5-thiophen-2-yl-4H-[1,2,4]triazole-3-thiol (78 mg, 0.39 mmol), 3-chloromethyl-5-(3-trifluoromethoxy-phenyl)-[1,2,4]oxadiazole (100 mg, 0.36 mmol) and potassium carbonate (149 mg, 1.08 mmol) in acetonitrile (2 ml) at room temperature. Purification was performed by SPE (flash) chromatography using 55% ethyl acetate in hexane. ¹H NMR (CDCl₃), δ (ppm): 8.04 (d, 1H), 7.95 (s, 1H), 7.51 (m, 4H), 7.18 (m, 1H), 4.56 (s, 2H), 3.74 (s, 3H)

Example 87

3-(5-Cyclohexyl-4-methyl-4H-[1,2,4]triazol-3-ylsulfanylmethyl)-5-m-tolyl-[1,2,4]oxadiazole 3-(5-Cyclohexyl-4-methyl-4H-[1,2,4]triazol-3-ylsulfanylmethyl)-5-m-tolyl-[1,2,4]oxadiazole (10.5 mg, clear oil) was obtained from 3-chloromethyl-5-m-tolyl-[1,2,4]oxadiazole (50 mg, 0.24 mmol), potassium carbonate (165 mg, 1.20 mmol), 5-cyclohexyl-4-methyl-4H-[1,2,4]triazole-3-thiol (94.6 mg, 0.48 mmol) in acetonitrile (3 ml) at 60° C. overnight. Purification was performed on silica gel using 2% ammonia (2 N methanol) in dichloromethane. ¹H NMR (CDCl₃), δ (ppm): 7.88 (m, 2H), 7.39 (m, 2H), 4.42 (s, 2H), 3.46 (s, 3H), 2.60 (m, 1H), 2.42 (d, 3H), 1.74 (m, 7H), 1.34 (m, 3H).

Example 88

3-(5-tert-Butyl-4-methyl-4H-[1,2,4]triazol-3-ylsulfanylmethyl)-5-m-tolyl-[1,2,4]oxadiazole 3-(5-tert-Butyl-4-methyl-4H-[1,2,4]triazol-3-ylsulfanylmethyl)-5-m-tolyl-[1,2,4]oxadiazole (56.8 mg, white solid) was obtained from 3-chloromethyl-5-m-tolyl-[1,2,4]oxadiazole (50 mg, 0.24 mmol), potassium carbonate (100 mg, 0.72 mmol), 5-tert-butyl-4-methyl-4H-[1,2,4]triazole-3-thiol (41 mg, 0.24 mmol) in acetonitrile (2 ml) at 60° C. overnight. Purification was performed on silica gel using 80% ethyl acetate in hexanes. ¹H NMR (CDCl₃), δ (ppm): 7.89 (m, 2H), 7.40 (m, 2H), 4.46 (s, 2H), 3.63 (s, 3H), 2.43 (m, 3H), 1.45 (s, 9H).

Example 89

5-(3-Bromo-phenyl)-3-(4-methyl-5-thiophen-2-yl-4H-[1,2,4]triazol-3-ylsulfanylmethyl)-[1,2,4]oxadiazole 5-(3-Bromo-phenyl)-3-(4-methyl-5-thiophen-2-yl-4H-[1,2,4]triazol-3-ylsulfanylmethyl)-[1,2,4]oxadiazole (83.4 mg, 86%, white solid) was obtained from 4-methyl-5-thiophen-2-yl-4H-[1,2,4]triazole-3-thiol (47 mg, 0.24 mmol), 5-(3-bromo-phenyl)-3-chloromethyl-[1,2,4]oxadiazole (60 mg, 0.22 mmol), and potassium carbonate (91 mg, 0.66 mmol) in acetonitrile (2 ml) at room temperature. Purification was performed by SPE (flash) chromatography using 60% ethyl acetate in hexane. ¹H NMR (CDCl₃), δ (ppm): 8.25 (t, 1H), 8.02 (d, 1H), 7.73 (d, 1H), 7.50 (m, 2H), 7.40 (t, 1H), 7.19 (m, 1H), 4.55 (s, 2H), 3.73 (s, 3H)

Example 90

2-[5-(3-Bromo-phenyl)-[1,2,4]oxadiazol-3-ylmethylsulfanyl]-1H-benzoimidazole

2-[5-(3-Bromo-phenyl)-[1,2,4]oxadiazol-3-ylmethylsulfanyl]-1H-benzoimidazole (71.1 mg, 84%, white solid) was obtained from 2-mercaptobenzimidazole (35 mg, 0.23 mmol), 5-(3-Bromo-phenyl)-3-chloromethyl-[1,2,4]oxadiazole (60 mg, 0.22 mmol) and potassium carbonate (91 mg, 0.66 mmol) in DMF (2 ml) at room temperature. Purification was performed by SPE (flash) chromatography using 35% ethyl acetate in hexane and titurated with ether. $^1$H NMR (DMSO-d$_6$), δ (ppm): 12.78 (broad s, 1H), 8.18 (s, 1H), 8.07 (d, 1H), 7.93 (d, 1H), 7.59 (t, 1H), 7.46 (s, 2H), 7.14 (m, 2H), 4.77 (s, 2H)

Example 91

5-(3-Methoxymethyl-phenyl)-3-(4-methyl-5-thiophen-2-yl-4H-[1,2,4]triazol-3-lsulfanylmethyl)-[1,2,4]oxadiazole 5-(3-Methoxymethyl-phenyl)-3-(4-methyl-5-thiophen-2-yl-4H-[1,2,4]triazol-3-lsulfanylmethyl)-[1,2,4]oxadiazole (76 mg, 90%, white solid) was obtained from 3-chloromethyl-5-(3-methoxymethyl-phenyl)-[1,2,4]oxadiazole (50 mg, 0.21 mmol), potassium carbonate (87 mg, 0.63 mmol), 4-methyl-5-thiophen-2-yl-4H-[1,2,4]triazole-3-thiol (50 mg, 0.25 mmol) in acetonitrile (2 ml) at room temperature. Purification was performed by SPE (flash) chromatography using 40-70% ethyl acetate in hexanes. $^1$H NMR (CDCl$_3$), δ (ppm): 8.06 (s, 1H), 8.01 (d, 1H), 7.59 (d, 1H), 7.50 (m, 3H), 7.18 (t, 1H), 4.54 (s, 2H), 4.50 (s, 2H), 3.72 (s, 3H), 3.43 (s, 3H).

Example 92

2-[5-(3-Methoxymethyl-phenyl)-[1,2,4]oxadiazol-3-ylmethylsulfanyl]-1H-benzoimidazole 2-[5-(3-Methoxymethyl-phenyl)-[1,2,4]oxadiazol-3-ylmethylsulfanyl]-1H-benzoimidazole (62 mg, 84%, white solid) was obtained from 3-chloromethyl-5-(3-methoxymethyl-phenyl)-[1,2,4]oxadiazole (50 mg, 0.21 mmol), potassium carbonate (87 mg, 0.63 mmol), 1H-benzoimidazole-2-thiol (32 mg, 0.21 mmol) in DMF (2 ml) at room temperature. Purification was performed by SPE (flash) chromatography using 40-100% ethyl acetate in hexanes. $^1$H NMR (DMSO), δ (ppm): 8.09 (d, 2H), 7.59 (m, 2H), 7.46 (bs, 2H), 7.14 (m, 2H), 4.77 (s, 2H), 4.51 (s, 2H), 3.35 (s, 3H).

Example 93

4-[3-Methyl-5-thiophen-2-yl-4H-[1,2,4]triazol-3-ylsulfanylmethyl)-[1,2,4]oxadiazol-5-yl]-pyridine A solution of isonicotinoyl chloride (2.0 g, 11.2 mmol) in dichloromethane was treated with 2-chloro-N-hydroxy-acetamidine (1.58 g, 14.6 mmol), followed by addition of triethylamine (4.67 ml, 33.6 mmol) in a dropwise manner. After stirring at room temperature 1 h, extraction with ethyl acetate using water and brine washes afforded the oxy-acyl intermediate (used without further purification, 150 mg, 0.7 mmol). A solution of the crude product in acetonitrile (2 ml) and DMSO (2 ml) with K$_2$CO$_3$ (292 mg, 2.1 mmol) and 4-methyl-5-thiophen-2-yl-4H-[1,2,4]triazole-3-thiol (140 mg, 0.7 mmol) was stirred at room temperature for 24 h followed by 1.5 h at 120° C. (sealed tube). Standard aqueous work-up with ethyl acetate using water and brine washes followed by silica gel chromatography afforded the title compound (110 mg, 44%). $^1$H NMR (CDCl$_3$), δ (ppm): 8.41 dd, 2H), 7.92 dd, 2H), 7.50 dd, 1H), 7.47 dd, 1H), 7.18 dd, 1H), 4.58 (s, 2H), 3.74 (s, 3H); LC-MS (M+H)$^+$: 357.

Example 94 was prepared in an analogous method to the procedure given in Example 93.

Example 94

4-[5-(4-Methyl-5-thiophen-2-yl-4H-[1,2,4]triazol-3-ylsulfanylmethyl)-[1,2,4]oxadiazol-3-yl]-pyridine 4-[5-(4-Methyl-5-thiophen-2-yl-4H-[1,2,4]triazol-3-ylsulfanylmethyl)-[1,2,4]oxadiazol-3-yl]-pyridine (12 mg, 5%) was obtained from N-hydroxy-isonicotinamidine (200 mg, 1.4 mmol) with chloroacetyl chloride (0.11 ml, 1.4 mmol) and triethylamine (0.5 ml, 3.5 mmol); aqueous work-up gave intermediate (150 mg, 0.7 mmol); treated with K$_2$CO$_3$ (292 mg, 2.1 mmol), and 4-methyl-5-thiophen-2-yl-4H-[1,2,4]triazole-3-thiol (140 mg, 0.7 mmol). Purification was performed by silica gel chromatography and recrystallization. $^1$H NMR (CDCl$_3$), δ (ppm): 8.76 (dd, 2H), 7.89 (dd, 2H), 7.53 (dd, 1H), 7.48 (dd, 1H), 7.18 (dd, 1H), 4.71 (s, 2H), 3.73 (s, 3H); LC-MS (M+H)+: 357.

Example 95

2-{1-[5-(3-Methoxy-phenyl)-[1,2,4]oxadiazol-3-yl]-ethylsulfanyl}-1-methyl-1H-imidazo[4,5b]pyridine and 2-[5-(3-Methoxy-phenyl)-[1,2,4]oxadiazol-3-ylmethylsulfanyl]-1-methyl-1H-imidazo[4,5-b]pyridine THF (3 ml) was added to a mixture of sodium hydride (60%, 8 mg, 0.2 mmol) and 2-[5-(3-methoxy-phenyl)-[1,2,4] oxadiazol-3-ylmethylsulfanyl]-1H-imidazo[4,5-b]pyridine (24.6 mg, 0.072 mmol) and the resulting mixture was stirred at 1° C. for about 15 min. Methyl iodide (20 µL, 0.32 mmol) was added the resulting mixture was stirred at 0° C. for 2 h. The reaction was quenched by the addition of dichloromethane (10 ml) and water (2 ml). After vigorous stirring, the organic extracts (10 ml, plus 3×5 ml) were eluted through a Chem Elut Extraction Column (Varian, cat #1219-8002). Purification using SPE chromatography (5 g silica) using 25/25/50 to 50/25/25 ethyl acetate/dichloromethane/hexane yielded two products. The first product to elute was 2-{1-[5-(3-methoxy-phenyl)-[1,2,4]oxadiazol-3-yl]-ethylsulfanyl}-1-methyl-1H-imidazo[4,5-b]pyridine (6 mg, 23%). $^1$H NMR (CDCl$_3$), δ (ppm): 8.46 (d, 1H), 7.72 (d, 1H), 7.62 (d, 1H), 7.55 (d, 1H), 7.42 (t, 1H), (m, 2H), 5.67 (q, 1H), 3.88 (s, 3H), 3.71 (s, 3H), 2.01 (d, 3H).

The second product to elute was 2-[5-(3-methoxy-phenyl)-[1,2,4]oxadiazol-3-ylmethylsulfanyl]-1-methyl-1H-imidazo[4,5-b]pyridine (12 mg, 47%). $^1$H NMR (CDCl$_3$), δ (ppm): 8.44 (d, 1H), 7.69 (d, 1H), 7.60 (d, 1H), 7.55 (d, 1H), 7.41 (t, 1H), 7.13 (m, 1H), 4.90 (s, 2H), 3.87 (s, 3H), 3.70 (s, 3H).

Example 96-97 was prepared in an analogous method to the procedure given in Example 95.

Example 96

3-[1-Methyl-1-(4-methyl-5-thiophen-2-yl-4H-[1,2,4]triazol-3-ylsulfanyl)-ethyl]-5-m-tolyl-[1,2,4]oxadiazole 3-[1-Methyl-1-(4-methyl-5-thiophen-2-yl-4H-[1,2,4]triazol-3-ylsulfanyl)-ethyl]-5-m-tolyl-[1,2,4]oxadiazole (13 mg, 47%) was obtained from 3-(4-methyl-5-thiophen-2-yl-4H-[1,2,4]triazol-3-ylsulfanylmethyl)-5-m-tolyl-[1,2,4]oxadiazole (25.5 mg, 0.069 mmol) with 60% sodium hydride (37 mg, 0.92 mmol) and methyl iodide (0.10 ml, 1.6 mmol) in THF (3 ml) at room temperature for 2 h. The product was extracted with ethyl acetate and purified by SPE 20-40% ethyl acetate in 1:1 dichloromethane:hexane. $^1$H NMR (CDCl$_3$), δ (ppm): 7.83 (br s, 2H), 7.48 (d, 1H), 7.42 (d, 1H), 7.36 (m, 2H), 7.13 (m, 1H), 3.50 (s, 3H), 2.35 (s, 3H), 1.95 (s, 6H).

Example 97

3-[1-(4-Methyl-5-thiophen-2-yl-4H-[1,2,4]triazol-3-ylsulfanyl)-ethyl]-5-m-tolyl-[1,2,4]oxadiazole 3-[1-(4-Methyl-5-thiophen-2-yl-4H-[1,2,4]triazol-3-ylsulfanyl)-ethyl]-5-m-tolyl-[1,2,4]oxadiazole (6.1 mg, 17%) was obtained from 3-(4-methyl-5-thiophen-2-yl-4H-[1,2,4]triazol-3-ylsulfanylmethyl)-5-m-tolyl-[1,2,4]oxadiazole (33.8 mg, 0.091 mmol) with 60% sodium hydride (17 mg, 0.42 mmol) and methyl iodide (20 μL, 0.32 mmol) in THF (2.5 ml) at room temperature for 1 h. The product was extracted with dichloromethane and purified by SPE 25-40% ethyl acetate in 1:1 chloroform:hexane. $^1$H NMR (CDCl$_3$), δ (ppm): 7.89 (br s, 2H), 7.50 (d, 1H), 7.46 (d, 1H), 7.38 (m, 2H), 7.16 (m, 1H), 4.89 (q, 1H), 3.64 (s, 3H), 2.37 (s, 3H), 1.90 (d, 3H).

Example 98

3-(4-Methyl-5-thiophen-2-yl-4H-[1,2,4]triazole-3-sulfinylmethyl)-5-m-tolyl-[1,2,4]oxadiazole and
3-(4-Methyl-5-thiophen-2-yl-4H-[1,2,4]triazole-3-sulfinylmethyl)-5-m-tolyl-1,2,4]oxadiazole Dichloromethane (2.5 ml) was added to a mixture of 3-chloro-benzenecarboperoxoic acid (57-85%, 49.5 mg, 0.16-0.25 mmol) and 3-(4-methyl-5-thiophen-2-yl-4H-[1,2,4]triazol-3-ylsulfanylmethyl)-5-m-tolyl-[1,2,4]oxadiazole (45 mg, 0.12 mmol) and the resulting mixture was stirred at room temperature overnight. The reaction was quenched by the addition of dichloromethane (10 ml) and 1 M sodium hydroxide (3 ml). After vigorous stirring, the organic extracts (10 ml, plus 3×5 ml) were eluted through a Chem Elut Extraction Column (Varian, cat #1219-8002). Purification was performed by SPE chromatography (5 g silica) using 10-30% ethyl acetate in 1:1 dichloromethane:hexane yielded two products. The first product to elute was 3-(4-methyl-5-thiophen-2-yl-4H-[1,2,4]triazole-3-sulfonylmethyl)-5-m-tolyl-[1,2,4]oxadiazole (12.3 mg, 25%). $^1$H NMR (CDCl$_3$), δ (ppm): 7.83 (br s, 2H), 7.63 (d, 1H), 7.56 (d, 1H), 7.36 (m, 2H), 7.24 (m, 1H), 5.12 (s, 2H), 3.94 (s, 3H), 2.36 (d, 3H).

The second product to elute was 3-(4-methyl-5-thiophen-2-yl-4H-[1,2,4]triazole-3-sulfinylmethyl)-5-m-tolyl-[1,2,4]oxadiazole (33.2 mg, 71%). $^1$H NMR (CDCl$_3$), δ (ppm): 7.87 (br s, 2H), 7.59 (d, 1H), 7.54 (d, 1H), 7.38 (m, 2H), 7.22 (m, 1H), 5.05 (d$_{AB}$, 1H), 4.90 (d$_{AB}$, 1H), 4.03 (s, 3H), 2.39 (d, 3H).

Example 99

5-(3-Furan-3-yl-phenyl)-3-(4-methyl-5-thiophen-2-yl-4H-[1,2,4]triazol-3-ylsulfanylmethyl)-[1,2,4]oxadiazole To 5-(3-Iodo-phenyl)-3-(4-methyl-5-thiophen-2-yl-4H-[1,2,4]triazol-3-ylsulfanylmethyl)-[1,2,4]oxadiazole (50 mg, 0.10 mmol) in a vial was added 3-furan boronic acid (17 mg, 0.16 mmol), tetrakis(triphenylphosphine)palladium(0) (6 mg, 0.0052 mmol), ethylene glycol dimethyl ether (1 ml) and 2 M sodium carbonate (1 ml). The vial was then sealed and heated at 90° C. for 1 h with vigorous stirring. The reaction was cooled, diluted with ethyl acetate, washed with water and saturated brine, filtered and concentrated. The residue was purified by flash column chromatography using 70% ethyl acetate in hexanes. Additional purification by trituration with a mixture of diethyl ether and hexanes and then filtration afforded the title compound as a beige solid 25 mg (57%). $^1$H NMR (CDCl$_3$), δ (ppm): 8.18 (s, 1H), 7.98 (d, 1H), 7.79 (s, 1H), 7.71 (d, 1H), 7.51 (m, 4H), 7.17 (m, 1H), 6.74 (s, 1H), 4.55 (s, 2H), 3.73 (s, 3H).

Intermediates

Example 100

Pyrimidine-4-carboxylic acid

3-Methyl-pyrimidine (9.41 g, 100 mmol), potassium permanganate (26.9 g) and sodium carbonate (10.6 g) was refluxed in water (100 ml) for 72 h followed by filtration through celite. The filtrate was washed with several portions of DCM and EtOAc before acidification with conc. HCl. The formed precipitate was collected and washed with water to yield 1.37 g of the title compound as a white solid. 1H NMR (DMSO-d6) d (ppm): 13.94 (br. s, 1H), 9.37 (d, 1H), 9.07 (d, 1H), 8.01 (dd, 1H).

Example 101

5-Chloro-thiophene-3-carboxylic acid

Thiophene-3-carboxylic acid (17.51 g, 136.6 mmol) and 1-chloro-pyrrolidine-2,5-dione (23.7 g) was refluxed in acetic acid (200 ml) for 4 h under argon before pouring onto water (700 ml). Repeated extraction with several small portions of DCM, followed by back extraction from the combined organics with several small portions of 2 M aqueous sodium hydroxide, gave a combined alkaline aqueous solution that was washed with DCM before acidified with conc. HCl to precipitate the crude material. This precipitate was recrystallized from water to yield 14.98 g of the title compound as a grey solid contaminated with approximately 20 mol % of a dichlorinated byproduct as judged from MS and 1H-NMR. 1H NMR (DMSO-d6) d (ppm): 8.15 (d, 1H), 7.37 (d, 1H).

Example 102

3-Methylsulfanyl-benzoic acid

Methyl iodide (0.972 mL) was added to a mixture of 3-mercapto-benzoic acid (601 mg, 3.9 mmol) and potassium carbonate (2.7 g, 19.5 mmol) in DMF (8 mL) in an ice-bath. After the reaction was warmed to room temperature and stirred for 1 hour, the reaction mixture was diluted with ethyl acetate, washed with water (3×), dried over anhydrous sodium sulfate, filtered, and concentrated to afford 3-methylsulfanyl-benzoic acid methyl ester (684 mg, 96%, yellow oil). $^1$H NMR (CDCl$_3$), δ (ppm): 7.90 (s, 1H), 7.80 (d, 1H), 7.44 (d, 1H), 7.35 (t, 1H), 3.92 (s, 3H), 2.53 (s, 3H).

3-Methylsulfanyl-benzoic acid methyl ester (684 mg, 3.8 mmol) and 1N NaOH (5.6 mL, 5.6 mmol) in methanol (8 mL) and THF (8 mL) were heated at 70° C. for 1 hour. The reaction mixture was concentrated and then the residue was diluted with water. After acidification with 1N HCl to pH~2, the aqueous layer was extracted with ethyl acetate and then washed with water and saturated brine, dried over anhydrous sodium sulfate, filtered, and concentrated to afford 3-methylsulfanyl-benzoic acid (616 mg, 97%, white solid). $^1$H NMR (DMSO), δ (ppm): 13.1 (bs, 1H), 7.76 (s, 1H), 7.70 (d, 1H), 7.51 (d, 1H), 7.44 (t, 1H), 2.52 (s, 3H).

Example 103

3-Cyclopropyl-benzoic acid 1.0 M Diethyl zinc in hexanes (27.3 ml, 27.3 mmol) was added to a solution of 2,4,6-trichlorophenol (5.4 g, 27.3 mmol) in dichloromethane (100 ml) at −40° C. After stirring for 15 minutes, diiodo-methane (2.2 mL, 27.3 mmol) was added at −40° C. and stirred for an additional 15 minutes. 1-Bromo-3-vinyl-benzene (2.5 g, 13.7 mmol) was then added to the reaction mixture, allowed to warm to room temperature, and left stirring overnight. The reaction mixture was diluted with dichloromethane, washed with 1N HCl (2×), saturated sodium bicarbonate (2×), saturated sodium sulfite, 1N sodium hydroxide, and saturated brine, dried over magnesium sulfate, filtered and concentrated. GC-MS revealed that the reaction mixture contained 1-Bromo-3-cyclopropyl-benzene and 1-bromo-3-vinyl-benzene. To remove the bromo-3-vinyl-benzene, the crude mixture was reacted with potassium permanganate. A solution of potassium permanganate/water (1.5 g/20 mL) was added drop-wise to a solution of the crude mixture (~3.5 g) in THF (40 mL) at 0° C. and then allowed to warm to room temperature. After 1 hour, the reaction was diluted with diethyl ether, washed with water and saturated brine, dried over anhydrous sodium sulfate filtered and concentrated. Purication by flash column chromatography eluted with 100 hexanes afforded 1-bromo-3-cyclopropyl-benzene (2.20 g, 81%). 1.6 M n-Butyllithium in hexanes (3.2 mL, 5.1 mmol) was added drop-wise to a solution of 1-bromo-3-cyclopropyl-benzene at −78° C. and stirred for 1 hour. This reaction mixture was then transferred via canula to a 250 mL round bottom flask equipped with a stirrer bar approximately ¼ full of solid carbon dioxide and stirred and for 1 hour. The reaction mixture was concentrated and then the residue was diluted with water. The aqueous layer was washed with dichloromethane (3×), acidified with 1 N HCl to pH~2, and extracted with ethyl acetate. The organic phase was washed with water and saturated brine, dried over anhydrous sodium sulfate, filtered and concentrated to afford 3-cyclopropyl-benzoic (356 mg, 43%, white solid). $^1$H NMR (DMSO), δ (ppm): 12.90 (bs, 1H), 7.71 (d, 1H), 7.64 (s, 1H), 7.34 (m, 2H), 2.01 (m, 1H), 0.99 (m, 2H), 0.70 (m, 2H).

Example 104

3-tert-Butoxycarbonylamino-benzoic acid

To a flask containing ethyl-3-aminobenzoate (1 g, 6.05 mmol) added di-tert-butyl dicarbonate (3.16 g, 14.5 mmol), triethyl amine (500 mg, 4.94 mmol), and THF (10 mL) and allowed to stir at 60° C. for two hours and then overnight at room temperature. The THF was removed in vacuo, and the crude ester was partitioned between ethyl acetate and water, washed with saturated brine, dried over anhydrous sodium sulfate and the solvent was removed in vacuo. The product was then purified by flash column chromatography using 15% ethyl acetate in hexane affording 2 g of 3-tert-butoxycarbonylamino-benzoic aid ethyl ester (white slurry).

To the crude 3-tert-butoxycarbonylamino-benzoic acid ethyl ester (~2.0 g, 0.00754 mmol) added THF (15 mL), and 0.5M LiOH (15 mL). The mixture was heated for two hours at 75° C. and the THF was removed in vacuo after cooling. The precipitate was filtered from the remaining mixture and the filtrate was transferred to a separatory funnel. The aqueous layer was washed with dichloromethane (3×) and was acidified to pH~5 using 1M HCl. The product was then extracted with ethyl acetate, washed with water, saturated brine, dried over anhydrous sodium sulfate, filtered and concentrated. 730 mg of 3-tert-Butoxycarbonylamino-benzoic acid (white solid) was isolated. 1H NMR (DMSO-d$_6$) δ (ppm): 9.58 (s, 1H), 8.16 (s, 1H), 7.63 (d, 1H), 7.54 (d, 1H), 7.37 (t, 1H), 1.49 (s, 9H)

Example 105

3-Acetyl-benzoic acid

6M Sodium hydroxide (25 mL) was added to 3-acetylbenzonitrile (850 mg, 5.82 mmol) in methanol (25 mL) and then heated at 90° C. overnight. After concentrating the reaction mixture, the aqueous layer was washed with dichloromethane (2×), then acidified pH~3 with 12M HCl. The precipitate was extracted with ethyl acetate then washed with water and saturated brine, dried over anhydrous sodium sulfate filtered and concentrated to afford 3-ethylbenzoic acid as a colorless oil; 0.800 g (92%). 1H NMR (CDCl$_3$) δ (ppm): 8.70 (s, 2H), 8.33 (d, 2H), 8.24 (d, 2H), 7.64 (t, 1H), 2.70 (s, 3H).

Example 106

2-Methyl-isonicotinic acid hydrazide

Dichloromethane (10 mL) was added to 2-methyl nicotinic acid hydrochloride salt (1.1 g, 6.34 mmol) and oxalyl chloride (6.95 mL, 13.9 mmol) was added slowly under Argon while the flask was cooled in ice. Dimethylformamide (2 drops) was added and the reaction was allowed to stir overnight during which time it warmed to room temperature. The reaction was concentrated and THF (10 mL) was added to the flask and it was placed in an ice bath. Methanol (5 mL) was added and the reaction was allowed to stir for one hour. The reaction was concentrated and the residue was partitioned between NaHCO$_3$ (sat) and EtOAc. The product was extracted with EtOAc three times. The combined organic layers were washed with brine, dried over Na$_2$SO$_4$, filtered and concentrated. Purification was performed by solid phase extraction tube (20% EtOAc/hexanes) gave the title compound as a clear oil. $^1$H NMR CDCl$_3$ δ (ppm): 8.51 (d, 1H), 7.57 (d, 1H), 7.51 (d, 1H), 3.82 (s, 3H), 2.50 (s, 3H).

2-Methyl-isonicotinic acid methyl ester (316.5 mg, 2.093 mmol) was dissolved in MEOH (7 mL) under Argon and hydrazine monohydrate 98% (1 mL, 20.93 mmol) was added. The reaction was allowed to stir under Argon at room temperature for eighteen hours. The reaction was concentrated to give the title compound (271.9 mg, 86%) as a white solid. $^1$H NMR CDCl$_3$ δ (ppm): 8.59 (d, 1H), 7.50 (s, 1H), 7.38 (d, 1H), 3.09 (br. s, 3H), 2.60 (s, 3H).

Example 107

5-Chloro-2-fluoro-benzoic acid hydrazide

Step 1: 5-Chloro-2-fluoro-benzoic acid methyl ester: Methanol (20 ml) was added to a solution 5-chloro-2-fluoro-benzoyl chloride (1.2 g, 6.2 mmol) in dichloromethane (10 ml) in an ice-bath. The reaction mixture was warmed to room temperature, stirred for 3 h and then concentrated to afford 5-chloro-2-fluoro-benzoic acid methyl ester (1.17 g, 100%). 1H NMR (CDCl$_3$), δ (ppm): 7.93 (m, 1H), 7.48 (m, 1H), 7.12 (m, 1H), 3.96 (s, 3H). Step 2: 5-Chloro-2-fluoro-benzoic acid hydrazide: A mixture of 5-chloro-2-fluoro-benzoic acid methyl ester (1.17 g, 6.2 mmol) and hydrazine monohydrate (0.451 ml, 9.3 mmol) in ethanol (20 ml) was stirred at room temperature overnight. The reaction mixture was concentrated and then the residue was triturated with diethyl ether to afford 5-chloro-2-fluoro-benzoic acid hydrazide (497 mg, 42%, white solid). 1H NMR (DMSO), δ (ppm): 9.66 (bs, 1H), 7.58 (m, 2H), 7.36 (m, 1H), 4.58 (bs, 2H).

Example 108 was prepared analogously to example 107.

Example 108

3-Cyano-benzoic acid hydrazide 3-cyano-benzoyl chloride (3 g, 18.12 mmol) in dichlormethane (5 mL) and methanol (20 mL) was stirred at room temperature and overnight. The solvent was removed using a rotevaporator to afford a white solid (3.76 g). $^1$H NMR (DMSO) δ (ppm): 8.33 (m, 1H), 8.24 (m, 1H), 8.14 (m, 1H), 7.76 (m, 1H), 3.89 (d, 3H).

A mixture of 3-cyano-benzoic acid methyl ester (2 g, 12 mmol) and hydrazine monohydrate (0.60 mL, 12 mmol) in ethanol (10 mL) was stirred at room temperature overnight. The reaction mixture was concentrated and then the residue was triturated with diethyl ether to afford 3-cyano-benzoic acid hydrazide (1.02 g, 51%, pink solid). $^1$H NMR (DMSO) δ (ppm): 10.31 (s, 1H), 8.21 (m, 1H), 8.11 (m, 1H), 7.99 (m, 1H), 7.70 (m, 1H), 4.50 (s, 1H).

Example 109

2-Chloro-isonicotinic acid hydrazide

HOBt (823 mg, 6.09 mmol), and EDCI (1.2 g, 6.09 mmol) were added to a suspension of 2-chloro-isonicotinic acid (800 mg, 5.08 mmol) in acetonitrile (10.3 ml) at room temperature. After two h a solution of hydrazine monohydrate (0.493 ml, 10.2 mmol) in acetonitrile (5.0 ml) was added drop-wise at 0° C. After 30 min, the solvent was removed using a roto-evaporator and the residue was diluted with ethyl acetate, quenched with water, dried over sodium sulfate, filtered and concentrated to afford 2-chloro-isonicotinic acid hydrazide (493 mg, 57%, yellow solid). 1H NMR (DMSO) d (ppm): 10.21 (bs, 1H), 8.55 (d, 1H), 7.82 (s, 1H), 7.75 (d, 1H), 4.69 (bs, 2H).

The following compounds were prepared analogously to example 109:

| Example No. | Name |
|---|---|
| 110 | 2-Fluoro-5-methyl-benzoic acid hydrazide |
| 111 | Pyrimidine-4-carboxylic acid hydrazide |

The following compounds were prepared analogously to example 6:

| Example No. | Name |
|---|---|
| 112 | 3-Fluoro-N-hydroxy-benzamidine |
| 113 | N-Hydroxy-thiophene-3-carboxamidine |
| 114 | 2-Chloro-N-hydroxy-propionamidine |
| 115 | 3,N-Dihydroxy-benzamidine |
| 116 | N-Hydroxy-2-methyl-benzamidine |
| 117 | N-Hydroxy-2-(4-methyl-5-thiophen-2-yl-4H-[1,2,4]triazol-3-ylsulfanyl)-acetamidine |
| 118 | 3-Chloro-N-hydroxy-benzamidine |
| 119 | N-Hydroxy-2-(4-methyl-5-thiophen-2-yl-4H-[1,2,4]triazol-3-ylsulfanyl)-acetamidine |
| 120 | 2,5-Difluoro-N-hydroxy-benzamidine |

The following compounds were prepared analogously to example 31:

| Example No. | Name |
|---|---|
| 121 | 4-Methyl-5-pyridin-3-yl-4H-[1,2,4]triazole-3-thiol |
| 122 | 4-Butyl-5-thiophen-2-yl-4H-[1,2,4]triazole-3-thiol |
| 123 | 4-(3-Methoxy-propyl)-5-thiophen-2-yl-4H-[1,2,4]triazole-3-thiol |
| 124 | 4-Benzyl-5-thiophen-2-yl-4H-[1,2,4]triazole-3-thiol |
| 125 | 4-Furan-2-ylmethyl-5-thiophen-2-yl-4H-[1,2,4]triazole-3-thiol |
| 126 | 5-Thiophen-2-yl-4-thiophen-2-ylmethyl-4H-[1,2,4]triazole-3-thiol |
| 127 | 4-Ethyl-5-thiophen-2-yl-4H-[1,2,4]triazole-3-thiol |
| 128 | 4-Furan-2-ylmethyl-5-pyridin-4-yl-4H-[1,2,4]triazole-3-thiol |
| 129 | 4-Ethyl-5-pyridin-4-yl-4H-[1,2,4]triazole-3-thiol |
| 130 | 4-Ethyl-5-pyridin-3-yl-4H-[1,2,4]triazole-3-thiol |
| 131 | 4-Ethyl-5-thiophen-2-yl-4H-[1,2,4]triazole-3-thiol |
| 132 | 4-Furan-2-ylmethyl-5-pyridin-3-yl-4H-[1,2,4]triazole-3-thiol |
| 133 | 4-Ethyl-5-furan-2-yl-4H-[1,2,4]triazole-3-thiol |
| 134 | 4-Ethyl-5-(3-fluoro-phenyl)-4H-[1,2,4]triazole-3-thiol |
| 135 | 4-Ethyl-5-(4-fluoro-phenyl)-4H-[1,2,4]triazole-3-thiol |
| 136 | 5-(2-Fluoro-5-methyl-phenyl)-4-furan-2-ylmethyl-4H-[1,2,4]triazole-3-thiol |
| 137 | 4-Ethyl-5-(3-methyl-thiophen-2-yl)-4H-[1,2,4]triazole-3-thiol |
| 138 | 4-Ethyl-5-(5-methyl-thiophen-2-yl)-4H-[1,2,4]triazole-3-thiol |
| 139 | 5-(2-Chloro-6-methyl-pyridin-4-yl)-4-ethyl-4H-[1,2,4]triazole-3-thiol |
| 140 | 5-(5-Bromo-furan-2-yl)-4-ethyl-4H-[1,2,4]triazole-3-thiol |
| 141 | 4-Ethyl-5-(3-methoxy-thiophen-2-yl)-4H-[1,2,4]triazole-3-thiol |
| 142 | 4-Ethyl-5-(tetrahydro-furan-2-yl)-2,4-dihydro-[1,2,4]triazole-3-thione |
| 143 | 4-Ethyl-5-thioxo-4,5-dihydro-1H-[1,2,4]triazole-3-carboxylic acid methyl ester |

The following compounds were prepared analogously to example 36:

| Example No. | Name |
|---|---|
| 144 | 5-(2-Chloro-pyridin-4-yl)-4-ethyl-4H-[1,2,4]triazole-3-thiol |
| 145 | 5-(2-Chloro-6-methoxy-pyridin-4-yl)-4-ethyl-4H-[1,2,4]triazole-3-thiol |
| 146 | 4-Ethyl-5-(3-methyl-3H-imidazol-4-yl)-4H-[1,2,4]triazole-3-thiol |
| 147 | 4-Propyl-5-pyridin-4-yl-4H-[1,2,4]triazole-3-thiol |
| 148 | 4-Ethyl-5-(1-methyl-1H-imidazol-2-yl)-4H-[1,2,4]triazole-3-thiol |
| 149 | 4-Ethyl-5-(1-methyl-1H-imidazol-4-yl)-4H-[1,2,4]triazole-3-thiol |
| 150 | 3-(5-Mercapto-4-methyl-4H-[1,2,4]triazol-3-yl)-benzonitrile |
| 151 | 5-(3-Chloro-phenyl)-4-methyl-4H-[1,2,4]triazole-3-thiol |
| 152 | 5-(4-Chloro-phenyl)-4-methyl-4H-[1,2,4]triazole-3-thiol |
| 153 | 5-(2-fluoro-phenyl)-4-methyl-4H-[1,2,4]triazole-3-thiol |
| 154 | 5-(3-fluoro-phenyl)-4-methyl-4H-[1,2,4]triazole-3-thiol |
| 155 | 5-(4-fluoro-phenyl)-4-methyl-4H-[1,2,4]triazole-3-thiol |
| 156 | 5-Benzo[b]thiophen-2-yl-4-methyl-4H-[1,2,4]triazole-3-thiol |
| 157 | 5-(3-methoxy-phenyl)-4-methyl-4H-[1,2,4]triazole-3-thiol |
| 158 | 5-(4-methoxy-phenyl)-4-methyl-4H-[1,2,4]triazole-3-thiol |
| 159 | 4-Ethyl-5-(4-methoxy-phenyl)-4H-[1,2,4]triazole-3-thiol |
| 160 | 5-(3,5-Difluoro-phenyl)-4-ethyl-4H-[1,2,4]triazole-3-thiol |
| 161 | 5-(2,6-Difluoro-phenyl)-4-ethyl-4H-[1,2,4]triazole-3-thiol |
| 162 | 5-(4-Butoxy-phenyl)-4-ethyl-4H-[1,2,4]triazole-3-thiol |
| 163 | 5-Benzo[1,3]dioxol-5-yl-4-ethyl-4H-[1,2,4]triazole-3-thiol |
| 164 | 4-Ethyl-5-pyrimidin-5-yl-2,4-dihydro-[1,2,4]triazole-3-thione |
| 165 | 4-Ethyl-5-furan-3-yl-2,4-dihydro-[1,2,4]triazole-3-thione |
| 166 | 4-(Tetrahydrofuran-2-ylmethyl)-5-thiophene-2-yl-2,4-dihydro-[1,2,4]triazole-3-thione |
| 167 | 5-Cyclopentyl-4-ethyl-2,4-dihydro-[1,2,4]triazole-3-thione |
| 168 | 4-Ethyl-5-[2-(4-methoxy-phenyl)-ethyl]-2,4-dihydro-[1,2,4]triazole-3-thione |

Example 169

5-(3,5-Dichloro-phenyl)-4-ethyl-4H-[1,2,4]triazole-3-thiol 3,5-Dichloro-benzoic acid (382 mg, 2 mmol) was mixed with triethylamine (606 mg, 3 mmol) in THF (6 ml) at 10° C. Then isobutyl chloroformate (300 mg, 2.2 mmol) was added dropwise and stirred for 45 min. To the reaction mixture, 4-methyl-3-thiosemicarbazide (238.4 mg, 2 mmol) was added. After being stirred at room temperature for 10 min, the reaction mixture was heated to 70° C. overnight. Standard work-up. The product was purified by column chromatography with 25~30% ethyl acetate in hexanes to give 46.4 mg (8.5%) of 5-(3,5-dichloro-phenyl)-4-ethyl-4H-[1,2,4]triazole-3-thiol.

The following compounds were prepared analogously to Example 169:

| Example No. | Name |
|---|---|
| 170 | 5-(3-Methylphenyl)-4-ethyl-4H-[1,2,4]triazole-3-thiol |
| 171 | 5-(4-Methylphenyl)-4-ethyl-4H-[1,2,4]triazole-3-thiol |
| 172 | 4-Ethyl-5-(3-nitrophenyl)-4H-[1,2,4]triazole-3-thiol |
| 173 | 5-(2,5-Difluorophenyl)-4-ethyl-4H-[1,2,4]triazole-3-thiol |
| 174 | 5-(3-Chlorophenyl)-4-ethyl-4H-[1,2,4]triazole-3-thiol |
| 175 | 5-(4-Chlorophenyl)-4-ethyl-4H-[1,2,4]triazole-3-thiol |

Example 176

4-Ethyl-5-methoxymethyl-2,4-dihydro-[1,2,4]triazole-3-thione

Step 1: N-Ethyl-2-(methoxyacetyl)hydrazinecarbothioamide: Methoxyacetic acid (360 mg, 3.99 mol), 4-ethyl-3-thiosemicarbazide (581 mg, 4.87 mmol), diisopropylcarbodiimide (615 mg, 4.87 mmol) and hydroxybenzotriazole (69.6 mg, 0.51 mmol) were mixed in dimethylformamide (10 ml) and stirred under argon at ambient temperatures for 19 h. After evaporation to dryness the crude was used directly in the next step. MS (ESI) m/z 192 (M+1). Step 2: 4-Ethyl-5-methoxymethyl-2,4-dihydro-[1,2,4]triazole-3-thione: N-Ethyl-2-(methoxyacetyl)hydrazinecarbothioamide (760 mg crude, 4 mmol) and sodium bicarbonate (560 mg, 6.6 mmol) were suspended in water (15 ml) and refluxed for 5 h. After cooling and filtration the filtrate was acidified with concentrated hydrochloric acid, followed by extraction with ethyl acetate. After evaporation to dryness the crude was recrystallized in ethyl acetate/heptane. Filtration and recrystallization of the mother liquor gave a combined yield of 325 mg (47%) of the title compound. 1H NMR (CDCl$_3$), δ (ppm): 4.47 (s, 2H), 4.13 (q, 2H), 3.37 (s, 3H), 1.38 (t, 3H).

The following compounds were prepared analogously to Example 176:

| Example No. | Name |
|---|---|
| 177 | 4-Methyl-5-pyridin-4-yl-2,4-dihydro-[1,2,4]triazole-3-thione |
| 178 | 4-Allyl-5-furan-2-yl-2,4-dihydro-[1,2,4]triazole-3-thione |
| 179 | 4-Ethyl-5-(4-methoxy-phenoxymethyl)-2,4-dihydro-[1,2,4]triazole-3-thione |
| 180 | 4-Ethyl-5-phenoxymethyl-2,4-dihydro-[1,2,4]triazole-3-thione |
| 181 | 4-Ethyl-5-hydroxymethyl-2,4-dihydro-[1,2,4]triazole-3-thione |
| 182 | 4-Ethyl-5-(2-methoxy-ethyl)-2,4-dihydro-[1,2,4]triazole-3-thione |
| 183 | 4-Ethyl-5-methylsulfanylmethyl-2,4-dihydro-[1,2,4]triazole-3-thione |
| 184 | 5-Ethoxymethyl-4-ethyl-2,4-dihydro-[1,2,4]triazole-3-thione |
| 185 | 5-Furan-3-yl-4-methyl-2,4-dihydro-[1,2,4]triazole-3-thione |
| 186 | 4-Methyl-5-pyrimidin-4-yl-2,4-dihydro-[1,2,4]triazole-3-thione |
| 187 | 4-Ethyl-5-pyridazin-4-yl-2,4-dihydro-[1,2,4]triazole-3-thione |
| 188 | 4-Ethyl-5-pyridin-4-ylmethyl-2,4-dihydro-[1,2,4]triazole-3-thione |
| 189 | 4-Ethyl-5-(6-hydroxy-pyridin-3-yl)-2,4-dihydro-[1,2,4]triazole-3-thione |
| 190 | 4-Ethyl-5-(4-hydroxy-phenyl)-2,4-dihydro-[1,2,4]triazole-3-thione |
| 191 | 4-Ethyl-5-p-tolyloxymethyl-2,4-dihydro-[1,2,4]triazole-3-thione |
| 192 | 4-Ethyl-5-(6-methoxy-pyridin-3-yl)-2,4-dihydro-[1,2,4]triazole-3-thione |
| 193 | 4-Ethyl-5-(2-methoxy-pyridin-4-yl)-2,4-dihydro-[1,2,4]triazole-3-thione |
| 194 | 4-Ethyl-5-pyrimidin-2-yl-2,4-dihydro-[1,2,4]triazole-3-thione |
| 195 | 4-Ethyl-5-(5-methoxy-pyrimidin-2-yl)-2,4-dihydro-[1,2,4]triazole-3-thione |

Example 196

4-Furan-2-ylmethyl-4H-[1,2,4]triazole-3-thiol

A solution of formic acid hydrazide (439 mg, 7.809 mmol) in pyridine (20 ml) was added to a solution of 2-isothiocyanatomethyl-furan (1 g, 7.185 mmol) in pyridine (20 ml). Reaction took place at room temperature overnight, and ethanol (20 ml) was added directly to the reaction and placed in 80 C bath overnight. Solvent was evaporated and the title compound (1.09 g, 83%) was obtained from purification by SPE chromatography on silica gel with 500 ml 20%, 250 ml 25%, 250 ml 30%, 250 ml 35%, 250 ml 40%, and 250 ml 50% ethyl acetate in hexanes. 1H NMR (CD3OD), δ (ppm): 14.0 (bs, 1H), 8.19 (s, 1H), 7.52 (q, 1H), 6.52 (m, 1H), 6.42 (m, 1H), 4.90 (s, 2H).

The following compounds were prepared analogously to Example 196:

| Example No. | Name |
|---|---|
| 197 | 4-Cyclopropyl-5-pyridin-4-yl-4H-[1,2,4]triazole-3-thiol |
| 198 | 4-Cyclopropylmethyl-5-pyridin-4-yl-4H-[1,2,4]triazole-3-thiol |

Example 199

4-Cyclopropyl-5-thiophen-2-yl-2,4-dihydro[1,2,4]triazole-3-thione

To a slurry of thiophene-2-carboxylic acid hydrazide (866 mg, 6.09 mmol) in iPrOH (25 ml) was added isothiocyanatocyclopropane (602 mg, 6.08 mmol). The mixture was stirred at 70° C. for 72 h and then cooled to room temperature. The white precipitate was filtered off and suspended in a MeOH:H$_2$O (9:1, 40 ml) together with aq. NaOH (2%, 5 ml). The reaction mixture was stirred at 70° C. overnight and then cooled to room temperature. The pH was adjusted to around 4 with aq. HCl (1N). The formed white precipitate was filtered off, washed with water and dried under vacuum (829 mg, 61%). 1H NMR (CD3OD), δ (ppm): 7.67 (dd, 1H), 7.63 (dd, 1H), 7.17 (dd, 1H), 3.15 (m, 1H), 1.14 (m, 2H), 0.86 (m, 2H).

The following compounds were prepared analogously to Example 199:

| Example No. | Name |
| --- | --- |
| 200 | 5-Furan-2-yl-4-(2-methoxy-ethyl)-2,4-dihydro-[1,2,4]triazole-3-thione |
| 201 | 4-Cyclopropyl-5-furan-2-yl-2,4-dihydro-[1,2,4]triazole-3-thione |
| 202 | (3-Thiophen-2-yl-5-thioxo-1,5-dihydro-[1,2,4]triazol-4-yl)-acetic acid methyl ester |
| 203 | 4-Cyclopropylmethyl-5-thiophene-2-yl-2,4-dihydro-[1,2,4]triazole-3-thione |
| 204 | 4-(2-Methoxy-ethyl)-5-thiophen-2-yl-2,4-dihydro-[1,2,4]triazole-3-thione |
| 205 | Thiophen-2-yl-4-(2,2,2-trifluoroethyl)-2,4-dihydro-[1,2,4]triazole-3-thione |
| 206 | 4-Cyclopropyl-5-pyrimidin-4-yl-2,4-dihydro-[1,2,4]triazole-3-thione |
| 207 | 4-Cyclopropyl-5-pyridin-3-yl-2,4-dihydro-[1,2,4]triazole-3-thione |

Example 208

4-Ethyl-5-trifluoromethyl-4H-[1,2,4]triazole-3-thiol

To a solution of 4-ethyl-3-thiosemicarbazide(2.38 g, 20 mmol) and triethylamine (6.06 g, 60 mmol) in THF (30 ml), trifluoroacetic anhydride (5.04 g, 24 mmol) was added. The reaction mixture was stirred at room temperature for an h and and heated at 60° C. overnight. Standard work-up, the product was triturated with hexanes to give 564 g of as 4-ethyl-5-trifluoromethyl-4H-[1,2,4]triazole-3-thiol pale-brown solid. 1H-NMR(CDCl3) d(ppm): 12.64 (w, 1H), 4.22 (q, 2H) and 1.44 (t, 3H).

Example 209

4-Ethyl-3-methanesulfonyl-5-thiophen-2-yl-4H-[1,2,4]triazole

The title compound was synthesized according to the method described in Åkerblom et al. J. Med. Chem. 16, 312 (1973). 4-Ethyl-3-methylsulfanyl-5-thiophen-2-yl-4H-[1,2,3]triazole (1.14 g, 5.06 mmol) was dissolved in glacial acetic acid (20 ml) followed by the addition of 30% hydrogen peroxide (5 ml). After stirring at ambient temperatures for 16 h additional 30% hydrogen peroxide (5 ml) was added. The mixture was stirred for 3 h at ambient temperature, then heated to 100° C. for 2.5 h. After cooling in an ice/water bath the reaction was neutralized with sodium hydroxide and extracted twice with dichloromethane. The organic layers were combined, evaporated to dryness and dried in vacuo yielding the title compound (0.78 g, 60%). 1H NMR (CDCl3), δ (ppm): 7.60 (d, 1H), 7.56 (d, 1H), 7.22 (m, 1H), 4.51 (q, 2H), 3.58 (s, 3H), 1.55 (t, 3H).

The following compound was prepared analogously to Example 209:

| Example No. | Name |
| --- | --- |
| 210 | 4-(5-Methanesulfonyl-4-methyl-4H-[1,2,4]triazol-3-yl)-pyridine |

Example 211

4-(2-Hydroxy-ethyl)-5-thiophen-2-yl-2,4-dihydro-[1,2,4]triazole-3-thione

To a slurry of LAH (38.1 mg, 1.00 mmol) in anhydrous THF (8 ml) was drop wise added (3-thiophen-2-yl-5-thioxo-1,5-dihydro-[1,2,4]triazol-4-yl)-acetic acid (101 mg, 0.42 mmol) in anhydrous THF (4 ml). The mixture was reacted for 2 h and then quenched with saturated aq. $Na_2SO_4$ (10 ml). THF was removed under reduced pressure and the residue was made acidic with aq. HCl (3N) and partitioned between EtOAc and water. The aqueous layer was extracted with EtOAc (3×20 ml). The combined organic layers were washed with brine (15 ml), dried ($MgSO_4$) and concentrated under reduced pressure. The crude product was used without purification in the next step. 1H NMR (DMSO-d6), δ (ppm): 13.94 (s, 1H), 7.86 (d, 1H); 7.81 (d, 1H), 7.24 (dd, 1H), 5.09 (t, 1H), 4.16 (t, 2H), 3.76 (app. q, 2H).

Example 212

4-(4,5-Dimethyl-4H-[1,2,4]triazol-3-yl)-pyridine

860 μl (10 mmol) oxalyl chloride was slowly added to a solution of 731 mg (10 mmol) N-methyl-acetamide and 2.33 ml (20 mmol) 2,6-lutidine in 20 ml $CH_2Cl_2$ at 0° C. After 15 min 1.37 g (10 mmol) isonicotinic acid hydrazide was added in one portion. The resulting mixture was stirred at room temperature for 1 h and the neutralized with $NaHCO_3$(sat). The phases were separated and the water phase was extracted with $CH_2Cl_2$. The combined organic phases were dried and concentrated. The residue was dissolve in 20 ml acetic acid and heated at 120° C. for 2 h. After cooling the solvent was removed. Flashchromatography (CH2Cl2/MeOH 10:1) afforded 765 mg (44%) of a grey/white solid. 1H NMR (CDCl3), d (ppm): 2.52 (s, 3 H) 3.66 (s, 3 H) 7.58 (d, 2 H) 8.76 (d, 2 H).

Example 213

Methyl-(4-methyl-5-pyridin-4-yl-4H-[1,2,4]triazol-3-yl)-amine

A mixture of 1000 mg (4.35 mmol) N-amino-N', N"-dimethyl-guanidine hydriodide (Henry; Smith; J. Amer. Chem. Soc.; 73; 1951; 1858) and 774 mg (4.35 mmol) isonicotinoyl chloride hydrochloride in 3 ml of pyridine was heated with microwaves for 5 min at 160° C. $K_2CO_3$(sat) was added and the mixture was extracted 4 times with $CHCl_3$. The organic phase was dried and concentrated. Recrystallization from ethanol, water and EtOAc gave 216 mg (26%) of a yellow white solid. 1H NMR (DMSO), d (ppm): 2.85 (d, 3 H) 3.45 (s, 3 H) 6.25 (d, 1 H) 7.65 (m, 2 H) 8.67 (m, 2 H).

Example 214

3-Pyridin-4-yl-5,6,7,8-tetrahydro-[1,2,4]triazolo[4,3-a]pyrimidine

A solution of 750 mg (3.1 mmol) (1,4,5,6-tetrahydro-pyrimidin-2-yl)-hydrazine hydroiodide (ref. Krezel, Izabella; Pharmazie; EN; 49; 1; 1994; 27-31) and 552 mg (3.1 mmol) isonicotinoyl chloride hydrochloride in 3 ml pyridine was heated at 120° C. over night. The reaction mixture was cooled and diluted with $K_2CO_3$(sat) and extracted with 3×10 ml chloroform. The combined organic extracts were dried and concentrated. Flashchromatography ($CH_2Cl_2$/MeOH 10:1) afforded 83 mg (18%) of a white solid. 1H NMR ($CDCl_3$), d (ppm): 1.91 (m, 2 H) 3.24 (m, 2 H) 4.13 (m, 2 H) 7.67 (m, 2 H) 8.65 (m, 2 H).

The following compound was prepared analogously to Example 214:

| Example No. | Name |
|---|---|
| 215 | 3-Furan-2-yl-5,6,7,8-tetrahydro-[1,2,4]triazolo[4,3-a]pyrimidine |

Example 216

4-Ethyl-5-(6-methoxy-pyridazin-3-yl)-2,4-dihydro-[1,2,4]triazole-3-thione

Step 1: 6-Chloro-pyridazine-3-carboxylic acid: Potassium dichromate (3.3 g, 11.2 mmol) was added in portions to a solution of 3-Chloro-6-methyl-pyridazine (1.2 g, 9.3 mmol) in $H_2SO_4$ (10 ml). After addition the mixture is stirred at 50° C. on. The reaction was pored on ice and the mixture was extracted three times with diethyl ether. The combined organic phases were dried and concentrated to give the title compound (840 mg, 57%). LC-MS (M++1): 159 and 161 (3:1). Step 2: 6-Chloro-pyridazine-3-carboxylic acid methyl ester: A solution of 6-chloro-pyridazine-3-carboxylic acid (700 mg, 4.53 mmol) in thionyl chloride (15 ml) was refluxed for 3 h. The reaction was cooled to ambient temperature and evaporated to dryness. Sodium methoxide (244 mg, 4.53 mmol) in MeOH (20 ml) was added to the residue and the solution was stirred on at room temperature (rt). $H_2O$ was added and the mixture was extracted three times with DCM. The combined organic phases were dried and concentrated. Flashchromatography ($SiO_2$, Heptane/EtOAc 1:1) afforded 560 mg (72%) of the title compound. 1H NMR ($CDCl_3$), δ (ppm): 4.09 (s, 3 H), 7.69 (d, 1 H), 8.18 (d, 1 H).LC-MS (M++1): 173 and 175 (3:1). Step 3: 6-Methoxy-pyridazine-3-carboxylic acid methyl ester: A solution of 6-chloro-pyridazine-3-carboxylic acid methyl ester in NaOMe in MeOH (1M, 10 ml) was refluxed on. $H_2O$ was added and the mixture was extracted three times with DCM to give organic phase I. The combined organic phases I were dried and concentrated to give the title compound (40 mg, 10%). The water phase was acidified with concentrated hydrochloric acid and extracted three times with DCM to give organic phase II. The combined organic phases II were dried and concentrated to give 6-methoxy-pyridazine-3-carboxylic acid (LC-MS (M++1): 155) (230 mg, 65%). A solution of 6-methoxy-pyridazine-3-carboxylic acid in thionyl chloride (6 ml) was refluxed for 3 h. The reaction was cooled to ambient temperature and evaporated to dryness. MeOH (10 ml) was added to the residue and the solution was stirred on at rt. Saturated $NaHCO_3$ (aq) was added and the mixture was extracted three times with DCM. The combined organic phases were dried and concentrated to give the title compound (253 mg, 100%). LC-MS (M++1): 169. Step 4: 4-Ethyl-5-(6-methoxy-pyridazin-3-yl)-2,4-dihydro-[1,2,4]triazole-3-thione: NaOMe (86 mg, 1.6 mmol) was added to a solution of 6-methoxy-pyridazine-3-carboxylic acid methyl ester (210 mg, 1.25 mmol) and 4-ethyl-3-thiosemicarbazide (190 mg, 1.6 mmol) in MeOH (6 ml) and the mixture was heated to 70° C. at 72 h. The reaction was cooled to ambient temperature and evaporated to dryness. $H_2O$ (10 ml) was added to the residue and the mixture was acidified with concentrated hydrochloric acid and the title compound 35 mg (12%) was collected by filtration. LC-MS (M++1): 238.

Example 217

4-Ethyl-5-(5-methoxy-pyridin-2-yl)-2,4-dihydro-[1,2,4]triazole-3-thione

Step 1: 5-Methoxy-pyridine-2-carboxylic acid methyl ester: 5-Methoxy-2-methyl-pyridine (700 mg, 5.69 mmol) was dissolved in $H_2O$ (20 ml) and heated to 80° C. $KMnO_4$ (4 g, 25.3 mmol) was added in portion to the solution over 1 h. After stirring at 80° C. for 5 h the mixture was filtrated and the filtrate was washed with $H_2O$ (60° C.). The combined water phase was concentrated. DMF (20 ml), $K_2CO_3$ (785 mg, 5.7 mmol) followed by MeI (540 ml, 8.6 mmol) was added to the remaining residue and the mixture was heated to 80° C. on. The reaction was cooled to ambient temperature and $H_2O$ was added and the mixture was extracted three times with toluene. The combined organic phases were dried and concentrated. Flashchromatography ($SiO_2$, Heptane/EtOAc 1:1) afforded 210 mg (22%) of the title compound. 1H NMR ($CDCl_3$): d ppm 3.93 (s, 3 H) 4.00 (s, 3 H) 7.23 (m, 1 H) 8.13 (d, 1 H) 8.40 (d, 1 H). Step 2: 4-Ethyl-5-(5-methoxy-pyridin-2-yl)-2,4-dihydro-[1,2,4]triazole-3-thione: NaOMe (4 ml, 4.0 mmol, 1M) was added to a solution of 5-Methoxy-pyridine-2-carboxylic acid methyl ester (200 mg, 1.2 mmol), 4-ethyl-3-thiosemicarbazide (145 mg, 1.2 mmol) in MeOH (10 ml) and the mixture was heated to 70° C. on. The reaction was cooled to ambient temperature and evaporated to dryness. $H_2O$ (10 ml) was added to the residue and the mixture was acidified with concentrated hydrochloric acid and the title compound 50 mg (18%) was collected by filtration. LC-MS (M++1): 237.

The following compounds were prepared analogously to example 10:

| Example No. | Name |
|---|---|
| 218 | 5-Chloromethyl-3-phenyl-[1,2,4]oxadiazole |
| 219 | 5-Chloromethyl-3-(3-fluoro-phenyl)-[1,2,4]oxadiazole |
| 220 | 5-Chloromethyl-3-(2-fluoro-5-methyl-phenyl)-[1,2,4]oxadiazole |
| 221 | 5-Chloromethyl-3-thiophen-2-yl-[1,2,4]oxadiazole |
| 222 | 5-Chloromethyl-3-thiophen-3-yl-[1,2,4]oxadiazole |
| 223 | 3-(5-Chloromethyl-[1,2,4]oxadiazol-3-yl)-phenol |
| 224 | 5-Chloromethyl-3-o-tolyl-[1,2,4]oxadiazole |
| 225 | 5-Chloromethyl-3-(3-chloro-phenyl)-[1,2,4]oxadiazole |
| 226 | 5-Chloromethyl-3-(2,5-difluoro-phenyl)-[1,2,4]oxadiazole |

The following compounds were prepared analogously to example 16:

| Example No. | Name |
|---|---|
| 227 | 3-(3-Chloromethyl-[1,2,4]oxadiazol-5-yl)-benzonitrile |
| 228 | 2-Chloro-4-(3-chloromethyl-[1,2,4]oxadiazol-5-yl)-pyridine |
| 229 | 3-Chloromethyl-5-(2,5-dimethyl-phenyl)-[1,2,4]oxadiazole |
| 230 | 3-Chloromethyl-5-(2-fluoro-5-methyl-phenyl)-[1,2,4]oxadiazole |
| 231 | 3-Chloromethyl-5-(2,5-dichloro-phenyl)-[1,2,4]oxadiazole |
| 232 | 3-Chloromethyl-5-(2-fluoro-5-bromo-phenyl)-[1,2,4]oxadiazole |
| 233 | 3-Chloromethyl-5-(3-methyl-phenyl)-[1,2,4]oxadiazole |
| 234 | 3-Chloromethyl-5-(2,5-difluoro-phenyl)-[1,2,4]oxadiazole |
| 235 | 3-Chloromethyl-5-(3-methylsulfanyl-phenyl)-[1,2,4]oxadiazole |
| 236 | 3-Chloromethyl-5-(3-cyclopropyl-phenyl)-[1,2,4]oxadiazole |
| 237 | 3-(3-Chloromethyl-[1,2,4]oxadiazol-5-yl)-phenyl]-carbamic acid tert-butyl ester |
| 238 | 1-[3-(3-Chloromethyl-[1,2,4]oxadiazol-5-yl)-phenyl]-ethanone |
| 239 | 5-(5-Chloro-2-fluoro-phenyl)-3-chloromethyl-[1,2,4]oxadiazole |
| 240 | 2-(3-Chloromethyl-[1,2,4]oxadiazol-5-yl)-4-methyl-phenol |

Example 241

3-Chloromethyl-5-(2-chloro-5-methyl-phenyl)-[1,2,4]oxadiazole

2-Chloro-5-methyl-benzoic acid (1 g, 5.8 mmol) was treated with 5 ml thionyl chloride at reflux for two h. Excess thionyl chloride was removed under reduced pressure. The residue was added to a suspension of 2-chloro-N-hydroxy-acetamidine (638 mg, 5.8 mmol) in dichloromethane (10 ml) at room temperature. After stirring for 30 min, triethylamine (2.04 ml, 14.6 mmol) was added and stirred for an additional h. The reaction mixture was diluted with ethyl acetate, washed with water and brine, dried over anhydrous sodium sulfate, filtered and concentrated. Flash column chromatography using 10-20% ethyl acetate in hexanes afforded 460 mg of the acyclic ester intermediate. DMF was added to this intermediate and then heated at 135° C. for 4 h to effect cyclization to oxadiazole. After cooling the reaction mixture was washed with water (3 times) and brine, dried over anhydrous sodium sulfate, filtered, and concentrated. Purification by flash column chromatography on silica gel using 5% ethyl acetate in hexanes afforded the title compound 160 mg (12% over 2 steps) as a white solid. m/z 244 (GCMS).

The following compounds were prepared analogously to Example 241:

| Example No. | Name |
|---|---|
| 242 | 3-Chloromethyl-5-(2,5-dichloro-thiophen-3-yl)-[1,2,4]oxadiazole |
| 243 | 3-(3-Chloromethyl-[1,2,4]oxadiazol-5-yl)-benzonitrile |
| 244 | 3-Chloromethyl-5-(3-fluoro-phenyl)-[1,2,4]oxadiazole |
| 245 | 3-Chloromethyl-5-(2-methyl-thiazol-4-yl)-[1,2,4]oxadiazole |
| 246 | 3-Chloromethyl-5-(4-fluoro-phenyl)-[1,2,4]oxadiazole |
| 247 | 5-(5-Bromo-2-fluoro-phenyl)-3-chloromethyl-[1,2,4]oxadiazole |
| 248 | 3-Chloromethyl-5-(4-methyl-thiophen-2-yl)-[1,2,4]oxadiazole |
| 249 | 5-(3-chloromethyl-[1,2,4]oxadiazol-5-yl)-thiophene-3-carbonitrile |
| 250 | 2-(3-Chloromethyl-[1,2,4]oxadiazol-5-yl)-4-methyl-benzonitrile |
| 251 | 3-(3-Chloromethyl-[1,2,4]oxadiazol-5-yl)-5-fluoro-benzonitrile |
| 252 | 3-(3-Chloromethyl-[1,2,4]oxadiazol-5-yl)-4-fluoro-benzonitrile |
| 253 | 4-Chloro-2-(3-chloromethyl-[1,2,4]oxadiazol-5-yl)-phenol |
| 254 | 3-(1-Chloro-ethyl)-5-(3-chloro-phenyl)-[1,2,4]oxadiazole |
| 255 | 3-(1-Chloro-ethyl)-5-(3-fluoro-phenyl)-[1,2,4]oxadiazole |
| 256 | 3-(1-Chloro-ethyl)-5-(5-chloro-2-fluoro-phenyl)-[1,2,4]oxadiazole |

Example 257

[3-(3-Chloromethyl-[1,2,4]oxadiazol-5-yl)-phenyl]-methanol

3-Hydroxymethylbenzoic acid, described in Reed, G. A.; Dimmel, D. R.; Malcolm, E. W. J. Org. Chem. 1993, 58 (23), 6372-6376, (175 mg, 1.15 mmol), 2-chloro-N-hydroxy-acetamidine (125 mg, 1.15 mmol) and HBTU was dissolved in anhydrous DMF (4 ml). Triethylamine (0.48 ml, 3.5 mmol) was added and the reaction was stirred at ambient temperature over night. The crude product was partitioned between dichloromethane and NaHCO$_3$ (aq), the organic phase was dried (MgSO$_4$) and the dichloromethane was removed in vacuo. The resulting DMF-solution was heated at 120° C. over night. The reaction mixture was concentrated in vacuo and the title compound (64 mg, 25%) was isolated by flash chromatography using 25-50% ethyl acetate in heptane. 1H NMR (CDCl3), δ (ppm): 8.15 (s, 1H), 8.06 (d, 1H), 7.62 (d, 1H), 7.53 (t, 1H); 4.80 (d, 2H), 4.66 (s, 1H); 1.99 (br. t, 1H).

The following compounds were prepared analogously to Example 257:

| Example No. | Name |
|---|---|
| 258 | 3-Chloromethyl-5-[1-(toluene-4-sulfonyl)-1H-pyrrol-3-yl]-[1,2,4]oxadiazole |
| 259 | 3-Chloromethyl-5-furan-3-yl-[1,2,4]oxadiazole |
| 260 | 3-Chloromethyl-5-(5-chloro-thiophen-2-yl)-[1,2,4]oxadiazole |

Example 261

1-[5-(3-Chloro-phenyl)-[1,3,4]oxadiazol-2-yl]-ethanol

Step 1: 1-{1-[5-(3-Chloro-phenyl)-[1,3,4]oxadiazol-2-yl]-ethoxy}-1H-benzotriazole: 2-(1-Chloro-ethyl)-5-(3-chloro-phenyl)-[1,3,4]oxadiazole (109 mg, 0.45 mmol), hydroxy-benzotriazole (76.4 mg, 0.56 mmol) and potassium iodide (23.0 mg, 0.14 mmol) were dissolved in DMF (2.5 ml), followed by the addition of potassium carbonate (74.0 mg, 0.53 mmol). After stirring under argon at ambient temperatures for 24 h the reaction mixture was diluted with ethyl acetate and washed with 2N ammonium chloride solution. After reextraction of the aqueous layer with ethyl acetate, the combined organic layers were washed with brine and evaporated to dryness. Column chromatography over 12 g silica using heptane/ethyl acetate=4/1 gave after drying in vacuo the title compound (129 mg, 84%). 1H NMR (CDCl$_3$), δ (ppm): 7.94 (d, 1 H), 7.82 (m, 1 H), 7.76 (m, 1 H), 7.46 (m, 1 H), 7.39-7.27

(m, 4 H), 5.98 (q, 1 H), 2.04 (d, 3 H). Step 2: 1-[5-(3-Chlorophenyl)-[1,3,4]oxadiazol-2-yl]-ethanol: 1-{1-[5-(3-Chlorophenyl)-[1,3,4]oxadiazol-2-yl]-ethoxy}-1H-benzotriazole (58.4 mg, 0.17 mmol) was dissolved under argon in dry THF (3 ml). To this mixture a 0.1 molar solution of samarium diiodide in THF (5 ml, 0.5 mmol) was slowly added over 20 min. After stirring for 80 min additional samarium diioide solution (4 ml, 0.4 mmol) was added during 5 min. The reaction mixture was quenched after further 15 min of stirring with aqueous $Na_2S_2O_3$, diluted with diethyl ether and washed with 1 molare aqueous hydrochloric acid, dried over sodium sulfate and evaporated to dryness. After drying in vacuo crude title compound was obtained (36.0 mg, 92%) which was used in the next step without further purification. 1H NMR ($CDCl_3$), δ (ppm): 7.98-7.75 (m, 2 H), 7.50-7.38 (m, 2 H), 5.25 (q, 1 H), 1.74 (d, 3 H).

The following compounds were prepared analogously to Example 261:

| Example No. | Name |
|---|---|
| 262 | [5-(5-Chloro-2-fluoro-phenyl)-[1,2,4]oxadiazol-3-yl]-methanol |

Example 263

1-[5-(3-Chloro-phenyl)-[1,2,4]oxadiazol-3-yl]-ethanol

To a solution of 3.19 g (30.6 mmol) 2,N-dihydroxy-propionamidine in 25 ml pyridine was added 4.3 ml (33.7 mmol) 3-chloro-benzoyl chloride at 0° C. Cooling was removed and the mixture was stirred at room temperature for 25 min and at reflux for 25 min. After cooling the mixture was poured into water and extracted twice with $CH_2Cl_2$. The organic phase was dried and concentrated. Recrystallization from heptane/EtOAc afforded 4.12 g (60%) of a white solid. 1H NMR ($CDCl_3$), d (ppm): 1.68 (d, 3 H) 2.67 (m, 1 H) 5.09 (m, 1 H) 7.46 (t, 1 H) 7.56 (d, 1 H) 8.01 (d, 1 H) 8.13 (s, 1 H).

Example 264

[5-(3-Chloro-phenyl)-[1,2,4]oxadiazol-3-yl]-methanol

Step 1: N-{4-[(Z)-{[5-(3-chlorophenyl)-1,2,4-oxadiazol-3-yl]methylene}(oxido)amino]phenyl}-N,N-dimethylamine: The title compound was synthesized according to the method described in Palazzo et al. J. Heterocycl. Chem. (1979) 16:1469. 1-[5-(3-Chloro-phenyl)-[1,2,4]oxadiazol-3-ylmethyl]-pyridinium chloride (1.81 g, 5.87 mmol) was dissolved in water (20 ml). To this solution, 4-nitroso-N,N-dimethylanilin (0.88 g, 5.86 mmol) dissolved in ethanol (50 ml) was added, followed by slow addition of 1 molar aq. sodium hydroxide (5.9 ml, 5.9 mmol) over a 3 min period. After 1 h the formed precipitate was filtered, washed with water and air-dried to give the title compound (2.08 g, wet) which was used immediately in the next step MS (ESI) m/z 344 (M+1). Step 2: [5-(3-Chloro-phenyl)-[1,2,4]oxadiazol-3-yl]-methanediol: N-{4-[(Z)-{[5-(3-Chlorophenyl)-1,2,4-oxadiazol-3-yl]methylene}(oxido)amino]phenyl}-N,N-dimethylamine (2.08 g wet) was suspended in diethyl ether (30 ml), followed by the addition of 1 molar aqueous hydrochloric acid. The mixture was stirred vigorously for 20 min, transferred to a separation funnel and diluted with diethyl ether and 1 molar aqueous hydrochloric acid. After extraction, the aqueous layer was extracted two more times with diethyl ether. Combining the organic layers, drying over magnesium sulfate, followed by evaporation to dryness and drying in vacuo gave the title compound as crude (0.56 g, 42% from 1-[5-(3-chloro-phenyl)-[1,2,4]oxadiazol-3-ylmethyl]-pyridinium chloride). MS (ESI) m/z 227 (M+1). Step 3: [5-(3-Chloro-phenyl)-[1,2,4]oxadiazol-3-yl]-methanol: Step 3: [5-(3-Chloro-phenyl)-[1,2,4]oxadiazol-3-yl]-methanol: 1-[5-(3-Chloro-phenyl)-[1,2,4]oxadiazol-3-ylmethyl]-pyridinium chloride (99.3 mg, 0.44 mmol) was dissolved in methanol (4 ml) followed by the addition of sodium borohydride (32 mg, 0.84 mmol). More sodium borohydride was added after 2 h and the reaction was allowed to run over night. The reaction mixture was diluted with dichloromethane and aq. ammonium chloride and stirred vigorously. After separation of the layers and washing of the organic layer with brine, followed by evaporation to dryness, crude product was obtained. This was purified by flash chromatography using heptane/ethyl acetate which gave the title compound (32.0 mg, 32%). 1H NMR ($CDCl_3$), δ (ppm): 8.11 (s, 1H), 8.00 (apparent d, 1H), 7.56 (apparent d, 1H), 7.46 (apparent t, 1H), 4.87 (d, 2H), 2.91 (t, 1H).

Example 265

2-Chloromethyl-5-(2-fluoro-5-methyl-phenyl)-[1,3,4]oxadiazole

2-Fluoro-5-methyl-benzoic acid hydrazide (320 mg, 1.9 mmol) and 2-chloro-1,1,1-triethoxy-ethane (1.9 ml) were heated in a sealed vial at 120° C. for 30 min. The reaction mixture was place directly onto a flash column (silica gel) and purified by using 0-5% ethyl acetate in hexanes to afford 2-chloromethyl-5-(2-fluoro-5-methyl-phenyl)-[1,3,4]oxadiazole (284.5 mg, 66%). 1H NMR (CDCl3) d (ppm): 7.89 (q, 1H), 7.36 (m, 1H), 7.16 (t, 1H), 4.81 (s, 2H), 2.43 (s, 3H).

The following compounds were prepared analogously to Example 265:

| Example No. | Name |
|---|---|
| 266 | 2-Chloromethyl-5-(3-chloro-phenyl)-[1,3,4]oxadiazole |
| 267 | 4-(5-Chloromethyl-[1,3,4]oxadiazol-2-yl)-2-methyl-pyridine |
| 268 | 2-Chloromethyl-5-m-tolyl-[1,3,4]oxadiazole |
| 269 | 3-(5-Chloromethyl-[1,3,4]oxadiazol-2-yl)-benzonitrile |
| 270 | 2-Chloro-4-(5-chloromethyl-[1,3,4]oxadiazol-2-yl)-pyridine |
| 271 | 2-(5-Chloro-2-fluoro-phenyl)-5-chloromethyl-[1,3,4]oxadiazole |

Example 272

2-(1-Bromo-ethyl)-5-(3-chloro-phenyl)-[1,3,4]oxadiazole

3-Chloro-benzoic acid hydrazide (170 mg, 1 mmol) and 2-bromo-1,1,1-triethoxypropane (1 ml) were heated in a sealed vial at 120° C. for 10 min. The reaction mixture was place directly onto a flash column (silica gel) and purified using 0-50% dichloromethane in hexanes. The product was re-purified by flash column chromatography using a mixture of ethyl acetate:hexanes:dichloromethane (1:19:20) to afford 2-(1-bromo-ethyl)-5-(3-chloro-phenyl)-[1,3,4]oxadiazole (93 mg, 32%, colorless oil). 1H NMR (CDCl$_3$) d (ppm): 8.09 (t, 1H), 7.99 (t, 1H), 7.55 (m, 3H), 5.30 (m, 1H), 2.21 (q, 3H).

The following compounds were prepared analogously to Example 272:

| Example No. | Name |
|---|---|
| 273 | 2-(1-Bromo-ethyl)-5-(5-chloro-2-fluoro-phenyl)-[1,3,4]oxadiazole |
| 274 | 4-[5-(1-Bromo-ethyl)-[1,3,4]oxadiazol-2-yl]-2-methyl-pyridine |
| 275 | 2-(1-Bromo-ethyl)-5-(2-fluoro-5-methyl-phenyl)-[1,3,4]oxadiazole |
| 276 | 2-(1-Bromo-ethyl)-5-(3-chloro-phenyl)-[1,3,4]oxadiazole |

Example 277

3-(1-Bromo-ethyl)-5-(3-chloro-phenyl)-[1,2,4]oxadiazole

A solution of 396 mg (2.22 mmol) N-bromosuccinimid in 2 ml THF was added dropwise to a solution of 583 mg (2.22 mmol) triphenylphosphine in 2 ml THF at 0° C. After stirring for 20 min 416 mg (1.85 mmol) 1-[5-(3-chloro-phenyl)-[1,2,4]oxadiazol-3-yl]-ethanol in 2 ml THF was added. Stirring was continued overnight at room temperature before the solvent was removed under reduced pressure. Flash chromatography (heptane/EtOAc 6:1) afforded 168 mg (32%). 1H NMR (CDCl$_3$), d (ppm): 2.12 (d, 3 H) 5.21 (q, 1 H) 7.47 (t, 1 H) 7.57 (m, 1 H) 8.03 (d, 1 H) 8.15 (s, 1 H).

Example 278

1-[5-(3-Chloro-phenyl)-isoxazol-3-yl]-ethanol

Step 1 4-(3-Chloro-phenyl)-2,4-dioxo-butyric acid ethyl ester: Sodium hydride (60% oil dispersion, 1.24 g, 31.1 mmol) was added in portions to a solution of 3-chloroacetophenone (4.0 g, 25.9 mmol) and diethyl oxalate (4.54 g, 31.1 mmol) in DMF (32 ml) at 0° C. The mixture stirred at room temperature for 1 h and was then heated at 80° C. for a half an h. After cooling, the mixture was treated with 3N HCl and then diluted with ethyl acetate. The organic layer was washed with water (3×) and saturated brine, dried over anhydrous sodium sulfate, filtered and concentrated. The resulting residue was then purified by flash column chromatography on silica using 0-10% ethyl acetate in hexanes to afford of 4-(3-chloro-phenyl)-2,4-dioxo-butyric acid ethyl ester (4.43 g, 67%, yellow solid). 1H NMR (CDCl$_3$) d (ppm): 15.12 (br s, 1H), 7.98 (s, 1H), 7.88 (d, 1H), 7.58 (d, 1H), 7.47 (t, 1H), 7.05 (s, 1H), 4.39 (m, 2H), 1.41 (m, 3H). Step 2: 5-(3-Chloro-phenyl)-isoxazole-3-carboxylic acid ethyl ester: A solution of 4-(3-chloro-phenyl)-2,4-dioxo-butyric acid ethyl ester (3.0 g, 11.8 mmol) and hydroxylamine hydrochloride (2.46 g, 35.4 mmol) in methanol (60 ml) was heated at 80° C. for 4 h. After cooling, the mixture was filtered and washed with cold methanol to afford 5-(3-chloro-phenyl)-isoxazole-3-carboxylic acid ethyl ester (2.0 g, 71%, white solid). 1H NMR (CDCl$_3$) d (ppm): 7.82 (s, 1H), 7.72 (m, 1H), 7.47 (m, 2H), 4.03 (s, 3H). Mixture of both methyl and ethyl ester (mostly methyl). Step 3: 1-[5-(3-Chloro-phenyl)-isoxazol-3-yl]-ethanone: In a screw cap vial equipped with stir bar added methyl magnesium iodide (3M in diethyl ether) (0.79 ml, 2.38 mmol), toluene (1 ml), tetrahydrofuran (0.39 ml, 4.77 mmol) and triethylamine (1 ml, 7.15 mmol). Cooled the solution down to 0° C. and to it added solution of 5-(3-chloro-phenyl)-isoxazole-3-carboxylic acid ethyl ester (300 mg, 1.19 mmol) in toluene (5 ml). Left the resulting mixture stirring at 0° C. for 5 h. Reaction mixture was quenched with 1N hydrochloric acid (aqueous, 6.5 ml, 6.5 mmol), diluted with toluene (35 ml), sequentially is washed with water (50 ml), saturated sodium bicarbonate (aqueous, 30 ml), water (50 ml) and brine (30 ml). The organic phase was concentrated, in-vacuo. The isolated residue was dissolved in methanol (8 ml) and 20% potassium hydroxide (aqueous, 1 ml). The mixture was stirred at 45° C. for 30 min. At this point the mixture was concentrated, in-vacuo. The isolated residue was dissolved in toluene (60 ml), sequentially washed with water (50 ml), saturated sodium bicarbonate (aqueous, 50 ml) and water (50 ml). The organic phase was concentrated, in-vacuo. The crude residue was purified on silica gel using 2% ethyl acetate in hexanes to isolate the desired compound as a white solid (156 mg, 60%). 1H-NMR (CDCl$_3$), d (ppm): 7.77 (m, 1H), 7.66 (m, 1H), 7.42 (m, 2H), 6.90 (s, 1H), 2.69 (s, 3H). Step 4: 1-[5-(3-Chloro-phenyl)-isoxazol-3-yl]-ethanol: In a screw cap vial equipped with stir bar added 1-[5-(3-chloro-phenyl)-isoxazol-3-yl]-ethanone (100 mg, 0.45 mmol), sodium borohydride (34 mg, 0.90 mmol) and methanol (3 ml). Left the resulting mixture stirring at room temperature for 3 h. Reaction was quenched with water (30 ml) and brine (30 ml), extracted with dichloromethane (3×30 ml). Combined organic phase was dried (sodium sulfate), filtered and concentrated, in-vacuo to isolate 1-[5-(3-Chloro-phenyl)-isoxazol-3-yl]-ethanol as a white solid (110 mg). 1H-NMR (CDCl3), d (ppm): 7.69 (m, 1H), 7.59 (m, 1H), 7.37 (m, 2H), 6.59 (s, 1H), 5.07 (q, 1H), 3.45 (bs, 1H), 1.58 (d, 3H).

The following compound was prepared analogously to Example 278:

| Example No. | Name |
|---|---|
| 279 | 1-[5-(2-Fluoro-5-methyl-phenyl)-isoxazol-3-yl]-ethanol |

The following compounds were prepared analogously to 5-(3-Chloro-phenyl)-isoxazole-3-carboxylic acid ethyl ester (step 2 in the synthesis of Example 279):

| Example No. | Name |
|---|---|
| 280 | 5-(2-Fluoro-5-methyl-phenyl)-isoxazole-3-carboxylic acid methyl ester |
| 281 | 5-Thiophen-3-yl-isoxazole-3-carboxylic acid methyl ester |
| 282 | 5-Phenyl-isoxazole-3-carboxylic acid methyl ester |
| 283 | 5-(3-Chloro-phenyl)-4-methyl-isoxazole-3-carboxylic acid ethyl ester |
| 284 | 5-(5-Chloro-thiophen-3-yl)-isoxazole-3-carboxylic acid methyl ester |

Example 285

[5-(3-Chloro-phenyl)-isoxazol-3-yl]-methanol

Lithium aluminum hydride (320 mg, 8.4 mmol) was slowly added to a solution of 5-(3-chloro-phenyl)-isoxazole-3-carcoxylic acid ethyl ester (2.0 g, 8.4) in THF (100 ml) at room temperature. After 1 h, the reaction mixture was quenched with water and then extracted with ethyl acetate. The organic layer was washed with water and saturated brine, dried over anhydrous sodium sulfate, filtered, and concentrated. The resulting residue was then purified by flash column chromatography using 15-40% ethyl acetate in hexane to afford [5-(3-chloro-phenyl)-isoxazol-3-yl]-methanol (1.32 g, 75%, yellow solid). 1H NMR (CDCl$_3$) d (ppm): 7.78 (s, 1H), 7.68 (m, 1H), 7.43 (m, 2H), 6.63 (s, 1H), 4.84 (d, 2H), 2.23 (t, 1H).

The following compounds were prepared analogously to Example 285:

| Example No. | Name |
|---|---|
| 286 | [2-(3-Chloro-phenyl)-oxazol-4-yl]-methanol |
| 287 | [3-(3-Chloro-phenyl)-isoxazol-5-yl]-methanol |
| 288 | 5-(Thiophen-3-yl-isoxazol-3-yl)methanol |
| 289 | [5-(2-Fluoro-5-methyl-phenyl)-isoxazol-3-yl]-methanol |
| 290 | (5-Phenyl-isoxazol-3-yl)-methanol |
| 291 | [5-(3-Chloro-phenyl)-4-methyl-isoxazol-3-yl]-methanol |
| 292 | [5-(5-Chloro-thiophen-3-yl)-isoxazol-3-yl)]-methanol |

Example 293

Methanesulfonic acid 1-[5-(3-Chloro-phenyl)-isoxazol-3-yl]-ethyl ester

In a screw cap vial equipped with stir bar was added 1-[5-(3-chloro-phenyl)-isoxazol-3-yl]-ethanol (110 mg, 0.49 mmol), dichloromethane (3 ml) and triethylamine (0.34 ml, 2.46 mmol). Cooled the mixture down to 0° C. and to it added methane sulfonyl chloride (0.08 ml, 0.98 mmol). Left the reaction mixture stirring at room temperature for 30 min. Reaction was quenched with saturated sodium bicarbonate (aqueous, 40 ml) and extracted with dichloromethane (3×30 ml). Combined organic phase was washed with brine (40 ml), dried (sodium sulfate), filtered and concentrated, in-vacuo to isolate the desired compound as brown oil.

The following compounds were prepared analogously to Example 293:

Example 307

Methanesulfonic acid 4-chloro-5-(3-chloro-phenyl)-isoxazol-3-ylmethyl ester

Sulfuryl chloride (1 ml) was added to methanesulfonic acid 5-(3-chloro-phenyl)-isoxazol-3-ylmethyl ester (200 mg, 0.70 mmol) and then stirred at 60° C. overnight. The reaction mixture was diluted with dichloromethane, washed saturated sodium bicarbonate, dried over anhydrous sodium sulfate, filtered and concentrated to afford methanesulfonic acid 4-chloro-5-(3-chloro-phenyl)-isoxazol-3-ylmethyl ester (219 mg, 97%, light brown solid). 1H NMR (CDCl$_3$) d (ppm): 8.07 (m, 1H), 7.92 (m, 1H), 7.50 (m, 2H), 5.38 (s, 2H), 3.16 (s, 3H).

Example 308

3-(3-Chlorophenyl)-isoxazole-5-carboxylic acid methyl ester

Step 1: 3-Chloro-N-hydroxy-benzamidine: A solution of 3-chlorobenzaldehyde (3.35 ml, 0.030 mmol) in ethanol (40 ml) was added to a solution of hydroxylamine hydrochloride (2.47 g, 0.036 mmol) and sodium hydroxide (1.42 g, 0.036) in water (20 ml) at room temperature and then heated at 90° C. for 24 h. After cooling, the reaction mixture was concentrated, the residue diluted with water and then the precipitate was filtered and dried to afford 3-chloro-N-hydroxy-benzamidine (1.13 g, 93%). 1H NMR (CDCl$_3$) d (ppm): 8.11 (s, 1H), 7.72 (s, 1H), 7.61 (m, 1H), 7.46 (m, 1H), 7.36 (m, 1H). Step 2: 3-Chloro-N-hydroxy-benzimidoyl chloride: N-chlorosuccinimide (858 mg, 6.4 mmol) was added to a solution of 3-chloro-N-hydroxy-benzamidine (1 g, 6.4 mmol) at room temperature and stirred for 1 h. The reaction mixture was diluted with diethyl ether and then washed with water (3×), dried over anhydrous magnesium sulfate, filtered, and concentrated to afford the titled compound (1.13 g, 93%). 1H NMR (CDCl$_3$) d (ppm): 8.03 (s, 1H), 7.87 (m, 1H), 7.76 (m,

| Example No. | Name |
|---|---|
| 294 | Methanesulfonic acid 2-(3-chloro-phenyl)-oxazol-4-ylmethyl ester |
| 295 | Methanesulfonic acid 3-(3-chloro-phenyl)-isoazol-5-ylmethyl ester |
| 296 | Methanesulfonic acid 5-(2-fluoro-5-methyl-phenyl)-isoxazol-3-ylmethyl ester |
| 297 | Methanesulfonic acid -phenyl)-isoxazol-5-yl]-ethyl ester |
| 298 | Methanesulfonic acid 5-(5-chloro-2-fluoro-phenyl)-isoxazol-3-ylmethyl ester |
| 299 | Methanesulfonic acid 5-(3-chloro-phenyl)-isoxazol-3-ylmethyl ester |
| 300 | Methanesulfonic acid 5-thiophen-3-yl-isoxazol-3-ylmethyl ester |
| 301 | Methanesulfonic acid 5-(2-fluoro-5-methyl-phenyl)-isoxazol-3-ylmethyl ester |
| 302 | Methanesulfonic acid 5-phenyl-isoxazol-3-ylmethyl ester |
| 303 | Methanesulfonic acid 5-(3-chloro-phenyl)-4-methyl-isoxazol-3-ylmethyl ester |
| 304 | Methanesulfonic acid 5-(5-chloro-thiophen-3-yl)-isoxazol-3-ylmethyl ester |
| 305 | Methanesulfonic acid 1-[5-(2-fluoro-5-methyl-phenyl)-isoxazol-3-yl]-ethyl ester |
| 306 | Methanesulfonic acid 1-[5-(5-chloro-2-fluoro-phenyl)-isoxazol-3-yl]-ethyl ester |

1H), 7.43 (m, 1H).: Step 3: 3-(3-Chloro-phenyl)-isoxazole-5-carboxylic acid methyl ester: Triethyl amine (0.73 ml, 5.3 mmol) was added drop-wise to a solution of 3-chloro-N-hydroxy-benzimidoyl chloride (1.0 g, 5.3 mmol) and methyl propiolate (2.2 ml, 25.3 mmol) in an ice-bath. The reaction mixture was warmed to room temperature and left to stir overnight. After diluting the reaction with dichloromethane, the organic layer was washed with water and saturated brine, dried over anhydrous sodium sulfate, filtered, and concentrated. Purification by flash column chromatography eluted with 50% hexanes in ethyl acetate and then recrystallization with methanol afforded 3-(3-chloro-phenyl)-isoxazole-5-carboxylic acid methyl ester (635 mg, 51%, white solid). 1H NMR (CDCl$_3$) d (ppm): 7.86 (m, 1H), 7.74 (m, 1H), 7.46 (2H), 7.2 (s, 1H), 4.05 (s, 3H).

Example 309

2-Bromomethyl-5-(3-chloro-phenyl)-oxazole

Step 1 5-(3-Chloro-phenyl)-2-methyl-oxazole: To a solution of Tl(OAc)3 (4.2 g, 11.1 mmol) in acetonitrile (80 ml), trifluoromethanesulfuric acid (5 g, 33.3 mmol) was added dropwise at room temperature and stirred for 15 min. The reaction mixture was then heated to 80° C. and 1-(3-chloro-phenyl)-ethanone (1.14 g, 7.4 mmol) in acetonitrile (40 ml) was added. After one h, the reaction was quenched with dichloromethane and saturated sodium bicarbonate. The organic layer was dried, purified by column chromatography with 5~19% ethyl acetate in hexanes to give 1.2 (83.9%) g of 5-(3-chloro-phenyl)-2-methyl-oxazole as yellow oil. 1H-NMR(CDCl$_3$) d(ppm): 7.60 (s, 1H), 7.48 (d, 1H), 7.29 (m, 2H), 7.23 (s, 1H) and 2.34 (s, 3H). Step 2: 2-Bromomethyl-5-(3-chloro-phenyl)-oxazole: 5-(3-chloro-phenyl)-2-methyl-oxazole (580 mg, 3 mmol) was mixed with NBS (531 mg, 3 mmol) and BPOA (36.3 mg, 0.15 mmol) in CCl$_4$ at room temperature. The reaction mixture was heated at 75° C. for 2 h and then quenched with water and dichloromethane. The organic layer was dried, concentrated, purified by column chromatography with 2~5% ethyl acetate in hexanes to give 562 mg (68.3%) of 2-bromomethyl-5-(3-chloro-phenyl)-oxazole as yellow oil. 1H-NMR(CDCl$_3$) d(ppm): 7.67 (s, 1H), 7.54 (d, 1H), 7.35(m, 3H) and 4.56 (s, 2H).

Example 310

2-(3-Chloro-phenyl)-oxazole-4-carboxylic acid methyl ester

To a mixture of 3-Chlorobenzoic acid (5.0 g, 31.9 mmol), serine methylester hydrochloride (6.1 g, 31.9 mmol) and HOBt (4.31 g, 31.9 mmol) in DMF (100 ml) was added N-methylmorpholine (NMM) (7.0 ml, 63.8 mmol) and EDCI (4.97 g, 31.9 mmol) at 0° C. The mixture was allowed to warm to room temperature and stirred for 18 h. The mixture was diluted with ethyl acetate (300 ml) and then washed with water (3×250 ml) followed by brine. The organic extract was dried over Na$_2$SO$_4$ (anhydrous) and then concentrated in vacuo giving 2-(3-Chloro-benzoylamino)-3-hydroxy-propionic acid methyl ester (7.2 g, 93%) of a pale yellow solid. 1H NMR (CDCl$_3$) d (ppm): 7.78 (s, 1 H), 7.66 (d, 1 H), 7.45, (dd, 1 H), 7.34 (t, 1 H), 7.25 (br, d, 1H), 4.82 (m, 1 H), 4.08 (m, 2 H), 3.79 (s, 3 H), 3.19 (br, t, 1 H).

To a solution of 2-(3-chloro-benzoylamino)-3-hydroxy-propionic acid methyl ester (7.2 g, 29.6 mmol) in CH$_2$Cl$_2$ at −20° C. was added dropwise De-oxofluor (7.2 g, 32.6 mmol). After stirring at this temperature for 30 min, BrCCl$_3$ (3.6 g, 18.1 mmol) was added dropwise followed by DBU (2.79 g, 18.1 mmol). The mixture was then stirred at 2-3° C. for 8 h ad then quenched with saturated NaHCO$_3$ followed by extraction with ethyl acetate. The organic extract as then washed with brine and dried over Na$_2$SO$_4$ (anhydrous). Purification was performed by flash column chromatography on silica gel using ethyl acetate in hexanes as eluant to afford 2-(3-chloro-phenyl)-oxazole-4-carboxylic acid methyl ester (4.1 g, 59%) as a yellow solid. 1H NMR (CDCl$_3$) d (ppm): 8.30 (s, 1 H), 8.12 (d, 1 H), 7.98 (dd, 1 H), 7.45 (m, 2 H), 3.96 (s, 3 H).

Example 311

2-(3-Chloro-phenyl)-oxazole-4-carboxylic acid methyl ester

To a mixture of 3-Chlorobenzoic acid (5.0 g, 31.9 mmol), serine methylester hydrochloride (6.1 g, 31.9 mmol) and HOBt (4.31 g, 31.9 mmol) in DMF (100 ml) was added N-methylmorpholine (NMM) (7.0 ml, 63.8 mmol) and EDCI (4.97 g, 31.9 mmol) at 0° C. The mixture was allowed to warm to room temperature and stirred for 18 h. The mixture was diluted with ethyl acetate (300 ml) and then washed with water (3×250 ml) followed by brine. The organic extract was dried over Na$_2$SO$_4$ (anhydrous) and then concentrated in vacuo giving 2-(3-Chloro-benzoylamino)-3-hydroxy-propionic acid methyl ester (7.2 g, 93%) of a pale yellow solid. 1H NMR (CDCl$_3$) d (ppm): 7.78 (s, 1 H), 7.66 (d, 1 H), 7.45, (dd, 1 H), 7.34 (t, 1 H), 7.25 (br, d, 1 H), 4.82 (m, 1 H), 4.08 (m, 2 H), 3.79 (s, 3 H), 3.19 (br, t, 1 H).

To a solution of 2-(3-chloro-benzoylamino)-3-hydroxy-propionic acid methyl ester (7.2 g, 29.6 mmol) in CH$_2$Cl$_2$ at −20° C. was added dropwise De-oxofluor (7.2 g, 32.6 mmol). After stirring at this temperature for 30 min, BrCCl$_3$ (3.6 g, 18.1 mmol) was added dropwise followed by DBU (2.79 g, 18.1 mmol). The mixture was then stirred at 2-3° C. for 8 h ad then quenched with saturated NaHCO$_3$ followed by extraction with ethyl acetate. The organic extract as then washed with brine and dried over Na$_2$SO$_4$ (anhydrous). Purification was performed by flash column chromatography on silica gel using ethyl acetate in hexanes as eluant to afford 2-(3-chloro-phenyl)-oxazole-4-carboxylic acid methyl ester (4.1 g, 59%) as a yellow solid. 1H NMR (CDCl$_3$) d (ppm): 8.30 (s, 1 H), 8.12 (d, 1 H), 7.98 (dd, 1 H), 7.45 (m, 2 H), 3.96 (s, 3 H).

Example 312

1-[5-(5-Chloro-2-fluoro-phenyl)-isoxazol-3-yl]-ethanol

Step 1: 5-(5-Chloro-2-fluoro-phenyl)-isoxazole-3-carbaldehyde: In a 50 ml round bottom flask equipped with stir bar and drying tube added 5-(5-chloro-2-fluoro-phenyl)-isoxazole-3-carboxylic acid ethyl ester (0.78 g, 2.89 mmol) and dichloromethane (10 ml). Cooled the solution down to −78° C. and to this stirred solution added diisobutylaluminum hydride (1M hexanes, 5.3 ml, 5.3 mmol). The resulting mixture was left stirring at −78° C. for 3 h. Reaction was quenched using sodium sulfate decahydrate. The resulting mixture was stirred at 63° C. for 15 min after which it was filtered through a celite pad. The filerate was concentrated in-vacuo to isolate an off-white solid, which was triturated with hexanes to isolate the title compound as a white solid (0.55 g, 84%). 1H-NMR (CDCl$_3$), d (ppm): 10.2 (s, 1H), 7.99 (m, 1H), 7.44 (m, 1H), 7.20 (m, 1H), 7.10 (d, 1H). Step 2: 1-[5-(5-Chloro-2-fluoro-phenyl)-isoxazol-3-yl]-ethanol: In a 50 ml round bottom flask equipped with stir bar added 5-(5- chloro-2-fluoro-phenyl)-isoxazole-3-carbaldehyde (0.5 g, 2.42 mmol) and tetrahydrofuran (6 ml). Cooled the mixture down to 0° C. and to it added methyl magnesium iodide (3M in diethyl ether, 3.23 ml, 9.67 mmol). The resulting mixture was left stirring at 0° C. for 3 h. Reaction mixture was quenched with hydrochloride acid (1N, aqueous, 10 ml), extracted with diethyl ether (3×50 ml). Combined organic phase was washed with water (50 ml), brine (50 ml), dried (sodium sulfate), filtered and concentrated in-vacuo. The crude residue was purified on silica gel using 10% ethyl acetate in hexanes to isolate the desired compound as clear oil (179 mg, 31%).

Example 313

1-[3-(3-Chloro-phenyl)-isoxazol-5-yl]-ethanol

3-Chloro-benzohydroximoyl chloride (e.g. Kim, Jae Nyoung; Ryu, Eung K; J. Org. Chem. (1992), 57(24), 6649-50) (2.84 g, 14.8 mmol) was suspended in benzene (50 ml) and cooled to 0° C. 3-Butyn-2-ol (2.10 g, 29.9 mmol) and triethylamine (1.89 ml, 26.7 mmol) were added. The mixture was heated to 60° C. for 1.5 houes, cooled and diluted with benzene and 1N aqueous hydrochloric acid. After stirring, the separated benzene layer was evaporated to dryness and the crude purified via flash chromatography over silica using heptane/ethyl acetate=5/1 giving after drying in vacuo the title compound (0.49 g, 15%). 1H NMR (CDCl$_3$), δ (ppm): 1.64 (d, 3 H), 5.07 (dq, 1 H), 6.50 (s, 1 H), 7.40 (m, 2 H), 7.68 (m, 1 H), 7.79 (m, 1 H)

Example 314

[5-(5-Chloro-2-fluoro-phenyl)-isoxazol-3-yl]-methanol

Step 1: (5-Chloro-2-fluoro-phenylethynyl)-trimethyl-silane: In a 250 ml round bottom flask equipped with a stir bar and reflux condenser added 4-chloro-2-bromo-1-fluoro-benzene (5 g, 23.9 mmol), triphenylphosphine (250 mg, 0.10 mmol), (trimethylsilyl)acetylene (5.2 ml, 36.5 mmol) and triethylamine (60 ml). The reaction mixture was purged with argon, followed by addition of palladium (II) acetate (108 mg, 0.05 mmol). The resulting mixture was left stirring at reflux under argon, overnight. The reaction mixture was filtered through a pad of celite using ethyl acetate and the filterate was concentrated in-vacuo. The isolated residue was absorbed on silica gel and filtered using hexanes. The filterate was concentrated in-vacuo to isolate the title compound as brown oil (5.42 g). Step 2: 4-Chloro-2-ethynyl-1-fluoro-benzene: In a 250 ml round bottom flask equipped with stir bar added (5-chloro-2-fluoro-phenylethynyl)-trimethyl-silane (5.42 g, 23.9 mmol), potassium carbonate (16.5 g, 120 mmol) and methanol (60 ml). The reaction mixture was left stirring at room temperature for 1 h. Diluted the reaction mixture with hexanes (200 ml) and washed with water (250 ml). The aqueous phase was extracted with hexanes (2×100 ml). Combined organic phase was washed with brine (200 ml), dried (sodium sulfate), filtered and concentrated in-vacuo to isolate the desired compound as brown oil (3.56 g). 1H-NMR (CDCl$_3$), d (ppm): 7.47 (dd, 1H), 7.30 (m, 1H), 7.05 (t, 1H), 3.36 (s, 1H). Step 3: Chloro-hydroxyimino-acetic acid ethyl ester: In 1 L round bottom flask equipped with stir bar added aminoacetic acid ethyl ester hydrochloride (20 g, 143 mmol) and water (30 ml). The solution was cooled down to 0° C. followed by sequential addition of concentrated hydrochloric acid (11.8 ml, 143 mmol) and dropwise addition of sodium nitrite (9.89 g, 143 mmol) solution in water (15 ml). After 10 min added another equivalent each of concentrated hydrochloric acid and sodium nitrite solution in water. The reaction mixture was left stirring at 0° C. for 1 h. Reaction mixture was extracted with ether (4×100 ml). Combined organic phase was dried (sodium sulfate), filtered and concentrated in-vacuo to isolate a lemon yellow solid. The solid was recrystallized from hexanes to isolate a white solid (11 g, 51%). 1H-NMR (CDCl$_3$), d (ppm): 9.98 (bs, 1H), 4.40 (q, 2H), 1.38 (t, 3H). Step 4: 5-(5-Chloro-2-fluoro-phenyl)-isoxazole-3-carboxylic acid ethyl ester: In a 250 ml round bottom flask equipped with stir bar added 4-chloro-2-ethynyl-1-fluoro-benzene (2 g, 12.9 mmol), chloro-hydroxyimino-acetic acid ethyl ester (3.92 g, 25.9 mmol), sodium bicarbonate (7.07 g, 84.1 mmol) and toluene (50 ml). Reaction mixture was left stirring at room temperature for 48 h, after which it was concentrated in-vacuo. Residue was taken up in ethyl acetate (200 ml), sequentially washed with water (150 ml), brine (150 ml), dried (sodium sulfate), filtered and concentrated in-vacuo. The crude residue was purified on silica gel using 3% acetone in hexanes to isolate the title compound as an off-white solid (1.56 g). 1H-NMR (CDCl$_3$), d (ppm): 8.00 (dd, 1H), 7.43 (m, 1H), 7.18 (m, 2H), 4.51 (q, 2H), 1.47 (t, 3H). Step 5: [5-(5-Chloro-2-fluoro-phenyl)-isoxazol-3-yl]-methanol: In a 50 ml round bottom flask equipped with stir bar and drying tube added 5-(5-chloro-2-fluoro-phenyl)-isoxazole-3-carboxylic acid ethyl ester (0.78 g, 2.89 mmol) and tetrahydrofuran (10 ml). To this stirred solution added solution of lithium aluminum hydride (0.12 g, 2.89 mmol) in tetrahydrofuran (2 ml). The resulting mixture was left stirring at room temperature for 1 h. Reaction was quenched using sodium sulfate decahydrate. The resulting mixture was stirred at 63° C. for 15 min after which it was filtered through a celite pad. The filterate was concentrated in-vacuo to isolate the title compound as yellow solid (0.65 g, 99%). 1H-NMR (CDCl$_3$), d (ppm): 7.73 (dd, 1H), 7.27 (m, 1H), 7.24 (t, 1H), 6.73 (d, 1H), 4.77 (s, 2H), 4.45 (bs, 1H).

Example 315

3-[5-(3-Chloro-phenyl)-[1,3,4]oxadiazol-2-yl]-propionic acid hydrazide

Step 1: 3-[5-(3-Chloro-phenyl)-[1,3,4]oxadiazol-2-yl]-propionic acid: 3-Chloro-benzoic acid hydrazide (3.4 g, 20 mmol) and succinic anhydride (2. g, 20 mmol) was mixed in ethyl acetate (50 ml) at room temperature for 15 min. The reaction mixture was diluted with ether and the precipitate was filtered to give 5.1 g of 4-[N'-(3-chloro-benzoyl)-hydrazino]-4-oxo-butyric acid. 1H-NMR(CDCl$_3$+DMSO-d6) d(ppm): 10.01 (s, 1H), 9.53 (s, 1H), 7.68 (s, 1H), 7.55 (d, 1H), 7.21 (d, 1H), 7.12 (t, 1H) and 2.35 (m, 4H). This solid was mixed with conc. H$_2$SO$_4$ and stirred at room temperature for 45 min and the reaction mixture was carefully added to crashed ice (400 g). The precipitate was filtered to give 4.07 g (80.6%) of 3-[5-(3-Chloro-phenyl)-[1,3,4]oxadiazol-2-yl]-propionic acid as white solid. 1H-NMR(DMSO-d6) d(ppm): 12.4 (w, 1H), 7.96 (s, 1H), 7.91 (d, 1H), 7.71 (d, 1H), 7.63 (t, 1H), 3.15 (t, 2H) and 2.82 (t, 2H). Step 2: 3-[5-(3-Chlorophenyl)-[1,3,4]oxadiazol-2-yl]-propionic acid hydrazide: 3-[5-(3-Chloro-phenyl)-[1,3,4]oxadiazol-2-yl]-propionic acid (2.52 g, 10 mmol) was mixed with iodomethane (5.68 g, 40 mmol) and K$_2$CO$_3$ (5.52 g, 40 mmol) in DMF (25 ml) at room temperature overnight. The reaction mixture was diluted with ethyl acetate and washed with water 3 times, dried with MgSO$_4$ and concentrated to give 2.57 g of 3-[5-(3-Chloro-phenyl)-[1,3,4]oxadiazol-2-yl]-propionic acid methyl ester. The methyl ester (2.54 g, 9.52 mmol) was mixed with 98% hydrazine hydrate (4.76 g, 95.2 mmol) in methanol (10 ml) for an h. The reaction mixture was concentrated, diluted with water, filtered to give 2.17 g (81.4%) of 3-[5-(3-Chloro-phenyl)-[1,3,4]oxadiazol-2-yl]-propionic acid hydrazide as white solid. 1H-NMR(CDCl$_3$+DMSO-d6) d(ppm): 8.75 (w, 1H), 7.91 (s, 1H), 7.82 (d, 1H), 7.42 (m, 2H), 3.45 (w, 2H), 3.19 (t, 2H) and 2.68 (t, 2H).

Example 316

3-[5-(3-Chloro-phenyl)-[1,3,4]oxadiazol-2-yl]-butyric acid hydrazide

Step 1: 2-{1-[5-(3-Chloro-phenyl)-[1,3,4]oxadiazol-2-yl]-ethyl}-malonic acid dimethyl ester: 2-(1-Chloro-ethyl)-5-(3-chloro-phenyl)-[1,3,4]oxadiazole (331 mg, 1.36 mmol) was mixed with dimethyl malonate (360 mg, 2/76 mmol) and DBU (207 mg, 1.36 mmol) in acetonitrile (3 ml) at 70° C. overnight. The reaction mixture was dilute with dichloromethane and washed with water. The organic layer was dried and concentrated. The residue was purified with 5~20% ethyl acetate in hexanes to give 357 mg (74.3%) 2-{1-[5-(3-Chloro-phenyl)-[1,3,4]oxadiazol-2-yl]-ethyl}-malonic acid dimethyl ester as white solid. 1H-NMR(CDCl$_3$) d(ppm): 8.03 (s, 1H), 7.95 (d, 1H), 7.53 (d, 1H), 7.47 (t, 1H), 4.06 (d, 1H), 3.95 (m, 1H), 3.84 (s, 3H), 3.74 (s, 3H) and 1.51 (d, 3H). Step 2: 3-[5-(3-Chloro-phenyl)-[1,3,4]oxadiazol-2-yl]-butyric acid methyl ester: 2-{1-[5-(3-Chloro-phenyl)-[1,3,4]oxadiazol-2-yl]-ethyl}-malonic acid dimethyl ester (352.8 mg, 1.0 mmol) was mixed with sodium chloride (76.3 mg, 1.3 mmol) and a drop of water in DMSO (1.5 ml) at 175° C. for an h. The reaction mixture was diluted with water and extracted with dichloromethane. The organic layer was washed with water and concentrated. The residue was purified with column chromatography with 10~20% ethyl acetate in hexanes to give 215 mg (76.8%)3-[5-(3-chloro-phenyl)-[1,3,4]oxadiazol-2-yl]-butyric acid methyl ester as clear oil. 1H-NMR(CDCl$_3$) d(ppm): 8.03 (s, 1H), 7.94 (d, 1H), 7.53 (d, 1H), 7.45 (t, 1H), 3.73 (s, 3H), 3.67 (m, 1H), 3.05 (dd, 1H), 2.73 (dd, 1H) and 1.50 (d, 3H). Step 3: 3-[5-(3-Chloro-phenyl)-[1,3,4]oxadiazol-2-yl]-butyric acid hydrazide: 3-[5-(3-Chloro-phenyl)-[1,3,4]oxadiazol-2-yl]-butyric acid hydrazide (146 mg, %) was obtained from 3-[5-(3-chloro-phenyl)-[1,3,4]oxadiazol-2-yl]-butyric acid methyl ester (215 mg, 0.766 mmol) reacted with hydrazine hydrate (0.74 ml) in methanol (3 ml) at room temperature for 2.5 h. 1H-NMR(CDCl$_3$) d(ppm): 8.03 (s, 1H), 7.94 (d, 1H), 7.53 (d, 1H), 7.46 (t, 1H), 7.23 (w, 1H), 3.93 (w, 2H), 3.71 (m, 1H), 2.90 (dd, 1H), 2.57 (dd, 1H) and 1.50 (d, 3H).

Example 317

3-[3-(3-Chloro-phenyl)-[1,2,4]oxadiazol-5-yl]-propionimidic acid ethyl ester hydrochloride Step 1: 3-[3-(3-Chloro-phenyl)-[1,2,4]oxadiazol-5-yl]-propionamide: 3-[3-(3-Chloro-phenyl)-[1,2,4]oxadiazol-5-yl]-propionic acid (1.6 g, 6.33 mmol) was reacted with SOCl$_2$ (10 ml) at room temperature overnight. The reaction mixture was concentrated by vacuum. The residue was mixed with THF (20 ml) and quenched with 28% NH$_3$.H$_2$O (5 ml) at 0° C. After being stirred for 2 h, the reaction mixture was dilute with dichloromethane and washed with water and brine. The organic layer was dried, concentrate and triturated with hexanes to give 1.21 g (76%) of 3-[3-(3-Chloro-phenyl)-[1,2,4] oxadiazol-5-yl]-propionamide. 1H-NMR(CDCl$_3$) d(ppm): 8.07 (s, 1H), 7.96 (d, 1H), 7.45 (m, 2H), 5.60 (dw, 2H), 3.32 (t, 2H) and 2.87 (t, 2H). Step 2: 3-[3-(3-Chloro-phenyl)-[1,2,4]oxadiazol-5-yl]-propionitrile: 3-[3-(3-Chloro-phenyl)-[1,2,4]oxadiazol-5-yl]-propionamide (1.2 g, 4.77 mmol) was mixed with pyridine (0.829 g, 10.5 mmol) and trifluoroacetic anhydride (1.2 g, 5.72 mmol) in dichloromethane(25 ml) at room temperature for 2 h. The reaction mixture was diluted with dichloromethane and washed with water and brine. The organic layer was dried to give 1.1 g (98%) of 3-[3-(3-chloro-phenyl)-[1,2,4]oxadiazol-5-yl]-propionitrile as pale-brown oil. 1H-NMR(CDCl$_3$) d(ppm): 8.09 (s, 1H), 7.98 (d, 1H), 7.45 (m, 2H), 5.60 (dw, 2H), 3.35 (t, 2H) and 3.01 (t, 2H). Step 3: 3-[3-(3-Chloro-phenyl)-[1,2,4]oxadiazol-5-yl]-propionimidic acid ethyl ester hydrochloride: 3-[3-(3-Chloro-phenyl)-[1,2,4]oxadiazol-5-yl]-propionitrile (1.1 g, 4.71 mmol) was mixed with 24% HCl in ethanol (8 ml) overnight. The precipitate was filtered and washed with ether to give 0.99 g (66%) of 3-[3-(3-chloro-phenyl)-[1,2,4]oxadiazol-5-yl]-propionimidic acid ethyl ester hydrochloride as white solid. 1H-NMR(DMSO-d6) d(ppm): 11.70 (w, 2H), 7.78 (m, 2H), 7.64 (m, 2H), 4.41 (q, 2H), 3.45 (t, 2H), 3.22 (t, 2H) and 1.28 (t, 3H).

Example 318

3-[3-(3-Chlorophenyl)-[1,2,4]oxadiazol-5-yl]-propionic acid hydrazide

Step 1: 3-[3-(3-chloro-phenyl)-[1,2,4]oxadiazol-5-yl]-propionic acid: 3-Chloro-N-hydroxy-benzamidine 4.52 g, 26.5 mmol) was heated with succinic anhydride (2.65 mg, 26.5 mmol) in DMF (5 ml) at 150° C. for an h. The reaction mixture was cooled down and diluted with ethyl acetate. The organic solution was washed with water and brine, concentrated by vacuum. The residue was triturated with 20% ethyl acetate in hexanes to give 4.0 g (60%) of 3-[3-(3-chloro-phenyl)-[1,2,4]oxadiazol-5-yl]-propionic acid as white solid. ). 1H-NMR(CDCl$_3$) d(ppm): 8.08 (s, 1H), 7.96 (d, 1H), 7.49 (d, 1H), 7.42 (t, 1H), 3.28 (t, 2H) and 3.04 (t, 2H). Step 2: 3-[3-(3-Chloro-phenyl)-[1,2,4]oxadiazol-5-yl]-propionic acid hydrazide: This acid was reacted with iodoethane (1.6 g, 10.5 mmol) and K$_2$CO$_3$ (1.46 10.5 mmol) in DMF (5 ml) for 5 min to form 3-[3-(3-chloro-phenyl)-[1,2,4]oxadiazol-5-yl]-propionic acid ethyl ester. The ethyl ester was then treated with 37% hydrazine (2 ml) in ethanol (5 ml) at 80° C. for 2 h to give 595 mg (65% in 3 steps) of 3-[3-(3-chloro-phenyl)-[1,2,4]oxadiazol-5-yl]-propionic acid hydrazide as off-white solid 1H-NMR(CDCl$_3$) d(ppm): 8.07 (s, 1H), 7.96 (d, 1H), 7.49 (d, 1H), 7.43 (t, 1H), 7.00 (w, 1H), 3.95 (w, 2H), 3.34 (t, 2H) and 2.79 (t, 2H).

Example 319

[5-(3-Chloro-phenyl)-[1,2,4]oxadiazol-3-yl]-acetic acid hydrazide

Step 1: (N-Hydroxycarbamimidoyl)-acetic acid ethyl ester: To a ethanol solution (40 ml) of cyano-acetic acid ethyl ester (9.9 g, 0.1 mol), the mixture solution of sodium hydroxide (4 g, 0.1 mol) in water (40 ml) and 5 M hydroxylamine hydrochloride (20 ml) was added and the reaction mixture was stirred at 50° C. overnight. After being concentrated, the reaction mixture was diluted with water and extrated with ethyl acetate. The organic layer was dried, concentrated again. The residue was purified by column chromatography with 30~70% ethyl acetate in hexanes to give 3.32 g (22.7%) of (N-Hydroxycarbamimidoyl)-acetic acid ethyl ester as white solid. 1H-NMR(CDCl₃) d(ppm): 5.04 (ws, 2H), 4.20 (q, 2H), 3.19 (s, 2H) and 1.30 (t, 3H). Step 2: [5-(3-Chloro-phenyl)-[1,2,4]oxadiazol-3-yl]-acetic acid ethyl ester: To a dichloromethane solution (10 ml) of (N-hydroxycarbamimidoyl)-acetic acid ethyl ester (1.46 g, 10 mmol) and triethylamine, 3-chlorobenzoyl chloride (1.75 g, 10 mmol) was added slowly at 5° C. and the reaction mixture was stirred for 10 min. DMF (8 ml) was added to the reaction mixture was heated to 135° C. for 2 h. Standard work-up, the product was passed column with dichloromethane to give 1.2 g (45%) of [5-(3-chloro-phenyl)-[1,2,4]oxadiazol-3-yl]-acetic acid ethyl ester as pale-yellow oil. 1H-NMR(CDCl₃) d(ppm): 8.168 (s, 1H), 8.04 (d, 1H), 7.59 (d, 1H), 7.49 (t, 1H), 4.26 (q, 2H), 3.91 (s, 2H) and 1.31 (t, 3H). Step 3: [5-(3-Chloro-phenyl)-[1,2,4]oxadiazol-3-yl]-acetic acid hydrazide: 5-(3-Chloro-phenyl)-[1,2,4]oxadiazol-3-yl]-acetic acid ethyl ester (0.64 g, 2.4 mmol) was mixed with 37% hydrazine (1.6 ml) in ethabol (10 ml) at 80° C. for 4 h. The reaction mixture was concentrated and diluted with water. The precipitate was filtered, washed with water to give 0.51 g (83.3%) of [5-(3-chloro-phenyl)-[1,2,4]oxadiazol-3-yl]-acetic acid hydrazide.

Example 320

(R)-3-[3-(3-Chloro-phenyl)-[1,2,4]oxadiazol-5-yl]-butyric acid hydrazide

Step 1: (R)-3-[3-(3-Chloro-phenyl)-[1,2,4]oxadiazol-5-yl]-butyric acid methyl ester: To a solution of (R)-2-methyl-succinic acid 4-methyl ester (2.2 g, 15 mmol) and triethylamine (4.54 g, 45 mmol) in THF (30 ml), isobutylchloroformate (2.16 g, 15.8 mmol) was added dropwise at 0° C. After being stirred for 30 min, the 3-chloro-N-hydroxy-benzamidine (2.56 g, 15 mmol) was added. The reaction mixture was stirred at room temperature for another 30 min and then heated to 135° C. with DMF for 45 min. The reaction mixture was diluted with ethyl acetate and washed with water and brine. The organic layer was dried and concentrated to give 4.0 g (95%) of (R)-3-[3-(3-chloro-phenyl)-[1,2,4]oxadiazol-5-yl]-butyric acid methyl ester as pale-yellow oil. Step 2: (R)-3-[3-(3-Chloro-phenyl)-[1,2,4]oxadiazol-5-yl]-butyric acid hydrazide: (R)-3-[3-(3-Chloro-phenyl)-[1,2,4]oxadiazol-5-yl]-butyric acid hydrazide (430 mg, 77%) was obtained from (R)-3-[3-(3-chloro-phenyl)-[1,2,4]oxadiazol-5-yl]-butyric acid methyl ester (461.4 mg, 2.0 mmol) reacted with hydrazine hydrate (2 mL) in methanol (2 mL) at 65° C. for 1 h. 1H-NMR(CDCl₃) d (ppm): 8.07 (s, 1H), 7.96 (d, 1H), 7.46 (m, 2H), 6.98 (w, 1H), 3.93 (w, 2H), 3.78 (m, 1H), 2.86 (dd, 1H), 2.55 (dd, 1H) and 1.59 (d, 3H).

The following compounds were prepared analogously to Example 320:

| Example No. | Name |
| --- | --- |
| 321 | 3-[3-(3-Chloro-phenyl)-[1,2,4]oxadiazol-5-yl]-3-methyl-butyric acid hydrazide |

Example 322

3-[5-(3-Chloro-phenyl)-[1,2,4]oxadiazol-3-ylmethyl]-piperidin-2-one 1.33 ml (3.32 mmol) n-BuLi (2.5 M in hexanes) was added dropwise to a solution of 157 mg (1.58 mmol) d-valerolactone in 5.3 ml THF at 0° C. After stirring for 2 h at 0° C., 400 mg (1.58 mmol) 3-chloromethyl-5-[3-chloro-phenyl)-[1,2,4]oxadiazole was added in one portion and stirring was continued for 3 h. NH₄Cl(sat) was added to quench the reaction and the mixture was extracted twice with CH₂Cl₂. The combined organic phases were dried and concentrated. Flashchromatography (SiO₂, Heptane/EtOAc 1:8) afforded 113 mg (25%) of a yellow-white solid. 1H NMR (CDCl₃):d ppm 1.80 (m, 1 H) 1.89 (m, 1 H) 2.00 (m, 1 H) 2.91 (m, 1 H) 2.98 (m, 1 H) 3.35 (m, 1 H) 3.52 (m, 1 H) 5.83 (s, 1 H) 7.46 (t, 1 H) 7.55 (d, J=8.08 Hz, 1 H) 8.00 (d, 1 H) 8.11 (s, 1 H).

The following compounds were prepared analogously to Example 322:

| Example No. | Name |
| --- | --- |
| 323 | 3-[5-(5-Chloro-2-fluoro-phenyl)-[1,2,4]oxadiazol-3-ylmethyl]-piperidin-2-one |

Example 324

3-Chloromethyl-5-(5-chloro-thiophen-3-yl)-[1,2,4]oxadiazole and 1-[5-(5-Chloro-thiophen-3-yl)-[1,2,4]oxadiazol-3-ylmethoxy]-1H-benzotriazole A solution of 2-chloro-N-hydroxy-acetamidine (781 mg, 7.2 mmol), 5-chloro-thiophene-3-carboxylic acid (1.4 g), HBTU (3.55 g) and DIPEA (1.3 g) in DMF (20 ml) was stirred at ambient temperature for 1 h before heated at 120° C. for 4 h under argon. Removal of the solvent in vacuo followed by silica gel chromatography of the obtained residue using 0-20% EtOAc in n-heptane yielded 38.5 mg of the faster eluting 3-chloromethyl-5-(5-chloro-thiophen-3-yl)-[1,2,4]oxadiazole as a syrup, followed by 65 mg of the slower eluting 1-[5-(5-chloro-thiophen-3-yl)-[1,2,4]oxadiazol-3-ylmethoxy]-1H-benzotriazole as a white solid. 3-Chloromethyl-5-(5-chloro-thiophen-3-yl)-[1,2,4]oxadiazole: 1H NMR (CDCl₃) d (ppm): 8.01 (d, 1H), 7.50 (d, 1H), 4.63 (s, 2H). 1-[5-(5-Chloro-thiophen-3-yl)-[1,2,4]oxadiazol-3-ylmethoxy]-1H-benzotriazole: 1H NMR (CDCl₃) d (ppm): 7.97 (m, 2H), 7.52 (dt, 1H), 7.44 (m, 2H), 7.34 (m, 1H), 5.70 (s, 2H).

Example 325

(4-Methyl-5-thiophen-2-yl-4H-[1,2,4]triazol-3-ylsulfanyl)-acetonitrile

4-Methyl-5-thiophene-3-yl-4H-[1,2,4]triazole-3-thiol (197 mg, 1.0 mmol), chloroacetonitrile (95 ml, 1.5 mmol), sodium carbonate (424 mg, 4 mmol) and potassium iodide (332 mg, 2.0 mmol) were stirred together at 100° C. for 3 h with an additional addition of chloroacetonitrile (60 ml, 0.5 mmol) after 2 h. The reaction was cooled, diluted with ethyl acetate and washed with water. The organic solution was dried, filtered and evaporated. Silica gel chromatography (dichloromethane:methanol 19:1) yielded 150 mg of the desired compound.

Example 326

2-(4-Methyl-5-thiophen-2-yl-4H-[1,2,4]triazol-3-ylsulfanyl)-propionic acid (R)-2-chloro-propionic acid (500 mg, 4.6 mmol), 4-methyl-5-thiophen-2-yl-4H-[1,2,4]triazole-3-thiol (1.09 g, 5.58 mmol) and potassium carbonate (1.94 g, 14.03 mmol) were dissolved in acetonitrile (15 ml) at room temperature. Reaction proceeded for 2.5 h and was partitioned between ethyl acetate (350 ml) and water 3 times, washed with 1 M HCl, once with saturated brine, dried over anhydrous sodium sulphate, filtered and concentrated in vacuo. Reaction was not completed at this stage and the crude was stirred in DMF (10 ml) overnight. Extraction was repeated and purification was performed by SPE (solid phase extraction) chromatography on silica gel using 300 ml ethyl acetate, 100 ml 1%, and 100 ml 3% formic acid in ethyl acetate, yielding title compound (150.7 mg, 12%) 1H-NMR (CDCl$_3$), d (ppm): 7.52 (dd, 2H), 7.19 (m, 1H), 4.21 (q, 1H), 3.78 (s, 3H), 1.64 (d, 3H).

The following compounds were prepared analogously to Example 326:

| Example No. | Name |
|---|---|
| 327 | 2-(4-Methyl-5-pyridin-3-yl-4H-[1,2,4]triazol-3-ylsulfanyl)-propionic acid |

Example 328

3-(3-Chloro-phenyl)-5-(4-methyl-4H-[1,2,4]triazol-3-ylsulfanylmethyl)-[1,2,4]oxadiazole The title compound (2.08 g, 81.5%) was obtained form 5-chloromethyl-3-(3-chloro-phenyl)-[1,2,4]oxadiazole (1.9 g, 8.29 mmol) reacted with 4-methyl-4H-[1,2,4]triazole-3-thiol (1.0 g, 8.71 mmol) and K$_2$CO$_3$ (4.58 g, 33.2 mmol) in DMF (19 ml) at room temperature overnight. 1H-NMR (CDCl$_3$) d (ppm): 8.21 (s, 1H), 8.05 (s, 1H), 7.94 (d, 1H), 7.49(d, 1H), 7.43 (t, 1H), 4.69 (s, 2H) and 3.64(s, 3H).

Example 329

{3-[3-(4-Methyl-5-thiophen-2-yl-4H-[1,2,4]triazol-3-ylsulfanylmethyl)-[1,2,4]oxadiazol-5-yl-phenyl]}-carbamic acid tert-butyl ester The title compound was prepared from 4-methyl-5-thiophen-2-yl-4H-[1,2,4]triazole-3-thiol (53 mg, 0.27 mmol), 3-(3-chloromethyl-[1,2,4]oxadiazol-5-yl)-phenyl]-carbamic acid tert-butyl ester (75 mg, 0.24 mmol), and potassium carbonate (101 mg, 0.73 mmol) in acetonitrile (2.5 ml). The product was purified by SPE (flash) chromatography using 65% ethyl acetate in hexane (88.0 mg, 79%, white solid). 1H NMR (CDCl$_3$) d (ppm): 8.06 (s, 1H), 7.73 (d, 1H), 7.66 (d, 1H), 7.51 (t, 2H), 7.42 (t, 1H), 7.18 (m, 1H), 6.68 (s, 1H), 4.51 (s, 2H), 3.73 (s, 3H), 1.53 (s, 9H).

The following compounds were prepared analogously to Example 41:

| Example No. | Name | 1H NMR | MS |
|---|---|---|---|
| 330 | 4-(4-Cyclopropyl-5-{1-[5-(2,5-difluoro-phenyl)-[1,2,4]oxadiazol-3-yl]-ethylsulfanyl}-4H-[1,2,4]triazol-3-yl)-pyridine | 8.88(d, 2H), 7.81(m, 1H), 7.75(m, 2H), 7.22(m, 2H), 5.42(q, 1H), 3.22(m, 1H), 1.98(d, 3H), 1.17(m, 2H), 0.79(m, 2H) | |
| 331 | 4-(5-{1-[5-(3-Methoxy-phenyl)-[1,2,4]oxadiazol-3-yl]-ethylsulfanyl}-4-methyl-4H-[1,2,4]triazol-3-yl)-pyridine | 8.69(m, 2H), 7.6(m, 1H), 7.52(m, 3H), 7.35(t, 1H), 7.04(m, 1H), 4.93(q, 1H), 3.78(t, 3H), 3.55(s, 3H), 1.86(d, 3H) | |
| 332 | 4-{4-Methyl-5-[1-(5-m-tolyl-[1,2,4]oxadiazol-3-yl)-ethylsulfanyl]-4H-[1,2,4]triazol-3-yl}-pyridine | 8.71(m, 2H), 7.82(m, 2H), 7.53(m, 2H), 7.32(m, 2H), 4.94(q, 1H), 3.54(s, 3H), 2.33(s, 3H), 1.87(d, 3H) | |
| 333 | 5-(4-Methyl-5-thiophen-2-yl-4H-[1,2,4]triazol-3-ylsulfanylmethyl)-3-o-tolyl-[1,2,4]oxadiazole | 2.58(s, 3H) 3.70(s, 3H) 4.65(s, 2H) 7.17(s, 1H) 7.29(s, 2H) 7.36(s, 1H) 7.46(s, 1H) 7.51(s, 1H) 7.90(s, 1H) | 370.0 |
| 334 | 5-(3-Chloro-phenyl)-3-(4-cyclopropyl-5-thiophen-2-yl-4H-[1,2,4]triazol-3-ylsulfanylmethyl)-[1,2,4]oxadiazole | 0.87(m, 1H) 1.18(m, 2H) 3.47(ddd, J=6.95, 3.41, 3.28Hz, 1H) 4.70(s, 2H) 7.23(m, 1H) 7.67(m, 2H) 7.77(m, 2H) 8.04(d, 2H) | 415.9 |
| 335 | 2-{3[5-(2-Fluoro-5-methyl-phenyl)-[1,2,4]oxadiazol-3-ylmethylsulfanyl]-5-thiophen-2-yl-[1,2,4]triazol-4-yl}-ethanol | 2.36(s, 3H) 4.03(t, 2H) 4.30(t, 2H) 4.57(s, 2H) 7.11(m, 2H) 7.35(s, 1H) 7.47(d, 1H) 7.64(d, 1H) 7.81(d, 1H) | 417.9 |
| 336 | 4-{4-Ethyl-5-[5-(2-fluoro-5-methyl-phenyl)-[1,2,4]oxadiazol-3-ylmethylsulfanyl]-4H-[1,2,4]triazol-3-yl}-pyrimidine | 1.38(t, 3H) 2.34(s, 3H) 4.66(m, 4H) 7.19(m, 1H) 7.47(m, 1H) 7.83(d, 1H) 8.23(d, 1H) 8.94(d, 1H) 9.28(s, 1H) | 398.0 |
| 337 | 3-(4-Ethyl-5-furan-3-yl-4H-[1,2,4]triazol-3-ylsulfanylmethyl)-5-(2-fluoro-5-methyl-phenyl)-[1,2,4]oxadiazole | 1.34(t, 3H) 2.37(s, 3H) 4.06(q, 2H) 4.61(s, 2H) 6.82(s, 1H) 7.12(m, 1H) 7.36(ddd, 1H) 7.55(s, 1H) 7.85(d, 2H). | 386.0 |

-continued

| Example No. | Name | 1H NMR | MS |
|---|---|---|---|
| 338 | {3-[5-(2-Fluoro-5-methyl-phenyl)-[1,2,4]oxadiazol-3-ylmethylsulfanyl]-5-thiophen-2-yl-[1,2,4]triazol-4-yl}-acetic acid methyl ester | 2.36(s, 3H) 3.70(s, 3H) 4.46(s, 2H) 5.10(s, 2H) 7.21(m, 2H) 7.47(m, 2H) 7.73(d, 1H) 7.86(m, 1H) | 445.9 |
| 339 | 5-(2-Fluoro-5-methyl-phenyl)-3-[5-furan-2-yl-4-(2-methoxy-ethyl)-4H-[1,2,4]triazol-3-ylsulfanylmethyl]-[1,2,4]oxadiazole | 2.26(s, 3H) 3.16(s, 3H) 3.57(t, 2H) 4.42(t, 2H) 4.44(s, 2H) 6.60(s, 1H) 7.10(m, 2H) 7.37(m, 1H) 7.70(s, 1H) 7.73(d, 1H) | 416.0 |
| 340 | 3-(4-Cyclopropyl-5-furan-2-yl-4H-[1,2,4]triazol-3-ylsulfanylmethyl)-5-(2-fluoro-5-methyl-phenyl)-[1,2,4]oxadiazole | 0.87(m, 2H) 1.14(m, 2H) 2.35(s, 3H) 3.39(dt, 1H) 4.71(s, 2H) 6.72(s, 1H) 7.09(d, 1H) 7.39(m, 1H) 7.56(m, 1H) 7.87(d, 1H) 7.93(s, 1H) | 398.0 |
| 341 | 3-(5-Chloro-2-fluoro-phenyl)-5-(4-cyclopropylmethyl-5-thiophen-2-yl-4H-[1,2,4]triazol-3-ylsulfanylmethyl)-[1,2,4]oxadiazole | 0.32(m, 2H) 0.56(m, 2H) 1.14(d, 1H) 4.00(d, 2H) 4.76(s, 2H) 7.16(ddd, 2H) 7.43(m, 1H) 7.50(t, 2H) 7.99(dd, 1H) | 448.1 |
| 342 | 4-{5-[3-(5-Chloro-2-fluoro-phenyl)-[1,2,4]oxadiazol-5-ylmethylsulfanyl]-4-ethyl-4H-[1,2,4]triazol-3-yl}-pyrimidine | 1.40(t, 3H) 4.63(q, 2H) 4.72(s, 2H) 7.20(m, 1H) 7.53(m, 1H) 8.06(dd, 1H) 8.29(d, 1H) 8.86(d, 1H) 9.26(s, 1H). | 417.8 |
| 343 | 3-(5-Cyclopentyl-4-ethyl-4H-[1,2,4]triazol-3-ylsulfanylmethyl)-5-m-tolyl-[1,2,4]oxadiazole | 1.29(t, 3H) 1.66(m, 3H) 1.87(m, 2H) 2.02(m, 3H) 2.42(s, 3H) 3.01(s, 2H) 3.90(d, 2H) 4.52(s, 2H) 7.39(d, 2H) 7.90(d, 2H) | 370.2 |
| 344 | 3-(3-Chloro-phenyl)-5-{4-ethyl-5-[2-(4-methoxy-phenyl)-ethyl]-4H-[1,2,4]triazol-3-ylsulfanylmethyl}-[1,2,4]oxadiazole | 1.18(t, 3H) 2.95(t, 2H) 3.09(t, 2H) 3.72(q, 2H) 3.76(s, 3H) 4.66(s, 2H) 6.81(d, 2H) 7.09(d, 2H) 7.40(t, 1H) 7.47(m, 1H) 7.92(d, 1H) 8.03(s, 1H) | 456.1 |
| 345 | 5-(3-Chloro-phenyl)-3-(4-ethyl-5-p-tolyloxymethyl-4H-[1,2,4]triazol-3-ylsulfanylmethyl)-[1,2,4]oxadiazole | 1.23(t, 3H) 2.22(s, 3H) 4.02(d, 2H) 4.60(s, 2H) 5.22(s, 2H) 6.92(d, 2H) 7.09(d, 2H) 7.65(t, 1H) 7.79(d, 1H) 8.04(m, 2H) | 442.1 |
| 346 | 5-(3-Chloro-phenyl)-3-[4-(2-methoxy-ethyl)-5-thiophen-2-yl-4H-[1,2,4]triazol-3-ylsulfanylmethyl]-[1,2,4]oxadiazole | 3.14(s, 3H) 3.57(t, 2H) 4.30(t, 2H) 4.58(s, 2H) 7.23(m, 1H) 7.64(m, 2H) 7.78(m, 2H) 8.03(d, 2H) | 433.9 |
| 347 | 3-(5-Chloro-2-fluoro-phenyl)-5-(4-ethyl-5-methoxymethyl-4H-[1,2,4]triazol-3-ylsulfanylmethyl)-[1,2,4]oxadiazole | 7.98(m, 1H), 7.43(m, 1H), 7.16(apparent t, 1H), 4.73(s, 2H), 4.62(s, 2H), 4.01(q, 2H), 3.33(s, 3H), 1.34(t, 3H). | 384.9 |
| 348 | 5-(5-Chloro-2-fluoro-phenyl)-3-(4-ethyl-5-methoxymethyl-4H-[1,2,4]triazol-3-ylsulfanylmethyl)-[1,2,4]oxadiazole | 8.05(m, 1H), 7.53(m, 1H), 7.21(apparent t, 1H); 4.62(s, 2H), 4.61(s, 2H), 4.02(q, 2H), 3.34(s, 3H), 1.32(t, 3H). | 384.9 |
| 349 | 5-(3-Chloro-phenyl)-3-(4-ethyl-5-methoxymethyl-4H-[1,2,4]triazol-3-ylsulfanylmethyl)-[1,2,4]oxadiazole | 8.07(apparent s, 1H), 7.97(m, 1H), 7.55(m, 1H), 7.45(apparent t, 1H), 4.62(s, 2H), 4.59(s, 2H), 4.01(q, 2H), 3.34(s, 3H), 1.32(t, 3H). | 366.9 |
| 350 | 3-(3-Chloro-phenyl)-5-(4-ethyl-5-methoxymethyl-4H-[1,2,4]triazol-3-ylsulfanylmethyl)-[1,2,4]oxadiazole | 8.02(m, 1H), 7.92(m, 1H), 7.46(m, 1H), 7.39(apparent t, 1H), 4.71(s, 2H), 4.62(s, 2H), 4.01(q, 2H), 3.34(s, 3H), 1.34(t, 3H). | 366.9 |

-continued

| Example No. | Name | 1H NMR | MS |
|---|---|---|---|
| 351 | 4-(5-{1-[3-(3-Chloro-phenyl)-isoxazol-5-yl]-ethylsulfanyl}-4-methyl-4H-[1,2,4]triazol-3-yl)-pyridine | 1.82(d, 3H), 3.46(s, 3H), 4.93(q, 1H), 6.33(s, 1H), 7.23–7.31(m, 2H), 7.44(d, 2H), 7.49(m, 1H), 7.61(s, 1H), 8.63(d, 2H). | 399.1 |
| 352 | 3-(4-Allyl-5-furan-2-yl-4H-[1,2,4]triazol-3-ylsulfanylmethyl)-5-(3-chloro-phenyl)-[1,2,4]oxadiazole | 4.6(s, 2H), 4.8(d, 2H), 5.0(d, 1H), 5.2(d, 1H), 5.9(m, 1H), 6.5(m, 1H), 7.1(d, 1H), 7.4(t, 1H), 7.5(m, 2H), 8.0(d, 1H), 8.1(s, 1H) | 399.95 |
| 353 | 3-(4-Allyl-5-furan-2-yl-4H-[1,2,4]triazol-3-ylsulfanylmethyl)-5-thiophen-3-yl-[1,2,4]oxadiazole | 4.5(s, 2H) 4.8(d, 2H) 5.0(d, 1H) 5.2(d, 1H) 5.9(m, 1H) 6.5(m, 1H) 7.0(d, 1H) 7.4(m, 1H) 7.5(s, 1H) 7.6(d, 1H) 8.2(m, 1H) | 371.98 |
| 354 | 5-(4-Allyl-5-furan-2-yl-4H-[1,2,4]triazol-3-ylsulfanylmethyl)-3-furan-2-yl-[1,2,4]oxadiazole | 4.7(s, 2H) 4.8(m, 2H) 5.0(d, 1H) 5.2(d, 1H) 5.9(m, 1H) 6.5(dt, 2H) 7.1(dd, 2H) 7.6(dd, 2H) | 356.01 |
| 355 | 5-(3-Chloro-phenyl)-3-[4-ethyl-5-(4-methoxy-phenoxymethyl)-4H-[1,2,4]triazol-3-ylsulfanylmethyl]-[1,2,4]oxadiazole | 1.4(t, 3H) 3.7(s, 3H) 4.1(q, 2H) 4.6(s, 2H) 5.2(s, 2H) 6.8(d, 2H) 6.9(d, 2H) 7.4(t, 1H) 7.6(d, 1H) 8.0(d, 1H) 8.1(s, 1H) | 457.91 |
| 356 | 3-(3-Chloro-phenyl)-5-[4-ethyl-5-(4-methoxy-phenoxymethyl)-4H-[1,2,4]triazol-3-ylsulfanylmethyl]-[1,2,4]oxadiazole | 1.4(t, 3H) 3.7(s, 3H) 4.1(q, 2H) 4.8(s, 2H) 5.2(s, 2H) 6.8(d, 2H) 6.9(d, 2H) 7.4(t, 1H) 7.5(m, 1H) 7.9(d, 1H) 8.0(s, 1H) | 457.97 |
| 357 | {5-[3-(3-Chloro-phenyl)-[1,2,4]oxadiazol-5-ylmethylsulfanyl]-4-ethyl-4H-[1,2,4]triazol-3-yl}-methanol | 1.4(t, 3H) 4.2(d, 2H) 4.7(s, 2H) 4.9(s, 2H) 7.4(t, 1H) 7.5(m, 1H) 7.9(d, 1H) 8.0(s, 1H) | 352.09 |
| 358 | 3-(3-Chloro-phenyl)-5-[4-ethyl-5-(2-methoxy-ethyl)-4H-[1,2,4]triazol-3-ylsulfanylmethyl]-[1,2,4]oxadiazole | 1.3(t, 3H) 3.0(t, 2H) 3.3(s, 3H) 3.8(t, 2H) 3.9(q, 2H) 4.7(s, 2H) 7.4(t, 1H) 7.5(ddd, 1H) 7.9(dt, 1H) 8.0(t, 1H) | 380.12 |
| 359 | 3-(3-Chloro-phenyl)-5-(4-ethyl-5-methylsulfanylmethyl-4H-[1,2,4]triazol-3-ylsulfanylmethyl)-[1,2,4]oxadiazole | 1.4(t, 3H) 2.1(s, 3H) 3.8(s, 2H) 4.0(q, 2H) 4.7(s, 2H) 7.4(t, 1H) 7.5(ddd, 1H) 7.9(dt, 1H) 8.0(t, 1H) | 382.07 |
| 360 | 3-(3-Chloro-phenyl)-5-(5-ethoxymethyl-4-ethyl-4H-[1,2,4]triazol-3-ylsulfanylmethyl)-[1,2,4]oxadiazole | .2(t, 3H) 1.3(t, 3H) 3.5(q, 2H) 4.0(q, 2H) 4.7(s, 2H) 4.7(s, 2H) 7.4(t, 1H) 7.5(ddd, 1H) 7.9(dt, 1H) 8.0(t, 1H) | 379.13 |
| 361 | 5-[3-(3-Chloro-phenyl)-[1,2,4]oxadiazol-5-ylmethylsulfanyl]-4-ethyl-4H-[1,2,4]triazole-3-carboxylic acid methyl ester | | |
| 362 | 2-(5-Chloro-2-fluoro-phenyl)-5-(4-ethyl-5-furan-2-yl-4H-[1,2,4]triazol-3-ylsulfanylmethyl)-[1,3,4]oxadiazole | 1.4(t 3H) 4.2(q, 2H) 4.7(s, 2H) 6.6(dd, 1H) 7.1(d, 1H) 7.2(m, 1H) 7.5(ddd, 1H) 7.6(d, 1H) 8.0(dd, 1H) | 406.07 |
| 363 | 2-(3-Chloro-phenyl)-5-(4-cyclopropyl-5-furan-2-yl-4H-[1,2,4]triazol-3-ylsulfanylmethyl)-[1,3,4]oxadiazole | 0.9(m, 2H) 1.2(m, 2H) 3.2(m, 1H) 4.8(s, 2H) 6.6(m, 1H) 7.0(d, 1H) 7.4(t, 1H) 7.5(m, 1H) 7.6(m, 1H) 7.9(m, 1H) 8.0(m, 1H) | 399.86 |
| 364 | 5-(3-Chloro-phenyl)-3-{1-[4-ethyl-5-(tetrahydro-furan-2-yl)-4H-[1,2,4]triazol-3-ylsulfanyl]-ethyl}-[1,2,4]oxadiazole | 1.3(t, 3H) 1.9(d, 3H) 2.0(m, 1H) 2.1(m, 1H) 2.3(m, 1H) 2.8(m, 1H) 3.8(m, 2H) 4.0(m, 1H) 4.1(m, 1H) | 406.04 |

-continued

| Example No. | Name | 1H NMR | MS |
|---|---|---|---|
| | | 5.0(m, 1H) 5.1(m, 1H) 7.4(t, 1H) 7.6(m, 1H) 8.0(m, 1H) 8.1(s, 1H) | |
| 365 | 4-(5-{1-[5-(3-Chloro-phenyl)-[1,2,4]oxadiazol-3-yl]-ethylsulfanyl}-4-ethyl-4H-[1,2,4]triazol-3-yl)-pyridazine | 1.4(t, 3H) 1.9(d, 3H) 4.1(m, 2H) 5.2(q, 1H) 7.4(t, 1H) 7.5(m, 1H) 7.8(m, 1H) 8.0(m, 1H) 8.1(m, 1H) 9.4(m, 1H) 9.5(s, 1H) | 414.12 |
| 366 | 4-(5-{1-[5-(3-Chloro-phenyl)-[1,2,4]oxadiazol-3-yl]-ethylsulfanyl}-4-ethyl-4H-[1,2,4]triazol-3-ylmethyl)-pyridine | 1.0(t, 3H) 1.9(d, 3H) 3.7(m, 2H) 4.2(m, 2H) 5.0(q, 1H) 7.1(m, 2H) 7.4(t, 1H) 7.5(m, 1H) 7.9(d, 1H) 8.1(s, 1H) 8.5(m, 2H) | 427.06 |
| 367 | 5-(5-{1-[5-(3-Chloro-phenyl)-[1,2,4]oxadiazol-3-yl]-ethylsulfanyl}-4-ethyl-4H-[1,2,4]triazol-3-yl)-pyridin-2-ol | 1.3(t, 3H) 1.9(d, 3H) 3.9(m, 2H) 5.1(q, 1H) 6.7(d, 1H) 7.5(t, 1H) 7.6(m, 1H) 7.7(m, 1H) 7.7(s, 1H) 8.0(d, 1H) 8.1(s, 1H) 13.1(s, 1H) | 429.1 |
| 368 | 4-(5-{1-[5-(3-Chloro-phenyl)-[1,2,4]oxadiazol-3-yl]-ethylsulfanyl}-4-ethyl-4H-[1,2,4]triazol-3-yl)-phenol | 1.2(t, 3H) 1.9(d, 3H) 3.9(q, 2H) 5.1(q, 1H) 6.9(d, 2H) 7.3(d, 2H) 7.4(t, 1H) 7.5(m, 1H) 7.9(m, 1H) 8.1(m, 1H) 10.2(s, 1H) | 428.08 |
| 369 | 5-(3-Chloro-phenyl)-3-[5-(4-methoxy-phenoxymethyl)-4-(tetrahydro-furan-2-ylmethyl)-4H-[1,2,4]triazol-3-ylsulfanylmethyl]-[1,2,4]oxadiazole | 1.54(m, 1H) 1.86(m, 2H) 2.02(m, 1H) 3.71(m, 4H) 3.79(m, 1H) 4.13(m, 3H) 4.60(m, 2H) 5.30(s, 2H) 6.82(m, 2H) 6.92(m, 2H) 7.44(t, 1H) 7.55(d, 1H) 7.95(d, 1H) 8.07(s, 1H) | |
| 370 | 5-(3-Chloro-phenyl)-3-[4-cyclopropyl-5-(4-methoxy-phenoxymethyl)-4H-[1,2,4]triazol-3-ylsulfanylmethyl]-[1,2,4]oxadiazole | 1.14(m, 4H) 3.10(s, 1H) 3.75(s, 3H) 4.70(s, 2H) 5.21(s, 2H) 6.82(d, 2H) 6.95(d, 2H) 7.45(t, 1H) 7.56(m, 1H) 7.99(d, 1H) 8.10(s, 1H) | |
| 371 | 5-(5-Chloro-2-fluoro-phenyl)-3-(4-ethyl-5-furan-2-yl-4H-[1,2,4]triazol-3-ylsulfanylmethyl)-[1,2,4]oxadiazole | 1.38(t, 3H) 4.27(q, 2H) 4.64(s, 2H) 6.58(m, 1H) 7.21(m, 2H) 7.53(m, 1H) 7.59(m, 1H) 8.06(m, 1H) | |
| 372 | 3-(4-Ethyl-5-methoxymethyl-4H-[1,2,4]triazol-3-ylsulfanylmethyl)-5-m-tolyl-[1,2,4]oxadiazole | 1.29(t, 3H) 2.40(s, 3H) 3.31(s, 3H) 3.99(m, 2H) 4.56(s, 2H) 4.60(s, 2H) 7.37(m, 2H) 7.87(m, 2H) | 346 |
| 373 | 3-[4-Ethyl-5-(tetrahydro-furan-2-yl)-4H-[1,2,4]triazol-3-ylsulfanylmethyl]-5-m-tolyl-[1,2,4]oxadiazole | 1.30(t, 3H) 1.97(m, 1H) 2.10(m, 1H) 2.24(m, 1H) 2.39(s, 3H) 2.80(m, 1H) 3.79(m, 1H) 3.86(m, 1H) 3.99(m, 1H) 4.08(m, 1H) 4.54(m, 2H) 4.98(m, 1H) 7.36(m, 2H) 7.86(m, 1H) 7.88(s, 1H) | 372 |
| 374 | 2-(3-Chloro-phenyl)-5-{1-[4-ethyl-5-(4-methoxy-phenyl)-4H-[1,2,4]triazol-3-ylsulfanyl]-ethyl}-[1,3,4]oxadiazole | 1.18(m, 3H) 1.95(d, 3H) 3.81(s, 3H) 3.90(q, 2H) 5.15(q, 1H) 6.94(m, 2H) 7.35(m, 1H) 7.45(m, 3H) 7.81(m, 1H) 7.92(m, 1H) | |
| 375 | 4-{5-[3-(2,5-Difluoro-phenyl)-[1,2,4]oxadiazol-5-ylmethylsulfanyl]-4-ethyl-4H-[1,2,4]triazol-3-yl}-pyrimidine | 1.43(t, 3H), 4.64(q, 2H), 4.87(s, 2H), 7.18(m, 2H), 7.72(m, 1H), 8.29(dd, 1H), 8.89(d, 1H), 9.30(d, 1H) | 402.1 |
| 376 | 4-{5-[5-(5-Chloro-2-fluoro-phenyl)-[1,2,4]oxadiazol-3-ylmethylsulfanyl]-4-methyl-4H-[1,2,4]triazol-3-yl}-pyrimidine | 4.12(s, 3H), 4.64(s, 2H), 7.21(t, 1H), 7.57(m, 1H), 8.06(dd, 1H), 8.28(dd, 1H), 8.92(d, 1H), 9.30(d, 1H) | 404.1 |

| Example No. | Name | 1H NMR | MS |
|---|---|---|---|
| 377 | 3-(3-Chloro-phenyl)-5-(4-methyl-5-thiophen-2-yl-4H-[1,2,4]triazol-3-ylsulfanylmethyl)-[1,2,4]oxadiazole | 8.03(s, 1H), 7.92(d, 1H), 7.53(d, 1H), 7.48(m, 2H), 7.40(t, 1H), 7.18(t, 1H), 4.87(s, 2H), 3.72(s, 3H). | 390.96 |
| 378 | 5-(3-Methylsulfanyl-phenyl)-3-(4-methyl-5-thiophen-2-yl-4H-[1,2,4]triazol-3-ylsulfanylmethyl)-[1,2,4]oxadiazole | 7.92(s, 1H), 7.84(d, 1H), 7.53(m, 2H), 7.43(m, 2H), 7.18(m, 1H), 4.53(s, 2H), 3.73(s, 3H), 2.52(s, 3H). | |
| 379 | 2-[5-(3-Methylsulfanyl-phenyl)-[1,2,4]oxadiazol-3-ylmethylsulfanyl]-1H-benzoimidazole | | |
| 380 | 5-(2,5-Dimethyl-phenyl)-3-(4-methyl-5-thiophen-2-yl-4H-[1,2,4]triazol-3-ylsulfanylmethyl)-[1,2,4]oxadiazole | 7.87(s, 1H), 7.49(m, 2H), 7.22(m, 3H), 4.56(d, 2H), 3.74(s, 3H), 2.61(s, 3H), 2.37(s, 3H). | |
| 381 | 5-(2-Fluoro-5-methyl-phenyl)-3-(4-methyl-5-thiophen-2-yl-4H-[1,2,4]triazol-3-ylsulfanylmethyl)-[1,2,4]oxadiazole | 7.83(dd, 1H), 7.49(m, 2H), 7.35(m, 1H), 7.16(m, 2H), 4.53(s, 2H), 3.73(s, 3H), 2.35(s, 3H). | 388.10 |
| 382 | 5-(3-Cyclopropyl-phenyl)-3-(4-methyl-5-thiophen-2-yl-4H-[1,2,4]triazol-3-ylsulfanylmethyl)-[1,2,4]oxadiazole | 7.87(d, 1H), 7.79(s, 1H), 7.51(m, 2H), 7.40(t, 1H), 7.30(m, 1H), 7.20(m, 1H), 4.53(s, 2H), 3.73(s, 3H), 1.96(m, 1H), 1.04(m, 2H), 0.77(m, 2H). | |
| 383 | 4-{5-[2-(3-Chloro-phenyl)-oxazol-4-ylmethylsulfanyl]-4-methyl-4H-[1,2,4]triazol-3-yl}-pyridine | 8.80(d, 2H), 8.02(dd, 1H), 7.88(dd, 1H), 7.80(s, 1H), 7.60(d, 2H), 7.42(m, 2H), 4.51(s, 2H, 3.64(s, 3H). | |
| 384 | 4-[4-Methyl-5-(5-thiophen-2-yl-[1,2,4]oxadiazol-3-ylmethylsulfanyl)-4H-[1,2,4]triazol-3-yl]-pyridine | 8.82(bs, 2H), 7.90(m, 1H), 7.66(m, 3H), 7.22(m, 1H), 4.58(s, 2H), 3.73(s, 3H). | |
| 385 | 4-{4-Methyl-5-[5-(3-methylsulfanyl-phenyl)-[1,2,4]oxadiazol-3-ylmethylsulfanyl]-4H-[1,2,4]triazol-3-yl}-pyridine | 8.81(m, 2H), 7.95(s, 1H), 7.86(m, 1H), 7.64(m, 2H), 7.45(m, 2H), 4.63(s, 2H), 3.72(s, 3H), 2.55(3H). | |
| 386 | 4-{5-[5-(3-Chloro-phenyl)-[1,2,4]oxadiazol-3-ylmethylsulfanyl]-4-methyl-4H-[1,2,4]triazol-3-yl}-pyridine | 8.83(d, 2H), 8.11(s, 1H), 8.00(d, 1H), 7.64(m, 2H), 7.60(m, 1H), 7.49(t, 1H), 4.64(s, 2H), 3.73(s, 3H). | |
| 387 | 2-Methyl-4-[3-(4-methyl-5-pyridin-4-yl-4H-[1,2,4]triazol-3-ylsulfanylmethyl)-[1,2,4]oxadiazol-5-yl]-pyridine | 8.82(d, 2H), 8.74(d, 1H), 7.82(s, 1H), 7.76(d, 1H), 7.64(d, 2H), 4.68(s, 2H), 3.74(s, 3H), 2.68(s, 3H). | |
| 388 | 1-{3-[3-(4-Methyl-5-thiophen-2-yl-4H-[1,2,4]triazol-3-ylsulfanylmethyl)-[1,2,4]oxadiazol-5-yl]-phenyl}-ethanone | 8.67(s, 1H), 8.29(d, 1H) 8.20(d, 1H), 7.68(t, 1H), 7.52(m, 2H), 7.20(m, 1H), 4.58(s, 2H), 3.76(s, 3H), 2.68(s, 3H). | |
| 389 | 4-{5-[5-(2-Fluoro-5-methyl-phenyl)-[1,2,4]oxadiazol-3-ylmethylsulfanyl]-4-methyl-4H-[1,2,4]triazol-3-yl}-pyridine | 8.81(dd, 2H), 7.86(d, 1H), 7.64(m, 2H), 7.39(m, 1H), 7.14(dd, 1H), 4.63(s, 2H), 3.73(s, 3H), 2.39(s, 3H). | 383.09 |
| 390 | 2-Methyl-4-[4-methyl-5-(5-m-tolyl-[1,2,4]oxadiazol-3-ylmethylsulfanyl)-4H-[1,2,4]triazol-3-yl]-pyridine | 8.68(dd, 1H), 7.92(m, 2H), 7.52(bs, 1H), 7.4(m, 3H), 4.61(s, 2H), 3.7(s, 3H), 2.67(s, 3H), 2.44(s, 3913H). | |
| 391 | 3-[5-(3-Chloro-phenyl)-isoxazol-3-ylmethylsulfanyl]-4-methyl-5-thiophen-2-yl-4H-[1,2,4]triazole | 7.76(s, 1H), 7.68(m, 1H), 7.54(m, 1H), 7.48(m, 1H), 7.40(m, 2H), 7.20(m, 1H), 6.76(s, 1H), 4.56(s, 2H), 3.70(s, 3H). | |

-continued

| Example No. | Name | 1H NMR | MS |
|---|---|---|---|
| 392 | 4-{5-[5-(3-Chloro-phenyl)-isoxazol-3-ylmethylsulfanyl]-4-methyl-4H-[1,2,4]triazol-3-yl}-pyridine | 8.82(m, 2H), 7.76(m, 1H), 7.65(m, 3H), 7.41(m, 2H), 6.77(s, 1H), 4.61(s, 2H), 3.69(s, 3H). | |
| 393 | 3-(4-Butyl-5-thiophen-2-yl-4H-[1,2,4]triazol-3-ylsulfanylmethyl)-5-(3-chloro-phenyl)-[1,2,4]oxadiazole | 8.07(s, 1H), 7.95(dd, 1H), 7.48(m, 4H), 7.17(dd, 1H), 4.59(s, 2H), 4.05(t, 2H), 1.67(m, 2H), 1.30(m, 2H), 0.88(t, 3H). | |
| 394 | 5-(3-Chloro-phenyl)-3-[4-(3-methoxy-propyl)-5-thiophen-2-yl-4H-[1,2,4]triazol-3-ylsulfanylmethyl]-[1,2,4]oxadiazole | 8.01(d, 1H), 7.91(dd, 1H), 7.48(m, 4H), 7.12(m, 1H), 4.51(s, 2H), 4.17(t, 2H), 3.34(t, 2H), 3.18(s, 3H), 1.90(m, 2H). | |
| 395 | 3-(4-Benzyl-5-thiophen-2-yl-4H-[1,2,4]triazol-3-ylsulfanylmethyl)-5-(3-chloro-phenyl)-[1,2,4]oxadiazole | 8.09(s, 1H), 7.97(dd, 1H), 7.57(m, 1H), 7.47(m, 2H), 7.24(m, 4H), 7.06(m, 3H), 5.37(s, 2H), 4.57(s, 2H). | |
| 396 | 5-(3-Chloro-phenyl)-3-(4-furan-2-ylmethyl-5-thiophen-2-yl-4H-[1,2,4]triazol-3-ylsulfanylmethyl)-[1,2,4]oxadiazole | 8.10(d, 1H), 8.03(dd, 1H), 7.55(m, 4H), 7.38(s, 1H), 7.20(dd, 1H), 6.32(m, 2H), 5.30(s, 2H), 4.60(s, 2H). | 457.02 |
| 397 | 3-{5-[5-(3-Chloro-phenyl)-[1,2,4]oxadiazol-3-ylmethylsulfanyl]-4-methyl-4H-[1,2,4]triazol-3-yl}-pyridine | 8.93(m, 1H), 8.78(m, 1H), 8.03(m, 3H), 7.59(m, 1H), 7.51(m, 2H), 4.63(s, 2H), 3.69(s, 3H). | |
| 398 | 5-(3-Chloro-phenyl)-3-(4-methyl-5-thiophen-3-yl-4H-[1,2,4]triazol-3-ylsulfanylmethyl)-[1,2,4]oxadiazole | 8.11(m, 1H), 8.05(m, 1H), 7.74(m, 1H), 7.59(m, 1H), 7.51(m, 3H), 4.57(s, 2H), 3.71(s, 3H). | |
| 399 | 4-{5-[5-(3-Chloro-phenyl)-[1,2,4]oxadiazol-3-ylmethylsulfanyl]-4-methyl-4H-[1,2,4]triazol-3-yl}-2-methyl-pyridine | 8.69(d, 1H), 8.10(s, 1H), 8.00(m, 1H), 7.49(m, 4H), 4.63(s, 2H), 3.71(s, 3H), 2.67(s, 3H). | |
| 400 | 5-(5-Chloro-2-fluoro-phenyl)-3-(4-methyl-5-thiophen-2-yl-4H-[1,2,4]triazol-3-ylsulfanylmethyl)-[1,2,4]oxadiazole | 8.08(m, 1H), 7.51(m, 1H) 7.21(m, 1H), 4.59(s, 2H), 3.77(s, 3H). | 409.00 |
| 401 | 4-{5-[5-(5-Chloro-2-fluoro-phenyl)-[1,2,4]oxadiazol-3-ylmethylsulfanyl]-4-methyl-4H-[1,2,4]triazole-3-yl}-pyridine | 8.82(d, 2H), 8.08(m, 1H) 8.29(d, 1H), 7.64(d, 2H), 7.56(m, 1H), 7.24(t, 1H), 4.66(s, 2H), 3.75(s, 3H). | 404.07 |
| 402 | 3-{5-[5-(2-Fluoro-5-methyl-phenyl)-[1,2,4]oxadiazol-3-ylmethylsulfanyl]-4-methyl-4H-[1,2,4]triazol-3-yl}-pyridine | 8.92(s, 1H), 8.76(d, 1H), 8.07(d, 1H), 7.87(d, 1H), 7.36(m, 3H), 4.59(s, 2H), 3.69(s, 3H), 2.39(s, 3H). | |
| 403 | 5-(3-Chloro-phenyl)-3-(5-thiophen-2-yl-4-thiophen-2-ylmethyl-4H-[1,2,4]triazol-3-ylsulfanylmethyl)-[1,2,4]oxadiazole | (CD3OD as solvent): 8.05(m, 1H), 8.00(dd, 1H), 7.75(dd, 1H), 7.58(m, 1H), 7.54(m, 1H), 7.53(m, 1H), 7.26(m, 1H), 7.22(m, 1H), 6.86(m, 2H), 5.63(s, 2H), 4.51(s, 2H). | |
| 404 | 5-(3-Chloro-phenyl)-3-(4-ethyl-5-thiophen-2-yl-4H-[1,2,4]triazol-3-ylsulfanylmethyl)-[1,2,4]oxadiazole | (CD3OD as solvent):8.08(m, 1H), 8.07(dd, 1H), 7.75(m, 1H), 7.67(m, 1H), 7.60(m, 2H), 7.28(dd, 1H), 4.57(s, 2H), 4.27(m, 2H), 1.29(m, 3H). | 405.10 |
| 405 | 3-{5-[3-(2-Fluoro-5-methyl-phenyl)-[1,2,4]oxadiazol-5-ylmethylsulfanyl]-4-methyl-4H-[1,2,4]triazol-3-yl}-pyridine | 8.90(m, 1H), 8.77(dd, 1H), 8.03(m, 1H), 7.78(m, 1H), 7.48(m, 1H), 7.28(m, 1H), 7.12(m, 1H), 4.73(s, 2H), 3.68(s, 3H), 2.36(s, 3H). | |

-continued

| Example No. | Name | 1H NMR | MS |
|---|---|---|---|
| 406 | 4-{5-[3-(2-Fluoro-5-methyl-phenyl)-[1,2,4]oxadiazol-5-ylmethylsulfanyl]-4-methyl-4H-[1,2,4]triazol-3-yl}-pyridine | 8.81(m, 2H), 7.77(m, 1H), 7.62(m, 2H), 7.31(m, 1H), 7.11(dd, 1H), 4.75(s, 2H), 3.72(s, 3H), 2.37(s, 3H). | |
| 407 | 4-{5-[5-(5-Bromo-2-fluoro-phenyl)-[1,2,4]oxadiazol-3-ylmethylsulfanyl]-4-methyl-4H-[1,2,4]triazol-3-yl}-pyridine | 8.82(m, 2H), 8.23(m, 1H), 7.71(m, 2H), 7.65(m, 1H), 7.18(d, 1H), 4.66(s, 2H), 3.75(s, 3H). | 448.02 |
| 408 | 3-{5-[5-(5-Bromo-2-fluoro-phenyl)-[1,2,4]oxadiazol-3-ylmethylsulfanyl]-4-methyl-4H-[1,2,4]triazol-3-yl}-pyridine | 8.92(m, 1H), 8.76(m, 1H), 8.22(m, 1H), 8.05(m, 1H), 7.50(m, 1H), 7.48(m, 1H), 7.17(dd, 1H), 4.63(s, 2H), 3.70(s, 3H). | |
| 409 | 5-(5-Bromo-2-fluoro-phenyl)-3-(4-methyl-5-thiophen-2-yl-4H-[1,2,4]triazol-3-ylsulfanylmethyl)-[1,2,4]oxadiazole | 8.23(dd, 1H), 7.70(m, 1H), 7.52(m, 2H), 7.19(m, 2H), 4.49(s, 2H), 3.77(s, 3H). | 452.90 |
| 410 | 5-(4-Methyl-5-thiophen-3-yl-4H-[1,2,4]triazol-3-ylsulfanylmethyl)-3-phenyl-[1,2,4]oxadiazole | 8.06(d, 2H) 7.34(d, 1H), 7.51(m, 5H), 4.68(s, 2H), 3.68(s, 3H). | |
| 411 | 3-{5-[5-(3-Fluoro-phenyl)-[1,2,4]oxadiazol-3-ylmethylsulfanyl]-4-methyl-4H-[1,2,4]triazol-3-yl}-pyridine | 8.92(s, 1H), 8.78(d, 1H) 8.05(d, 1H), 7.93(d, 1H), 7.91(d, 1H), 7.50(m, 2H), 7.28(t, 1H), 4.64(s, 2H), 3.70(s, 3H). | |
| 412 | 4-{5-[5-(3-Fluoro-phenyl)-[1,2,4]oxadiazol-3-ylmethylsulfanyl]-4-methyl-4H-[1,2,4]triazol-3-yl}-pyridine | 8.82(d, 2H), 7.93(d, 1H) 7.90(d, 1H), 7.64(d, 2H), 7.52(m, 1H), 7.33(m, 1H), 4.64(s, 2H), 3.73(s, 3H). | |
| 413 | 5-(3-Fluoro-phenyl)-3-(4-methyl-5-thiophen-3-yl-4H-[1,2,4]triazol-3-ylsulfanylmethyl)-[1,2,4]oxadiazole | 7.90(d, 1H) 7.82(d, 1H), 7.74(d, 1H), 7.51(m, 3H), 4.58(s, 2H), 3.71(s, 3H). | |
| 414 | 3-[4-Methyl-5-(5-thiophen-3-yl-[1,2,4]oxadiazol-3-ylmethylsulfanyl)-4H-[1,2,4]triazol-3-yl]-pyridine | 8.91(s, 1H), 8.78(d, 1H) 8.23(d, 1H), 8.04(d, 1H), 7.66(d, 1H), 7.49(m, 2H), 4.60(s, 2H), 3.69(s, 3H). | |
| 415 | 3-(4-Methyl-5-thiophen-3-yl-4H-[1,2,4]triazol-3-ylsulfanylmethyl)-5-thiophen-3-yl-[1,2,4]oxadiazole | 8.22(d, 1H) 7.74(d, 1H), 7.63(d, 1H), 7.49(m, 3H), 4.54(s, 2H), 3.70(s, 3H). | |
| 416 | 2-Chloro-4-[3-(4-methyl-5-pyridin-3-yl-4H-[1,2,4]triazol-3-ylsulfanylmethyl)-[1,2,4]oxadiazol-5-yl]-pyridine | 8.92(s, 1H), 8.78(d, 1H) 8.65(d, 1H), 8.04(t, 2H), 7.89(d, 1H), 7.51(m, 1H), 4.69(s, 2H), 3.71(s, 3H). | |
| 417 | 2-Chloro-4-[3-(4-methyl-5-pyridin-4-yl-4H-[1,2,4]triazol-3-ylsulfanylmethyl)-[1,2,4]oxadiazol-5-yl]-pyridine | 8.82(d, 2H), 8.65(d, 1H) 8.02(s, 1H), 7.89(d, 1H), 7.64(d, 2H), 4.70(s, 2H), 3.74(s, 3H). | |
| 418 | 2-Chloro-4-[3-(4-methyl-5-thiophen-3-yl-4H-[1,2,4]triazol-3-ylsulfanylmethyl)-[1,2,4]oxadiazol-5-yl]-pyridine | 8.64(d, 1H) 8.01(s, 1H), 7.88(d, 1H), 7.75(d, 1H), 7.52(m, 2H), 4.62(s, 2H), 3.72(s, 3H). | |
| 419 | 4-[4-Methyl-5-(5-phenyl-[1,2,4]oxadiazol-3-ylmethylsulfanyl)-4H-[1,2,4]triazol-3-yl]-pyridine | 8.82(d, 2H), 8.12(d, 2H) 7.63(m, 3H), 7.55(m, 2H), 4.63(s, 2H), 3.72(s, 3H). | |
| 420 | 3-(4-Methyl-5-thiophen-3-yl-4H-[1,2,4]triazol-3-ylsulfanylmethyl)-5-phenyl-[1,2,4]oxadiazole | 8.11(d, 2H) 7.74(d, 1H), 7.57(m, 1H), 7.52(m, 4H), 4.56(s, 2H), 3.70(s, 3H). | |
| 421 | 5-(5-Bromo-2-fluoro-phenyl)-3-(4-methyl-5-thiophen-3-yl-4H-[1,2,4]triazol-3-ylsulfanylmethyl)-[1,2,4]oxadiazole | (CD3OD as solvent):8.21(m, 1H), 8.02(m, 1H), 7.82(m, 1H), 7.68(m, 1H), 7.56(m, 1H), 7.33(t, 1H), 4.50(s, 2H), 3.82(s, 3H). | |

| Example No. | Name | 1H NMR | MS |
|---|---|---|---|
| 422 | 3-[5-(3-Chloro-phenyl)-isoxazol-3-ylmethylsulfanyl]-4-ethyl-5-thiophen-2-yl-4H-[1,2,4]triazole | (CD3OD as solvent): 7.84(s, 1H), 7.75(m, 2H), 7.60(m, 1H) 7.50(m, 2H), 7.27(m, 1H), 6.92(s, 1H), 4.51(s, 2H), 4.23(q, 2H), 1.33(t, 3H). | 404.05 |
| 423 | 2-Chloro-4-[3-(4-methyl-5-thiophen-2-yl-4H-[1,2,4]triazol-3-ylsulfanylmethyl)-[1,2,4]oxadiazol-5-yl]-pyridine | 8.64(d, 1H), 8.01(s, 1H) 7.98(d, 1H), 7.54(d, 1H), 7.50(d, 1H), 7.20(m, 1H), 4.61(s, 2H), 3.76(s, 3H). | 392.00 |
| 424 | 4-{5-[3-(3-Fluoro-phenyl)-[1,2,4]oxadiazol-5-ylmethylsulfanyl]-4-methyl-4H-[1,2,4]triazol-3-yl}-pyridine | 8.83(d, 2H), 7.85(d, 1H) 7.78(d, 1H), 7.62(d, 2H), 7.46(m, 1H), 7.22(m, 1H), 4.76(s, 2H), 3.72(s, 3H). | |
| 425 | 3-(3-Fluoro-phenyl)-5-(4-methyl-5-thiophen-3-yl-4H-[1,2,4]triazol-3-ylsulfanylmethyl)-[1,2,4]oxadiazole | 7.84(d, 1H) 7.74(m, 1H), 7.51(m, 3H), 7.24(m, 1H), 4.70(s, 2H), 3.70(s, 3H). | |
| 426 | 3-(4-Ethyl-5-thiophen-2-yl-4H-[1,2,4]triazol-3-ylsulfanylmethyl)-5-m-tolyl-[1,2,4]oxadiazole | (CD3OD as solvent):7.89(m, 2H), 7.76(m, 1H), 7.60(m, 1H), 7.47(m, 2H), 7.27(m, 1H), 4.55(s, 2H), 4.25(q, 2H), 2.41(s, 3H), 1.32(s, 3H) | 384.13 |
| 427 | 3-(4-Ethyl-5-thiophen-2-yl-4H-[1,2,4]triazol-3-ylsulfanylmethyl)-5-(2-fluoro-5-methyl-phenyl)-[1,2,4]oxadiazole | (CD3OD as solvent):7.85(m, 1H), 7.75(m, 1H), 7.60(m, 1H), 7.55(m, 1H), 7.27(m, 1H), 7.22(m, 1H), 4.57(s, 2H), 4.27(q, 2H), 2.36(s, 3H), 1.33(s, 3H). | 402.09 |
| 428 | 4-{5-[5-(3-Chloro-phenyl)-[1,2,4]oxadiazol-3-ylmethylsulfanyl]-4-furan-2-ylmethyl-4H-[1,2,4]triazol-3-yl}-pyridine | (CD3OD as solvent):8.75(m, 2H), 8.04(m, 2H), 7.78(m, 2H), 7.66(m, 1H), 7.60(m, 1H), 7.37(m, 1H), 6.30(m, 2H), 5.42(s, 2H), 4.56(s, 2H). | 452.10 |
| 429 | 4-{5-[5-(3-Chloro-phenyl)-[1,2,4]oxadiazol-3-ylmethylsulfanyl]-4-ethyl-4H-[1,2,4]triazol-3-yl}-pyridine | 8.80(m, 2H), 8.09(m, 1H), 7.98(m, 1H), 7.58(m, 3H), 7.50(dd, 1H), 4.69(s, 2H), 4.12(m, 2H), 1.36(m, 3H). | |
| 430 | 3-{5-[5-(3-Chloro-phenyl)-[1,2,4]oxadiazol-3-ylmethylsulfanyl]-4-ethyl-4H-[1,2,4]triazol-3-yl}-pyridine | (CD3OD as solvent):8.87(s, 1H), 8.77(d, 1H), 8.07(m, 3H), 7.67(m, 2H), 7.61(dd, 1H), 4.62(s, 2H), 4.13(m, 2H), 1.26(m, 3H). | 400.12 |
| 431 | 5-(3-Chloro-phenyl)-3-(4-ethyl-5-thiophen-3-yl-4H-[1,2,4]triazol-3-ylsulfanylmethyl)-[1,2,4]oxadiazole | (CD3OD as solvent):7.79(m, 3H), 7.67(m, 2H), 7.51(m, 2H), 4.56(s, 2H), 4.22(q, 2H), 1.30(t, 3H). | 405.07 |
| 432 | 3-{5-[5-(3-Chloro-phenyl)-[1,2,4]oxadiazol-3-ylmethylsulfanyl]-4-furan-2-ylmethyl-4H-[1,2,4]triazol-3-yl}-pyridine | (CD3OD as solvent):8.86(s, 1H), 8.76(d, 1H), 8.07(m, 1H), 8.01(m, 2H), 7.64(m, 3H), 7.36(s, 1H), 6.29(s, 2H), 5.37(s, 2H), 4.55(s, 2H). | 452.12 |
| 433 | 3-(4-Furan-2-ylmethyl-5-thiophen-2-yl-4H-[1,2,4]triazol-3-ylsulfanylmethyl)-5-m-tolyl-[1,2,4]oxadiazole | (CD3OD as solvent):7.87(m, 2H), 7.73(m, 1H), 7.63(m, 1H), 7.45(m, 3H), 7.25(m, 1H), 6.31(m, 2H), 5.42(s, 2H), 4.49(s, 2H), 2.40(s, 3H). | 436.16 |
| 434 | 5-(5-Fluoro-2-methyl-phenyl)-3-(4-furan-2-ylmethyl-5-thiophen-2-yl-4H-[1,2,4]triazol-3- | (CD3OD as solvent):7.75(dd, 1H), 7.69(m, 1H), 7.66(m, | 454.12 |

| Example No. | Name | 1H NMR | MS |
|---|---|---|---|
| | ylsulfanylmethyl)-[1,2,4]oxadiazole | 1H), 7.41(m, 1H), 7.38(m, 1H), 7.25(m, 2H), 6.32(s, 2H), 5.44(s, 2H), 4.51(s, 2H), 2.36(s, 3H). | |
| 435 | 5-(3-Chloro-phenyl)-3-(4-furan-2-ylmethyl-4H-[1,2,4]triazol-3-ylsulfanylmethyl)-[1,2,4]oxadiazole | 8.23(s, 1H), 8.09(m, 1H), 7.97(m, 1H), 7.48(m, 1H), 7.45(m, 1H), 7.37(s, 1H), 6.39(m, 1H), 6.34(m, 1H), 5.12(s, 2H), 4.55(s, 2H). | 375.09 |
| 436 | 3-[3-(4-Methyl-5-pyridin-3-yl-4H-[1,2,4]triazol-3-ylsulfanylmethyl)-[1,2,4]oxadiazol-5-yl]-benzonitrile | 8.92(s, 1H), 8.78(d, 1H) 8.43(s, 1H), 8.35(d, 1H), 8.05(d, 1H), 7.91(d, 1H), 7.72(t, 1H), 7.52(m, 1H), 4.67(s, 2H), 3.71(s, 3H). | 376.20 |
| 437 | 3-[3-(4-Methyl-5-pyridin-4-yl-4H-[1,2,4]triazol-3-ylsulfanylmethyl)-[1,2,4]oxadiazol-5-yl]-benzonitrile | 8.82(d, 2H), 8.43(s, 1H) 8.35(d, 1H), 7.90(t, 1H), 7.64(d, 2H), 4.68(s, 2H), 3.74(s, 3H). | 376.10 |
| 438 | 3-[3-(4-Methyl-5-thiophen-3-yl-4H-[1,2,4]triazol-3-ylsulfanylmethyl)-[1,2,4]oxadiazol-5-yl]-benzonitrile | 8.42(s, 1H), 8.35(d, 1H) 7.89(d, 1H), 7.72(m, 2H), 7.52(s, 1H), 4.61(s, 2H), 3.73(s, 3H). | |
| 439 | 5-(5-Chloro-2-fluoro-phenyl)-3-(4-ethyl-5-thiophen-2-yl-4H-[1,2,4]triazol-3-ylsulfanylmethyl)-[1,2,4]oxadiazole | 8.08(m, 1H), 7.54(m, 2H), 7.48(d, 1H), 7.20(m, 2H), 4.69(s, 2H), 4.18(m, 2H), 1.39(t, 3H). | 423.12 |
| 440 | 2-Chloro-4-[3-(4-ethyl-5-thiophen-2-yl-4H-[1,2,4]triazol-3-ylsulfanylmethyl)-[1,2,4]oxadiazol-5-yl]-pyridine | 8.64(d, 1H), 8.02(s, 1H), 7.89(d, 1H), 7.53(d, 1H), 7.48(d, 1H), 7.20(t, 1H), 4.69(s, 2H), 4.17(m, 2H), 1.40(t, 3H). | 406.00 |
| 441 | 3-(4-Ethyl-5-thiophen-2-yl-4H-[1,2,4]triazol-3-ylsulfanylmethyl)-5-thiophen-3-yl-[1,2,4]oxadiazole | 8.23(s, 1H), 7.66(d, 1H), 7.53(d, 1H), 7.48(m, 2H), 7.19(t, 1H), 4.63(s, 2H), 4.17(m, 2H), 1.40(t, 3H). | 376.10 |
| 442 | 3-(4-Ethyl-5-thiophen-3-yl-4H-[1,2,4]triazol-3-ylsulfanylmethyl)-5-m-tolyl-[1,2,4]oxadiazole | 7.93(m, 2H), 7.71(m, 1H), 7.49(m, 2H), 7.42(m, 2H), 4.63(s, 2H), 4.10(q, 2H), 2.43(s, 3H), 1.36(t, 3H). | 384.10 |
| 443 | 4-[4-Ethyl-5-(5-m-tolyl-[1,2,4]oxadiazol-3-ylmethylsulfanyl)-4H-[1,2,4]triazol-3-yl]-pyridine | 8.80(m, 2H), 7.91(m, 2H), 7.60(m, 2H), 7.41(m, 2H), 4.68(s, 2H), 4.09(m, 2H), 2.43(s, 3H), 1.29(s, 3H). | 379.20 |
| 444 | 3-[4-Ethyl-5-(5-m-tolyl-[1,2,4]oxadiazol-3-ylmethylsulfanyl)-4H-[1,2,4]triazol-3-yl]-pyridine | (CD3OD as solvent): 8.87(s, 1H), 8.77(d, 1H), 8.02(m, 1H), 7.92(m, 2H), 7.49(m, 1H), 7.42(m, 2H), 4.67(s, 2H), 4.05(q, 2H), 2.43(s, 3H), 1.35(t, 3H). | 379.20 |
| 445 | 3-(4-Ethyl-5-thiophen-3-yl-4H-[1,2,4]triazol-3-ylsulfanylmethyl)-5-(2-fluoro-5-methyl-phenyl)-[1,2,4]oxadiazole | 7.88(dd, 1H), 7.71(m, 1H), 7.49(m, 2H), 7.28(m, 1H), 7.14(dd, 1H), 4.66(s, 2H), 4.11(q, 2H), 2.39(s, 3H), 1.34(t, 3H). | |
| 446 | 4-{4-Ethyl-5-[5-(2-fluoro-5-methyl-phenyl)-[1,2,4]oxadiazol-3-ylmethylsulfanyl]-4H-[1,2,4]triazol-3-yl}-pyridine | 8.80(m, 2H), 7.86(m, 1H), 7.60(m, 2H), 7.38(m, 1H), 7.14(dd, 1H), 4.70(s, 2H), 4.11(q, 2H), 2.39(s, 3H), 1.36(t, 3H). | 398.20 |
| 447 | 3-{4-Ethyl-5-[5-(2-fluoro-5-methyl-phenyl)-[1,2,4]oxadiazol-3-ylmethylsulfanyl]-4H-[1,2,4]triazol-3-yl}-pyridine | 8.87(s, 1H), 8.76(d, 1H), 8.01(m, 1H), 7.88(m, 1H), 7.49(m, 1H), 7.28(m, 1H), 7.14(dd, | |

-continued

| Example No. | Name | 1H NMR | MS |
|---|---|---|---|
| | | 1H), 4.69(s, 2H), 4.07(q, 2H), 2.39(q, 2H), 1.35(t, 3H). | |
| 448 | 3-[5-(3-Chloro-phenyl)-[1,2,4]oxadiazol-3-ylmethylsulfanyl]-5-pyridin-4-yl-[1,2,4]triazol-4-ylamine | (DMSO-D6 as solvent): 8.75(dd, 2H), 8.05(m, 4H), 7.79(m, 1H), 7.66(dd, 1H), 6.33(s, 2H), 4.65(s, 2H). | 387.05 |
| 449 | 4-{5-[5-(5-Bromo-2-fluoro-phenyl)-[1,2,4]oxadiazol-3-ylmethylsulfanyl]-4-ethyl-4H-[1,2,4]triazol-3-yl}-pyridine | 8.81(dd, 2H), 8.24(m, 1H), 7.71(m, 1H), 7.61(m, 2H), 7.18(dd, 1H), 4.72(s, 2H), 4.13(m, 2H), 1.29(m, 3H). | 464.02 |
| 450 | 5-(4-Methyl-5-thiophen-3-yl-4H-[1,2,4]triazol-3-ylsulfanylmethyl)-3-thiophen-2-yl-[1,2,4]oxadiazole | 7.75(m, 2H), 7.51(m, 3H), 7.16(m, 1H), 4.64(s, 2H), 3.70(s, 3H). | |
| 451 | 3-[3-(4-Ethyl-5-thiophen-2-yl-4H-[1,2,4]triazol-3-ylsulfanylmethyl)-[1,2,4]oxadiazol-5-yl]-benzonitrile | 8.42(s, 1H), 8.35(d, 1H), 7.89(d, 1H), 7.71(t, 1H), 7.54(d, 1H), 7.48(d, 1H), 7.20(t, 1H), 4.68(s, 2H), 4.16(m, 2H), 1.40(t, 3H). | 395.10 |
| 452 | 3-(4-Ethyl-5-thiophen-2-yl-4H-[1,2,4]triazol-3-ylsulfanylmethyl)-5-phenyl-[1,2,4]oxadiazole | 8.13(d, 2H), 7.49(br m, 5H), 7.20(m, 1H), 4.65(s, 2H), 4.16(m, 2H), 1.40(t, 3H). | 370.09 |
| 453 | 4-[3-(4-Ethyl-5-thiophen-2-yl-4H-[1,2,4]triazol-3-ylsulfanylmethyl)-[1,2,4]oxadiazol-5-yl]-2-methoxy-pyridine | 8.36(d, 1H), 7.51(br m, 3H), 7.42(s, 1H), 7.19(m, 1H), 4.68(s, 2H), 4.16(m, 2H), 1.42(t, 3H). | |
| 454 | 3-(3-Chloro-phenyl)-5-(4-ethyl-5-thiophen-2-yl-4H-[1,2,4]triazol-3-ylsulfanylmethyl)-[1,2,4]oxadiazole | 8.06(s, 1H), 7.95(d, 1H), 7.54(m, 1H), 7.49(m, 1H), 7.42(m, 2H), 7.20(m, 1H), 4.78(s, 2H), 4.17(q, 2H), 1.41(t, 3H). | |
| 455 | 4-{5-[5-(3-Chloro-phenyl)-isoxazol-3-ylmethylsulfanyl]-4-ethyl-4H-[1,2,4]triazol-3-yl}-pyridine | 8.82(m, 2H), 7.76(m, 1H), 7.66(m, 1H), 7.60(m, 2H), 7.41(m, 2H), 6.78(s, 1H), 4.65(s, 2H), 4.07(q, 2H), 1.40(t, 3H). | 399.10 |
| 456 | 2-Methyl-4-[3-(4-methyl-5-thiophen-3-yl-4H-[1,2,4]triazol-3-ylsulfanylmethyl)-[1,2,4]oxadiazol-5-yl]-pyridine | 8.73(d, 1H), 7.81(s, 1H), 7.75(s, 2H), 7.51(m, 2H), 4.60(s, 2H), 3.71(s, 3H) 2.68(s, 3H). | |
| 457 | 4-[3-(4-Ethyl-5-thiophen-2-yl-4H-[1,2,4]triazol-3-ylsulfanylmethyl)-[1,2,4]oxadiazol-5-yl]-2-methyl-pyridine | 8.73(d, 1H), 7.82(s, 1H), 7.76(d, 1H), 7.54(d, 1H), 7.48(d, 1H), 7.29(m, 1H), 4.68(s, 2H), 4.16(m, 2H), 2.68(s, 3H), 1.41(t, 3H). | |
| 458 | 5-(4-Ethyl-5-thiophen-2-yl-4H-[1,2,4]triazol-3-ylsulfanylmethyl)-3-thiophen-2-yl-[1,2,4]oxadiazole | 7.78(d, 1H), 7.53(t, 2H), 7.48(d, 1H), 7.18(m, 2H), 4.74(s, 2H), 4.17(m, 2H), 1.41(t, 3H). | 376.00 |
| 459 | 4-{5-[5-(5-Chloro-2-fluoro-phenyl)-[1,2,4]oxadiazol-3-ylmethylsulfanyl]-4-ethyl-4H-[1,2,4]triazol-3-yl}-pyridine | 8.82(d, 2H), 8.09(m, 1H), 7.58(m, 3H), 7.24(m, 1H), 4.73(s, 2H), 4.13(m, 2H), 1.41(t, 3H). | 418.10 |
| 460 | 4-[3-(4-Ethyl-5-pyridin-4-yl-4H-[1,2,4]triazol-3-ylsulfanylmethyl)-[1,2,4]oxadiazol-5-yl]-2-methyl-pyridine | 8.82(d, 2H), 8.75(d, 1H), 7.84(s, 1H), 7.76(d, 1H), 7.60(d, 2H), 4.74(s, 2H), 4.13(m, 2H), 1.41(t, 3H). | |
| 461 | 3-{5-[5-(3-Chloro-phenyl)-[1,2,4]oxadiazol-3-ylmethylsulfanyl]-4-methyl-4H-[1,2,4]triazol-3-yl}-benzonitrile | 8.11(s, 1H), 7.97(m, 3H), 7.83(d, 1H), 7.63(m, 3H), 7.50(t, 1H), 4.63(s, 2H) and 3.68(s, 3H) | |
| 462 | 5-(3-Chloro-phenyl)-3-[5-(3-chloro-phenyl)-4-methyl-4H-[1,2,4]triazol- | 8.11(s, 1H), 8.00(d, 1H), 7.67(m, 1H), | |

-continued

| Example No. | Name | 1H NMR | MS |
|---|---|---|---|
| | 3-ylsulfanylmethyl]-[1,2,4]oxadiazole | 7.50(m, 5H), 4.61(s, 2H) and 3.66(s, 3H). | |
| 463 | 5-(3-Chloro-phenyl)-3-[5-(4-chloro-phenyl)-4-methyl-4H-[1,2,4]triazol-3-ylsulfanylmethyl]-[1,2,4]oxadiazole | 8.11(s, 1H), 8.01(d, 1H), 7.55(m, 6H), 4.61(s, 2H) and 3.64(s, 3H). | |
| 464 | 4-{5-[5-(2,5-Dichloro-phenyl)-[1,2,4]oxadiazol-3-ylmethylsulfanyl]-4-ethyl-4H-[1,2,4]triazol-3-yl}-pyridine | 8.80(dd, 2H), 8.05(m, 1H), 7.59(m, 2H), 7.47(s, 2H), 4.73(s, 2H), 4.11(m, 2H), 1.32(m, 3H). | |
| 465 | 5-(2,5-Dichloro-phenyl)-3-(4-ethyl-5-thiophen-2-yl-4H-[1,2,4]triazol-3-ylsulfanylmethyl)-[1,2,4]oxadiazole | 8.06(dd, 1H), 7.50(m, 4H), 7.19(dd, 1H), 4.68(s, 2H), 4.17(q, 2H), 1.39(t, 3H). | |
| 466 | 5-(2,5-Difluoro-phenyl)-3-(4-ethyl-5-thiophen-2-yl-4H-[1,2,4]triazol-3-ylsulfanylmethyl)-[1,2,4]oxadiazole | 8.80(dd, 2H), 7.79(m, 1H), 7.60(m, 2H), 7.28(m, 1H), 4.68(s, 2H), 4.11(q, 2H), 1.39(t, 3H). | 406.10 |
| 467 | 4-{5-[5-(2,5-Difluoro-phenyl)-[1,2,4]oxadiazol-3-ylmethylsulfanyl]-4-ethyl-4H-[1,2,4]triazol-3-yl}-pyridine | 7.80(m, 1H), 7.52(m, 1H), 7.48(m, 1H), 7.20(m, 4H), 4.68(s, 2H), 4.17(m, 2H), 1.40(t, 3H). | |
| 468 | 5-(2,5-Dichloro-phenyl)-3-(4-ethyl-5-thiophen-3-yl-4H-[1,2,4]triazol-3-ylsulfanylmethyl)-[1,2,4]oxadiazole | 8.07(dd, 1H), 7.71(dd, 1H), 7.49(m, 4H), 4.69(s, 2H), 4.12(m, 2H), 1.38(t, 3H). | |
| 469 | 5-(2,5-Difluoro-phenyl)-3-(4-ethyl-5-thiophen-3-yl-4H-[1,2,4]triazol-3-ylsulfanylmethyl)-[1,2,4]oxadiazole | 7.80(m, 1H), 7.72(m, 1H), 7.49(m, 2H), 7.28(m, 2H), 4.68(s, 2H), 4.12(q, 2H), 1.37(t, 3H). | 406.10 |
| 470 | 4-{5-[5-(3-Chloro-phenyl)-[1,2,4]oxadiazol-3-ylmethylsulfanyl]-4-propyl-4H-[1,2,4]triazol-3-yl}-pyridine | 8.80(dd, 2H), 8.11(m, 1H), 7.99(m, 1H), 7.57(m, 3H), 7.48(t, 1H), 4.70(s, 2H), 3.99(q, 2H), 1.72(m, 2H), 0.91(t, 3H). | |
| 471 | 4-{5-[5-(2-Fluoro-5-methyl-phenyl)-[1,2,4]oxadiazol-3-ylmethylsulfanyl]-4-propyl-4H-[1,2,4]triazol-3-yl}-pyridine | 8.80(dd, 2H), 7.87(dd, 1H), 7.58(m, 2H), 7.39(m, 1H), 7.15(q, 1H), 4.70(s, 2H), 4.01(m, 2H), 2.40(s, 3H), 1.70(m, 2H), 0.87(t, 3H). | |
| 472 | 3-(4-Ethyl-5-thiophen-2-yl-4H-[1,2,4]triazol-3-ylsulfanylmethyl)-5-thiophen-2-yl-[1,2,4]oxadiazole | 7.91(d, 1H), 7.67(d, 1H), 7.52(d, 1H), 7.48(d, 1H), 7.20(m, 2H), 4.62(s, 2H), 4.18(m, 2H), 1.38(t, 3H). | 376.10 |
| 473 | 3-(4-Methyl-5-thiophen-3-yl-4H-[1,2,4]triazol-3-ylsulfanylmethyl)-5-thiophen-2-yl-[1,2,4]oxadiazole | 7.90(s, 1H), 7.74(d, 1H), 7.67(d, 1H), 7.52(m, 2H), 7.21(m, 1H), 4.60(s, 2H), 3.71(s, 3H) 2.68(s, 3H). | |
| 474 | 4-[4-Methyl-5-(3-thiophen-3-yl-[1,2,4]oxadiazol-5-ylmethylsulfanyl)-4H-[1,2,4]triazol-3-yl]-pyridine | 8.82(d, 2H), 8.05(s, 1H), 7.61(m, 3H), 7.44(m, 1H), 4.73(s, 2H), 3.70(s, 3H). | |
| 475 | 5-(4-Methyl-5-thiophen-3-yl-4H-[1,2,4]triazol-3-ylsulfanylmethyl)-3-thiophen-3-yl-[1,2,4]oxadiazole | 8.05(s, 1H), 7.73(d, 1H), 7.62(d, 1H), 7.51(s, 2H), 7.44(m, 1H), 4.66(s, 2H), 3.68(s, 3H). | |
| 476 | 5-(4-Ethyl-5-thiophen-2-yl-4H-[1,2,4]triazol-3-ylsulfanylmethyl)-3-thiophen-3-yl-[1,2,4]oxadiazole | 8.05(d, 1H), 7.62(d, 1H), 7.53(d, 1H), 7.47(d, 1H), 7.44(m, 1H), 7.19(m, 1H), 4.75(s, 2H), 4.15(m, 2H), 1.40(t, 3H). | 376.10 |
| 477 | 5-[3-(4-Ethyl-5-thiophen-2-yl-4H-[1,2,4]triazol-3-ylsulfanylmethyl)-[1,2,4]oxadiazol-5-yl]-thiophene-3-carbonitrile | 8.18(d, 1H), 8.03(d, 1H), 7.51(m, 1H), 7.46(m, 1H), 7.18(m, 1H), 4.63(s, 2H), 4.16(q, 2H), 1.40(t, 3H). | 401.00 |

-continued

| Example No. | Name | 1H NMR | MS |
|---|---|---|---|
| 478 | 5-(3-Chloro-phenyl)-3-[5-(2-fluoro-phenyl)-4-methyl-4H-[1,2,4]triazol-3-ylsulfanylmethyl]-[1,2,4]oxadiazole | 8.13(s, 1H), 8.01(d, 1H), 7.52(m, 4H), 7.34(t, 1H), 7.27(m, 1H), 4.63(s, 2H) and 3.54(s, 3H). | |
| 479 | 5-(3-Chloro-phenyl)-3-[5-(3-fluoro-phenyl)-4-methyl-4H-[1,2,4]triazol-3-ylsulfanylmethyl]-[1,2,4]oxadiazole | 8.11(s, 1H), 8.00(d, 1H), 7.52(m, 5H), 7.27(m, 1H), 4.62(s, 2H) and 3.66(s, 3H). | 403.00 |
| 480 | 5-(3-Chloro-phenyl)-3-[5-(4-fluoro-phenyl)-4-methyl-4H-[1,2,4]triazol-3-ylsulfanylmethyl]-[1,2,4]oxadiazole | 8.11(s, 1H), 8.00(d, 1H), 7.59(m, 4H), 7.49(t, 1H), 7.22(m, H), 4.61(s, 2H) and 3.64(s, 3H). | 403.10 |
| 481 | 3-(5-Benzo[b]thiophen-2-yl-4-methyl-4H-[1,2,4]triazol-3-ylsulfanylmethyl)-5-(3-chloro-phenyl)-[1,2,4]oxadiazole | 8.11(s, 1H), 8.01(d, 1H), 7.87(m, 2H), 7.72(s, 1H), 7.58(d, 1H), 7.45(m, 3H), 4.60(s, 2H) and 3.85(s, 3H). | |
| 482 | 5-(3-Chloro-phenyl)-3-[5-(3-methoxy-phenyl)-4-methyl-4H-[1,2,4]triazol-3-ylsulfanylmethyl]-[1,2,4]oxadiazole | 8.12(s, 1H), 8.01(d, 1H), 7.59(dd, 1H), 7.49(t, 1H), 7.44(t, 1H), 7.2(m, 2H), 7.05(dd, 1H), 4.60(s, 2H), 3.88(s, 3H) and 3.65(s, 3H). | |
| 483 | 5-(3-Chloro-phenyl)-3-[5-(4-methoxy-phenyl)-4-methyl-4H-[1,2,4]triazol-3-ylsulfanylmethyl]-[1,2,4]oxadiazole | 8.12(s, 1H), 8.01(d, 1H), 7.59(m, 3H), 7.49(t, 1H), 7.03(d, 2H), 4.59(s, 2H), 3.89(s, 3H) and 3.63(s, 3H). | 415.00 |
| 484 | 3-(4-Ethyl-5-furan-2-yl-4H-[1,2,4]triazol-3-ylsulfanylmethyl)-5-(2-fluoro-5-methyl-phenyl)-[1,2,4]oxadiazole | 7.86(dd, 1H), 7.59(m, 1H), 7.37(m, 1H), 7.14(m, 2H), 6.58(q, 1H), 4.63(s, 2H), 4.26(q, 2H), 2.39(s, 3H), 1.37(t, 3H). | 386.10 |
| 485 | 3-(4-Ethyl-5-furan-2-yl-[1,2,4]triazol-3-ylsulfanylmethyl)-5-m-tolyl-[1,2,4]oxadiazole | 7.91(m, 2H), 7.59(m, 1H), 7.40(m, 2H), 7.10(q, 2H), 6.58(q, 1H), 4.61(s, 2H), 4.24(q, 2H), 2.43(s, 3H), 1.36(t, 3H). | 368.20 |
| 486 | 3-(4-Ethyl-5-trifluoromethyl-4H-[1,2,4]triazol-3-ylsulfanylmethyl)-5-(2-fluoro-5-methyl-phenyl)-[1,2,4]oxadiazole | 7.97(m, 1H), 7.47(m, 1H), 7.16(t, 1H), 4.72(d, 2H), 4.16(m, 2H), 2.41(d, 3H), 1.37(m, 3H). | |
| 487 | 3-[5-(2-Fluoro-5-methyl-phenyl)-[1,2,4]oxadiazol-3-ylmethylsulfanyl]-5-pyridin-4-yl-[1,2,4]triazol-4-ylamine | (CD3OD as solvent):8.72(m, 2H), 8.17(m, 2H), 7.86(dd, 1H), 7.49(m, 1H), 7.23(dd, 1H), 4.59(s, 2H), 2.35(s, 3H). | |
| 488 | 3-[5-(2-Fluoro-5-methyl-phenyl)-[1,2,4]oxadiazol-3-ylmethylsulfanyl]-5-thiophen-2-yl-[1,2,4]triazol-4-ylamine | (CD3OD as solvent):8.05(s, 1H), 7.84(dd, 1H), 7.69(m, 1H), 7.47(m, 1H), 7.22(m, 2H), 4.52(s, 2H), 2.33(s, 3H). | |
| 489 | 3-Pyridin-4-yl-5-(5-m-tolyl-[1,2,4]oxadiazol-3-ylmethylsulfanyl)-[1,2,4]triazol-4-ylamine | (CD3OD as solvent):8.73(dd, 2H), 8.17(dd, 2H), 7.89(m, 2H), 7.46(m, 2H), 4.58(s, 2H), 2.389(s, 3H). | |
| 490 | 3-Thiophen-2-yl-5-(5-m-tolyl-[1,2,4]oxadiazol-3-ylmethylsulfanyl)-[1,2,4]triazol-4-ylamine | (CD3OD as solvent):8.05(dd, 1H), 7.87(d, 2H), 7.70(dd, 1H), 7.45(m, 2H), 7.23(q, 1H), 4.50(s, 2H), 2.39(s, 3H). | |
| 491 | 3-(4-Ethyl-5-furan-2-yl-4H-[1,2,4]triazol-3-ylsulfanylmethyl)-5-thiophen-3-yl-[1,2,4]oxadiazole | 8.23(m, 1H), 7.66(m, 1H), 7.60(m, 1H), 7.47(m, 1H), 7.11(m, 1H), 6.60(m, 1H), 4.61(s, 2H), 4.26(q, 2H), 1.38(t, 3H). | 360.10 |

-continued

| Example No. | Name | 1H NMR | MS |
|---|---|---|---|
| 492 | 5-(3-Chloro-phenyl)-3-(4-ethyl-5-furan-2-yl-4H-[1,2,4]triazol-3-ylsulfanylmethyl)-[1,2,4]oxadiazole | 8.11(m, 1H), 8.00(m, 1H), 7.59(m, 2H), 7.51(t, 1H), 7.12(m, 1H), 6.60(m, 1H), 4.63(s, 2H), 4.26(q, 2H), 1.38(t, 3H). | 389.00 |
| 493 | 4-[3-(4-Ethyl-5-furan-2-yl-4H-[1,2,4]triazol-3-ylsulfanylmethyl)-[1,2,4]oxadiazol-5-yl]-2-methyl-pyridine | 8.73(d, 1H), 7.82(s, 1H), 7.75(m, 1H), 7.60(m, 1H), 7.12(m, 1H), 6.60(m, 1H), 4.65(s, 2H), 4.26(q, 2H), 2.68(s, 3H), 1.39(t, 3H). | |
| 494 | 5-(2,5-Difluoro-phenyl)-3-(4-ethyl-5-furan-2-yl-4H-[1,2,4]triazol-3-ylsulfanylmethyl)-[1,2,4]oxadiazole | 7.80(m, 1H), 7.61(m, 1H), 7.29(m, 2H), 7.12(m, 1H), 6.60(m, 1H), 4.65(s, 2H), 4.28(q, 2H), 1.39(t, 3H). | 390.09 |
| 495 | 4-[4-Ethyl-5-(5-thiophen-3-yl-isoxazol-3-ylmethylsulfanyl-4H-[1,2,4]triazol-3-yl]-pyridine | 8.81(m, 2H), 7.63(m, 1H), 7.59(m, 2H), 7.41(m, 2H), 6.58(s, 1H), 4.63(s, 2H), 4.06(q, 2H), 1.38(t, 3H). | 371.00 |
| 496 | 4-Ethyl-3-furan-2-yl-5-(5-thiophen-3-yl-isoxazol-3-ylmethylsulfanyl)-4H-[1,2,4]triazole | 7.77(m, 1H), 7.60(m, 1H) 7.40(m, 2H), 7.10(m, 1H), 6.60(m, 1H), 6.55(s, 1H), 4.58(s, 2H), 4.21(q, 2H), 1.38(t, 3H). | 359.10 |
| 497 | 5-(3-Chloro-phenyl)-3-[5-(3,5-dichloro-phenyl)-4-ethyl-4H-[1,2,4]triazol-3-ylsulfanylmethyl]-[1,2,4]oxadiazole | 8.12(s, 1H), 8.01(d, 1H), 7.60(d, 1H), 7.54(s, 3H), 7.47(t, 1H), 4.69(s, 2H), 4.06(q, 2H) and 1.36(t, 3H). | |
| 498 | 5-(3-Chloro-phenyl)-3-(4-ethyl-5-p-tolyl-4H-[1,2,4]triazol-3-ylsulfanylmethyl)-[1,2,4]oxadiazole | 8.13(s, 1H), 8.01(d, 1H), 7.53(m, 4H), 7.20(d, 2H), 4.68(s, 2H), 4.03(q, 3H), 2.45(s, 1H) and 1.32(t, 3H). | |
| 499 | 5-(3-Chloro-phenyl)-3-(4-ethyl-5-m-tolyl-4H-[1,2,4]triazol-3-ylsulfanylmethyl)-[1,2,4]oxadiazole | 8.11(s, 1H), 8.00(d, 1H), 7.58(d, 1H), 7.29–7.50(m, 5H), 4.66(s, 2H), 4.02(q, 2H), 2.45(s, 1H) and 1.32(t, 3H). | |
| 500 | 5-(3-Chloro-phenyl)-3-[4-ethyl-5-(3-nitro-phenyl)-4H-[1,2,4]triazol-3-ylsulfanylmethyl]-[1,2,4]oxadiazole | 8.52(s, 1H), 8.40(d, 1H), 8.12(s, 1H), 8.05(dd, 2H), 7.76(t, 1H), 7.60(d, 1H), 7.50(t, 1H), 4.72(s, 2H), 4.10(q, 2H) and 1.41(t, 3H). | |
| 501 | 4-{5-[3-(3-Chloro-phenyl)-isoxazol-5-ylmethylsulfanyl]-4-methyl-4H-[1,2,4]triazol-3-yl}-pyridine | 7.80(m, 2H), 7.78(m, 1H), 7.65(m, 1H), 7.59(m, 2H), 7.40(m, 2H), 6.65(s, 1H), 4.67(s, 2H), 3.64(s, 3H). | |
| 502 | 5-(3-Chloro-phenyl)-3-[5-(2,5-difluoro-phenyl)-4-ethyl-4H-[1,2,4]triazol-3-ylsulfanylmethyl]-[1,2,4]oxadiazole | 8.14(s, 1H), 8.02(d, 1H), 7.60(d, 1H), 7.52(t, 1H), 7.32(m, 1H), 7.23(m, 2H), 4.70(s, 2H), 3.96(q, 2H) and 1.27(t, 3H). | |
| 503 | 5-(3-Chloro-phenyl)-3-[5-(3-chloro-phenyl)-4-ethyl-4H-[1,2,4]triazol-3-ylsulfanylmethyl]-[1,2,4]oxadiazole | 8.11(s, 1H), 8.06(d, 1H), 7.63(s, 1H), 7.58(d, 1H), 7.49(m, 4H), 7.23(m, 2H), 4.68(s, 2H), 4.04(q, 2H) and 1.34(t, 3H). | |
| 504 | 5-(3-Chloro-phenyl)-3-[5-(4-chloro-phenyl)-4-ethyl-4H-[1,2,4]triazol-3-ylsulfanylmethyl]-[1,2,4]oxadiazole | 8.13(s, 1H), 8.01(d, 1H), 7.3(m, 6H), 4.68(s, 2H), 4.03(q, 2H) and 1.34(t, 3H). | |
| 505 | 4-{5-[5-(3-Chloro-phenyl)-oxazol-2-ylmethylsulfanyl]-4-ethyl-4H-[1,2,4]triazol-3-yl}-pyridine | 8.78(d, 2H), 7.55(m, 3H), 7.44(m, 1H), 7.29(m, 3H), 4.69(s, 2H), 4.04(q, 2H) and 1.34(t, 3H). | |

-continued

| Example No. | Name | 1H NMR | MS |
|---|---|---|---|
| 506 | 3-[5-(3-Chloro-phenyl)-oxazol-2-ylmethylsulfanyl]-4-ethyl-5-thiophen-2-yl-4H-[1,2,4]triazole | 7.55(s, 1H), 7.50(d, 1H), 7.44(m, 2H), 7.28(m, 3H), 7.18(dd, 1H), 4.64(s, 2H), 4.10(q, 2H) and 1.35(t, 3H). | 404.00 |
| 507 | 3-[5-(3-Chloro-phenyl)-oxazol-2-ylmethylsulfanyl]-4-ethyl-5-furan-2-yl-4H-[1,2,4]triazole | 7.58(s, 1H), 7.53(s, 1H), 7.40(m, 1H), 7.27(m, 3H), 7.10(d, 1H), 6.68(d, 1H), 4.62(s, 2H), 4.19(q, 2H) and 1.33(t, 3H). | 388.00 |
| 508 | 5-(2-Chloro-5-methyl-phenyl)-3-(4-ethyl-5-thiophen-2-yl-4H-[1,2,4]triazol-3-ylsulfanylmethyl)-[1,2,4]oxadiazole | 7.83(s, 1H), 7.53(d, 1H), 7.44(m, 2H), 7.32(d, 1H), 7.18(t, 2H), 4.63(s, 2H), 4.17(q, 2H), 2.37(s, 3H), 1.38(t, 3H). | |
| 509 | 4-{5-[3-(3-Chloro-phenyl)-isoxazol-5-ylmethylsulfanyl]-4-ethyl-4H-[1,2,4]triazol-3-yl}-pyridine | 8.80(m, 2H), 7.78(m, 1H), 7.66(m, 1H), 7.57(m, 2H), 7.41(m, 2H), 6.67(s, 1H), 4.71(s, 2H), 4.03(q, 2H), 1.36(t, 3H). | |
| 510 | 3-[3-(3-Chloro-phenyl)-isoxazol-5-ylmethylsulfanyl]-4-ethyl-5-thiophen-2-yl-4H-[1,2,4]triazole | 7.78(s, 1H), 7.64(m, 1H) 7.52(m, 1H), 7.41(m, 3H), 7.18(m, 1H), 6.65(s, 1H), 4.66(s, 2H), 4.08(q, 2H), 1.36(t, 3H). | 404.00 |
| 511 | 3-[3-(3-Chloro-phenyl)-isoxazol-5-ylmethylsulfanyl]-4-ethyl-5-furan-2-yl-4H-[1,2,4]triazole | 7.77(s, 1H), 7.64(d, 1H), 7.59(m, 1H), 7.39(m, 2H), 7.10(m, 1H), 6.62(s, 1H), 6.59(m, 1H), 4.65(s, 2H), 4.17(q, 2H), 1.35(t, 3H). | 388.10 |
| 512 | 4-{5-[5-(2-Fluoro-5-methyl-phenyl)-isoxazol-3-ylmethylsulfanyl]-4-methyl-4H-[1,2,4]triazol-3-yl}-pyridine | | |
| 513 | 5-(2,5-Dichloro-thiophen-3-yl)-3-(4-ethyl-5-thiophen-2-yl-4H-[1,2,4]triazol-3-ylsulfanylmethyl)-[1,2,4]oxadiazole | (DMSO-D6 as solvent): 7.82(dd, 1H), 7.65(d, 1H), 7.58(m, 1H), 7.25(m, 1H), 4.60(s, 2H), 4.16(q, 2H), 1.24(t, 3H). | |
| 514 | 4-{5-[5-(2,5-Dichloro-thiophen-3-yl)-[1,2,4]oxadiazol-3-ylmethylsulfanyl]-4-ethyl-4H-[1,2,4]triazol-3-yl}-pyridine | 8.78(d, 2H), 7.71(d, 2H), 7.68(m, 1H), 4.67(s, 2H), 4.10(q, 2H), 1.21(t, 3H). | |
| 515 | 4-{4-Ethyl-5-[5-(2-fluoro-5-methyl-phenyl)-isoxazol-3-ylmethylsulfanyl]-4H-[1,2,4]triazol-3-yl}-pyridine | 8.81(m, 2H), 7.73(m, 1H), 7.60(m, 2H), 7.21(m, 1H), 7.07(m, 1H), 6.76(m, 1H), 4.63(s, 2H), 4.02(q, 2H), 2.40(s, 3H), 1.38(t, 3H). | |
| 516 | 4-Ethyl-3-[5-(2-fluoro-5-methyl-phenyl)-isoxazol-3-ylmethylsulfanyl]-5-thiophen-2-yl-4H-[1,2,4]triazole | 7.71(d, 1H), 7.53(m, 1H), 7.47(m, 1H), 7.46(m, 2H), 7.07(m, 1H), 6.77(d, 1H), 4.63(s, 2H), 4.12(q, 2H), 2.40(s, 3H), 1.39(t, 3H). | |
| 517 | 4-Ethyl-3-[5-(2-fluoro-5-methyl-phenyl)-isoxazol-3-ylmethylsulfanyl]-5-furan-2-yl-4H-[1,2,4]triazole | 7.72(d, 1H), 7.60(m, 1H), 7.10(m, 1H), 7.05(m, 2H), 6.77(d, 1H), 6.60(m, 1H), 4.61(s, 2H), 4.21(q, 2H), 2.39(s, 3H), 1.38(t, 3H). | |
| 518 | 5-(3-Chloro-phenyl)-3-(4-ethyl-5-trifluoromethyl-4H-[1,2,4]triazol-3-ylsulfanylmethyl)-[1,2,4]oxadiazole | 8.11(s, 1H), 8.01(d, 1H), 7.60(d, 1H), 7.50(t, 1H), 4.72(s, 2H), 4.12(q, 2H) and 1.42(t, 3H). | 391.00 |
| 519 | 3-(3-Chloro-phenyl)-5-(4-ethyl-5-trifluoromethyl-4H-[1,2,4]triazol-3-ylsulfanylmethyl)-[1,2,4]oxadiazole | 8.05(s, 1H), 7.94(d, 1H), 7.50(d, 1H), 7.43(t, 1H), 4.83(s, 2H), 4.13(q, 2H) and 1.44(t, 3H). | |
| 520 | 3-(4-Ethyl-5-trifluoromethyl-4H-[1,2,4]triazol-3-ylsulfanylmethyl)-5- | 8.23(s, 1H), 7.65(d, 1H), 7.48(m, 1H), | |

-continued

| Example No. | Name | 1H NMR | MS |
|---|---|---|---|
| | thiophen-3-yl-[1,2,4]oxadiazole | 4.69(s, 2H), 4.12(q, 2H) and 1.41(t, 3H). | |
| 521 | 5-(4-Ethyl-5-trifluoromethyl-4H-[1,2,4]triazol-3-ylsulfanylmethyl)-3-thiophen-3-yl-[1,2,4]oxadiazole | 8.05(s, 1H), 7.61(d, 1H), 7.43(m, 1H), 4.81(s, 2H), 4.12(q, 2H) and 1.43(t, 3H). | |
| 522 | 5-(3-Chloro-phenyl)-3-[4-ethyl-5-(3-fluoro-phenyl)-4H-[1,2,4]triazol-3-ylsulfanylmethyl]-[1,2,4]oxadiazole | 8.12(d, 1H), 8.00(d, 1H), 7.52(m, 4H), 7.25(m, 2H), 4.67(s, 2H), 4.06(q, 2H), 1.31(t, 3H). | |
| 523 | 5-(3-Chloro-phenyl)-3-[4-ethyl-5-(4-fluoro-phenyl)-4H-[1,2,4]triazol-3-ylsulfanylmethyl]-[1,2,4]oxadiazole | 8.10(s, 1H), 7.99(d, 1H), 7.59(m, 4H), 7.48(t, 1H), 7.22(d, 1H), 4.67(s, 2H), 4.01(q, 2H), 1.30(t, 3H). | |
| 524 | 3-(4-Ethyl-5-trifluoromethyl-4H-[1,2,4]triazol-3-ylsulfanylmethyl)-5-thiophen-2-yl-[1,2,4]oxadiazole | 7.91(s, 1H), 7.68(d, 1H), 7.21(m, 1H), 4.67(s, 2H), 4.13(q, 2H) and 1.41(t, 3H). | |
| 525 | 3-{3-[5-(3-Chloro-thiophen-2-yl)-4-ethyl-4H-[1,2,4]triazol-3-ylsulfanylmethyl]-[1,2,4]oxadiazol-5-yl}-benzonitrile | 8.35(m, 2H), 7.89(d, 1H), 7.87(t, 1H), 7.58(d, 1H), 7.09(d, 1H), 4.70(s, 2H), 4.00(q, 2H), 1.27(t, 3H). | |
| 526 | 4-{5-[5-(3-Chloro-phenyl)-[1,3,4]oxadiazol-2-ylmethylsulfanyl]-4-ethyl-4H-[1,2,4]triazol-3-yl}-pyridine | 8.82(d, 2H), 8.01(d, 1H), 9.93(m, 1H), 7.59(m, 2H), 7.52(m, 1H), 7.47(m, 1H), 4.83(s, 2H), 4.11(q, 2H), 1.40(t, 3H). | 400.10 |
| 527 | 2-(3-Chloro-phenyl)-5-(4-ethyl-5-furan-2-yl-4H-[1,2,4]triazol-3-ylsulfanylmethyl)-[1,3,4]oxadiazole | 8.00(s, 1H), 7.89(d, 1H), 7.60(m, 1H), 7.50(m, 1H), 7.44(m, 1H), 7.13(m, 1H), 6.60(m, 1H), 4.76(s, 2H), 4.25(q, 2H), 1.38(t, 3H). | 389.00 |
| 528 | 5-(3-Chloro-phenyl)-3-[4-ethyl-5-(4-methoxy-phenyl)-4H-[1,2,4]triazol-3-ylsulfanylmethyl]-[1,2,4]oxadiazole | 8.12(s, 1H), 8.01(d, 1H), 7.57(m, 3H), 7.51(t, 1H), 7.05(d, 2H), 4.67(s, 2H), 4.02(q, 2H), 3.89(s, 3H), 1.31(t, 3H). | |
| 529 | 5-(3-Chloro-phenyl)-3-[5-(2-fluoro-5-methyl-phenyl)-4-furan-2-ylmethyl-4H-[1,2,4]triazol-3-ylsulfanylmethyl]-[1,2,4]oxadiazole | 8.12(s, 1H), 8.02(d, 1H), 7.58(d, 1H), 7.52(d, 1H), 7.35(d, 2H), 7.23(s, 1H), 7.22(d, 1H), 6.19(s, 1H), 6.04(s, 1H), 5.13(s, 2H), 4.61(s, 2H), 2.37(s, 3H). | |
| 530 | 4-[3-(4-Ethyl-5-trifluoromethyl-4H-[1,2,4]triazol-3-ylsulfanylmethyl)-[1,2,4]oxadiazol-5-yl]-2-methyl-pyridine | 8.74(d, 1H), 7.81(s, 1H), 7.74(d, 1H), 4.74(s, 2H), 4.12(q, 2H) 2.69(s, 1H) and 1.42(t, 3H). | |
| 531 | 3-(4-Ethyl-5-trifluoromethyl-4H-[1,2,4]triazol-3-ylsulfanylmethyl)-5-(3-methoxy-phenyl)-[1,2,4]oxadiazole | 7.70(d, 1H), 7.60(s, 1H), 7.44(t, 1H), 7.16(d, 1H), 4.70(s, 2H), 4.12(q, 2H), 3.90(s, 3H) and 1.41(t, 3H). | |
| 532 | 5-(4-Ethyl-5-trifluoromethyl-4H-[1,2,4]triazol-3-ylsulfanylmethyl)-3-(3-methoxy-phenyl)-[1,2,4]oxadiazole | 7.63(d, 1H), 7.56(s, 1H), 7.39(t, 1H), 7.07(d, 1H), 4.82(s, 2H), 4.12(q, 2H) and 1.42(t, 3H). | |
| 533 | 5-(4-Ethyl-5-trifluoromethyl-4H-[1,2,4]triazol-3-ylsulfanylmethyl)-3-thiophen-2-yl-[1,2,4]oxadiazole | 7.77(s, 1H), 7.52(d, 1H), 7.16(m, 1H), 4.79(s, 2H), 4.13(q, 2H) and 1.42(t, 3H). | |
| 534 | 5-(5-Chloro-2-fluoro-phenyl)-3-(4-ethyl-5-trifluoromethyl-4H-[1,2,4]triazol-3-ylsulfanylmethyl)-[1,2,4]oxadiazole | 8.07(dd, 1H), 7.56(m, 1H), 7.24(dd, 1H), 4.73(s, 2H), 4.13(q, 2H) and 1.42(t, 3H). | |
| 535 | 3-[3-(4-Ethyl-5-trifluoromethyl-4H-[1,2,4]triazol-3-ylsulfanylmethyl)-[1,2,4]oxadiazol-5-yl]-benzonitrile | 8.40(s, 1H), 8.34(d, 1H), 7.91(d, 1H), 7.01(t, 1H), 4.73(s, 2H), | 381.10 |

-continued

| Example No. | Name | 1H NMR | MS |
|---|---|---|---|
| | | 4.12(q, 2H) and 1.42(t, 3H). | |
| 536 | 3-[5-(3-Chloro-phenyl)-isoxazol-3-ylmethylsulfanyl]-4-ethyl-5-trifluoromethyl-4H-[1,2,4]triazole | 7.75(s, 1H), 7.63(m, 1H), 7.40(m, 2H), 6.73(s, 1H), 4.65(s, 2H), 4.07(q, 2H) and 1.40(t, 3H). | |
| 537 | 3-[5-(3-Chloro-phenyl)-oxazol-2-ylmethylsulfanyl]-4-ethyl-5-trifluoromethyl-4H-[1,2,4]triazole | 7.58(s, 1H), 7.46(d, 1H), 7.32(d, 3H), 4.74(s, 2H), 4.09(q, 2H) and 1.39(t, 3H). | |
| 538 | 4-Ethyl-3-(5-thiophen-3-yl-isoxazol-3-ylmethylsulfanyl)-5-trifluoromethyl-4H-[1,2,4]triazole | 7.78(s, 1H), 7.39(m, 1H), 6.53(d, 1H), 4.63(s, 2H), 4.07(q, 2H) and 1.39(t, 3H). | |
| 539 | 4-{3-[5-(3-Fluoro-phenyl)-4-methyl-4H-[1,2,4]triazol-3-ylsulfanylmethyl]-[1,2,4]oxadiazol-5-yl}-2-methyl-pyridine | 8.73(d, 1H), 7.83(s, 1H), 7.76(d, 1H), 7.47(m, 3H), 7.27(s, 1H), 4.65(s, 2H), 3.67(s, 3H), 2.69(s, 3H). | |
| 540 | 4-{3-[5-(3-Chloro-phenyl)-4-methyl-4H-[1,2,4]triazol-3-ylsulfanylmethyl]-[1,2,4]oxadiazol-5-yl}-2-methyl-pyridine | 8.74(d, 1H), 7.82(s, 1H), 7.67(d, 1H), 7.56(d, 1H), 7.51(m, 1H), 7.48(m, 1H), 7.46(s, 1H), 4.65(s, 2H), 3.67(s, 3H), 2.69(s, 3H). | |
| 541 | 4-{3-[5-(4-Chloro-phenyl)-4-methyl-4H-[1,2,4]triazol-3-ylsulfanylmethyl]-[1,2,4]oxadiazol-5-yl}-2-methyl-pyridine | 8.73(d, 1H), 7.82(s, 1H), 7.75(d, 1H), 7.63(d, 2H), 7.51(d, 2H), 4.65(s, 2H), 3.65(s, 3H), 2.69(s, 3H). | |
| 542 | 4-{3-[5-(4-Methoxy-phenyl)-4-methyl-4H-[1,2,4]triazol-3-ylsulfanylmethyl]-[1,2,4]oxadiazol-5-yl}-2-methyl-pyridine | 8.73(d, 1H), 7.83(s, 1H), 7.45(d, 1H), 7.61(d, 2H), 7.04(d, 2H), 4.62(s, 2H), 3.89(s, 3H), 3.64(s, 3H), 2.69(s, 3H). | |
| 543 | 4-[3-(4-Ethyl-5-p-tolyl-4H-[1,2,4]triazol-3-ylsulfanylmethyl)-[1,2,4]oxadiazol-5-yl]-2-methyl-pyridine | 8.74(d, 1H), 7.85(s, 1H), 7.77(d, 1H), 7.51(d, 2H), 7.32(d, 2H), 4.70(s, 2H), 4.03(q, 2H), 2.70(s, 3H), 2.45(s, 3H), 1.31(t, 3H). | |
| 544 | 3-(4-Ethyl-5-thiophen-2-yl-4H-[1,2,4]triazol-3-ylsulfanylmethyl)-5-(3-fluoro-phenyl)-[1,2,4]oxadiazole | (DMSO-D6 as solvent): 7.93(m, 1H), 7.86(m, 2H), 7.80(m, 1H), 7.67(m, 2H), 7.25(m, 1H), 4.61(s, 2H), 4.16(q, 2H), 1.24(t, 3H). | 388.10 |
| 545 | 4-{4-Ethyl-5-[5-(3-fluoro-phenyl)-[1,2,4]oxadiazol-3-ylmethylsulfanyl]-4H-[1,2,4]triazol-3-yl}-pyridine | 8.78(bs, 2H), 7.92(m, 2H), 7.71(d, 2H), 7.68(m, 1H), 7.27(m, 1H), 4.70(s, 2H), 4.10(q, 2H), 1.39(t, 3H). | 383.10 |
| 546 | 5-(3-Chloro-phenyl)-3-[5-(3,5-difluoro-phenyl)-4-ethyl-4H-[1,2,4]triazol-3-ylsulfanylmethyl]-[1,2,4]oxadiazole | 8.11(s, 1H), 8.01(d, 1H), 7.58(d, 1H), 7.50(t, 1H), 7.21(m, 2H), 7.00(t, 1H), 4.68(s, 2H), 4.07(q, 2H), 1.35(t, 3H). | |
| 547 | 5-(3-Chloro-phenyl)-3-[5-(2,6-difluoro-phenyl)-4-ethyl-4H-[1,2,4]triazol-3-ylsulfanylmethyl]-[1,2,4]oxadiazole | 8.12(s, 1H), 8.02(d, 1H), 7.59(m, 2H), 7.52(d, 1H), 7.41(d, 1H), 7.04(d, 1H), 4.73(s, 2H), 4.21(q, 2H), 1.42(t, 3H). | |
| 548 | 2-[3-(4-Ethyl-5-thiophen-2-yl-4H-[1,2,4]triazol-3-ylsulfanylmethyl)-[1,2,4]oxadiazol-5-yl]-4-methyl-phenol | 9.89(s, 1H), 7.70(s, 1H), 7.56(d, 1H), 7.54(d, 1H), 7.30(m, 1H), 7.18(m, 1H), 6.98(d, 1H), 4.66(s, 2H), 4.12(q, 2H), 2.34(s, 3H), 1.37(t, 3H). | 399.90 |
| 549 | 3-{1-[5-(3-Chloro-phenyl)-isoxazol-3-yl]-ethylsulfanyl}-4-ethyl-5-furan-2-yl-4H-[1,2,4]triazole | 7.73(bs, 1H), 7.59(m, 2H), 7.41(m, 2H), 7.10(dd, 1H), 6.59(m, 2H), 5.05(q, 1H), 4.13(q, | 401.10 |

-continued

| Example No. | Name | 1H NMR | MS |
|---|---|---|---|
| | | 2H), 1.91(d, 3H), 1.27(t, 3H). | |
| 550 | 4-(5-{1-[5-(3-Chloro-phenyl)-isoxazol-3-yl]-ethylsulfanyl}-4-ethyl-4H-[1,2,4]triazol-3-yl)-pyridine | 8.8(dd, 2H), 7.74(bs, 1H), 7.63(m, 1H), 7.57(dd, 2H), 7.40(m, 2H), 6.62(s, 2H), 5.15(q, 1H), 4.05(q, 2H), 1.95(d, 3H), 1.34(t, 3H). | |
| 551 | 3-[5-(4-Butoxy-phenyl)-4-ethyl-4H-[1,2,4]triazol-3-ylsulfanylmethyl]-5-(3-chloro-phenyl)-[1,2,4]oxadiazole | 8.12(s, 1H), 8.01(d, 1H), 7.58(d, 1H), 7.52(d, 2H), 7.49(d, 1H), 7.01(d, 2H), 4.69(s, 2H), 4.02(q, 4H), 1.82(m, 2H), 1.51(q, 2H), 1.32(t, 3H), 1.01(t, 3H). | |
| 552 | 3-(5-Benzo[1,3]dioxol-5-yl-4-ethyl-4H-[1,2,4]triazol-3-ylsulfanylmethyl)-5-(3-chloro-phenyl)-[1,2,4]oxadiazole | 8.12(s, 1H), 8.00(d, 1H), 7.58(d, 1H), 7.51(d, 1H), 7.09(d, 2H), 6.96(s, 1H), 6.08(s, 2H), 4.67(s, 2H), 4.02(q, 2H), 1.31(t, 2H). | |
| 553 | 3-(4-Ethyl-5-thiophen-2-yl-4H-[1,2,4]triazol-3-ylsulfanylmethyl)-5-(2-methyl-thiazol-4-yl)-[1,2,4]oxadiazole | 8.11(s, 1H), 7.48(m, 2H), 7.16(t, 1H), 4.63(s, 2H), 4.13(q, 2H), 2.82(s, 3H), 1.37(t, 3H). | 391.90 |
| 554 | 3-(4-Ethyl-5-thiophen-2-yl-4H-[1,2,4]triazol-3-ylsulfanylmethyl)-5-(4-fluoro-phenyl)-[1,2,4]oxadiazole | (DMSO-D6 as solvent): 8.21(m, 2H), 7.51(m, 2H), 7.21(m, 3H), 4.63(s, 2H), 4.16(q, 2H), 1.38(t, 3H). | |
| 555 | 4-Ethyl-3-{1-[5-(2-fluoro-5-methyl-phenyl)-isoxazol-3-yl]-ethylsulfanyl}-5-furan-2-yl-4H-[1,2,4]triazole | 7.71(dd, 1H), 7.59(dd, 1H), 7.26(m, 1H), 7.06(m, 2H), 6.66(d, 1H), 6.58(dd, 1H), 5.06(q, 1H), 4.13(q, 2H), 2.39(s, 3H), 1.91(d, 3H), 1.28(t, 3H). | |
| 556 | 4-(4-Ethyl-5-{1-[5-(2-fluoro-5-methyl-phenyl)-isoxazol-3-yl]-ethylsulfanyl}-4H-[1,2,4]triazol-3-yl)-pyridine | 8.79(dd, 2H), 7.71(dd, 1H), 7.59(dd, 2H), 7.23(m, 1H), 7.06(m, 1H), 6.64(d, 1H), 5.15(q, 1H), 4.01(q, 2H), 2.39(s, 3H), 1.94(d, 3H), 1.30(t, 3H). | 410.10 |
| 557 | 5-(3-Chloro-phenyl)-3-[4-ethyl-5-(3-methyl-3H-imidazol-4-yl)-4H-[1,2,4]triazol-3-ylsulfanylmethyl]-[1,2,4]oxadiazole | 8.11(s, 1H), 8.00(d, 1H), 7.66(s, 1H), 7.58(d, 1H), 7.52(t, 1H), 7.37(s, 1H), 4.69(s, 2H), 4.09(q, 2H), 3.93(s, 3H), 1.37(t, 3H). | |
| 558 | 5-(3-Chloro-phenyl)-3-[4-ethyl-5-(1-methyl-1H-imidazol-2-yl)-4H-[1,2,4]triazol-3-ylsulfanylmethyl]-[1,2,4]oxadiazole | 8.12(s, 1H), 8.01(d, 1H), 7.57(d, 1H), 7.51(t, 1H), 7.17(s, 1H), 7.04(s, 1H), 4.69(s, 2H), 4.56(q, 2H), 4.12(s, 3H), 1.40(t, 3H). | |
| 559 | 5-(3-Chloro-phenyl)-3-[4-ethyl-5-(1-methyl-1H-imidazol-4-yl)-4H-[1,2,4]triazol-3-ylsulfanylmethyl]-[1,2,4]oxadiazole | 8.12(s, 1H), 8.01(d, 1H), 7.65(s, 1H), 7.57(d, 1H), 7.48(d, 2H), 4.60(s, 2H), 4.50(q, 2H), 3.79(s, 3H), 1.36(t, 3H). | |
| 560 | 4-{5-[5-(3-Chloro-phenyl)-4-methyl-isoxazol-3-ylmethylsulfanyl]-4-ethyl-4H-[1,2,4]triazol-3-yl}-pyridine | 8.81(bs, 2H), 7.70(m, 1H), 7.61(m, 3H), 7.44(m, 2H), 4.65(s, 2H), 4.09(q, 2H), 2.31(s, 3H), 1.40(t, 3H). | |
| 561 | 3-[5-(3-Chloro-phenyl)-4-methyl-isoxazol-3-ylmethylsulfanyl]-4-ethyl-5-furan-2-yl-4H-[1,2,4]triazole | 7.70(s, 1H), 7.60(m, 2H), 7.43(m, 2H), 7.10(m, 1H), 6.59(m, 1H), 4.59(s, 2H), 4.23(q, 2H), 2.28(s, 3H), 1.38(t, 3H). | |
| 562 | 3-(4-Ethyl-5-thiophen-2-yl-4H-[1,2,4]triazol-3-ylsulfanylmethyl)-5- | 7.61(d, 1H), 7.49(m, 2H), 7.22(m, 2H), | |

-continued

| Example No. | Name | 1H NMR | MS |
|---|---|---|---|
| | (4-methyl-thiophen-2-yl)-[1,2,4]oxadiazole | 4.59(s, 2H), 4.16(q, 2H), 2.32(s, 3H), 1.38(t, 3H). | |
| 563 | 5-(3-Chloro-phenyl)-3-[4-ethyl-5-(3-methyl-thiophen-2-yl)-4H-[1,2,4]triazol-3-ylsulfanylmethyl]-[1,2,4]oxadiazole | 8.13(s, 1H), 8.01(d, 1H), 7.58(d, 1H), 7.52(d, 1H), 7.45(d, 1H), 7.02(d, 1H), 4.69(s, 2H), 3.97(q, 2H), 2.32(s, 3H), 1.28(t, 3H). | |
| 564 | 5-(3-Chloro-phenyl)-3-[4-ethyl-5-(5-methyl-thiophen-2-yl)-4H-[1,2,4]triazol-3-ylsulfanylmethyl]-[1,2,4]oxadiazole | 8.11(s, 1H), 8.01(d, 1H), 7.58(d, 1H), 7.51(t, 1H), 7.28(s, 1H), 6.83(d, 1H), 4.64(s, 2H), 4.14(q, 2H), 2.56(s, 3H), 1.39(t, 3H). | |
| 565 | 4-{5-[4-Chloro-5-(3-chloro-phenyl)-isoxazol-3-ylmethylsulfanyl]-4-ethyl-4H-[1,2,4]triazol-3-yl}-pyridine | 8.81(d, 2H), 7.99(m, 1H), 7.90(m, 1H), 7.60(m, 2H), 7.48(m, 2H), 4.65(s, 2H), 4.10(q, 2H), 1.39(t, 3H). | |
| 566 | 3-[4-Chloro-5-(3-chloro-phenyl)-isoxazol-3-ylmethylsulfanyl]-4-ethyl-5-furan-2-yl-4H-[1,2,4]triazole | 7.99(s, 1H), 7.90(m, 1H), 7.60(m, 1H), 7.47(m, 2H), 7.12(m, 1H), 6.60(m, 1H), 4.59(s, 2H), 4.25(q, 2H), 1.38(t, 3H). | |
| 567 | 2-Chloro-4-{5-[5-(3-chloro-phenyl)-[1,2,4]oxadiazol-3-ylmethylsulfanyl]-4-ethyl-4H-[1,2,4]triazol-3-yl}-6-methyl-pyridine | 8.11(s, 1H), 8.00(d, 1H), 7.58(d, 1H), 7.52(d, 1H), 7.40(d, 2H), 4.71(s, 2H), 4.10(q, 2H), 2.64(s, 3H), 1.40(t, 3H). | |
| 568 | 3-[5-(5-Bromo-furan-2-yl)-4-ethyl-4H-[1,2,4]triazol-3-ylsulfanylmethyl]-5-(3-chloro-phenyl)-[1,2,4]oxadiazole | 8.11(s, 1H), 7.99(d, 1H), 7.58(d, 1H), 7.51(t, 1H), 7.07(d, 1H), 6.52(d, 1H), 4.64(s, 2H), 4.23(q, 2H), 1.40(t, 3H). | |
| 569 | 2-Chloro-4-{5-[5-(3-chloro-phenyl)-[1,2,4]oxadiazol-3-ylmethylsulfanyl]-4-ethyl-4H-[1,2,4]triazol-3-yl}-pyridine | 8.59(d, 1H), 8.10(s, 1H), 8.00(d, 1H), 7.66(s, 1H), 7.59(d, 1H), 7.54(d, 1H), 7.50(d, 1H), 4.72(s, 2H), 4.11(q, 2H), 1.42(t, 3H). | |
| 570 | 2-Chloro-4-{5-[5-(3-chloro-phenyl)-[1,2,4]oxadiazol-3-ylmethylsulfanyl]-4-ethyl-4H-[1,2,4]triazol-3-yl}-6-methoxy-pyridine | 8.11(s, 1H), 8.00(d, 1H), 7.58(d, 1H), 7.50(t, 1H), 7.24(s, 1H), 6.91(s, 1H), 4.70(s, 2H), 4.08(q, 2H), 4.02(s, 3H), 1.39(t, 3H). | 464.10 |
| 571 | 2-[3-(4-Ethyl-5-thiophen-2-yl-4H-[1,2,4]triazol-3-ylsulfanylmethyl)-[1,2,4]oxadiazol-5-yl]-4-methyl-benzonitrile | 8.02(s, 1H), 7.76(d, 2H), 7.47(m, 3H), 7.17(t, 1H), 4.68(s, 2H), 4.19(q, 2H), 2.51(s, 3H), 1.39(t, 3H). | |
| 572 | 5-(3-Chloro-phenyl)-3-[4-ethyl-5-(3-methoxy-thiophen-2-yl)-4H-[1,2,4]triazol-3-ylsulfanylmethyl]-[1,2,4]oxadiazole | 8.14(s, 1H), 8.03(d, 1H), 7.58(d, 1H), 7.50(d, 1H), 7.44(d, 1H), 6.94(1H), 4.67(s, 2H), 4.03(q, 2H), 3.88(s, 3H), 1.29(t, 3H). | |
| 573 | 3-[5-(5-Chloro-thiophen-3-yl)-isoxazol-3-ylmethylsulfanyl]-4-ethyl-5-furan-2-yl-4H-[1,2,4]triazole | 7.61(m, 1H), 7.52(d, 1H), 7.21(d, 1H), 7.11(m, 1H), 7.61(m, 1H), 6.55(s, 1H), 4.57(s, 2H), 4.21(q, 2H), 1.38(t, 3H). | 393.10 |
| 574 | 3-[3-(4-Ethyl-5-furan-2-yl-4H-[1,2,4]triazol-3-ylsulfanylmethyl)-[1,2,4]oxadiazol-5-yl]-5-fluoro-benzonitrile | 8.21(m, 1H), 8.04(dd, 1H), 7.59(m, 2H), 7.10(dd, 1H), 6.59(dd, 1H), 4.64(s, 2H), 4.25(q, 2H), 1.38(t, 3H). | |
| 575 | 4-Ethyl-3-(5-phenyl-isoxazol-3-ylmethylsulfanyl)-5-thiophen-2-yl-4H-[1,2,4]triazole | 7.77(m, 2H), 7.53(d, 1H), 7.47(m, 4H), 7.19(dd, 1H), 6.71(s, 1H), 4.61(s, 2H), 4.12(q, 2H) and 1.39(t, 3H). | |

| Example No. | Name | 1H NMR | MS |
|---|---|---|---|
| 576 | 4-Methyl-3-(5-phenyl-isoxazol-3-ylmethylsulfanyl)-5-thiophen-3-yl-4H-[1,2,4]triazole | 7.77(m, 3H), 7.50(m, 5H), 6.69(s, 1H), 4.56(s, 2H) and 3.67(s, 3H) | |
| 577 | 4-Ethyl-3-furan-2-yl-5-(5-phenyl-isoxazol-3-ylmethylsulfanyl)-4H-[1,2,4]triazole | 7.77(m, 2H), 7.61(s, 1H), 7.46(m, 3H), 7.14(d, 1H), 6.69(s, 1H), 6.60(d, 1H), 4.60(s, 2H), 4.22(q, 2H) and 1.38(t, 3H). | |
| 578 | 4-[4-Ethyl-5-(5-phenyl-isoxazol-3-ylmethylsulfanyl)-4H-[1,2,4]triazol-3-yl]-pyridine | 8.82(w, 2H), 7.77(m, 2H), 7.61(d, 2H), 7.45(m, 3H), 6.71(s, 1H), 4.65(s, 2H), 4.06(q, 2H) and 1.39(t, 3H). | |
| 579 | 4-[4-Methyl-5-(5-phenyl-isoxazol-3-ylmethylsulfanyl)-4H-[1,2,4]triazol-3-yl]-pyridine | 8.81(w, 2H), 7.77(m, 2H), 7.63(d, 2H), 7.46(m, 3H), 6.70(s, 1H), 4.60(s, 2H) and 3.68(s, 3H). | |
| 580 | 2-(4-Ethyl-5-furan-2-yl-4H-[1,2,4]triazol-3-ylsulfanylmethyl)-5-m-tolyl-[1,3,4]oxadiazole | 7.80(m, 2H), 7.70(m, 1H), 7.35(m, 2H), 7.13(m, 2H), 6.60(m, 1H), 4.74(s, 2H), 4.23(q, 2H), 2.40(s, 3H), 1.36(t, 3H). | 368.10 |
| 581 | 4-[4-Methyl-5-(5-m-tolyl-[1,3,4]oxadiazol-2-ylmethylsulfanyl)-4H-[1,2,4]triazol-3-yl]-pyridine | 8.81(m, 2H), 7.80(m, 2H), 7.61(d, 2H), 7.39(m, 2H), 4.74(s, 2H), 3.71(s, 3H), 2.4(s, 3H). | 365.10 |
| 582 | 4-[4-Ethyl-5-(5-m-tolyl-[1,3,4]oxadiazol-2-ylmethylsulfanyl)-4H-[1,2,4]triazol-3-yl]-pyridine | 8.81(d, 2H), 7.81(m, 2H), 7.58(m, 2H), 7.37(m, 2H), 4.81(s, 2H), 4.41(q, 2H), 2.42(s, 3H), 1.33(t, 3H). | 379.10 |
| 583 | 4-{5-[5-(5-Chloro-thiophen-3-yl)-[1,2,4]oxadiazol-3-ylmethylsulfanyl]-4-ethyl-4H-[1,2,4]triazol-3-yl}-pyridine | 8.80(d, 2H), 7.98(m, 1H), 7.58(d, 2H), 7.46(d, 1H), 4.66(s, 2H), 4.10(q, 2H), 1.38(t, 3H). | 405.90 |
| 584 | 3-[3-(4-Ethyl-5-pyridin-4-yl-4H-[1,2,4]triazol-3-ylsulfanylmethyl)-[1,2,4]oxadiazol-5-yl]-4-fluoro-benzonitrile | 8.79(bs, 2H), 8.46(m, 1H), 7.91(m, 1H), 7.59(d, 2H), 7.43(t, 1H), 4.74(s, 2H), 4.12(q, 2H), 1.41(t, 3H). | |
| 585 | 3-[3-(4-Ethyl-5-furan-2-yl-4H-[1,2,4]triazol-3-ylsulfanylmethyl)-[1,2,4]oxadiazol-5-yl]-4-fluoro-benzonitrile | 8.45(dd, 1H), 7.91(m, 1H), 7.59(d, 1H), 7.43(t, 1H), 7.10(d, 1H), 6.58(dd, 1H), 4.65(s, 2H), 4.27(q, 2H), 1.39(t, 3H). | 397.10 |
| 586 | 3-[3-(4-Ethyl-5-thiophen-2-yl-4H-[1,2,4]triazol-3-ylsulfanylmethyl)-[1,2,4]oxadiazol-5-yl]-4-fluoro-benzonitrile | 8.45(dd, 1H), 7.90(m, 1H), 7.47(m, 3H), 7.18(t, 1H), 4.68(s, 2H), 4.17(q, 2H), 1.41(t, 3H). | |
| 587 | 3-[3-(4-Ethyl-5-furan-2-yl-4H-[1,2,4]triazol-3-ylsulfanylmethyl)-[1,2,4]oxadiazol-5-yl]-benzonitrile | 8.41(m, 2H), 7.89(d, 1H), 7.69(d, 1H), 7.13(m, 1H), 6.60(m, 1H), 4.65(s, 2H), 4.27(q, 2H), 1.40(t, 3H). | 379.10 |
| 588 | 3-[5-(4-Ethyl-5-furan-2-yl-4H-[1,2,4]triazol-3-ylsulfanylmethyl)-[1,2,4]oxadiazol-3-yl]-benzonitrile | 8.36(m, 2H), 7.80(t, 1H), 7.62(m, 2H), 7.15(m, 1H), 6.61(m, 1H), 4.78(s, 2H), 4.2(q, 2H), 1.40(t, 3H). | 379.10 |
| 589 | 3-[3-(4-Methyl-5-trifluoromethyl-4H-[1,2,4]triazol-3-ylsulfanylmethyl)-[1,2,4]oxadiazol-5-yl]-benzonitrile | 8.41(m, 2H), 7.90(m, 1H), 7.72(t, 1H), 4.68(s, 2H), 3.73(s, 3H). | |
| 590 | 5-(5-Chloro-2-fluoro-phenyl)-3-(4-methyl-5-trifluoromethyl-4H-[1,2,4]triazol-3-ylsulfanylmethyl)-[1,2,4]oxadiazole | 8.08(m, 1H), 7.58(m, 1H), 7.25(m, 1H), 4.67(s, 2H), 3.74(s, 3H). | 394.90 |
| 591 | 2-Chloro-4-[3-(4-ethyl-5-furan-2-yl-4H-[1,2,4]triazol-3-ylsulfanylmethyl)-[1,2,4]oxadiazol-5-yl]-pyridine | 8.63(m, 1H), 8.02(m, 1H), 7.89(m, 1H), 7.61(m, 1H), 7.14(m, 1H), 6.61(m, 1H), 4.67(s, | 390.00 |

-continued

| Example No. | Name | 1H NMR | MS |
|---|---|---|---|
| | | 2H), 4.27(q, 2H), 1.40(t, 3H). | |
| 592 | 2-Chloro-4-[3-(5-furan-2-yl-4-methyl-4H-[1,2,4]triazol-3-ylsulfanylmethyl]-[1,2,4]oxadiazol-5-yl]-pyridine | 8.63(d, 1H), 8.00(d, 1H), 7.88(m, 1H), 7.62(d, 1H), 7.14(d, 1H), 6.61(m, 1H), 4.60(s, 2H), 3.82(s, 3H). | |
| 593 | 2-(3-Chloro-phenyl)-5-[4-methyl-5-(2-methyl-thiazol-4-yl)-4H-[1,2,4]triazol-3-ylsulfanylmethyl]-[1,3,4]oxadiazole | 7.98(m, 2H), 7.89(d, 1H), 7.49(m, 1H), 7.44(m, 1H), 4.69(s, 2H), 3.92(s, 3H), 2.77(s, 3H). | |
| 594 | 2-(3-Chloro-phenyl)-5-(4-methyl-5-thiazol-4-yl-4H-[1,2,4]triazol-3-ylsulfanylmethyl)-[1,3,4]oxadiazole | 8.91(s, 1H), 8.24(s, 1H), 7.98(s, 1H), 7.91(d, 1H), 7.49(m, 1H), 7.43(m, 1H), 4.72(s, 2H), 3.96(s, 3H). | |
| 595 | 2-(3-Chloro-phenyl)-5-(5-furan-2-yl-4-methyl-4H-[1,2,4]triazol-3-ylsulfanylmethyl)-[1,3,4]oxadiazole | 8.00(s, 1H), 7.89(d, 1H), 7.60(s, 1H), 7.53(m, 1H), 7.43(m, 1H), 7.12(d, 1H), 6.60(d of d, 1H), 4.68(s, 2H), 3.80(s, 3H). | |
| 596 | 2-(3-Chloro-phenyl)-5-(4-ethyl-5-trifluoromethyl-4H-[1,2,4]triazol-3-ylsulfanylmethyl)-[1,3,4]oxadiazole | 8.00(s, 1H), 7.90(d, 1H), 7.52(m, 2H), 4.86(s, 2H), 4.13(q, 2H), 1.42(t, 3H). | |
| 597 | 4-{4-Ethyl-5-[5-(4-methyl-thiophen-2-yl)-[1,2,4]oxadiazol-3-ylmethylsulfanyl]-4H-[1,2,4]triazol-3-yl}-pyridine | 8.79(d, 2H), 7.68(s, 1H), 7.59(d, 2H), 7.23(m, 1H), 4.63(s, 2H), 4.10(q, 2H), 2.32(d, 3H), 1.37(t, 3H). | |
| 598 | 3-(4-Ethyl-5-furan-2-yl-4H-[1,2,4]triazol-3-ylsulfanylmethyl)-5-(4-methyl-thiophen-2-yl)-[1,2,4]oxadiazole | 7.67(d, 1H), 7.59(m, 1H), 7.2(s, 1H), 7.09(d, 1H), 6.58(dd, 1H), 4.56(s, 2H), 4.24(q, 2H), 2.32(s, 3H), 1.36(t, 3H). | 374.00 |
| 599 | 3-(3-Chloro-phenyl)-5-(4-ethyl-5-furan-2-yl-4H-[1,2,4]triazol-3-ylsulfanylmethyl)-[1,2,4]oxadiazole | 8.02(m, 1H), 7.91(m, 1H), 7.57(d, 1H), 7.35(m, 2H), 7.08(d, 1H), 6.56(dd, 1H), 4.72(s, 2H), 4.22(q, 2H), 2.32(s, 3H), 1.36(t, 3H). | |
| 600 | 4-{5-[3-(3-Chloro-phenyl)-[1,2,4]oxadiazol-5-ylmethylsulfanyl]-4-ethyl-4H-[1,2,4]triazol-3-yl}-pyridine | 8.79(dd, 2H), 8.02(m, 1H), 7.92(m, 1H), 7.57(dd, 2H), 7.42(m, 2H), 4.80(s, 2H), 4.08(q, 2H), 1.38(t, 3H). | |
| 601 | 4-{4-Ethyl-5-[5-(3-nitro-phenyl)-[1,3,4]oxadiazol-2-ylmethylsulfanyl]-4H-[1,2,4]triazol-3-yl}-pyridine | 8.87(m, 3H), 8.42(m, 2H), 7.75(t, 1H), 7.66(d, 2H), 4.88(s, 2H), 4.15(q, 2H), 1.45(t, 3H). | |
| 602 | 2-(4-Ethyl-5-furan-2-yl-4H-[1,2,4]triazol-3-ylsulfanylmethyl)-5-(3-nitro-phenyl)-[1,3,4]oxadiazole | 8.87(t, 1H), 8.39(m, 2H), 7.73(t, 1H), 7.61(m, 1H), 7.15(m, 1H), 6.61(m, 1H), 4.28(q, 2H), 1.78(s, 2H), 1.41(t, 3H). | |
| 603 | 4-{5-[5-(3-Chloro-phenyl)-isoxazol-3-ylmethylsulfanyl]-4-cyclopropyl-4H-[1,2,4]triazol-3-yl}-pyridine | 8.79(d, 2H), 7.78(m, 3H), 7.66(m, 1H), 7.39(m, 2H), 6.84(s, 1H), 4.69(s, 2H), 3.27(m, 1H), 1.20(q, 2H), 0.83(m, 2H). | 411.00 |
| 604 | 3-[5-(3-Chloro-phenyl)-isoxazol-3-ylmethylsulfanyl]-4-ethyl-5-(4-methoxy-phenyl)-4H-[1,2,4]triazole | 7.77(m, 1H), 7.65(m, 1H), 7.56(m, 2H), 7.41(m, 2H), 7.04(m, 2H), 6.79(s, 1H), 4.61(s, 2H), 3.97(q, 2H), 3.89(s, 3H), 1.32(t, 3H). | 428.20 |
| 605 | 5-(3-Chloro-phenyl)-3-[1-(4-methyl-5-thiophen-2-yl-4H-[1,2,4]triazol-3-ylsulfanyl)-ethyl]- | 8.08(m, 1H), 7.96(dd, 1H), 7.45(m, 4H), 7.17(m, 1H), 4.93(q, 1H), | 404.92 |

| Example No. | Name | 1H NMR | MS |
|---|---|---|---|
| | [1,2,4]oxadiazole | 3.67(s, 3H), 1.91(d, 3H). | |
| 606 | 5-(3-Chloro-phenyl)-3-[1-(4-ethyl-5-thiophen-2-yl-4H-[1,2,4]triazol-3-ylsulfanyl)-ethyl]-[1,2,4]oxadiazole | 8.1(d, 1H), 7.98(d, 1H), 7.51(m, 4H), 7.17(t, 1H), 5.11(q, 1H), 4.11(q, 2H), 1.93(d, 3H), 1.34(t, 3H). | 418.90 |
| 607 | 4-(5-{1-[5-(3-Chloro-phenyl)-[1,2,4]oxadiazol-3-yl]-ethylsulfanyl}-4-methyl-4H-[1,2,4]triazol-3-yl)-pyridine | 8.79(dd, 2H), 8.08(m, 1H), 7.98(dd, 1H), 7.59(m, 3H), 7.46(t, 1H), 5.05(q, 1H), 3.66(s, 3H), 1.94(d, 3H). | 400.07 |
| 608 | 4-(5-{1-[5-(3-Chloro-phenyl)-[1,2,4]oxadiazol-3-yl]-ethylsulfanyl}-4-ethyl-4H-[1,2,4]triazol-3-yl)-pyridine | 8.79(dd, 2H), 8.10(m, 1H), 7.99(dd, 1H), 7.58(m, 3H), 7.47(t, 1H), 5.20(q, 1H), 4.06(q, 2H), 1.96(d, 3H), 1.33(t, 3H). | 414.05 |
| 609 | 3-[5-(4-Ethyl-5-pyridin-4-yl-4H-[1,2,4]triazol-3-ylsulfanylmethyl)-[1,3,4]oxadiazol-2-yl]-benzonitrile | 8.84(s, 2H), 8.30(m, 2H), 7.85(m, 1H), 7.66(m, 3H), 4.84(s, 2H), 4.14(q, 2H), 1.43(t, 3H). | |
| 610 | 3-[5-(4-Ethyl-5-furan-2-yl-4H-[1,2,4]triazol-3-ylsulfanylmethyl)-[1,3,4]oxadiazol-2-yl]-benzonitrile | 8.27(m, 2H), 7.82(m, 1H), 7.62(m, 2H), 7.18(t, 1H), 6.62(m, 1H), 4.79(s, 2H), 4.27(q, 2H), 1.40(t, 3H). | |
| 611 | 3-[5-(4-Methyl-5-pyridin-4-yl-4H-[1,2,4]triazol-3-ylsulfanylmethyl)-[1,3,4]oxadiazol-2-yl]-benzonitrile | 8.83(d, 2H), 8.31(m, 2H), 7.84(m, 4H), 4.81(s, 2H), 3.77(s, 3H). | |
| 612 | 3-[5-(4-Cyclopropyl-5-pyridin-4-yl-4H-[1,2,4]triazol-3-ylsulfanylmethyl)-[1,3,4]oxadiazol-2-yl]-benzonitrile | 8.82(s, 2H), 8.33(m, 2H), 7.86(t, 3H), 7.67(t, 1H), 4.91(d, 2H), 1.24(m, 3H), 0.88(m, 2H). | 402.20 |
| 613 | 4-{5-[5-(3-Chloro-phenyl)-[1,3,4]oxadiazol-2-ylmethylsulfanyl]-4-methyl-4H-[1,2,4]triazol-3-yl}-pyridine | (CD3OD as solvent): 8.80(s(br), 2H), 7.96(m, 2H), 7.81(d, 2H), 7.61(m, 2H), 4.73(s, 2H), 3.84(s, 3H). | |
| 614 | 4-{5-[5-(3-Chloro-phenyl)-[1,3,4]oxadiazol-2-ylmethylsulfanyl]-4-cyclopropyl-4H-[1,2,4]triazol-3-yl}-pyridine | (CD3OD as solvent): 8.75(d, 2H), 8.02(s, 1H), 7.96(d, 1H), 7.89(d, 2H), 7.60(m, 2H), 4.89(s, 2H), 3.59(m, 1H), 1.21(m, 2H), 0.84(m, 2H). | 412.16 |
| 615 | 4-{5-[5-(5-Chloro-2-fluoro-phenyl)-[1,3,4]oxadiazol-2-ylmethylsulfanyl]-4-cyclopropyl-4H-[1,2,4]triazol-3-yl}-pyridine | 7.80(m, 2H), 8.04(m, 1H), 7.77(d, 2H), 7.51(m, 1H), 7.21(t, 1H), 4.92(s, 2H), 3.32(m, 1H), 1.21(m, 2H), 0.85(m, 2H). | 430.11 |
| 616 | 2-(5-Chloro-2-fluoro-phenyl)-5-[4-ethyl-5-(4-methoxy-phenyl)-4H-[1,2,4]triazol-3-ylsulfanylmethyl]-[1,3,4]oxadiazole | 8.02(m, 1H), 7.52(m, 3H), 7.20(t, 1H), 7.04(m, 2H), 4.81(s, 2H), 4.03(q, 2H), 3.89(s, 3H), 1.33(t, 3H). | |
| 617 | 4-{5-[5-(5-Chloro-2-fluoro-phenyl)-[1,3,4]oxadiazol-2-ylmethylsulfanyl]-4-methyl-4H-[1,2,4]triazol-3-yl}-pyridine | 8.83(d, 2H), 8.03(m, 1H), 7.65(m, 2H), 7.51(m, 1H), 7.20(t, 1H), 4.78(s, 2H), 3.75(s, 3H). | |
| 618 | 4-{5-[5-(5-Chloro-2-fluoro-phenyl)-[1,3,4]oxadiazol-2-ylmethylsulfanyl]-4-ethyl-4H-[1,2,4]triazol-3-yl}-pyridine | 8.82(bs, 2H), 8.02(m, 1H), 7.61(m, 2H), 7.51(m, 1H), 7.20(t, 1H), 4.85(s, 2H), 4.13(q, 2H), 1.41(t, 3H). | |
| 619 | 2-(3-Chloro-phenyl)-5-[4-ethyl-5-(4-methoxy-phenyl)-4H-[1,2,4]triazol-3-ylsulfanylmethyl]-[1,3,4]oxadiazole | 8.01(d of d collapsed, 1H), 7.85(d, 1H), 7.51(m, 4H), 7.00(d, 2H), 4.79(s, 2H), 4.00(q, 2H), 3.88(s, 3H), 1.30(t, 3H). | |
| 620 | 2-(3-Chloro-phenyl)-5-[1-(4-ethyl-5-furan-2-yl-4H-[1,2,4]triazol-3- | 7.97(s, 1H), 7.84(d, 1H), 7.58(d, 1H), | |

-continued

| Example No. | Name | 1H NMR | MS |
|---|---|---|---|
| | ylsulfanyl)-ethyl]-[1,3,4]oxadiazole | 7.49(m, 1H), 7.40(m, 1H), 7.12(d, 1H), 6.59(d of d, 1H), 5.16(q, 1H), 4.17(q, 2H), 2.02(d, 3H), 1.28(t, 3H). | |
| 621 | 5-(5-Chloro-2-fluoro-phenyl)-3-[1-(4-methyl-5-thiophen-2-yl-4H-[1,2,4]triazol-3-ylsulfanyl)-ethyl]-[1,2,4]oxadiazole | 8.06(m, 1H), 7.54(m, 3H), 7.23(m, 2H), 4.93(q, 1H), 3.72(s, 3H), 1.91(d, 3H). | |
| 622 | 4-(5-{1-[5-(5-Chloro-2-fluoro-phenyl)-[1,2,4]oxadiazol-3-yl]-ethylsulfanyl}-4-methyl-4H-[1,2,4]triazol-3-yl)-pyridine | 8.79(dd, 2H), 8.07(dd, 1H), 7.62(dd, 2H), 7.54(m, 1H), 7.21(t, 1H), 5.07(q, 1H), 3.69(s, 3H), 1.95(d, 3H). | 418.10 |
| 623 | 4-(5-{1-[5-(5-Chloro-2-fluoro-phenyl)-[1,2,4]oxadiazol-3-yl]-ethylsulfanyl}-4-ethyl-4H-[1,2,4]triazol-3-yl)-pyridine | 8.79(dd, 2H), 8.08(m, 1H), 7.57(m, 3H), 7.22(t, 1H), 5.21(q, 1H), 4.08(q, 2H), 1.97(d, 3H), 1.35(t, 3H). | |
| 624 | 2-Chloro-4-[3-(4-cyclopropyl-5-pyridin-4-yl-4H-[1,2,4]triazol-3-ylsulfanylmethyl)-[1,2,4]oxadiazol-5-yl]-pyridine | 8.83(m, 2H), 8.65(m, 1H), 8.05(t, 1H), 7.92(t, 1H), 7.76(t, 2H), 4.82(2H), 3.31(m, 1H), 1.23(m, 2H), 0.86(m, 2H). | |
| 625 | 4-{5-[5-(2-Fluoro-5-methyl-phenyl)-[1,3,4]oxadiazol-2-ylmethylsulfanyl]-4-methyl-4H-[1,2,4]triazol-3-yl}-pyridine | 8.83(t, 2H), 7.82(m, 1H), 7.63(m, 2H), 7.32(m, 1H), 7.10(m, 1H), 4.75(s, 2H), 3.73(s, 3H), 2.39(s, 3H), 1.61(d, 1H). | |
| 626 | 4-{4-Ethyl-5-[5-(2-fluoro-5-methyl-phenyl)-[1,3,4]oxadiazol-2-ylmethylsulfanyl]-4H-[1,2,4]triazol-3-yl}-pyridine | 8.82(d, 2H), 7.82(m, 1H), 7.59(t, 2H), 7.33(m, 1H), 7.11(m, 1H), 4.82(s, 2H), 4.10(m, 2H), 2.39(s, 3H), 1.38(t, 3H). | 397.08 |
| 627 | 4-{4-Cyclopropyl-5-[5-(2-fluoro-5-methyl-phenyl)-[1,3,4]oxadiazol-2-ylmethylsulfanyl]-4H-[1,2,4]triazol-3-yl}-pyridine | 8.80(s, 2H), 7.84(m, 1H), 7.76(d, 2H), 7.32(m, 1H), 7.12(q, 1H), 4.91(s, 2H), 3.31(m, 1H), 2.39(s, 3H), 1.21(m, 2H), 0.84(m, 2H). | 409.15 |
| 628 | 2-(4-Ethyl-5-furan-2-yl-4H-[1,2,4]triazol-3-ylsulfanylmethyl)-5-(2-fluoro-5-methyl-phenyl)-[1,3,4]oxadiazole | 7.77(m, 1H), 7.61(m, 1H), 7.32(d, 1H), 7.12(m, 2H), 6.61(m, 1H), 4.76(s, 2H), 4.26(q, 2H), 2.37(d, 3H), 1.23(t, 3H). | |
| 629 | 2-[4-Ethyl-5-(4-methoxy-phenyl)-4H-[1,2,4]triazol-3-ylsulfanylmethyl]-5-(2-fluoro-5-methyl-phenyl)-[1,3,4]oxadiazole | 7.81(m, 1H), 7.54(m, 2H), 7.32(d, 1H), 7.11(m, 1H), 7.03(m, 2H), 4.79(s, 2H), 4.02(q, 2H), 3.89(s, 3H), 2.37(d, 3H), 1.31(t, 3H). | 426.15 |
| 630 | 4-{5-[5-(5-Chloro-2-fluoro-phenyl)-isoxazol-3-ylmethylsulfanyl]-4-ethyl-4H-[1,2,4]triazol-3-yl}-pyridine | 8.82(dd, 2H), 7.91(dd, 1H), 7.60(dd, 2H), 7.38(m, 1H), 7.15(m, 1H), 6.86(d, 1H), 4.67(s, 2H), 4.05(q, 2H), 1.37(t, 3H). | 417.02 |
| 631 | 4-(5-{1-[5-(5-Chloro-2-fluoro-phenyl)-isoxazol-3-yl]-ethylsulfanyl}-4-ethyl-4H-[1,2,4]triazol-3-yl)-pyridine | 8.81(dd, 2H), 7.91(dd, 1H), 7.59(dd, 2H), 7.38(m, 1H), 7.15(m, 1H), 6.74(d, 1H), 5.20(q, 1H), 4.05(q, 2H), 1.95(d, 3H), 1.34(t, 3H). | 431.10 |
| 632 | 4-{5-[5-(5-Chloro-2-fluoro-phenyl)-isoxazol-3-ylmethylsulfanyl]-4-methyl-4H-[1,2,4]triazol-3-yl}-pyridine | 8.82(dd, 2H), 7.91(dd, 1H), 7.63(dd, 2H), 7.39(m, 1H), 7.15(m, 1H), 6.85(d, 1H), 4.62(s, 2H), 3.69(s, 3H). | 403.10 |
| 633 | 4-(5-{1-[5-(5-Chloro-2-fluoro-phenyl)-isoxazol-3-yl]-ethylsulfanyl}-4-methyl-4H-[1,2,4]triazol-3-yl)-pyridine | 8.81(dd, 2H), 7.91(dd, 1H), 7.60(dd, 2H), 7.38(m, 1H), 7.15(m, 1H), 6.72(d, 1H), 5.06(q, | 417.10 |

-continued

| Example No. | Name | 1H NMR | MS |
|---|---|---|---|
| | | 1H), 3.64(s, 3H), 1.93(d, 3H). | |
| 634 | 4-{5-[5-(5-Chloro-2-fluoro-phenyl)-isoxazol-3-ylmethylsulfanyl]-4-cyclopropyl-4H-[1,2,4]triazol-3-yl}-pyridine | 8.80(dd, 2H), 7.92(dd, 1H), 7.76(dd, 2H), 7.38(m, 1H), 7.15(m, 1H), 6.95(d, 1H), 4.71(s, 2H), 3.27(m, 1H), 1.18(m, 2H), 0.82(m, 2H). | 429.10 |
| 635 | 4-(5-{1-[5-(5-Chloro-2-fluoro-phenyl)-isoxazol-3-yl]-ethylsulfanyl}-4-cyclopropyl-4H-[1,2,4]triazol-3-yl)-pyridine | 8.78(dd, 2H), 7.92(dd, 1H), 7.76(dd, 2H), 7.38(m, 1H), 7.15(m, 1H), 6.85(d, 1H), 5.40(q, 1H), 3.24(m, 1H), 1.98(d, 3H), 1.88(m, 2H), 0.80(m, 2H). | 443.20 |
| 636 | 3-[5-(5-Chloro-2-fluoro-phenyl)-isoxazol-3-ylmethylsulfanyl]-4-ethyl-5-furan-2-yl-4H-[1,2,4]triazole | 7.90(dd, 1H), 7.60(dd, 1H), 7.39(m, 1H), 7.11(m, 2H), 6.85(d, 1H), 6.59(dd, 1H), 4.62(s, 2H), 4.20(q, 2H), 1.38(t, 3H). | |
| 637 | 3-{1-[5-(5-Chloro-2-fluoro-phenyl)-isoxazol-3-yl]-ethylsulfanyl}-4-ethyl-5-furan-2-yl-4H-[1,2,4]triazole | 7.88(dd, 1H), 7.59(dd, 1H), 7.39(m, 1H), 7.11(m, 2H), 6.74(d, 1H), 6.58(dd, 1H), 5.08(q, 1H), 4.20(q, 2H), 1.92(d, 3H), 1.34(t, 3H). | |
| 638 | 4-(5-{1-[5-(3-Chloro-phenyl)-[1,3,4]oxadiazol-2-yl]-ethylsulfanyl}-4-methyl-4H-[1,2,4]triazol-3-yl)-pyridine | 1.96(d, 3H) 3.61(s, 3H) 5.10(q, 1H) 7.38(t, 1H) 7.47(m, 1H) 7.54(m, 2H) 7.84(m, 1H) 7.93(m, 1H) 8.74(d, 2H) | |
| 639 | 4-(5-{1-[5-(3-Chloro-phenyl)-[1,3,4]oxadiazol-2-yl]-ethylsulfanyl}-4-ethyl-4H-[1,2,4]triazol-3-yl)-pyridine | 8.80(bs, 2H), 7.99(m, 1H), 7.90(m, 1H), 7.58(d, 2H), 7.51(m, 1H), 7.46(t, 1H), 5.31(q, 1H), 4.06(q, 2H), 2.04(d, 3H), 1.31(t, 3H). | 414.10 |
| 640 | 4-(5-{1-[5-(3-Chloro-phenyl)-[1,3,4]oxadiazol-2-yl]-ethylsulfanyl}-4-cyclopropyl-4H-[1,2,4]triazol-3-yl)-pyridine | 8.79(bs, 2H), 8.03(m, 1H), 7.94(d, 1H), 7.76(d, 2H), 7.51(m, 1H), 7.45(t, 1H), 7.54(q, 1H), 3.25(m, 1H), 2.06(d, 3H), 1.19(m, 2H), 0.81(m, 2H). | 426.07 |
| 641 | 5-(5-Chloro-2-fluoro-phenyl)-3-(5-furan-2-yl-4-methyl-4H-[1,2,4]triazol-3-ylsulfanylmethyl)-[1,2,4]oxadiazole | 8.06(dd, 1H), 7.60(d, 1H), 7.55(m, 1H), 7.22(t, 1H), 7.09(d, 1H), 6.58(m, 1H), 4.55(s, 2H), 3.81(s, 3H). | |
| 642 | 5-(5-Chloro-2-fluoro-phenyl)-3-(5-furan-3-yl-4-methyl-4H-[1,2,4]triazol-3-ylsulfanylmethyl)-[1,2,4]oxadiazole | 8.06(dd, 1H), 7.89(d, 1H), 7.55(m, 2H), 7.22(t, 1H), 6.88(dd, 1H), 4.55(s, 2H), 3.67(s, 3H). | |
| 643 | 4-Chloro-2-[3-(4-ethyl-5-thiophen-2-yl-4H-[1,2,4]triazol-3-ylsulfanylmethyl)-[1,2,4]oxadiazol-5-yl]-phenol | 10.08(s, 1H), 7.88(d, 1H), 7.47(m, 3H), 7.17(t, 1H), 7.06(d, 1H), 4.68(s, 2H), 4.14(q, 2H), 1.38(t, 3H). | |
| 644 | 2-Chloro-4-[5-(4-methyl-5-pyridin-4-yl-4H-[1,2,4]triazol-3-ylsulfanylmethyl)-[1,3,4]oxadiazol-2-yl]-pyridine | 8.83(d, 2H), 8.60(m, 1H), 7.94(m, 1H), 7.85(m, 1H), 7.62(m, 2H), 4.82(s, 2H), 3.75(s, 3H). | |
| 645 | 2-Chloro-4-[5-(4-ethyl-5-pyridin-4-yl-4H-[1,2,4]triazol-3-ylsulfanylmethyl)-[1,3,4]oxadiazol-2-yl]-pyridine | 8.82(d, 2H), 8.60(m, 1H), 7.94(m, 1H), 7.86(m, 1H), 7.59(m, 2H), 4.87(s, 2H), 4.12(q, 2H), 1.43(t, 3H). | |
| 646 | 2-Chloro-4-[5-(4-cyclopropyl-5-pyridin-4-yl-4H-[1,2,4]triazol-3-ylsulfanylmethyl)-[1,3,4]oxadiazol-2-yl]-pyridine | 8.81(d, 2H), 8.60(m, 1H), 7.96(m, 1H), 7.86(m, 1H), 7.75(m, 2H), 4.92(s, 2H), 3.32(m, 1H), 1.21(m, 2H), 0.87(q, 2H). | |

-continued

| Example No. | Name | 1H NMR | MS |
|---|---|---|---|
| 647 | 2-Chloro-4-[5-(4-ethyl-5-furan-2-yl-4H-[1,2,4]triazol-3-ylsulfanylmethyl)-[1,3,4]oxadiazol-2-yl]-pyridine | 8.57(m, 1H), 7.92(m, 1H), 7.81(m, 1H), 7.61(m, 1H), 7.12(m, 1H), 6.61(m, 1H), 4.79(s, 2H), 4.26(q, 2H), 1.40(t, 3H). | |
| 648 | 2-Chloro-4-{5-[4-ethyl-5-(4-methoxy-phenyl)-4H-[1,2,4]triazol-3-ylsulfanylmethyl]-[1,3,4]oxadiazol-2-yl}-pyridine | 8.59(m, 1H), 7.94(m, 1H), 7.84(m, 1H), 7.55(m, 2H), 7.05(m, 2H), 4.83(s, 2H), 4.02(q, 2H), 1.34(t, 3H). | |
| 649 | 2-(3-Chloro-phenyl)-5-{1-[5-(4-methoxy-phenyl)-4-methyl-4H-[1,2,4]triazol-3-ylsulfanyl]-ethyl}-[1,3,4]oxadiazole | 8.00(m, 1H), 7.87(d, 1H), 7.53(m, 3H), 7.42(t, 1H), 7.01(m, 2H), 5.07(q, 1H), 3.88(s, 3H), 3.54(s, 3H), 2.00(d, 3H). | |
| 650 | 4-(5-{1-[5-(5-Chloro-2-fluoro-phenyl)-[1,3,4]oxadiazol-2-yl]-ethylsulfanyl}-4-methyl-4H-[1,2,4]triazol-3-yl)-pyridine | 8.81(bs, 2H), 8.01(m, 1H), 7.63(d, 2H), 7.50(m, 1H), 7.18(m, 1H), 5.17(q, 1H), 3.69(s, 3H), 2.02(d, 3H). | |
| 651 | 5-(5-Bromo-2-fluoro-phenyl)-3-(4-ethyl-5-furan-2-yl-4H-[1,2,4]triazol-3-ylsulfanylmethyl)-[1,2,4]oxadiazole | 8.20(m, 1H), 7.65(m, 1H), 7.60(s, 1H), 7.13(m, 2H), 6.56(m, 1H), 4.64(s, 2H), 4.25(q, 2H), 1.38(t, 3H). | |
| 652 | 2-(3-Chloro-phenyl)-5-[5-(4-methoxy-phenyl)-4-methyl-4H-[1,2,4]triazol-3-ylsulfanylmethyl]-[1,3,4]oxadiazole | 8.02(d, 1H), 7.90(d, 1H), 7.50(m, 4H), 7.03(d, 2H), 4.71(s, 2H), 3.88(s, 3H), 3.61(s, 3H). | |
| 653 | 4-{5-[3-(3-Chloro-phenyl)-[1,2,4]oxadiazol-5-ylmethylsulfanyl]-4-cyclopropyl-4H-[1,2,4]triazol-3-yl}-pyridine | 8.79(d, 2H), 8.09(t, 1H), 7.97(m, 1H), 7.76(d, 2H), 7.45(m, 2H), 4.89(s, 2H), 3.30(m, 1H), 1.22(m, 2H), 0.86(m, 2H). | 412.07 |
| 654 | 4-{5-[5-(3-Chloro-phenyl)-[1,2,4]oxadiazol-3-ylmethylsulfanyl]-4-cyclopropyl-4H-[1,2,4]triazol-3-yl}-pyridine | 8.78(s, 2H), 8.14(m, 1H), 8.04(m, 1H), 7.77(t, 2H), 7.54(m, 2H), 4.79(s, 2H), 3.29(m, 1H), 1.21(m, 2H), 0.85(d, 2H). | |
| 655 | 4-(5-{1-[5-(2-Fluoro-5-methyl-phenyl)-[1,3,4]oxadiazol-2-yl]-ethylsulfanyl}-4-methyl-4H-[1,2,4]triazol-3-yl)-pyridine | 8.79(s, 2H), 7.79(t, 1H), 7.61(t, 2H), 7.33(m, 1H), 7.08(m, 1H), 5.09(m, 1H), 3.65(s, 3H), 2.37(s, 3H), 2.02(d, 3H). | |
| 656 | 4-(4-Ethyl-5-{1-[5-(2-fluoro-5-methyl-phenyl)-[1,3,4]oxadiazol-2-yl]-ethylsulfanyl}-4H-[1,2,4]triazol-3-yl)-pyridine | 8.81(m, 2H), 8.23(m, 1H), 7.79(d, 2H), 7.32(m, 1H), 7.09(m, 1H), 5.28(m, 1H), 4.07(m, 2H), 2.37(s, 3H), 2.04(d, 3H), 1.24(m, 3H). | |
| 657 | 4-(4-Cyclopropyl-5-{1-[5-(2-fluoro-5-methyl-phenyl)-[1,3,4]oxadiazol-2-yl]-ethylsulfanyl}-4H-[1,2,4]triazol-3-yl)-pyridine | 8.78(m, 2H), 7.82(d, 1H), 7.74(d, 2H), 7.31(m, 1H), 7.11(m, 1H), 5.51(m, 1H), 3.23(m, 1H), 2.38(s, 3H), 2.06(d, 3H), 1.16(m, 2H), 0.78(m, 2H). | |
| 658 | 4-(4-Cyclopropylmethyl-5-{1-[5-(2-fluoro-5-methyl-phenyl)-[1,3,4]oxadiazol-2-yl]-ethylsulfanyl}-4H-[1,2,4]triazol-3-yl)-pyridine | 8.83(m, 2H), 7.78(m, 1H), 7.59(m, 2H), 7.33(m, 1H), 7.10(m, 1H), 5.26(m, 1H), 3.90(m, 2H), 2.37(s, 3H), 2.03(d, 3H), 0.92(m, 1H), 0.48(m, 2H), 0.21(m, 2H). | |
| 659 | 2-(2-Fluoro-5-methyl-phenyl)-5-{1-[4-methyl-5-(2-methyl-thiazol-4-yl)-4H-[1,2,4]triazol-3-ylsulfanyl]-ethyl}-[1,3,4]oxadiazole | 7.98(s, 1H), 7.75(m, 1H), 7.31(m, 1H), 7.08(m, 1H), 5.03(q, 1H), 3.85(s, 3H), 2.75(s, 3H), 2.35(s, 3H), 1.98(d, 3H). | |

-continued

| Example No. | Name | 1H NMR | MS |
|---|---|---|---|
| 660 | 4-(5-{1-[5-(5-Chloro-2-fluoro-phenyl)-[1,3,4]oxadiazol-2-yl]-ethylsulfanyl}-4-ethyl-4H-[1,2,4]triazol-3-yl)-pyridine | 8.80(m, 2H), 8.01(m, 1H), 7.58(m, 2H), 7.49(m, 1H), 7.19(m, 1H), 5.32(q, 1H), 4.08(q, 2H), 2.04(d, 3H), 1.35(t, 3H). | |
| 661 | 4-(5-{1-[5-(5-Chloro-2-fluoro-phenyl)-[1,3,4]oxadiazol-2-yl]-ethylsulfanyl}-4-cyclopropyl-4H-[1,2,4]triazol-3-yl)-pyridine | 8.79(d, 2H), 8.03(m, 1H), 7.75(m, 2H), 7.50(m, 1H), 7.20(m, 1H), 5.55(q, 1H), 3.26(s, 1H), 2.06(d, 3H), 1.18(m, 2H), 0.81(m, 2H). | |
| 662 | 2-(5-Chloro-2-fluoro-phenyl)-5-[1-(4-ethyl-5-furan-2-yl-4H-[1,2,4]triazol-3-ylsulfanyl)-ethyl]-[1,3,4]oxadiazole | 8.97(m, 1H), 7.59(m, 1H), 7.47(m, 1H), 7.17(m, 1H), 7.12(m, 1H), 6.59(m, 1H), 5.18(q, 1H), 4.21(q, 2H), 2.00(d, 3H), 1.33(t, 3H). | |
| 663 | 2-(5-Chloro-2-fluoro-phenyl)-5-{1-[4-methyl-5-(2-methyl-thiazol-4-yl)-4H-[1,2,4]triazol-3-ylsulfanyl]-ethyl}-[1,3,4]oxadiazole | 7.99(s, 1H), 7.96(m, 1H), 7.48(m, 1H), 7.17(t, 1H), 7.06(q, 1H), 3.86(s, 3H), 2.75(s, 3H), 1.98(d, 3H). | |
| 664 | 4-(4-Cyclopropylmethyl-5-{1-[5-(2-fluoro-5-methyl-phenyl)-isoxazol-3-yl]-ethylsulfanyl}-4H-[1,2,4]triazol-3-yl)-pyridine | 8.78(dd, 2H), 7.71(dd, 1H), 7.58(dd, 2H), 7.25(m, 1H), 7.08(m, 1H), 6.62(d, 1H), 5.12(q, 1H), 3.87(dd, 2H), 2.40(s, 3H), 1.94(d, 3H), 0.90(m, 1H), 0.49(m, 2H), 0.19(m, 2H). | |
| 665 | 4-(5-{1-[5-(3-Fluoro-phenyl)-[1,2,4]oxadiazol-3-yl]-ethylsulfanyl}-4-methyl-4H-[1,2,4]triazol-3-yl)-pyridine | 8.78(bs, 2H), 7.92(d, 1H), 7.80(dd, 1H), 7.60(d, 2H), 7.50(m, 1H), 7.25(m, 1H), 5.05(q, 2H), 3.65(s, 3H), 1.94(d, 3H). | |
| 666 | 4-(4-Cyclopropyl-5-{1-[5-(3-fluoro-phenyl)-[1,2,4]oxadiazol-3-yl]-ethylsulfanyl}-4H-[1,2,4]triazol-3-yl)-pyridine | 8.76(d, 2H), 7.95(d, 1H), 7.85(dd, 1H), 7.75(d, 2H), 7.50(m, 1H), 7.25(m, 1H), 5.45(q, 2H), 3.20(m, 1H), 1.98(d, 3H) 1.22(m, 2H), 0.88(m, 2H). | |
| 667 | 4-(5-{1-[5-(4-Methoxy-phenyl)-4-methyl-4H-[1,2,4]triazol-3-ylsulfanyl]-ethyl}-[1,3,4]oxadiazol-2-yl)-2-methyl-pyridine | 8.65(d, 1H), 7.71(s, 1H), 7.63(d, 1H), 7.54(d, 2H), 7.00(d, 2H), 5.10(q, 1H), 3.87(s, 3H), 3.53(s, 3H), 2.58(s, 3H), 2.00(d, 3H). | |
| 668 | 4-(5-{1-[4-Ethyl-5-(4-methoxy-phenyl)-4H-[1,2,4]triazol-3-ylsulfanyl]-ethyl}-[1,3,4]oxadiazol-2-yl)-2-methyl-pyridine | 8.65(d, 1H), 7.71(s, 1H), 7.63(d, 1H), 7.49(d, 2H), 7.01(d, 2H), 5.26(q, 1H), 3.96(q, 2H), 3.88(s, 3H), 2.62(s, 3H), 2.02(d, 3H), 1.24(t, 3H). | |
| 669 | 4-{5-[1-(4-Ethyl-5-pyridin-4-yl-4H-[1,2,4]triazol-3-ylsulfanyl)-ethyl]-[1,3,4]oxadiazol-2-yl}-2-methyl-pyridine | 8.79(d, 2H), 8.67(d, 1H), 7.73(s, 1H), 7.65(d, 1H), 7.55(d, 2H), 5.33(q, 1H), 4.08(q, 2H), 2.64(s, 3H), 2.03(d, 3H), 1.30(t, 3H). | |
| 670 | 4-{5-[1-(4-Cyclopropyl-5-pyridin-4-yl-4H-[1,2,4]triazol-3-ylsulfanyl)-ethyl]-[1,3,4]oxadiazol-2-yl}-2-methyl-pyridine | 8.77(d, 2H), 8.68(d, 1H), 7.72(m, 4H), 5.55(q, 1H), 3.24(m, 1H), 2.64(s, 3H), 2.04(d, 3H), 1.16(m, 2H), 0.81(m, 2H). | |
| 671 | 4-{5-[1-(5-Furan-2-yl-4-methyl-4H-[1,2,4]triazol-3-ylsulfanyl)-ethyl]-[1,3,4]oxadiazol-2-yl}-2-methyl-pyridine | 8.61(d, 1H), 7.57(m, 3H), 7.08(d, 1H), 6.57(d, 1H), 5.02(q, 1H), 3.70(s, 3H), 1.96(d, 3H). | |
| 672 | 2-(3-Chloro-phenyl)-5-{1-[4-methyl-5-(2-methyl-thiazol-4-yl)-4H-[1,2,4]triazol-3-ylsulfanyl]- | 7.99(s, 1H), 7.94(m, 1H), 7.86(m, 1H), 7.48(m, 1H), 7.39(m, | |

-continued

| Example No. | Name | 1H NMR | MS |
|---|---|---|---|
| | ethyl}-[1,3,4]oxadiazole | 1H), 5.03(q, 1H), 3.82(t, 3H), 2.73(d, 3H), 1.98(d, 3H). | |
| 673 | 3-(5-{1-[5-(3-Chloro-phenyl)-[1,3,4]oxadiazol-2-yl]-ethylsulfanyl}-4-methyl-4H-[1,2,4]triazol-3-yl)-pyridine | 8.88(s, 1H), 8.76(d, 1H), 8.00(m, 2H), 7.90(d, 1H), 7.48(m, 3H), 5.14(q, 1H), 3.60(s, 3H), 2.02(d, 3H). | |
| 674 | 4-(5-{1-[5-(3-Chloro-phenyl)-[1,3,4]oxadiazol-2-yl]-ethylsulfanyl}-4-methyl-4H-[1,2,4]triazol-3-yl)-2-methyl-pyridine | 8.66(d, 1H), 7.99(m, 1H), 7.88(m, 1H), 7.51(m, 1H), 7.43(m, 2H), 7.34(d, 1H), 5.13(q, 1H), 3.61(s, 3H), 2.63(s, 3H), 2.00(d, 3H). | |
| 675 | 4-(5-{1-[5-(3-Chloro-phenyl)-[1,2,4]oxadiazol-3-yl]-ethylsulfanyl}-4-cyclopropyl-4H-[1,2,4]triazol-3-yl)-pyridine | 8.68(dd, 2H), 8.05(d, 1H), 7.92(d, 1H), 7.67(dd, 2H), 7.51(d, 1H), 7.37(t, 1H) 5.37(q, 1H), 3.18(m, 1H), 1.90(d, 3H), 1.08(m, 2H), 0.74(m, 2H). | |
| 676 | 5-(3-Chloro-phenyl)-3-{1-[5-(4-methoxy-phenyl)-4-methyl-4H-[1,2,4]triazol-3-ylsulfanyl]-ethyl}-[1,2,4]oxadiazole | 8.01(s, 1H), 7.90(d, 1H), 7.50(m, 3H), 7.38(t, 1H), 6.92(d, 2H), 4.88(q, 1H) 3.78(s, 3H), 3.47(s, 3H), 1.83(d, 3H). | |
| 677 | 4-(5-{1-[5-(5-Chloro-2-fluoro-phenyl)-[1,2,4]oxadiazol-3-yl]-ethylsulfanyl}-4-cyclopropyl-4H-[1,2,4]triazol-3-yl)-pyridine | 8.70(dd, 2H), 8.05(m, 1H), 7.67(m, 2H), 7.46(m, 1H), 7.18(m, 1H), 5.41(q, 1H), 3.18(m, 1H), 1.90(d, 3H), 1.08(m, 2H), 0.74(m, 2H). | |
| 678 | 5-(5-Chloro-2-fluoro-phenyl)-3-{1-[5-(4-methoxy-phenyl)-4-methyl-4H-[1,2,4]triazol-3-ylsulfanyl]-ethyl}-[1,2,4]oxadiazole | 8.05(m, 1H), 7.56(m, 3H), 7.21(t, 1H), 7.00(m, 3H), 5.01(q, 1H), 3.85(s, 3H), 3.56(s, 3H), 1.90(d, 3H). | |
| 679 | 4-[5-(4-Ethyl-5-pyridin-4-yl-4H-[1,2,4]triazol-3-ylsulfanylmethyl)-[1,3,4]oxadiazol-2-yl]-2-methyl-pyridine | 8.79(d, 2H), 8.67(d, 1H), 7.75(s, 1H), 7.67(d, 1H), 7.56(d, 2H), 4.82(s, 2H), 4.10(q, 2H), 2.64(s, 3H), 1.39(t, 3H). | |
| 680 | 4-[5-(4-Cyclopropyl-5-pyridin-4-yl-4H-[1,2,4]triazol-3-ylsulfanylmethyl)-[1,3,4]oxadiazol-2-yl]-2-methyl-pyridine | 8.78(d, 3H), 8.68(d, 1H), 7.74(m, 4H), 4.90(s, 2H), 3.30(m, 1H), 2.65(s, 3H), 1.21(m, 2H), 0.84(m, 2H). | |
| 681 | 4-{5-[5-(5-Chloro-2-fluoro-phenyl)-[1,2,4]oxadiazol-3-ylmethylsulfanyl]-4-cyclopropyl-4H-[1,2,4]triazol-3-yl}-pyridine | 8.79(d, 2H), 8.12(m, 1H), 7.76(m, 2H), 7.57(m, 1H), 7.25(m, 1H), 4.81(s, 2H), 3.31(m, 1H), 1.20(m, 2H), 0.85(m, 2H). | |
| 682 | 4-[5-(5-Furan-2-yl-4-methyl-4H-[1,2,4]triazol-3-ylsulfanylmethyl)-[1,3,4]oxadiazol-2-yl]-2-methyl-pyridine | 8.66(d, 1H), 7.72(s, 1H), 7.65(d, 1H), 7.60(d, 1H), 7.11(d, 1H), 6.60(d of d, 1H), 4.70(s, 2H), 3.80(s, 3H), 2.64(s, 3H). | |
| 683 | 4-(5-{1-[5-(3-Chloro-phenyl)-[1,3,4]oxadiazol-2-yl]-ethylsulfanyl}-4-cyclopropylmethyl-4H-[1,2,4]triazol-3-yl)-pyridine | 8.79(bs, 2H), 7.98(m, 1H), 7.88(m, 1H), 7.51(m, 4H), 5.30(q, 1H), 3.90(m, 2H), 2.05(t, 3H), 0.94(ms, 1H), 0.50(m, 2H), 0.19(m, 2H). | |
| 684 | 4-(5-{1-[5-(4-Fluoro-phenyl)-4-methyl-4H-[1,2,4]triazol-3-ylsulfanyl]-ethyl}-[1,3,4]oxadiazol-2-yl)-2-methyl-pyridine | 8.66(d, 1H), 7.72(s, 1H), 7.60(m, 3H), 7.17(m, 3H), 5.13(q, 1H), 3.57(s, 3H), 2.63(s, 3H), 2.00(d, 3H). | |
| 685 | 4-(5-{1-[5-(3-Fluoro-phenyl)-4-methyl-4H-[1,2,4]triazol-3-ylsulfanyl]-ethyl}-[1,3,4]oxadiazol-2-yl)-2-methyl-pyridine | 8.65(d, 1H), 7.72(s, 1H), 7.66(d, 1H), 7.48–7.20(m, 4H), 5.15(q, 1H), 3.60(s, 3H), 2.63(s, 3H), 2.01(d, 3H). | |

| Example No. | Name | 1H NMR | MS |
|---|---|---|---|
| 686 | 3-[3-(4-Cyclopropyl-5-pyridin-4-yl-4H-[1,2,4]triazol-3-ylsulfanylmethyl)-[1,2,4]oxadiazol-5-yl]-4-fluoro-benzonitrile | 8.77(dd, 2H), 8.49(dd, 1H), 7.90(m, 1H), 7.74(dd, 2H), 7.43(t, 1H), 4.81(s, 2H), 3.31(m, 1H), 1.21(m, 2H), 0.83(m, 2H). | |
| 687 | 4-Chloro-2-[3-(4-cyclopropyl-5-pyridin-4-yl-4H-[1,2,4]triazol-3-ylsulfanylmethyl)-[1,2,4]oxadiazol-5-yl]-phenol | 10.15(bs, 1H), 8.77(dd, 2H), 7.89(d, 1H), 7.75(dd, 2H), 7.45(dd, 1H), 7.06(d, 1H), 4.79(s, 2H), 3.29(m, 1H), 1.21(m, 2H), 0.83(m, 2H). | |
| 688 | 4-{4-Cyclopropyl-5-[5-(3-methoxy-phenyl)-[1,2,4]oxadiazol-3-ylmethylsulfanyl]-4H-[1,2,4]triazol-3-yl}-pyridine | 8.77(dd, 2H), 7.72(m, 3H), 7.62(dd, 1H), 7.43(t, 1H), 7.14(m, 1H), 4.77(s, 2H), 3.88(s, 3H), 3.28(m, 1H), 1.17(m, 2H), 0.84(m, 2H). | |
| 689 | 4-{4-Cyclopropyl-5-[5-(2-fluoro-5-methyl-phenyl)-[1,2,4]oxadiazol-3-ylmethylsulfanyl]-4H-[1,2,4]triazol-3-yl}-pyridine | 8.7(q, 2H), 7.81(d, 1H), 7.7(q, 2H), 7.29(m, 1H), 7.1(t, 1H), 4.71(s, 2H), 3.23(m, 1H), 2.32(s, 3H), 1.11(m, 2H), 0.76(m, 2H) | |
| 690 | 4-{4-Cyclopropyl-5-[5-(3-fluoro-phenyl)-[1,2,4]oxadiazol-3-ylmethylsulfanyl]-4H-[1,2,4]triazol-3-yl}-pyridine | 8.67(m, 2H), 7.82(m, 1H), 7.72(m, 1H), 7.66(m, 1H), 7.42(m, 1H), 7.21(m, 1H), 4.68(s, 1H), 3.23(m, 1H), 1.11(m, 2H), 0.75(m, 2H) | |
| 691 | 4-[4-Cyclopropyl-5-(5-m-tolyl-[1,2,4]oxadiazol-3-ylmethylsulfanyl)-4H-[1,2,4]triazol-3-yl]-pyridine | 8.69(q, 2H), 7.85(m, 2H), 7.67(q, 2H), 7.32(m, 2H), 4.69(s, 2H), 3.2(m, 1H), 2.35(s, 3H), 1.11(m, 2H), 0.76(m, 2H) | |
| 692 | 3-[3-(4-Cyclopropyl-5-pyridin-4-yl-4H-[1,2,4]triazol-3-ylsulfanylmethyl)-[1,2,4]oxadiazol-5-yl]-benzonitrile | 8.71(b s, 2H), 8.36(m, 1H), 8.28(d, 1H), 7.83(d d, 1H), 7.67(m, 3H), 4.72(s, 2H), 3.23(m, 1H), 1.14(m, 2H), 0.77(m, 2H) | |
| 693 | 4-{4-Cyclopropyl-5-[5-(2,5-difluoro-phenyl)-[1,2,4]oxadiazol-3-ylmethylsulfanyl]-4H-[1,2,4]triazol-3-yl}-pyridine | 8.75(t, 2H), 7.79(m, 2H), 7.26(m, 2H), 4.78(s, 2H), 3.28(m, 1H), 1.14(m, 2H), 0.82(m, 2H) | |
| 694 | 4-{4-Cyclopropyl-5-[1-(5-m-tolyl-[1,2,4]oxadiazol-3-yl)-ethylsulfanyl]-4H-[1,2,4]triazol-3-yl}-pyridine | 8.67(d d, 2H), 7.87(m, 2H), 7.67(d d, 2H), 7.33(m, 2H), 5.36(q, 1H), 3.15(m, 1H), 2.36(s, 3H), 1.92(d, 3H), 1.07(m, 2H), 0.72(m, 2H) | |
| 695 | 4-(4-Cyclopropyl-5-{1-[5-(3-methoxy-phenyl)-[1,2,4]oxadiazol-3-yl]-ethylsulfanyl}-4H-[1,2,4]triazol-3-yl)-pyridine | 8.69(m, 2H), 7.6(m, 3H), 7.52(m, 1H), 7.35(t, 1H), 7.04(d d, 1H), 5.35(q, 1H), 3.81(s, 3H), 3.15(m, 1H), 1.91(d, 3H), 1.11(m, 2H), 0.7(m, 2H) | |
| 696 | 4-{5-[5-(2-Chloro-5-methyl-phenyl)-[1,2,4]oxadiazol-3-ylmethylsulfanyl-4-cyclopropyl-4H-[1,2,4]triazol-3-yl}-pyridine | 8.69(d, 2H), 7.78(m, 1H), 7.67(m, 2H), 7.35(d, 1H), 7.24(m, 1H), 4.72(s, 2H), 3.22(m, 1H), 2.31(s, 3H), 1(m, 2H), 0.76(m, 2H) | |
| 697 | 2-[3-(4-Cyclopropyl-5-pyridin-4-yl-4H-[1,2,4]triazol-3-ylsulfanylmethyl)-[1,2,4]oxadiazol-5-yl]-4-methyl-phenol | 9.89(s, 1H), 8.7(m, 2H), 7.68(m, 3H), 7.2(m, 1H), 6.92(d, 1H), 4.72(s, 2H), 3.22(m, 1H), 2.26(s, 3H), 1.01(m, 2H), 0.74(m, 2H) | |

| Example No. | Name | 1H NMR | MS |
|---|---|---|---|
| 698 | 4-(5-{1-[5-(2-Chloro-5-methyl-phenyl)-[1,2,4]oxadiazol-3-yl]-ethylsulfanyl}-4-cyclopropyl-4H-[1,2,4]triazol-3-yl)-pyridine | 8.69(d d, 2H), 7.8(q, 1H), 7.67(m, 2H), 7.35(d, 1H), 7.22(m, 1H), 5.4(q, 1H), 3.16(m, 1H), 2.32(s, 3H), 1.93(d, 3H), 1.09(m, 2H), 0.73(m, 2H) | |

Example 699

{3-[3-(4-Methyl-5-thiophen-2-yl-4H-[1,2,4]triazol-3-ylsulfanylmethyl)-[1,2,4]oxadiazol-5-yl]-phenyl}-methanol

[3-(3-Chloromethyl-[1,2,4]oxadiazol-5-yl)-phenyl]-methanol (32 mg, 0.14 mmol), 4-methyl-5-thiophene-3-yl-4H-[1,2,4]triazole-3-thiol (41 mg, 0.21 mmol) and potassium carbonate (29 mg, 0.21 mmol) was dissolved in anhydrous acetonitrile and refluxed under nitrogen atmosphere for 1 h. The solvent was removed in vacuo and the residue was dissolved in NaHCO3 (aq) and extracted with dichloromethane ('3). The organic phase was dried (MgSO4), filtered and concentrated. The title compound was isolated as an colorless oil (43 mg, 80%) by flash chromatography using 3% methanol in dichloromethane. 1H NMR (CDCl3), δ (ppm): 8.07 (s, 1H), 7.98 (d, 1H), 7.60 (d, 1H), 7.52-7.45 (m, 3H), 7.16 (dd, 1H), 5.29 (s, 2H), 4.75 (s, 2H), 4.50 (s, 2H), 3.71 (s, 1H).

The following compounds were prepared analogously to Example 699:

Example 704

3-(2,5-Difluoro-phenyl)-5-(4-ethyl-5-thiophen-2-yl-4H-[1,2,4]triazol-3-ylsulfanylmethyl)-[1,2,4]oxadiazole 5-Chloromethyl-3-(2,5-difluoro-phenyl)-[1,2,4]oxadiazole (23 mg, 0.10 mmol) and 4-ethyl-5-thiophen-2-yl-2,4-dihydro-[1,2,4]triazole-3-thione (23 mg, 0.11 mmol) was dissolved in anhydrous DMF (1 ml) and potassium carbonate (21 mg, 0.15 mmol) was added. After stirring for 22 h ethyl acetate was added, the resulting mixture was washed twice with water and once with brine, dried over MgSO4 and evaporated. Flash chromatography using heptane:ethyl acetate 1:1 yielded the title compound (20 mg, 50%).

1H NMR (CDCl3) d (ppm): 7.64 (m, 1H), 7.45 (d, 1H), 7.39 (d, 1H), 7.10 (m, 3H), 4.70 (s, 2H), 4.08 (q, 2H), 1.32 (t, 3H).

The following compounds were prepared analogously to Examples 704:

| Example No. | Name | 1H NMR | MS |
|---|---|---|---|
| 700 | 3-[5-(4-Methyl-5-thiophen-2-yl-4H-[1,2,4]triazol-3-ylsulfanylmethyl)-[1,2,4]oxadiazol-3-yl]-phenol | | |
| 701 | 5-(3-Chloro-phenyl)-3-[4-(tetrahydro-furan-2-ylmethyl)-5-thiophen-2-yl-4H-[1,2,4]triazol-3-ylsulfanylmethyl]-[1,2,4]oxadiazole | 1.5(m, 1H) 1.8(m, 2H) 2.0(m, 1H) 3.7(m, 1H) 3.8(m, 1H) 4.1(s, m, 3H) 4.5(dd, 2H) 7.1(dd, 1H) 7.4(t, 2H) 7.5(m, 2H) 7.9(dd, 1H) 8.0(m, 1H | 460 |
| 702 | (2-Chloro-phenyl)-{5-[5-(3-chloro-phenyl)-[1,2,4]oxadiazol-3-ylmethylsulfanyl]-4-isobutyl-4H-[1,2,4]triazol-3-yl}-methanol | 0.8(2d, 6H) 2.0(m, 1H) 3.5(dd, 1H) 3.6(dd, 1H) 4.5(s, 2H) 6.3(d, 1H) 7.3(m, 3H) 7.5(apparent triplett, 1H) 7.6(m, 2H) 8.0(apparent d, 1H) 8.1(m, 1H) | 490 |
| 703 | 5-(2-Fluoro-5-methyl-phenyl)-3-[5-thiophen-2-yl-4-(2,2,2-trifluoro-ethyl)-4H-[1,2,4]triazol-3-ylsulfanylmethyl]-[1,2,4]oxadiazole | 2.4(s, 3H) 4.6(s, 2H) 4.8(q, J=7.7Hz, 2H) 7.1(m, 1H) 7.2(m, 1H) 7.4(m, 1H) 7.5(m, 1H) 7.6(m, 1H) 7.8(m, 1H) | 455.9 |

| Example No. | Name | 1H NMR | MS |
|---|---|---|---|
| 705 | 5-Furan-3-yl-3-(4-methyl-5-thiophen-2-yl-4H-[1,2,4]triazol-3-ylsulfanylmethyl)-[1,2,4]oxadiazole | 3.71(s, 3H) 4.51(s, 2H) 6.88(dd, 1H) 7.17(dd, 1H) 7.48(dd, 1H) 7.51(dd, 1H) 7.54(t, 1H) 8.18(m, 1H) | 345.92 |
| 706 | 3-(3-Chloro-phenyl)-5-(5-furan-2-yl-4-methyl-4H-[1,2,4]triazol-3-ylsulfanylmethyl)-[1,2,4]oxadiazole | 3.78(s, 3H) 4.64(s, 2H) 6.57(dd, 1H) 7.09(d, 1H) 7.38(t, 1H) 7.46(m, 1H) 7.58(d, 1H) 7.91(d, 1H) 8.01(m, 1H) | 373.96 |
| 707 | 3-(3-Chloro-phenyl)-5-(5-furan-3-yl-4-methyl-4H-[1,2,4]triazol-3-ylsulfanylmethyl)-[1,2,4]oxadiazole | 3.63(s, 3H) 4.64(s, 2H) 6.85(d, 1H) 7.39(t, 1H) 7.47(dt, 1H) 7.56(t, 1H) 7.87(br. s, 1H) 7.91(dt, 1H) 8.01(t, 1H) | 373.96 |
| 708 | 5-(3-Chloro-phenyl)-3-(5-furan-2-yl-4-methyl-4H-[1,2,4]triazol-3-ylsulfanylmethyl)-[1,2,4]oxadiazole | 3.77(s, 3H) 4.50(s, 2H) 6.55(dd, 1H) 7.07(d, 1H) 7.43(t, 1H) 7.55(m, 2H) 7.95(dt, 1H) 8.05(t, 1H) | 373.96 |
| 709 | 5-(3-Chloro-phenyl)-3-(5-furan-3-yl-4-methyl-4H-[1,2,4]triazol-3-ylsulfanylmethyl)-[1,2,4]oxadiazole | 3.63(s, 3H) 4.49(s, 2H) 6.84(br. s, 1H) 7.43(t, 1H) 7.54(m, 2H) 7.87(s, 1H) 7.94(d, 1H) 8.04(m, 1H) | 373.97 |
| 710 | 4-{5-[5-(3-Chloro-phenyl)-[1,2,4]oxadiazol-3-ylmethylsulfanyl]-4-methyl-4H-[1,2,4]triazol-3-yl}-pyrimidine | 4.06(s, 3H) 4.63(s, 2H) 7.43(t, 1H) 7.53(m, 1H) 7.95(d, 1H) 8.05(t, 1H) 8.27(dd, 1H) 8.85(d, 1H) 9.25(d, 1H) | 385.97 |
| 711 | 4-{5-[3-(3-Chloro-phenyl)-[1,2,4]oxadiazol-5-ylmethylsulfanyl]-4-methyl-4H-[1,2,4]triazol-3-yl}-pyrimidine | 4.06(s, 3H) 4.75(s, 2H) 7.35(t, 1H) 7.42(ddd, 1H) 7.88(dt, 1H) 7.97(t, 1H) 8.24(dd, 1H) 8.84(d, 1H) 9.23(d, 1H) | 385.97 |
| 712 | 3-(5-Chloro-2-fluoro-phenyl)-5-(4-ethyl-5-thiophen-2-yl-4H-[1,2,4]triazol-3-ylsulfanylmethyl)-[1,2,4]oxadiazole | 1.29(t, 3H) 4.07(q, 2H) 4.68(s, 2H) 7.08(m, 2H) 7.35(m, 2H) 7.44(dd, 1H) 7.87(dd, 1H) | 421.99 |
| 713 | 3-(5-Chloro-2-fluoro-phenyl)-5-(4-ethyl-5-furan-2-yl-4H-[1,2,4]triazol-3-ylsulfanylmethyl)-[1,2,4]oxadiazole | 1.32(t, 3H) 4.18(q, 2H) 4.71(s, 2H) 6.51(dd, 1H) 7.02(dd, 1H) 7.10(dd, 1H) 7.37(ddd, 1H) 7.53(dd, 1H) 7.91(dd, 1H) | 406.02 |
| 714 | 5-(5-Chloro-thiophen-2-yl)-3-(4-ethyl-5-thiophen-2-yl-4H-[1,2,4]triazol-3-ylsulfanylmethyl)-[1,2,4]oxadiazole | 1.30(t, 3H) 4.09(q, 2H) 4.47(s, 2H) 6.96(d, 1H) 7.11(dd, 1H) 7.40(dd, 1H) 7.47(dd, 1H) 7.60(d, 1H) | 409.92 |
| 715 | 5-(5-Chloro-thiophen-2-yl)-3-(4-ethyl-5-furan-2-yl-4H-[1,2,4]triazol-3-ylsulfanylmethyl)-[1,2,4]oxadiazole | 1.33(t, 3H) 4.21(q, 2H) 4.52(s, 2H) 6.54(dd, 1H) 6.98(d, 1H) 7.05(dd, 1H) 7.55(dd, 1H) 7.62(d, 1H) | 393.96 |
| 716 | 5-(5-Chloro-thiophen-3-yl)-3-(4-ethyl-5-thiophen-2-yl-4H-[1,2,4]triazol-3-ylsulfanylmethyl)-[1,2,4]oxadiazole | 1.36(t, 3H) 4.12(q, 2H) 4.58(s, 2H) 7.15(dd, 1H) 7.43(m, 2H) 7.48(dd, 1H) 7.94(d, 1H) | 409.92 |
| 717 | 4-{5-[5-(3-Chloro-phenyl)-[1,2,4]oxadiazol-3-ylmethylsulfanyl]-4-ethyl-4H-[1,2,4]triazol-3-ylmethoxy}-phenol | 1.30(t, 3H) 4.02(q, 2H) 4.51(s, 2H) 5.07(s, 2H) 6.72(m, 4H) 7.39(t, 1H) 7.49(m, 1H) 7.89(m, 1H) 7.99(t, 1H) | 443.9 |
| 718 | 4-{5-[5-(5-Chloro-2-fluoro-phenyl)-[1,3,4]oxadiazol-2-ylmethylsulfanyl]-4-ethyl-4H-[1,2,4]triazol-3-ylmethoxy}-phenol | 1.33(t, 3H) 4.05(q, 2H) 4.70(s, 2H) 5.11(s, 2H) 6.74(m, 4H) 7.13(dd, 1H) 7.44(m, 1H) 7.93(dd, 1H) | 461.9 |
| 719 | 3-(2,5-Difluoro-phenyl)-5-(4-ethyl-5-furan-2-yl-4H-[1,2,4]triazol-3-ylsulfanylmethyl)-[1,2,4]oxadiazole | 7.75(m, 1H), 7.64(d, 1H), 7.23(m, 2H), 7.16(d, 1H), 6.63(dd, 1H), 4.80(s, 2H), 4.29(q, 2H), 1.43(t, 3H) | 389.9 |

-continued

| Example No. | Name | 1H NMR | MS |
|---|---|---|---|
| 720 | 3-(2,5-Difluoro-phenyl)-5-(5-furan-2-yl-4-methyl-4H-[1,2,4]triazol-3-ylsulfanylmethyl)-[1,2,4]oxadiazole | 8.17(dd, 1H), 7.87(m, 1H), 7.74(m, 2H), 7.33(dd, 1H), 6.95(dd, 1H), 5.01(s, 2H), 3.96(s, 3H) | 375.8 |
| 721 | 4-(5-{1-[3-(3-Chloro-phenyl)-[1,2,4]oxadiazol-5-yl]-ethylsulfanyl}-4-methyl-4H-[1,2,4]triazol-3-yl)-pyridine | 8.74(d, 2H), 7.97(s, 1H), 7.87(m, 1H), 7.56(d, 2H), 7.44(m, 1H), 7.36(apparent t, 1H), 5.06(q, 1H), 3.58(s, 3H), 1.96(d, 3H). | 400 |
| 722 | 4-{5-[5-(5-Chloro-2-fluoro-phenyl)-[1,2,4]oxadiazol-3-ylmethylsulfanyl]-4-cyclopropyl-4H-[1,2,4]triazol-3-yl}-pyrimidine | 0.90(m, 2H), 1.22(m, 2H), 3.49(m, 1H), 4.81(s, 2H), 7.26(t, 1H), 7.53(m, 1H), 8.11(m, 2H), 8.88(d, 1H) 9.33(s, 1H) | 430.1 |
| 723 | 2-(5-{1-[5-(3-Chloro-phenyl)-[1,2,4]oxadiazol-3-yl]-ethylsulfanyl}-4-ethyl-4H-[1,2,4]triazol-3-yl)-5-methoxy-pyrimidine | 1.32(t, 3H), 1.94(d, 3H), 4.00(s, 3H), 4.50(m, 2H), 5.20(q, 1H), 7.46(t, 1H), 7.56(m, 1H), 7.99(d, 1H), 8.10(t, 1H), 8.56(d, 2H). | 444.1 |
| 724 | 2-(5-{1-[5-(3-Chloro-phenyl)-[1,2,4]oxadiazol-3-yl]-ethylsulfanyl}-4-ethyl-4H-[1,2,4]triazol-3-yl)-pyrimidine | 1.34(t, 3H), 1.94(d, 3H), 4.50(m, 2H), 5.26(q, 1H), 7.36(t, 1H), 7.46(t, 1H), 7.57(d, 1H), 7.99(m, 1H), 8.10(m, 1H), 8.92(d, 2H). | 414 |
| 725 | 4-(5-{1-[5-(3-Chloro-phenyl)-[1,2,4]oxadiazol-3-yl]-ethylsulfanyl}-4-ethyl-4H-[1,2,4]triazol-3-yl)-2-methoxy-pyridine | 1.32(t, 3H), 1.97(d, 3H), 3.99(s, 3H), 4.06(m, 2H), 5.19(q, 1H), 6.98(bs, 1H), 7.16(m, 1H), 7.47(t, 1H), 7.58(m, 1H), 7.98(dt, 1H), 8.10(m, 1H) 8.31(d, 1H). | 443.1 |
| 726 | 5-(5-{1-[5-(3-Chloro-phenyl)-[1,2,4]oxadiazol-3-yl]-ethylsulfanyl}-4-ethyl-4H-[1,2,4]triazol-3-yl)-2-methoxy-pyridine | 1.30(t, 3H), 1.96(d, 3H), 3.99(m, 2H), 4.00(s, 3H), 5.16(q, 1H), 6.87(d, 1H), 7.47(t, 1H), 7.58(m, 1H), 7.86(dd, 1H), 8.00(d, 1H), 8.11(t, 1H) 8.40(d, 1H). | 443 |
| 727 | 2-(5-{1-[5-(3-Chloro-phenyl)-[1,2,4]oxadiazol-3-yl]-ethylsulfanyl}-4-ethyl-4H-[1,2,4]triazol-3-yl)-5-methoxy-pyridine | 1.30(t, 3H), 1.93(d, 3H), 3.92(s, 3H), 4.52(m, 2H), 5.13(q, 1H), 7.32(dd, 1H), 7.46(t, 1H), 7.56(m, 1H), 7.99(dt, 1H), 8.10(t, 1H), 8.25(d, 1H) 8.30(d, 1H). | 443.1 |
| 728 | 3-(5-{1-[5-(3-Chloro-phenyl)-[1,2,4]oxadiazol-3-yl]-ethylsulfanyl}-4-ethyl-4H-[1,2,4]triazol-3-yl)-6-methoxy-pyridazine | 1.38(t, 3H), 1.96(d, 3H), 4.20(s, 3H), 4.61(m, 2H), 5.20(q, 1H), 7.12(d, 1H), 7.46(t, 1H), 7.56(t, 1H), 8.00(d, 1H), 8.10(s, 1H), 8.40(d, 1H) | 444 |
| 729 | 3-(5-{1-[5-(3-Chloro-phenyl)-[1,2,4]oxadiazol-3-yl]-ethylsulfanyl}-4-cyclopropyl-4H-[1,2,4]triazol-3-yl)-pyridine | 0.77(m, 2H), 1.14(m, 2H), 1.99(d, 3H), 3.22(m, 1H), 5.44(q, 1H), 7.45(m, 2H), 7.58(d, 1H), 8.02(d, 1H), 8.15(m, 2H), 8.72(d, 1H) 9.05(s, 1H). | |
| 730 | 4-{5-[3-(3-Chloro-phenyl)-[1,2,4]oxadiazol-5-ylmethylsulfanyl]-4-methyl-4H-[1,2,4]triazol-3-yl}-pyridine | 3.69(s, 3H) 4.73(s, 2H) 7.39(t, 1H) 7.47(m, 1H) 7.60(m, 2H) 7.92(m, 1H) 8.02(t, 1H) 8.79(m, 2H) | 384.91 |

Example 731

5-(3-Chloro-phenyl)-3-(5-furan-2-yl-4-isobutyl-4H-[1,2,4]triazol-3-ylsulfanylmethyl)-[1,2,4]oxadiazole The title compound was synthesized according to the method described by Graybill et al. Tetrahedron lett. 2002 43, 5305-5309 from furan-2-carboxylic acid hydrazide (55.2 mg, 0.44 mmol), 1-isothiocyanato-2-methyl-propane (47 ml, 0.38 mmol) and 3-chloromethyl-5-(3-chloro-phenyl)-[1,2,4]oxadiazole (45.0 mg, 0.20 mmol) with P-BEMP (136 mg, 0.30 mmol) as base. Purification by flash chromatography (33-66% EtOAc in heptane) gave the product as an oil (12.7 mg, 15.6%). 1H NMR (CDCl$_3$) d (ppm): 8.08 (s, 1H), 7.97 (d, 1H), 7.55 (d, 2H), 7.45 (t, 1H), 7.10 (d, 1H), 6.56 (d, 1H), 4.62 (s, 2H), 4.01 (d, 2H), 2.03 (m, 1H), 0.86 (d, 6H).

General: Thiophene-2-carbohydrazide (1.5 equiv) and an isothiocyanate (1.3 equiv) were dissolved in DMF (1 ml). 2-tert-Butylimino-2-diethylamino-1,3-dimethyl-perhydro-1,3,2-diazaphosporine (1 equiv) on polystyrene was added and the reactions were shaken on a Bohdan miniblock at ambient temperature for 1 h and then for one additional h at 45° C. The resin was washed with dioxane:water 1:1 several times. The ring closure was carried out at 85° C. for 48 h in dioxane:water 1:1 on the miniblock. The resin was washed with acetonitrile (2'2 ml). The 3-(chloromethyl)-5-(3-chlorophenyl)-1,2,4-oxadiazole was added to the reaction and shaken in acetonitrile at 50° C. for 2 h. The product was filtrated and purified on MS-directed prep-HPLC, gradient 0-100% acetonitrile over 15 min.

The following compounds were prepared analogously to Example 731:

| Example No. | Name | 1H NMR | MS |
|---|---|---|---|
| 732 | 5-(3-Chloro-phenyl)-3-[4-(3-methylsulfanyl-propyl)-5-thiophen-2-yl-4H-[1,2,4]triazol-3-ylsulfanylmethyl]-[1,2,4]oxadiazole | | 464.0 |
| 733 | 5-(3-Chloro-phenyl)-3-(4-hexyl-5-thiophen-2-yl-4H-[1,2,4]triazol-3-ylsulfanylmethyl)-[1,2,4]oxadiazole | | 460.0 |
| 734 | 5-(3-Chloro-phenyl)-3-(4-cyclopropylmethyl-5-thiophen-2-yl-4H-[1,2,4]triazol-3-ylsulfanylmethyl)-[1,2,4]oxadiazole | | 430.0 |
| 735 | 5-(3-Chloro-phenyl)-3-[4-(3-fluoro-benzyl)-5-thiophen-2-yl-4H-[1,2,4]triazol-3-ylsulfanylmethyl]-[1,2,4]oxadiazole | | 484.0 |
| 736 | 5-(3-Chloro-phenyl)-3-[4-(3-methyl-benzyl)-5-thiophen-2-yl-4H-[1,2,4]triazol-3-ylsulfanylmethyl]-[1,2,4]oxadiazole | | 480.0 |
| 737 | 5-(3-Chloro-phenyl)-3-[4-(2-methyl-butyl)-5-thiophen-2-yl-4H-[1,2,4]triazol-3-ylsulfanylmethyl]-[1,2,4]oxadiazole | | 446.0 |
| 738 | 5-(3-Chloro-phenyl)-3-[4-(3-methyl-butyl)-5-thiophen-2-yl-4H-[1,2,4]triazol-3-ylsulfanylmethyl]-[1,2,4]oxadiazole | | 446.0 |
| 739 | 5-(3-Chloro-phenyl)-3-[4-(2-fluoro-benzyl)-5-thiophen-2-yl-4H-[1,2,4]triazol-3-ylsulfanylmethyl]-[1,2,4]oxadiazole | | 484.0 |

Example 740

5-(3-Chloro-phenyl)-3-(4-ethyl-5-thiophen-2-yl-4H-[1,2,4]triazol-3-yloxymethyl)-[1,2,4]oxadiazole

[5-(3-Chloro-phenyl)-[1,2,4]oxadiazol-3-yl]-methanol (28.0 mg, 0.13 mmol), 4-ethyl-3-methanesulfonyl-5-thiophen-2-yl-4H-[1,2,4]triazole (35.2 mg, 0.13 mmol) and cesium carbonate (130 mg) were dissolved in dimethylformamide and stirred under argon at ambient temperatures for 46 h. After evaporation to dryness the crude was chromatographed on 12 g silica, heptane/ethyl acetate 4/1 to 2/1. Collection of the appropriate fractions gave after evaporation to dryness and drying in vacuo the title compound (17.0 mg, 33%). 1H NMR (CDCl$_3$), δ (ppm): 8.13 (m, 1H), 8.02 (m, 1H), 7.58 (m, 1H), 7.47 (m, 2H), 7.40 (dd, 1H), 7.14 (dd, 1H), 5.74 (s, 2H), 4.04 (q, 2H), 1.38 (t, 3H).

The following compounds were prepared analogously to Example 740:

| Example No. | Name | 1H NMR | MS |
|---|---|---|---|
| 741 | 4-{5-[5-(5-Chloro-2-fluoro-phenyl)-[1,2,4]oxadiazol-3-ylmethoxy]-4-methyl-4H-[1,2,4]triazol-3-yl}-pyridine | 8.92(s broad, 2H), 8.12(apparent dd, 1H), 7.78(s, 1H), 7.56(s broad, 2H), 7.25(apparent t, 1H), 5.79(s, 2H), 3.66(s, 3H). | 388 |
| 742 | 4-(5-{1-[5-(3-Chloro-phenyl)-[1,3,4]oxadiazol-2-yl]-ethoxy}-4-methyl-4H-[1,2,4]triazol-3-yl)-pyridine | 8.82(s broad, 2H), 8.07–7.94(m, 2H), 7.69(s broad, 2H), 7.47(m, 2H), 6.47(q, 1H), 3.63(s, 3H), 2.02(d, 3H). | 384.1 |
| 743 | 4-(5-{1-[3-(3-Chloro-phenyl)-isoxazol-5-yl]-ethoxy}-4-methyl-4H-[1,2,4]triazol-3-yl)-pyridine | 1.92(d, 3H), 3.57(s, 3H), 6.36(q, 1H), 6.74(s, 1H), 7.39(m, 2H), 7.60(m, 2H), 7.66(m, 1H), 7.78(m, 1H), 8.75(m, 2H) | 383.1 |

| Example No. | Name | 1H NMR | MS |
|---|---|---|---|
| 744 | 3-(5-{1-[5-(3-Chloro-phenyl)-[1,2,4]oxadiazol-3-yl]-ethoxy}-4-cyclopropyl-4H-[1,2,4]triazol-3-yl)-pyridine | | |

The following compounds were prepared analogously to Example 740 with the exception that sodium hydride was employed as the base and the reaction was heated at 80° C.:

| | | | |
|---|---|---|---|
| 745 | 4-{5-[5-(3-Chloro-phenyl)-[1,2,4]oxadiazol-3-ylmethoxy]-4-cyclopropyl-4H-[1,2,4]triazol-3-yl}-pyridine | 8.77(d, 2H), 8.17(s, 1H), 8.05(d, 1H), 7.79(d, 2H), 7.62(dd, 1H), 7.52(t, 1H), 5.79(s, 2H), 3.25(m, 1H), 1.14(d, 2H), 0.89(m, 2H) | |
| 746 | 4-{5-[5-(3-Chloro-phenyl)-isoxazol-3-ylmethoxy]-4-cyclopropyl-4H-[1,2,4]triazol-3-yl}-pyridine | 8.77(d, 2H), 7.79(m, 3H), 7.7(m, 1H), 7.44(m, 2H), 6.84(s, 1H), 5.71(s, 2H), 3.21(m, 1H), 1.13(d, 2H), 0.82(m, 2H) | |

Example 747

5-(2-Methoxy-phenyl)-3-(4-methyl-5-thiophen-2-yl-4H-[1,2,4]triazol-3-ylsulfanylmethyl)-[1,2,4]oxadiazole HBTU (171 mg, 0.45 mmol) and HOBT (8 mg, 0.06 mmol) were added to a solution of 2-methoxy benzoic acid (68 mg, 0.45 mmol) and DIPEA (192 ml, 1.11 mmol) in DMF (3 ml). After 10 min N-hydroxy-2-(4-methyl-5-thiophen-2-yl-4H-[1,2,4]triazol-3-ylsulfanyl)-acetamidine (100 mg, 0.37 mmol) was added. The reaction mixture was stirred at RT for 7 h and then at 110° C. over night. After cooling the reaction mixture was diluted with water and extracted with $CH_2Cl_2$. The organic phase was dried and concentrated. Flash chromatography (heptane/EtOAc 1:2) afforded 1.9 mg (11%) of the desired product.

1H NMR ($CDCl_3$), d (ppm): 7.99 (m, 1H), 7.53 (m, 1H), 7.50 (m, 1H), 7.47 (m, 1H), 7.16 (m, 1H), 7.04 (m, 2H), 4.52 (s, 2H), 3.94 (s, 3H), 3.71 (s, 3H).

The following compounds were prepared analogously to Example 747:

| Example No. | Name | 1H NMR | MS |
|---|---|---|---|
| 748 | 5-Furan-2-yl-3-(4-methyl-5-thiophen-2-yl-4H-[1,2,4]triazol-3-ylsulfanylmethyl)-[1,2,4]oxadiazole | 3.72(s, 3H) 4.52(s, 2H) 6.61(dd, 1H) 7.16(dd, 1H) 7.30(dd, 1H) 7.47(dd, 1H) 7.50 (dd, 1H) 7.67(dd, 1H) | 345.92 |
| 749 | 3-[3-(4-Methyl-5-thiophen-2-yl-4H-[1,2,4]triazol-3-ylsulfanylmethyl)-[1,2,4]oxadiazol-5-yl]-benzoic acid methyl ester | | 414.0 |
| 750 | 5-(2-Fluoro-phenyl)-3-(4-methyl-5-thiophen-2-yl-4H-[1,2,4]triazol-3-ylsulfanylmethyl)-[1,2,4]oxadiazole | | 374.0 |
| 751 | 5-(2,5-Difluoro-phenyl)-3-(4-methyl-5-thiophen-2-yl-4H-[1,2,4]triazol-3-ylsulfanylmethyl)-[1,2,4]oxadiazole | | 392.0 |
| 752 | 3-(4-Methyl-5-thiophen-2-yl-4H-[1,2,4]triazol-3-ylsulfanylmethyl)-5-(3-vinyl-phenyl)-[1,2,4]oxadiazole | | 382.1 |
| 753 | 5-(3-Difluoromethoxy-phenyl)-3-(4-methyl-5-thiophen-2-yl-4H-[1,2,4]triazol-3-ylsulfanylmethyl)-[1,2,4]oxadiazole | | 422.0 |
| 754 | 5-(4-Methoxy-thiophen-3-yl)-3-(4-methyl-5-thiophen-2-yl-4H-[1,2,4]triazol-3-ylsulfanylmethyl)-[1,2,4]oxadiazole | | 392.0 |
| 755 | 5-(2-Chloro-phenyl)-3-(4-methyl-5-thiophen-2-yl-4H-[1,2,4]triazol-3-ylsulfanylmethyl)-[1,2,4]oxadiazole | | 390.0 |
| 756 | 5-(4-Fluoro-phenyl)-3-(4-methyl-5-thiophen-2-yl-4H-[1,2,4]triazol-3-ylsulfanylmethyl)-[1,2,4]oxadiazole | | 374.0 |

Example 757

3-(3-Chloro-phenyl)-5-[1-(4-methyl-5-thiophen-2-yl-4H-[1,2,4]triazol-3-ylsulfanyl)-ethyl]-[1,2,4]oxadiazole DMF was added to a mixture of 2-(4-Methyl-5-thiophen-2-yl-4H-[1,2,4]triazol-3-ylsulfanyl)-propionic acid (50 mg, 0.186 mmol), 1-(3-dimethylaminopropyl)-3-ethylcarbodiimide hydrochloride (EDCI) (35.7 mg, 0.186 mmol), 1-hydroxybenzotriazole hydrate (HOBT) (28.5 mg, 0.186 mmol) and 3-chloro-N-hydroxy-benzamidine (29.3 mg, 0.172 mmol) at room temperature and stirred overnight. The reaction mixture was diluted lo with ethyl acetate (75 ml), washed with water 3 times, once with 1.0 M HCl (30 ml), saturated NaHCO$_3$ (30 ml) and saturated brine (30 ml), dried over anhydrous sodium sulfate, filtered and concentrated in vacuo. DMF (1 ml) was added to the residue and the resulting solution was heated at 135° C. for 3 h to effect cyclization to oxadiazole. After cooling the reaction mixture was diluted with ethyl acetate (75 ml), washed with water 3 times, once with 1.0 M HCl (30 ml), saturated NaHCO$_3$ (30 ml) and saturated brine (30 ml), dried over anhydrous sodium sulfate, filtered and concentrated in vacuo. The title compound (46.5 mg, 66.9%) was purified by SPE chromatography on silica gel using 50 ml 40%, 150 ml 50% ethyl acetate in hexanes. 1H NMR (CDCl$_3$), a (ppm): 8.03 (s, 1H), 7.92 (m, 1H), 7.47 (m, 4H), 7.18 (dd, 1H), 4.99 (q, 1H), 3.64 (s, 3H), 1.97 (d, 3H).

The following compounds were prepared analogously to Example 757:

| Example No. | Name | 1H NMR | MS |
|---|---|---|---|
| 758 | 3-(5-{1-[3-(3-Chloro-phenyl)-[1,2,4]oxadiazol-5-yl]-ethylsulfanyl}-4-methyl-4H-[1,2,4]triazol-3-yl)-pyridine | 8.88(d, 1H), 8.76(dd, 1H), 8.03(m, 2H), 7.93(d, 1H), 7.74(m, 3H), 5.09(m, 1H), 3.58(s, 3H), 2.00(d, 3H) | |

The following compounds were prepared analogously to Example 10:

| Example No. | Name |
|---|---|
| 759 | 5-(1-Chloro-ethyl)-3-(3-chloro-phenyl)-[1,2,4]oxadiazole |
| 760 | 3-(1-Chloro-ethyl)-5-m-tolyl-[1,2,4]oxadiazole |
| 761 | 3-(1-Chloro-ethyl)-5-(3-methoxy-phenyl)-[1,2,4]oxadiazole |
| 762 | 3-(1-Chloro-ethyl)-5-(2-chloro-5-methyl-phenyl)-[1,2,4]oxadiazole |
| 763 | 3-(1-Chloro-ethyl)-5-(2,5-difluoro-phenyl)-[1,2,4]oxadiazole |
| 764 | 3-(1-Chloro-ethyl)-5-(2-fluoro-5-methyl-phenyl)-[1,2,4]oxadiazole |
| 765 | 3-[3-(1-Chloro-ethyl)-[1,2,4]oxadiazol-5-yl]-benzonitrile |

The following compounds were prepared analogously to Example 40:

| Example No. | Name | 1H NMR | MS |
|---|---|---|---|
| 766 | 4-(5-{1-[5-(2-Chloro-5-methyl phenyl)-[1,2,4]oxadiazol-3-yl]-ethylsulfanyl}-4-methyl-4H-[1,2,4]triazol-3-yl)-pyridine | 8.74(d, 2H), 7.79(s, 1H), 7.57(dd, 2H), 7.38(d, 1H), 7.25(d, 1H), 5(q, 1H), 3.62(s, 3H), 2.33(s, 3H), 1.92(d, 3H) | |
| 767 | 4-(5-{1-[5-(2,5-Difluoro-phenyl)-[1,2,4]oxadiazol-3-yl]-ethylsulfanyl}-4-methyl-4H-[1,2,4]triazol-3-yl)-pyridine | 8.67(d, 2H), 7.7(m, 1H), 7.57(dd, 2H), 7.2(m, 2H), 5(q, 1H), 3.61(s, 3H), 1.87(d, 3H) | |
| 768 | 4-(5-{1-[5-(2-Fluoro-5-methyl phenyl)-[1,2,4]oxadiazol-3-yl]-ethylsulfanyl}-4-methyl-4H-[1,2,4]triazol-3-yl)-pyridine | 8.77(d, 2H), 7.85(m, 1H), 7.61(m, 2H), 7.38(m, 1H), 7.06(t, 1H), 5.02(q, 1H), 3.66(s, 3H), 2.37(s, 3H), 1.94(d, 3H) | |
| 769 | 4-(4-Cyclopropyl-5-{1-[5-(2-fluoro-5-methyl-phenyl)-[1,2,4]oxadiazol-3-yl]-ethylsulfanyl}-4H-[1,2,4]triazol-3-yl)-pyridine | 8.75(d, 2H), 7.9(m, 1H), 7.74(m, 2H), 7.38(m, 1H), 7.13(m, 1H), 5.45(q, 1H), 3.24(m, 1H), 2.39(s, 3H), 2(d, 3H), 1.15(m, 2H), 0.79(m, 2H) | |
| 770 | 3-{3-[1-(4-Methyl-5-pyridin-4-yl 4H-[1,2,4]triazol-3-ylsulfanyl)-ethyl]-[1,2,4]oxadiazol-5-yl}-benzonitrile | 8.76(dd, 2H), 8.4(s, 1H), 8.32(d, 1H), 7.87(d, 1H), 7.65(t, 1H), 7.59(m, 2H), 5.07(q, 1H), 3.67(s, 3H), 2.59(s, 2H), 1.91(d, 3H) | |
| 771 | 3-{3-[1-(4-Cyclopropyl-5-pyridin-4-yl-4H-[1,2,4]triazol-3-ylsulfanyl)-ethyl]-[1,2,4]oxadiazol-5-yl}-benzonitrile | 8.77(m, 2H), 8.42(d, 1H), 8.38(m, 1H), 7.9(m, 1H), 7.71(m, 3H), 5.49(q, 1H), 3.25(m, 1H), 2(d, 3H), 1.17(m, 2H), 0.81(m, 2H) | |

-continued

| Example No. | Name | 1H NMR | MS |
|---|---|---|---|
| 772 | 3-{1-[5-(3-Chloro-phenyl)-[1,3,4]oxadiazol-2-yl]-ethylsulfanyl}-5-pyridin-4-yl-[1,2,4]triazol-4-ylamine | 8.77(br s, 2H), 8.18(d, 2H), 7.98(s, 1H), 7.87(d, 1H), 7.52(d, 1H), 7.44(t, 1H), 5.66(s, 2H), 4.88(q, 1H), 1.98(d, 3H) | |

The following compounds were prepared analogously to Example 316:

| Example No. | Name |
|---|---|
| 773 | 3-[3-(3-Chloro-phenyl)-[1,2,4]oxadiazol-5-yl]-2-methyl-propionic acid hydrazide |
| 774 | Rac-3-[3-(3-Chloro-phenyl)-[1,2,4]oxadiazol-5-yl]-butyric acid hydrazide |

The following compounds were prepared analogously to Example 318:

| Example No. | Name |
|---|---|
| 775 | 2-[3-(3-Chloro-phenyl)-[1,2,4]oxadiazol-5-yl]-cyclopropanecarboxylic acid hydrazide |

Example 776

3-[3-(3-Chloro-phenyl)-[1,2,4]oxadiazol-5-yl]-2,2-dimethyl-propionic acid hydrazide 3,3-Dimethyl-dihydro-furan-2,5-dione (6.4 g) was heated at 50° C. in ethanol (150 mL) overnight. The solvent was removed in vacuo and the residue triturated with hexane to yield 2,2-Dimethyl-succinic acid 4-ethyl ester (4.66 g) which was used without further purification. t-Butanol (7.5 mL) was added to a mixture of 2,2-Dimethyl-succinic acid 4-ethyl ester (2.74 g, 15.7 mmol) in dichloromethane (62 mL) containing magnesium sulfate (7.5 g) and conc. sulfuric acid (0.85 mL) and the mixture was stirred at room temperature overnight. Saturated sodium bicarbonate solution was added and the product was extracted into dichloromethane, washed with brine solution, dried and concentrated to yield the diested as a colorloess oil (1.89 g). The ethyl ester was hydrolyzed by trating the crude sample with potassium hydroxide (2.75 g) in a mixture of ethanol (50 mL) and water (25 mL) at room temperatire for 2 h. The reaction was acidified using 1N HCl (aq) and extracted into ether, dried and concentrated to yield 2,2-Dimethyl-succinic acid 1-tert-butyl ester (1.4 g). This acid was treated under the conditions of Example 320 (step 1) to yield 3-[3-(3-Chloro-phenyl)-[1,2,4]oxadiazol-5-yl]-2,2-dimethyl-propionic acid tert-butyl ester (1.9 g). This t-Bu ester was deprotected using formic acid (19 mL) at 50° C. for 20 min. The crude product was concentrated and triturated with a mixture of ether and hexane to yield 3-[3-(3-Chloro-phenyl)-[1,2,4]oxadiazol-5-yl]-2,2-dimethyl-propionic acid (1.12 g). To a solution of 3-[3-(3-Chloro-phenyl)-[1,2,4]oxadiazol-5-yl]-2,2-dimethyl-propionic acid (561 mg, 2 mmol) and triethylamine (1.1 mL, 8 mmol) in THF (9 ml), isobutyl chloroformate (0.31 mL, 2.4 mmol) was added dropwise at −78° C. After being stirred for 1 h, hydrazine hydrate (1 mL, 11 mmol) was added. The reaction mixture was stirred at room temperature for 1 h and concentrated. A small amount of ice was added to quence any excess reagent and precipitate the product, which was collected by filtration to give 482 mg of the title compound.

The following compounds were prepared analogously to Example 320:

| Example No. | Name |
|---|---|
| 777 | (S)-{1-[3-(3-Chloro-phenyl)-[1,2,4]oxadiazol-5-yl]-2-hydrazinocarbonyl-ethyl}-carbamic acid tert-butyl ester |

Example 778

3-(3-Chloro-phenyl)-5-[2-(4-methyl-5-thiophen-2-yl-4H-[1,2,4]triazol-3-yl)-ethyl]-[1,2,4]oxadiazole Step 1: 3-[3-(3-Chloro-phenyl)-[1,2,4]oxadiazol-5-yl]-propionic acid (ethoxy-thiophen-2-yl-methylene)-hydrazide: 3-[3-(3-chloro-phenyl)-[1,2,4]oxadiazol-5-yl]-propionic acid hydrazide (266.69 mg, 1 mmol) was mixed with thiophene-2-carboximidic acid ethyl ester (191.6 mg, 1 mmol) in ethanol (6 ml) and stirred at room temperature overnight. The reaction was quenched with water, extracted with ethyl acetate, dried and concentrated in vacuo. The crude product was triturated with hexane to yield 3-[3-(3-Chloro-phenyl)-[1,2,4]oxadiazol-5-yl]-propionic acid (ethoxy-thiophen-2-yl-methylene)-hydrazide as a white solid (305 mg, 75%). 1H-NMR(CDCl$_3$) d(ppm): 8.99 (ws, 1H), 8.09 (s, 1H), 7.98 (d, 1H), 7.41(m, 4H), 7.08 (dd, 1H), 4.27 (q, 2H), 3.34 (m, 4H) and 1.41 (t, 3H). Step 2: 3-(3-Chloro-phenyl)-5-[2-(4-methyl-5-thiophen-2-yl-4H-[1,2,4]triazol-3-yl)-ethyl]-[1,2,4]oxadiazole: 3-[3-(3-chloro-phenyl)-[1,2,4]oxadiazol-5-yl]-propionic acid (ethoxy-thiophen-2-yl-methylene)-hydrazide (81 mg, 0.2 mmol) was mixed with 2M methylamine (0.3 ml in THF) in ethanol (2 ml) at 70~80° C. overnight. The reaction mixture was concentrated with silica gel and purified by column chromatography with 0.5~2.0% methanol in ethyl acetate to give 54 mg (72.5%) of 3-(3-chloro-phenyl)-5-[2-(4-methyl-5-thiophen-2-yl-4H-[1,2,4]triazol-3-yl)-ethyl]-[1,2,4]oxadiazole. 1H-NMR(CDCl$_3$) d (ppm): 8.08 (s, 1H), 7.97 (d, 1H), 7.41 (m, 4H), 7.20 (dd, 1H), 3.80 (s, 3H), 3.68 (dd, 2H), 3.38 (dd, 2H).

The following compounds were prepared analogously to Example 778:

| Example No. | Name | 1H NMR | MS |
|---|---|---|---|
| 779 | 3-(3-Chloro-phenyl)-5-[2-(4-ethyl-5-thiophen-2-yl-4H-[1,2,4]triazol-3-yl)-ethyl]-[1,2,4]oxadiazole | 8.08(s, 1H), 7.97(d, 1H), 7.47(m, 4H), 7.20(dd, 1H), 4.20(q, 2H), 3.72(dd, 2H), 3.38(dd, 2H) and 1.47(t, 3H) | |
| 780 | 5-(3-Chloro-phenyl)-3-(5-furan-2-yl-4-methyl-4H-[1,2,4]triazol-3-ylmethyl)-[1,2,4]oxadiazole | 8.11(s, 1H), 8.01(d, 1H), 7.61(s, 1H), 7.58(d, 1H), 7.48(t, 1H), 7.11(d, 1H), 6.59(m, 1H), 4.48(s, 2H) and 3.92(s, 3H) | |
| 781 | 2-(3-Chloro-phenyl)-5-[2-(5-furan-2-yl-4-methyl-4H-[1,2,4]triazol-3-yl)-ethyl]-[1,3,4]oxadiazole | 8.04(s, 1H), 7.93(d, 1H), 7.60(s, 1H), 7.52(d, 1H), 7.46(t, 1H), 7.06(d, 1H), 6.59(m, 1H), 3.87(s, 3H), 3.65(t, 2H) and 3.38(t, 2H) | |
| 782 | 2-(3-Chloro-phenyl)-5-[2-(4-ethyl-5-furan-2-yl-4H-[1,2,4]triazol-3-yl)-ethyl]-[1,3,4]oxadiazole | 8.05(s, 1H), 7.94(d, 1H), 7.60(s, 1H), 7.52(d, 1H), 7.47(t, 1H), 7.10(d, 1H), 6.59(m, 1H), 4.30(q, 2H), 3.67(t, 2H), 3.39(t, 2H) and 1.43(t, 3H) | |
| 783 | 2-(3-Chloro-phenyl)-5-[2-(4-cyclopropyl-5-furan-2-yl-4H-[1,2,4]triazol-3-yl)-ethyl]-[1,3,4]oxadiazole | 8.05(s, 1H), 7.94(d, 1H), 7.63(s, 1H), 7.52(d, 1H), 7.46(t, 1H), 7.01(d, 1H), 6.58(m, 1H), 3.67(dd, 2H), 3.51(t, 2H), 3.33(m, 1H) 1.25(m, 2H) and 0.93(m, 2H) | 383.12 |

Example 784

4-(5-{2-[3-(3-Chloro-phenyl)-[1,2,4]oxadiazol-5-yl]-ethyl}-4-methy-4H-[1,2,4]triazol-3-yl)-pyridine Step 1: Isonicotinic acid {4-[3-(3-chloro-phenyl)-[1,2,4]oxadiazol-5-yl]-1-ethoxy-butylidene}-hydrazide: 3-[3-(3-chloro-phenyl)-[1,2,4]oxadiazol-5-yl]-propionimidic acid ethyl ester hydrochloride (473.3, 1.5 mmol) was mixed with isonicotinic acid hydrazide (205.7 mg, 1.5 mmol) in ethanol (8 ml) at 60° C. for an h and then at room temperature for 2 h. The reaction mixture was diluted with dichloromethane and washed with water. The organic layer was dried, concentrated with vacuum and the residue was triturated with ether to give 490 mg (78.9%) of isonicotinic acid {4-[3-(3-chloro-phenyl)-[1,2,4]oxadiazol-5-yl]-1-ethoxy-butylidene}-hydrazide as white solid. Step 2: 4-(5-{2-[3-(3-Chloro-phenyl)-[1,2,4]oxadiazol-5-yl]-ethyl}-4-methyl-4H-[1,2,4]triazol-3-yl)-pyridine (47.1 mg, 82%) as white solid was obtained from isonicotinic acid {4-[3-(3-chloro-phenyl)-[1,2,4]oxadiazol-5-yl]-1-ethoxy-butylidene}-hydrazide (60 mg, 0.15 mmol) reacted with 2M methylamine (0.45 ml, 0.9 mmol) in ethanol (1 ml) at 60° C. overnight.

1H-NMR(CDCl$_3$) d(ppm): 8.77 (d, 2H), 8.02 (s, 1H), 7.91 (d, 1H), 7.58(d, 2H), 7.42 (m, 2H), 3.76 (s, 3H), 3.66 (t, 2H) and 3.38 (t, 2H).

The following compounds were prepared analogously to Example 784:

| Example No. | Name | 1H NMR | MS |
|---|---|---|---|
| 785 | 4-(5-{2-[3-(3-Chloro-phenyl)-[1,2,4]oxadiazol-5-yl]-ethyl}-4-ethyl-4H-[1,2,4]triazol-3-yl)-pyridine | 8.79(d, 2H), 8.05(s, 1H), 7.94(d, 1H), 7.58(d, 2H), 7.43(m, 2H), 4.16(q, 2H), 3.72(t, 2H), 3.40(t, 2H) and 1.44(t, 3H) | |
| 786 | 4-(5-{2-[3-(3-Chloro-phenyl)-[1,2,4]oxadiazol-5-yl]-ethyl}-4-cyclopropyl-4H-[1,2,4]triazol-3-yl)-pyridine | 8.77(d, 2H), 8.05(s, 1H), 7.93(d, 1H), 7.73(d, 2H), 7.44(m, 2H), 3.72(t, 3H), 3.51(t, 2H), 3.38(m, 1H), | |

| Example No. | Name | 1H NMR | MS |
|---|---|---|---|
| | | 1.23(m, 2H) and 0.79(m, 2H) | |

Example 787

4-(5-{2-[3-(3-Chloro-phenyl)-[1,2,4]oxadiazol-5-yl]-propyl}-4-cyclopropyl-4H-[1,2,4]triazol-3-yl)-pyridine Step 1: N-Cyclopropyl-isonicotinamide: Isonicotinic acid ethyl ester (3.0 g, 20 mmol) was mixed with cyclopropylamine (2 ml) at 120° C. in a sealed vial for 40 h. The reaction mixture was triturated with ether to give 1.62 g (50%) of N-cyclopropyl-isonicotinamide as off-white solid. 1H-NMR (CDCl$_3$) d (ppm): 8.73 (d, 2H), 7.60 (d, 2H) and 6.55 (w, 1H), 2.92 (m, 1H), 0.90 (m, 2H) and 0.66 (m, 2H). Step 2: N-Cyclopropyl-isonicotinimidoyl chloride hydrochloride: N-Cyclopropyl-isonicotinamide (1.62 g, 10 mmol) was reacted with SOCl2 (12 g, 100 mol) at 80° C. overnight. The reaction mixture was concentrated and triturated with dichloromethane to give 1.3 g (64%) of N-cyclopropyl-isonicotinimidoyl chloride hydrochloride as yellow solid. Step 3: 4-(5-{2-[3-(3-Chloro-phenyl)-[1,2,4]oxadiazol-5-yl]-propyl}-4-cyclopropyl-4H-[1,2,4]triazol-3-yl)-pyridine: (R)-3-[3-(3-Chloro-phenyl)-[1,2,4]oxadiazol-5-yl]-butyric acid hydrazide (56 mg, 0.2 mmol) was mixed with N-cyclopropyl-isonicotinimidoyl chloride hydrochloride (40.6 mg, 0.2 mmol) and K$_2$CO$_3$ (60 mg, 0.43 mmol) in DM (1 ml) at 100° C. for 3 h. The reaction mixture was dilute with dichloromethane and then washed with water. The organic layer was concentrated and purified with 5~6% methanol in ethyl acetate to give 32 mg (39%) of the title comound. 1H-NMR (CDCl$_3$) d (ppm): 8.78 (d, 2H), 8.05 (s, 1H), 7.96(d, 1H), 7.73(d, 2H), 7.45(m, 2H), 4.15 (q, 1H), 3.64 (dd, 1H), 3.31 (m, 2H), 1.68 (d, 3H), 1.25 (m, 2H) and 0.79 (m, 2H).

The following compounds were prepared analogously to Example 787: It should be noted that some reactions provided 1,3,4-oxadiazole cyclization products with loss of the methylamino or cycopropylamino group instead of or as well as the triazole product.

| Example No. | Name | 1H NMR | MS |
|---|---|---|---|
| 788 | 4-(5-{2-[3-(3-Chloro-phenyl)-[1,2,4]oxadiazol-5-yl]-2-methyl-propyl}-4-cyclopropyl-4H-[1,2,4]triazol-3-yl)-pyridine | 8.74(d, 2H), 8.04(s, 1H), 7.94(d, 1H), 7.67(d, 2H), 7.43(m, 2H), 3.48(s, 2H), 3.09(m, 1H), 1.75(s, 6H), 1.16(m, 2H) and 0.68(m, 2H) | |
| 789 | 4-(5-{2-[5-(3-Chloro-phenyl)-[1,3,4]oxadiazol-2-yl]-propyl}-4-cyclopropyl-4H-[1,2,4]triazol-3-yl)-pyridine | 8.76(w, 2H), 8.03(s, 1H), 7.92(d, 1H), 7.72(d, 2H), 7.44(m, 2H), 4.13(m, 1H), 3.72(dd, 1H), 3.43(m, 1H), 3.27(dd, 1H), 1.66(d, 3H), 1.25(m, 2H) and 0.79(m, 2H) | |
| 790 | 4-(5-{2-[3-(3-Chloro-phenyl)-[1,2,4]oxadiazol-5-yl]-1-methyl-ethyl}-4-cyclopropyl-4H-[1,2,4]triazol-3-yl)-pyridine | 8.78(d, 2H), 8.01(s, 1H), 7.91(d, 1H), 7.73(d, 2H), 7.49(d, 1H), 7.42(t, 1H), 3.99(m, 1H), 3.83(dd, 1H), 3.48(m, 1H), 3.39(m, 1H), 1.61(d, 3H), 1.25(m, 2H), 0.98(m, 1H), 0.74(m, 1H) | |
| 791 | cis-4-(5-{2-[3-(3-Chloro-phenyl)-[1,2,4]oxadiazol-5-yl]-cyclopropyl}-4-cyclopropyl-4H-[1,2,4]triazol-3-yl)-pyridine | 8.73(d, 2H), 7.88(s, 1H), 7.78(d, 1H), 7.65(d, 2H), 7.41(d, 1H), 7.34(t, 1H), 3.20(m, 1H), 2.89(m, 2H), 2.54(dd, 1H), 2.00(td, 1H), 1.20(m, 2H), 0.83(m, 2H) | |
| 792 | 4-(5-{2-[3-(3-Chloro-phenyl)-[1,2,4]oxadiazol-5-yl]-1,1-dimethyl-ethyl}-[1,3,4]oxadiazol-2-yl)-pyridine | 8.82(m, 2H), 7.98(s, 1H), 7.90(m, 3H), 7.47(d, 1H), 7.39(t, 1H), 3.51(s, 2H), 1.70(s, 6H) | |
| 793 | 4-(5-{2-[3-(3-Chloro-phenyl)-[1,2,4]oxadiazol-5-yl]-2-methyl-propyl}-[1,3,4]oxadiazol-2-yl)-pyridine | 8.76(d, 2H), 8.07(s, 1H), 7.97(d, 1H), 7.77(d, 2H), 7.49(dd, 1H), 7.43(t, 1H), 3.53(s, 2H), 1.69(s, 6H) | |

-continued

| Example No. | Name | 1H NMR | MS |
|---|---|---|---|
| 794 | 4-(5-{2-[3-(3-Chloro-phenyl)-[1,2,4]oxadiazol-5-yl]-1-methyl-ethyl}-[1,3,4]oxadiazol-2-yl)-pyridine | 8.82(d, 2H), 8.05(m, 1H), 7.95(d, 1H), 7.91(d, 2H), 7.50(dd, 1H), 7.42(t, 1H), 3.94(dd, 1H), 3.67(dd, 1H), 3.41(dd, 1H), 1.66(d, 3H) | |
| 795 | 4-(5-{2-[3-(3-Chloro-phenyl)-[1,2,4]oxadiazol-5-yl]-cyclopropyl}-[1,3,4]oxadiazol-2-yl)-pyridine | 8.77(d, 2H), 7.81(m, 4H), 7.42(d, 1H), 7.32(t, 1H), 3.07(q, 1H), 2.99(q, 1H), 2.41(q, 1H), 2.08(td, 1H) | |
| 796 | 4-(5-{2-[3-(3-Chloro-phenyl)-[1,2,4]oxadiazol-5-yl]-cyclopropyl}-4-methyl-4H-[1,2,4]triazol-3-yl)-pyridine | 8.76(d, 2H), 7.85(m, 1H), 7.77(d, 1H), 7.55(d, 2H), 7.44(dd, 1H), 7.34(t, 1H), 3.70(s, 3H), 2.89(m, 1H), 2.72(m, 1H), 2.51(q, 1H), 2.02(dt, 1H) | |
| 797 | 4-(5-{2-[5-(3-Chloro-phenyl)-[1,3,4]oxadiazol-2-yl]-propyl}-4-methyl-4H-[1,2,4]triazol-3-yl)-pyridine | 8.79(d, 2H), 8.02(s, 1H), 7.93(d, 1H), 7.59(d, 2H), 7.53(d, 1H), 7.46(t, 1H), 4.03(m, 1H), 3.80(s, 3H), 3.52(m, 1H), 3.23(dd, 1H), 1.66(d, 3H) | |
| 798 | 4-(5-{2-[3-(3-Chloro-phenyl)-[1,2,4]oxadiazol-5-yl]-propyl}-[1,3,4]oxadiazol-2-yl)-pyridine | 8.81(d, 2H), 8.07(s, 1H), 7.97(d, 1H), 7.87(d, 2H), 7.50(d, 1H), 7.43(t, 1H), 3.91(q, 1H), 3.66(dd, 1H), 3.44(dd, 1H), 1.65(d, 3H) | |
| 799 | 4-(5-{2-[3-(3-Chloro-phenyl)-[1,2,4]oxadiazol-5-yl]-propyl}-4-methyl-4H-[1,2,4]triazol-3-yl)-pyridine | 8.80(d, 2H), 8.05(s, 1H), 7.95(d, 1H), 7.61(d, 2H), 7.51(d, 1H), 7.45(t, 1H), 4.07(q, 1H), 3.75(s, 3H), 3.48(dd, 1H), 3.23(dd, 1H), 1.68(d, 3H) | |
| 800 | 4-(5-{2-[3-(3-Chloro-phenyl)-[1,2,4]oxadiazol-5-yl]-propyl}-4-cyclopropyl-4H-[1,2,4]triazol-3-yl)-pyridine | 8.78(d, 2H), 8.05(s, 1H), 7.96(d, 1H), 7.74(d, 2H), 7.50(dd, 1H), 7.46(t, 1H), 4.15(q, 1H), 3.64(dd, 1H), 3.31(m, 2H), 1.67(d, 3H), 1.25(m, 2H), 0.81(m, 2H) | |
| 801 | (S)-[1-[3-(3-Chloro-phenyl)-[1,2,4]oxadiazol-5-yl]-2-(4-cyclopropyl-5-pyridin-4-yl-4H-[1,2,4]triazol-3-yl)-ethyl]-carbamic acid tert-butyl ester | | |

Example 802

(S)-1-[3-(3-Chloro-phenyl)-[1,2,4]oxadiazol-5-yl]-2-(4-cyclopropyl-5-pyridin-4-yl-4H-[1,2,4]triazol-3-yl)-ethylamine (S)-[1-[3-(3-Chloro-phenyl)-[1,2,4]oxadiazol-5-yl]-2-(4-cyclopropyl-5-pyridin-4-yl-4H-[1,2,4]triazol-3-yl)-ethyl]-carbamic acid tert-butyl ester (135 mg) was mixed with 96% formic acid (1.3 mL) and heated at 50° C. for 1 h. The reaction mixture was concentrated in vacuo. The residue was quenched with saturated sodium bicarbonate and extracted with ethyl acetate. The organic layer was dried with sodium sulfate and concentrated. Purification was performed by flash column silica gel chromatography with 2-3% (2 M ammonia methanol) in dichloromethane to give 106 mg of the title compound as an off-white solid. 1H NMR (CDCl$_3$): d ppm 8.73 (d, 2H), 8.03 (s, 1H), 7.93 (d, 1H), 7.69 (d, 2H), 7.46 (d, 1H), 7.42 (t, 1H), 5.02 (dd, 1H), 3.61 (dd, 1H), 3.49 (dd, 1H), 3.35 (m, 1H), 2.47 (br s, 2H), 1.20 (m, 2H), 0.75 (m, 2H)

Example 803

(S)-[1-[3-(3-Chloro-phenyl)-[1,2,4]oxadiazol-5-yl]-2-(4-cyclopropyl-5-pyridin-4-yl-4H-[1,2,4]triazol-3-yl)-ethyl]-dimethyl-amine Sodium cyanoborohydride (0.1 mL, 1M in THF) was added to a solution of (S)-1-[3-(3-Chloro-phenyl)-[1,2,4]oxadiazol-5-yl]-2-(4-cyclopropyl-5-pyridin-4-yl-4H-[1,2,4]triazol-3-yl)-ethylamine (30 mg) in methanol (0.8 mL) containing 96% formic acid (0.1 mL) and 37% formalin solution (0.1 mL). The residue was quenched with water and extracted with ethyl acetate. The organic layer was dried with sodium sulfate and concentrated. Purification was performed by flash column silica gel chromatography with 3% (2 M ammnonia methanol) in dichloromethane to give 22 mg of the title compound. 1H NMR (CDCl$_3$): d ppm 8.76 (d, 2H), 8.06 (s, 1H), 7.97 (d, 1H), 7.73 (d, 2H), 7.47 (d, 1H), 7.45 (t, 1H), 5.00 (dd, 1H), 3.76 (dd, 1H), 3.51 (dd, 1H), 3.42 (m, 1H), 2.45 (br s, 6H), 1.26 (m, 2H), 0.88 (m, 1H), 0.79 (m, 1H)

Example 804

8-[5-(3-Chloro-phenyl)-[1,2,4]oxadiazol-3-ylmethyl]-3-pyridin-4-yl-5,6,7,8-tetrahydro-[1,2,4]triazolo[4,3-a]pyridine 37 mg (0.25 mmol) Me3OBF4 was added to a solution of 60 mg (0.21 mmol) 3-[5-(3-chloro-phenyl)-[1,2,4]oxadiazol-3-ylmethyl]-piperidin-2-one in 2 ml CH$_2$Cl$_2$. The mixture was stirred overnight at room temperature. The reaction mixture was diluted with CH$_2$Cl$_2$, washed with NaHCO3 (sat), dried and concentrated. The residue was dissolved in 3 ml EtOH and 22 mg (0.16 mmol) isonicotinic hydrazide was added. The solution was heated with microwaves at 120° C. for 10 min. The reaction mixture was cooled and the volatiles were removed under reduced pressure. The crude product was purified by preparative HPLC to afford 17 mg (20%) of the desired product. 1H NMR (CDCl$_3$): d ppm 1.75 (m, 1 H) 1.99 (m, 1 H) 2.21 (m, 2 H) 3.16 (dd, 1 H) 3.73 (m, 1 H) 3.85 (dd, 1 H) 4.07 (m, 1 H) 4.19 (m, 1 H) 7.47 (t, 1 H) 7.56 (m, 1 H) 7.67 (m, 2 H) 8.01 (m, 1 H) 8.11 m, 1 H) 8.76 (d, 2 H).

The following compounds were prepared analogously to Example 804:

Example 808

3-[3-(4-Methyl-5-thiophen-2-yl-4H-[1,2,4]triazol-3-ylsulfanylmethyl)-[1,2,4]oxadiazol-5-yl]-phenylamine To {3-[3-(4-Methyl-5-thiophen-2-yl-4H-[1,2,4]triazol-3-ylsulfanylmethyl)[1,2,4]oxadiazole 5-yl-phenyl}-carbamic acid tert-butyl ester (88.0 mg, 0.19 mmol) in dichloromethane (3 ml) at 0° C. added TFA (1.5 ml) and allowed to stir for 1 h. The reaction mixture was warmed to room temperature and the solvent was removed under vacuum. Dichloromethane was added to the resulting residue and the mixture was cooled to 0° C. and saturated sodium bicarbonate was added to the stirring solution until turning basic (pH~8). The mixture was then transferred to a separatory funnel and the product was extracted with dichloromethane, dried using anhydrous sodium sulfate, and concentrated in vacuo. The resulting residue was titurated with ether and 61.1 mg (87%) of 3-[3-(4-methyl-5-thiophen-2-yl-4H-[1,2,4]triazol-3-ylsulfanylmethyl)-[1,2,4]oxadiazol-5-yl]-phenylamine was isolated (light yellow solid). 1H NMR (DMSO-d6) d (ppm): 7.81 (d, 1H), 7.64 (d, 1H), 7.23 (m, 4H), 6.84 (d, 1H), 5.57 (s, 2H), 4.50 (s, 2H), 3.72 (s, 3H).

The following compounds were prepared analogously to Example 98:

| Example No. | Name | 1H NMR | MS |
|---|---|---|---|
| 805 | 8-[5-(3-Chloro-phenyl)-[1,2,4]oxadiazol-3-ylmethyl]-3-thiophen-2-yl-5,6,7,8-tetrahydro-[1,2,4]triazolo[4,3-a]pyridine | 1.69(m, 1H) 1.99(m, 1H) 2.18(m, 2H) 3.11(m, 1H) 3.67(m, 1H) 3.87(m, 1H) 4.02(m, 1H) 4.24(m, 1H) 7.15(m, 1H) 7.47(m, 3H) 7.56(m, 1H) 8.01(d, J=7.83Hz, 1H) 8.12(d, J=1.77Hz, 1H) | |
| 806 | 8-[5-(5-Chloro-2-fluoro-phenyl)-[1,2,4]oxadiazol-3-ylmethyl]-3-pyridin-4-yl-5,6,7,8-tetrahydro-[1,2,4]triazolo[4,3-a]pyridine | 1.76(m, 1H) 2.00(m, 1H) 2.21(m, 2H) 3.22(dd,, 1H) 3.74(m, 1H) 3.87(dd, 1H) 4.09(m, 1H) 4.19(m, 1H) 7.23(m, 1H) 7.53(m, 1H) 7.68(m, 2H) 8.10(dd, 1H) 8.77(m, 2H) | |

Example 807

5-(5-Bromo-4-methyl-4H-[1,2,4]triazol-3-ylsulfanylmethyl)-3-(3-chloro-phenyl)-[1,2,4]oxadiazole 3-(3-Chloro-phenyl)-5-(4-methyl-4H-[1,2,4]triazol-3-ylsulfanylmethyl)-[1,2,4]oxadiazole was mixed with 30 ml of chloroform/pyridine(25/1) at room temperature. Then bromine in chloroform (0.5 ml) was added dropwise and the reaction mixture was heated at 70° C. overnight. The reaction mixture was diluted with chloroform and washed with saturated NH$_4$Cl twice and the organic layer was dried with sodium sulfate, concentrated, the residue was triturated with diethyl ether to give the title compound (1.5 g, 57.5%, yellow solid). 1H-NMR(CDCl$_3$) d(ppm): 8.05 (s, 1H), 7.94 (d, 1H), 7.47(d, 1H), 7.43 (t, 1H), 4.66 (s, 2H) and 3.59 (s, 3H).

| Example No. | Name | 1H NMR | MS |
|---|---|---|---|
| 809 | 5-(3-Chloro-phenyl)-3-(4-methyl-5-thiophen-2-yl-4H-[1,2,4]triazole-3-sulfonylmethyl)-[1,2,4]oxadiazole | | 423.01 |
| 810 | 5-(3-Chloro-phenyl)-3-(4-methyl-5-thiophen-2-yl-4H-[1,2,4]triazole-3-sulfinylmethyl)-[1,2,4]oxadiazole | | |

The following compounds were prepared analogously to Example 93:

| Example No. | Name | 1H NMR | MS |
|---|---|---|---|
| 811 | 2-Methyl-6-[3-(4-methyl-5-thiophen-2-yl-4H-[1,2,4]triazol-3-ylsulfanylmethyl)-[1,2,4]oxadiazol-5-yl]-pyridine | | |

Example 812

4-(5-{1-[5-(3-Chloro-phenyl)-[1,2,4]oxadiazol-3-yl]-ethylsulfanyl}-4-ethyl-4H-[1,2,4]triazol-3-yl)-pyridin-2-ol HBr (1 ml) and HOAc (1 ml) were added to 4-(5-{1-[5-(3-Chloro-phenyl)-[1,2,4]oxadiazol-3-yl]-ethylsulfanyl}-4-ethyl-4H-[1,2,4]triazol-3-yl)-2-methoxy-pyridine (9 mg, 0.02 mmol) and the reaction was stirred at 80° C. on. Saturated NaHCO₃ (aq) was added to the reaction and the mixture was extracted three times with dichloromethane. The combined organic phases were dried and concentrated to give the title compound (8.5 mg, 99%). 1H NMR (CDCl₃), δ (ppm): 1.37 (t, 3 H), 1.96 (d, 3 H), 4.10 (q, 2 H), 5.23 (q, 1 H), 6.80 (m, 2 H), 7.49 (t, 2 H), 7.59 (m, 1 H), 7.99 (d, 1 H), 8.11 (s, 1 H).

Example 813

4-(5-{2-[5-(3-Chloro-phenyl)-[1,2,4]oxadiazol-3-yl]-propyl}-4-methy-4H-[1,2,4]triazol-3-yl)-pyridine 84 microl (0.21 mmol, 2.5 M) n-BuLi was added dropwise to a solution of 37 mg (0.21 mmol) 4-(4,5-dimethyl-4H-[1,2,4]triazol-3-yl)-pyridine in 2.1 ml THF at 0° C. After 20 min a solution of 60 mg (0.21 mmol) 3-(1-bromo-ethyl)-5-(3-chloro-phenyl)-[1,2,4]oxadiazole was added dropwise. The reaction mixture was allowed to reach room temperature and stirred over night. NH₄Cl(sat) was added and the mixture was extracted twice with EtOAc. The organic phase was dried and concentrated. Flashchromatography (CH₂Cl₂/MeOH 20:1) afforded 7.7 mg (10%) of the desired product. 1H NMR (CDCl₃), d (ppm): 1.57 (d, 3 H) 3.16 (m, 1 H) 3.38 (m, 1 H) 3.71 (s, 3 H) 3.84 (d, 1 H) 7.46 (t, 1 H) 7.55 (m, 1 H) 7.58 (m, 2 H) 7.98 (m, 1 H) 8.10 (t, 1 H) 8.77 (d, 2 H)

Example 814

[5-(3-Chloro-phenyl)-[1,2,4]oxadiazol-3-ylmethyl]-methyl-(4-methyl-5-pyridin-4-yl-4H-[1,2,4]triazol-3-yl)-amine 10 mg (0.4 mmol) NaH was added to a solution of 38 mg (0.2 mmol) methyl-(4-methyl-5-pyridin-4-yl-4H-[1,2,4]triazol-3-yl)-amine in 3 ml DMF under an atmosphere of nitrogen. After 10 min a solution of 50 mg (0.22 mmol) 3-chloromethyl-5-(3-chloro-phenyl)-[1,2,4]oxadiazole in 2 ml DMF was added. After stirring for 45 min NH₄Cl(sat) was added and the mixture was extracted twice with CHCl₃. The organic phase was dried and concentrated. Flashchromatography (CH₂Cl₂/MeOH 20:1) afforded 41 mg (54%) of the desired product. 1H NMR (CDCl₃), d (ppm): 3.07 (s, 3 H) 3.71 (s, 3 H) 4.56 (s, 2 H) 7.45 (m, 1 H) 7.55 (m, 1 H) 7.62 (d, 2 H) 7.98 (d, 1 H) 8.09 (m, 1 H) 8.73 (d, 2 H).

Example 815

8-[5-(3-Chloro-phenyl)-[1,2,4]oxadiazol-3-ylmethyl]-3-pyridin-4-yl-5,6,7,8-tetrahydro-[1,2,4]triazolo[4,3-a]pyrimidine 32 mg (1.31 mmol) NaH was added to a solution of 193 mg (0.96 mmol) 3-pyridin-4-yl-5,6,7,8-tetrahydro-[1,2,4]triazolo[4,3-a]pyrimidine in 10 ml DMF at room temperature. After 10 min 200 mg (0.87 mmol) 5-(3-chloro-phenyl)-3-chloromethyl-[1,2,4]oxadiazole was added to the reaction mixture. The reaction mixture was stirred at room temperature over night. The reaction mixture was diluted with NH₄Cl (sat) and extracted twice with EtOAc. The combined organic phases were washed with water, dried and concentrated. Flashchromatography (CH₂Cl₂/MeOH 20:1) afforded 111 mg (32%) of a white solid. 1H NMR (CDCl₃), d (ppm): 2.24 (m, 2 H) 3.57 (m, 2 H) 4.15 (m, 2 H) 5.01 (s, 2 H) 7.46 (t, 1 H) 7.56 (d, 1 H) 7.62 (d, 2 H) 7.99 (d, 1 H) 8.10 (s, 1 H) 8.70 (d, 2 H).

The following compounds were prepared analogously to Example 815:

| Example No. | Name | 1H NMR | MS |
|---|---|---|---|
| 816 | 8-[5-(5-Chloro-2-fluoro-phenyl)-[1,2,4]oxadiazol-3-ylmethyl]-3-pyridin-4-yl-5,6,7,8-tetrahydro-[1,2,4]triazolo[4,3-a]pyrimidine | | |
| 817 | 8-[5-(3-Chloro-phenyl)-[1,3,4]oxadiazol-2-ylmethyl]-3-pyridin-4-yl-5,6,7,8-tetrahydro-[1,2,4]triazolo[4,3-a]pyrimidine | | |
| 818 | 8-{1-[5-(3-Chloro-phenyl)-[1,3,4]oxadiazol-2-yl]-ethyl}-3-pyridin-4-yl-5,6,7,8-tetrahydro-[1,2,4]triazolo[4,3-a]pyrimidine | 1.81(d, 3H) 2.19(m, 2H) 3.47(m, 2H) 4.12(m, 2H) 6.07(q, 1H) 7.42(m, 1H) 7.49(m, 1H) 7.61(m, 2H) 7.91(m, 1H) 8.00(m, 1H) 8.70(m, 2H) | |
| 819 | 8-[5-(5-Chloro-2-fluoro-phenyl)-[1,2,4]oxadiazol-3-ylmethyl]-3-furan-2-yl-5,6,7,8-tetrahydro-[1,2,4]triazolo[4,3-a]pyrimidine | 2.23(m, 2H) 3.50(m, 2H) 4.20(m, 2H) 4.97(s, 2H) 6.49(m, 1H) 6.89(d, 1H) 7.19(t, 1H) 7.48(m, 1H) 7.51/m, 1H) 8.06(m, 1H) | |

| Example No. | Name | 1H NMR | MS |
|---|---|---|---|
| 820 | 8-{1-[5-(3-Chloro-phenyl)-[1,2,4]oxadiazol-3-yl]-ethyl}-3-pyridin-4-yl-5,6,7,8-tetrahydro-[1,2,4]triazolo[4,3-a]pyrimidine | 1.74(d, 3H) 2.17(m, 2H) 3.45(m, 2H) 4.10(m, 2H) 5.96(m, 1H) 7.44(t, 1H) 7.53(m, 1H) 7.59(m, 2H) 7.97(m, 1H) 8.08(m, 1H) 8.67(d, 2H) | |

Example 821

3-(4-Ethyl-5-thiophen-2-yl-4H-[1,2,4]triazol-3-ylsulfanylmethyl)-5-(1H-pyrrol-3-yl)-[1,2,4]oxadiazole 3-Chloromethyl-5-[1-(toluene-4-sulfonyl)-1H-pyrrol-3-yl]-[1,2,4]oxadiazole (50 mg) and potassium hydroxide (50 mg) was heated for two h in methanol (5 ml). The mixture was diluted with ethyl acetate (10 ml), washed with water and brine, dried over MgSO$_4$, filtered and concentrated. The title compound was isolated in 57% yield by flash chromatography on silica gel using 40% ethyl acetate in heptane. 1H NMR (CDCl$_3$) d (ppm): 9.8 (s, 1H), 7.5 (m, 2H), 7.4 (d, 1H), 7.2 (dd, 1H), 6.8 (m, 1H), 6.7 (d, 1H), 4.5 (s, 2H), 4.1 (q, 2H), 1.4 (t, 3H).

Example 822

4-{5-[5-(3-Chloro-phenyl)-[1,2,4]oxadiazol-3-ylmethylsulfanyl]-4-methyl-4H-[1,2,4]triazol-3-yl}-pyridine 1-oxide 4-{5-[5-(3-Chloro-phenyl)-[1,2,4]oxadiazol-3-ylmethylsulfanyl]-4-methyl-4H-[1,2,4]triazol-3-yl}-pyridine and wet 57%-86% MCPBA (52.4 mg, 0.20-0.30 mmol) were dissolved in dichloromethane (4 ml) and stirred for 16 h. The reaction mixture was purified via reversed phase preparative LC to give the title compound (7.5 mg, 8%). 1H NMR (CDCl$_3$), δ (ppm): 8.33 (d, 2 H), 8.06 (m, 1 H), 7.96 (m, 1 H), 7.67 (d, 2 H), 7.57 (m, 1 H), 7.46 (apparent t, 1 H), 4.60 (s, 2 H), 3.71 (s, 3 H).

Example 823

5-(3-Chloro-phenyl)-3-(2-furan-2-yl-3-methyl-3H-imidazol-4-ylsulfanylmethyl)-[1,2,4]oxadiazole 2-Furan-2-yl-3-methyl-3,5-dihydro-imidazol-4-one (described in Takeuchi, H., Hagiwara, S., Eguchi, S., Tetrahedron (1989) 6375-6386) (50 mg, 0.30 mmol) was dissolved in dioxane (3 ml) and Lawesson reagent (136 mg, 0.34 mmol) was added. The reaction mixture was heated to reflux over night and then allowed to room temperature at which time DIPEA (212 ml, 1.22 mmol) and 3-chloromethyl-5-(3-chloro-phenyl)-[1,2,4]oxadiazole (140 mg, 0.61 mmol) was added. The resulting mixture was heated to reflux for 5 h and then kept at room temperature over night. Ethyl acetate was added and the reaction mixture was washed with water followed by brine. The organic phase was dried over MgSO$_4$ and evaporated. The title compound (13 mg, 11%) was obtained by flash chromatography using 1% methanol in chloroform. 1H NMR (CD$_3$OD) d (ppm): 7.96 (m, 1H), 7.90 (m, 1H), 7.60 (dd, 1H), 7.57 (ddd, 1H), 7.46 (t, 1H), 7.09 (s, 1H), 6.86 (dd, 1H), 6.52 (dd, 1H), 3.95 (s, 2H), 3.74 (s, 3H).

Example 824

5-(5-Chloro-2-fluoro-phenyl)-3-[4-(2-fluoro-ethyl)-5-thiophen-2-yl-4H-[1,2,4]triazol-3-ylsulfanylmethyl]-[1,2,4]oxadiazole To a cooled (−15° C.) solution of 2-{3-[5-(5-chloro-2-fluoro-phenyl)-[1,2,4]oxadiazol-3-ylmethylsulfanyl]-5-thiophen-2-yl-[1,2,4]triazol-4-yl}-ethanol (46 mg, 0.11 mmol) in anhydrous THF (15 ml) was dropwise added DAST (32 ml, 0.24 mmol). The mixture was stirred at room temperature for 1.5 h and was then quenched with MeOH (1 ml). The solvent was removed under reduced pressure and the residue was partitioned between brine and EtOAc. The aqueous layer was extracted with EtOAc (2×20 ml). The combined organic layers were washed with brine (10 ml), dried (MgSO$_4$) and concentrated under reduced pressure. Purification by flash chromatography (EtOAc:heptane 2:1) and preparative HPLC afforded the title compound as a white solid (11 mg, 22%). 1H NMR (CDCl$_3$) d (ppm): 8.05 (dd, 1H), 7.52 (m, 3H), 7.20 (m, 1H), 7.16 (m, 1H), 4.75 (t, 1H), 4.63 (m, 3H), 4.45 (m, 2H).

Example 825

5-(5-Chloro-thiophen-3-yl)-3-(4-ethyl-5-furan-2-yl-4H-[1,2,4]triazol-3-ylsulfanylmethyl)-[1,2,4]oxadiazole The title compound was prepared according to method for 2-[5-(3-Methoxy-phenyl)-[1,2,4]oxadiazol-3-ylmethylsulfanyl]-1H-benzoimidazole, with the exception of using molar equivalent cesium carbonate instead of potassium carbonate as the base, from 1-[5-(5-chloro-thiophen-3-yl)-[1,2,4]oxadiazol-3-ylmethoxy]-1H-benzotriazole (32.3 mg, 0.097 mmol) and 4-ethyl-5-furan-2-yl-2,4-dihydro-[1,2,4]triazole-3-thione (23 mg) by using 50% EtOAc in n-heptane as chromatography eluent to yield 21 mg. 1H NMR (CDCl$_3$) d (ppm): 7.95 (d, 1H), 7.57 (dd, 1H), 7.44 (d, 1H), 7.07 (dd, 1H), 6.56 (dd, 1H), 4.56 (s, 2H), 4.22 (q, 2H), 1.35 (t, 3H).

Example 826

3-[3-(4-Ethyl-5-furan-2-yl-4H-[1,2,4]triazol-3-ylsulfanylmethyl)-[1,2,4]oxadiazol-5-yl]-4-hydroxy-benzonitrile The title compound was prepared using the general procedure of Rogers et al., Tetrahedron Letters (2002) 43: 3585-3587. To a stirring solution of 3-[3-(4-Ethyl-5-furan-2-yl-4H-[1,2,4]triazol-3-ylsulfanylmethyl)-[1,2,4]oxadiazol-5-yl]-4-fluoro-benzonitrile (20 mg, 0.050 mmol), 2-(methylsulfonylethanol) (9.38 mg, 0.075 mmol), and DMF (0.05 M) at 0° C. was added NaH (5.8 mg, 0.150 mmol). Stirred for 20 min and removed the ice bath. Stirred an additional 20 min while warming to room temperature. The reaction mixture was quenched with 1 N HCl solution and partitioned between ethyl acetate and brine. The organic layer was dried (Na$_2$SO$_4$), filtered and concentrated to dryness. The crude organics were purified by flash column chromatography using ethyl acetate followed by 5% methanol in ethyl acetate to give the title compound (8.1 mg, 41%, white solid). 1H NMR (CDCl$_3$), δ (ppm): 8.25 (m, 1H), 7.75 (m, 1H), 7.60 (s, 1H), 7.18 (m, 2H), 6.60 (m, 1H), 4.64 (s, 2H), 4.25 (q, 2H), 1.38 (t, 3H).

Pharmaceutical Examples

FLIPR Assay of Group I Receptor Antagonist Activity

For FLIPR analysis, cells were seeded on collagen coated clear bottom 96-well plates with black sides and analysis of [Ca$^{2+}$]$_i$ mobilization was performed 24 hours following seeding. Cell cultures in the 96-well plates were loaded with a 4 µM solution of acetoxymethyl ester form of the fluorescent calcium indicator fluor-3 (Molecular Probes, Eugene, Oreg.) in 0.01% pluronic. All assays were performed in a buffer containing 127 mM NaCl, 5 mM KCl, 2 mM MgCl$_2$, 0.7 mM NaH$_2$PO$_4$, 2 mM CaCl$_2$, 0.422 mg/ml NaHCO$_3$, 2.4 mg/ml HEPES, 1.8 mg/ml glucose and 1 mg/ml BSA Fraction IV (pH 7.4). FLIPR experiments were done using a laser setting of 0.800 W and a 0.4 second CCD camera shutter speed with excitation and emission wavelengths of 488 nm and 562 nm, respectively. Each FLIPR experiment was initiated with 160 µL of buffer present in each well of the cell plate. A 40 µL addition from the antagonist plate was followed by a 50 µL addition from the agonist plate. After each addition the fluorescence signal was sampled 50 times at 1 second intervals followed by 3 samples at 5 second intervals. Responses were measured as the peak height of the response within the sample period. EC$_{50}$/IC$_{50}$ determinations were made from data obtained from 8 point concentration response curves (CRC) performed in duplicate. Agonist CRC were generated by scaling all responses to the maximal response observed for the plate. Antagonist block of the agonist challenge was normalized to the average response of the agonist challenge in 14 control wells on the same plate.

Measurement of Inositol Phosphate (IP3) Turnover in Intact Whole Cells

GHEK stably expressing the human mGluR5d receptor were seeded onto 24 well poly-L-lysine coated plates at 40×10$^4$ cells/well in media containing 1 µCi/well [3H] myoinositol. Cells were incubated overnight (16 h), then washed three times and incubated for 1 hour at 37° C. in HEPES buffered saline (146 mM NaCl, 4.2 mM KCl, 0.5 mM MgCl$_2$, 0.1% glucose, 20 mM HEPES, pH 7.4) supplemented with 1 unit/ml glutamate pyruvate transaminase and 2 mM pyruvate. Cells were washed once in HEPES buffered saline and pre-incubated for 10 minutes in HEPES buffered saline containing 10 mM LiCl. Compounds (agonists) were added and incubated at 37° C. for 30 minutes. Antagonist activity was determined by pre-incubating test compounds for 15 minutes, then incubating in the presence of glutamate (80 µM) or DHPG (30 µM) for 30 minutes. The reaction was terminated by the addition of 0.5 ml perchloric acid (5%) on ice, with incubation at 4° C. for at least 30 minutes. Samples were collected in 15 ml Falcon tubes and inositol phosphates were separated using Dowex columns, as described below.

Assay for Inositol Phosphates Using Gravity-Fed Ion-Exchange Columns a) Preparation of Ion-Exchange Columns Ion-exchange resin (Dowex AG1-X8 formate form, 200-400 mesh, BIORAD) was washed three times with distilled water and stored at 4° C. 1.6 ml resin was added to each column and washed with 3 ml 2.5 mM HEPES, 0.5 mM EDTA, pH 7.4.

b) Sample Treatment

Samples were collected in 15 ml Falcon tubes and neutralized with 0.375 M HEPES, 0.75 M KOH. 4 ml of HEPES/EDTA (2.5/0.5 mM, pH 7.4) were added to precipitate the potassium perchlorate. Supernatant was added to the prepared Dowex columns.

c) Inositol Phosphate Separation

Elute glycero phosphatidyl inositols with 8 ml 30 mM ammonium formate. Elute total inositol phosphates with 8 ml 700 mM ammonium formate/100 mM formic acid and collect eluate in scintillation vials. Count eluate mixed with 8 ml scintillant.

Results

Typical IC$_{50}$ values as measured in the assays described above are 10 µM or less. In one aspect of the invention the IC$_{50}$ is below 2 µM. In another aspect of the invention the IC$_{50}$ is below 0.2 µM. In a further aspect of the invention the IC$_{50}$ is below 0.05 µM.

The invention claimed is:

1. A compound of formula I

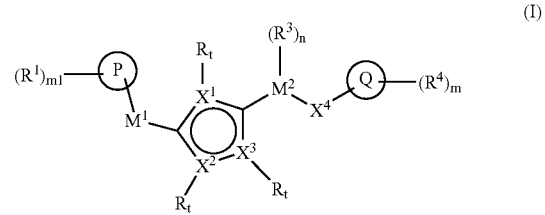

wherein:

P is phenyl, whereby the phenyl ring is substituted on position 3 or disubstituted on positions 2 and 5;

R$^1$ is attached to P via a carbon atom on ring P and is selected from the group consisting of hydrogen, hydroxy, halo, nitro, C$_{1-6}$alkylhalo, OC$_{1-6}$alkylhalo, C$_{1-6}$alkyl, OC$_{1-6}$alkyl, C$_{2-6}$alkenyl, OC$_{2-6}$alkenyl, C$_{2-6}$alkynyl, OC$_{2-6}$alkynyl, C$_{0-6}$alkylC$_{3-6}$cycloalkyl, OC$_{0-6}$alkylC$_{3-6}$cycloalkyl, C$_{0-6}$alkylaryl, OC$_{0-6}$alkylaryl, CHO, (CO)R$^5$, O(CO)R$^5$, O(CO)OR$^5$, O(CN)OR$^5$, C$_{1-6}$alkylOR$^5$, OC$_{2-6}$alkylOR$^5$, C$_{1-6}$alkyl(CO)R$^5$, OC$_{1-6}$alkyl(CO)R$^5$, C$_{0-6}$alkylCO$_2$R$^5$, OC$_{1-6}$alkylCO$_2$R$^5$, C$_{0-6}$alkylcyano, OC$_{2-6}$alkylcyano, C$_{0-6}$alkylNR$^5$R$^6$, OC$_{2-6}$alkylNR$^5$R$^6$, C$_{1-6}$alkyl(CO)NR$^5$R$^6$, OC$_{1-6}$alkyl(CO)NR$^5$R$^6$, C$_{0-6}$alkylNR$^5$(CO)R$^6$, OC$_{2-6}$alkylNR$^5$(CO)R$^6$, C$_{0-6}$alkylNR$^5$(CO)NR$^5$R$^6$, C$_{0-6}$alkylSR$^5$, OC$_{2-6}$alkylSR$^5$, C$_{0-6}$alkyl(SO)R$^5$, OC$_{2-6}$alkyl(SO)R$^5$, C$_{0-6}$alkylSO$_2$R$^5$, OC$_{2-6}$alkylSO$_2$R$^5$, C$_{0-6}$alkyl(SO$_2$)NR$^5$R$^6$, OC$_{2-6}$alkyl(SO$_2$)NR$^5$R$^6$, C$_{0-6}$alkylNR$^5$(SO$_2$)R$^6$, OC$_{2-6}$alkylNR$^5$(SO$_2$)R$^6$, C$_{0-6}$alkylNR$^5$(SO$_2$)NR$^5$R$^6$, OC$_{2-6}$alkylNR$^5$(SO$_2$)NR$^5$R$^6$, (CO)NR$^5$R$^6$, O(CO)NR$^5$R$^6$, NR$^5$OR$^6$, C$_{0-6}$alkylNR$^5$(CO)OR$^6$, OC$_{2-6}$alkylNR$^5$(CO)OR$^6$, SO$^3$R$^5$ and a 5- or 6-membered ring containing one or more atoms independently selected from the group consisting of C, N, O and S;

M¹ is a bond;
X¹ is C;
X² is selected from the group consisting of N, and O;
X³ is selected from the group consisting of N, and O;
where the ring containing X¹, X² and X³ forms an, isoxazole, chloro-isoxazole or a methyl-isoxazole;
R is selected from the group consisting of hydrogen, C$_{0-3}$alkyl, halo, C$_{0-3}$alkylOR$^5$, C$_{0-3}$alkylNR$^5$R$^6$, C$^{0-3}$alkyl(CO)OR$^5$ and C$_{0-3}$alkylaryl;
M² is selected from a group consisting of C$_{1-3}$alkyl, and C$_{2-3}$alkynyl;
R³ is selected from a group consisting of hydrogen, hydroxy, C$_{0-6}$alkylcyano, oxo, =NR$^5$, =NOR$^5$, C$_{1-4}$alkylhalo, halo, C$_{1-4}$alkyl, O(CO)C$_{1-4}$alkyl, C$_{1-4}$alkyl(SO)C$_{0-4}$alkyl, C$_{1-4}$alkyl(SO$_2$)C$_{0-4}$alkyl, (SO)C$_{0-4}$alkyl, (SO$_2$)C$_{0-4}$alkyl, OC$_{1-4}$alkyl, C$_{1-4}$alkylOR$^5$ and C$_{0-4}$alkylNR$^5$R$^6$;
X⁴ is wherein the bond between M² and X⁴ is a single bond;
Q is triazolyl, wherein any substitutable nitrogen atom in the ring is substituted with R⁴ on such nitrogen atom and any suitable carbon atom is optionally substituted with R⁴; and
R⁴ is selected from the group consisting of C$_{0-6}$alkylcyano, =NC$_{1-4}$alkyl, =NOR$^5$, C$_{1-4}$alkylhalo, halo, C$_{1-6}$alkyl, OC$_{1-4}$alkyl, C$_{2-4}$alkenyl, C$_{0-2}$alkylC$_{3-6}$cycloalkyl, C$_{0-6}$alkylaryl, C$_{0-6}$alkylheteroaryl, OC$_{0-6}$alkylaryl, OC$_{0-6}$alkylheteroaryl, NC$_{0-6}$alkylaryl, NC$_{0-6}$alkylheteroaryl, C$_{0-6}$alkylOaryl, C$_{0-6}$alkylOheteroaryl, C$_{0-6}$akylNaryl, C$_{0-6}$alkylNheteroaryl, OC$_{0-6}$alkylOaryl, OC$_{0-6}$alkylOheteroaryl, OC$_{0-6}$alkylNaryl, OC$_{0-6}$ alkylNheteroaryl, NC$_{0-6}$alkylOaryl, NC$_{0-6}$ alkylOheteroaryl, NC$_{0-6}$alkylNaryl, NC$_{0-6}$ alkylNheteroaryl, O(CO)C$_{1-4}$alkyl, C$_{0-4}$alkyl(CO)OC$_{1-4}$alkyl, C$_{1-4}$alkyl(S)C$_{0-4}$ alkyl, C$_{1-4}$alkyl(SO)C$_{0-4}$alkyl, C$_{1-4}$alkyl(SO$_2$)C$_{0-4}$ alkyl, (SO)C$_{0-4}$alkyl, (SO$_2$)C$_{0-4}$alkyl, C$_{1-4}$alkylOR$^5$, C$_{0-4}$alkylN(C$_{1-4}$alkyl)$_2$ and a 3- or 6-membered non-aromatic ring containing one or more atoms independently selected from C, N, O and S, which ring may optionally be fused with a 5-membered ring containing one or more atoms independently selected from the group consisting of C, N and O and wherein said ring and said fused ring may be substituted by one or two A; or
ii) selected from the group consisting of tetrahydrotriazolopyridyl, tetrahydrotriazolopyrimidinyl, and pyridonyl; and
R⁴ is selected from the group consisting of hydrogen, hydroxy, C$_{0-6}$alkylcyano, =NR$^5$, =NOR$^5$, C$_{1-4}$alkylhalo, halo, C$_{1-6}$alkyl, OC$_{1-4}$alkyl, OC$_{0-6}$alkylaryl, O(CO)C$_{1-4}$alkyl, C$_{0-4}$alkyl(S)C$_{0-4}$alkyl, C$_{1-4}$alkyl(SO)C$_{0-4}$alkyl, C$_{1-4}$alkyl(SO$_2$)C$_{0-4}$alkyl, (SO)C$_{0-4}$alkyl, (SO$_2$)C$_{0-4}$alkyl, C$_{1-4}$alkylOR$^5$, C$_{0-4}$alkylNR$^5$R$^6$ and a 5- or 6-membered ring containing one or more atoms independently selected from C, N, O and S, which ring may optionally be fused with a 5 or 6 membered ring containing one or more atoms independently selected from the group consisting of C, N and O and wherein said ring and said fused ring may be substituted by one or two A;
R⁵ and R⁶ are independently selected from the group consisting of hydrogen and C$_{1-6}$alkyl;
wherein any C$_{1-6}$alkyl defined under R¹, R² and R⁴ may be substituted by one or more A;
A is selected from the group consisting of hydrogen, hydroxy, halo, nitro, oxo, C$_{0-6}$alkylcyano, C$_{0-4}$alkylC$_{3-6}$cycloalkyl, C$_{1-6}$alkyl, C$_{1-6}$alkylhalo, OC$_{1-6}$alkylhalo, C$_{2-6}$alkenyl, C$_{0-3}$alkylaryl, C$_{0-6}$alkylOR$^5$, OC$_{2-6}$alkylOR$^5$, C$_{1-6}$alkylSR$^5$, OC$_{2-6}$alkylSR$^5$, (CO)R$^5$, O(CO)R$^5$, OC$_{2-6}$alkylcyano, OC$_{1-6}$alkylCO$_2$R$^5$, O(CO)OR$^5$, OC$_{1-6}$alkyl(CO)R$^5$, C$_{1-6}$alkyl(CO)R$^5$, NR$^5$OR$^6$, OC$_{2-6}$alkylNR$^5$R$^6$, C$_{0-6}$alkyl(CO)NR$^5$R$^6$, OC$_{1-6}$alkyl(CO)NR$^5$R$^6$, OC$_{2-6}$alkylNR$^5$(CO)R$^6$, C$_{0-6}$alkylNR$^5$(CO)R$^6$, C$_{0-6}$alkyl(CO)NR$^5$R$^6$, O(CO)NR$^5$R$^6$, C$_{0-6}$alkyl(SO$_2$)NR$^5$R$^6$, OC$_{2-6}$alkyl(SO$_2$)NR$^5$R$^6$, C$_{0-6}$alkylNR$^5$(SO$_2$)R$^6$, OC$_{2-6}$alkylNR$^5$(SO$_2$)R$^6$, SO$_3$R$^5$, C$_{1-6}$alkylNR$^5$(SO$_2$)NR$^5$R$^6$, OC$_{2-6}$alkyl(SO$_2$)R$^5$, C$_{0-6}$alkyl(SO$_2$)R$^5$, C$_{0-6}$alkyl(SO)R$^5$, OC$_{2-6}$alkyl(SO)R$^5$ and a 5-membered ring containing one or more atoms independently selected from the group consisting of C, N, O and S;
m1 is selected from 0, 1, 2, 3 and 4;
m2 is selected from 0, 1, 2 and 3;
n is selected from 0, 1 and 2; and
t is 0 or 1, and a salt thereof.

2. The compound according to claim 1, wherein P is phenyl substituted on position 3.

3. The compound according to claim 1, wherein P is phenyl disubstituted on positions 2 and 5.

4. The compound according to claim 1, wherein M² is C$_{1-3}$alkyl and R³ is hydrogen, methyl or dimethyl.

5. The compound according to claim 1, wherein R⁴ is selected from the group consisting of benzo[b]thiophenyl, benzodioxolyl, bromo, bromofuryl, butoxyphenyl, chloromethoxypyridyl, chlorophenyl, chlorophenylmethanol, chloropyridyl, chlorothiophene, cyanophenyl, cyclohexyl, cyclopentyl, dichloro-phenyl, dichloropyridyl, difluorophenyl, dimethylthiazolyl, ethanol, ethoxymethyl, fluoromethylphenyl, fluorophenyl, formic acid methyl ester, furyl, hydrogen, hydroxyphenoxymethyl, hydroxyphenyl, imidazolyl, methoxyethyl, methoxymethyl, methoxyphenoxymethyl, methoxyphenyl, methoxyphenylethyl, methoxypyridazinyl, methoxypyridyl, methoxypyrimidinyl, methoxythiophene, methylimidazolyl, methylpyridyl, methylsulfanylmethyl, methylthiazolyl, methylthiophene, nitrofuryl, nitrophenyl, phenyl, p-tolyloxymethyl, pyridazinyl, pyridine-oxidyl, benzylmorpholinyl, pyridinolyl, pyridyl, pyridylmethyl, pyrimidinyl, tert-butylphenyl, tetrahydrofuryl, thiazolyl, thiophene, tolyl, trifluoromethyl, acetic acid methylester, allyl, amino, benzyl, cyclopropylmethyl, ethyl, fluorobenzyl, fluoroethyl, furylmethyl, hydroxyethyl, isobutyl, methyl, methylbenzyl, methylbutyl, methylsulfanylpropyl, n-butyl, n-hexyl, n-propyl, tetrahydrofurylmethyl, thiophenylmethyl and trifluoroethyl.

6. The compound according to any one of claims 1-3, 4 and 5 wherein R¹ is selected from hydrogen, methyl, ethyl, cyclopropyl, hydroxy, methoxy, cyano, fluoro, chloro, bromo, iodo, trifluoromethyl, difluoromethoxy, trifluoromethoxy, amino, nitro, dimethylamino, methylsulfanyl, vinyl, acetyl, formic acid methyl ester, methoxymethyl, ethanol and furyl.

7. The compound according to any one of claims 1-3, 4 and 5 wherein m1 is 1.

8. The compound according to any one of claims 1-3, 4 and 5 wherein R³ is selected from hydrogen and C$_{1-4}$ alkyl.

9. The compound according to claim 8 wherein n is 0.

10. A compound which is selected from the group consisting of 4(5-{1-[3-(3Chloro-phenyl)-isoxazol-5-yl]ethylsulfanyl}-4-methyl-4H-[1,2,4]triazol-3-yl)-pyridine, 3-[5-(3-Chloro -phenyl)-isoxazol-3-ylmethylsulfanyl]-4-methyl-5-thiophen-2-yl-4H-[1,2,4]triazole, 4-{5-[5-(3-Chlorophenyl)-isoxazol-3-ylmethylsulfanyl]-4-methyl-4H-[1,2,4]triazol-3-yl}-pyridine, 3-[5-(3-Chloro-phenyl)-ixoxazol-3-ylmethylsulfanyl]-4-ethyl-5-thiophen-2-yl-4H-[1,2,4]triazole, 4-{5-[5-(3-Chloro-phenyl)-isoxazol-3-ylmethylsulfanyl]-4-ethyl-4H-[1,2,4]triazol-3-yl}pyridine, 4-{5-[3-(3-Chloro-phenyl)-isoxazol-5-ylmethylsulfanyl]-4-methyl-4H-[1,2,4]triazol-3-yl}-pyridine, 4-{5-[3-(3-Chlorophenyl)-isoxazol-5-ylmethylsulfanyl]-4-ethyl-4H-[1,2,4]triazol-3-yl}-pyridine, 3-[3-(3-Chloro-phenyl)-isoxazol-5-ylmethylsulfanyl]-4-ethyl-5-thiophen-2-yl-4H-[1,2,4]triazole, 3-[3-(3-Chloro-phenyl)-isoxazol-5-ylmethylsulfanyl]-4-ethyl-5-furan-2-yl-4H-[1,2,4]triazole, 4-{5-[5-(2-Fluoro-5-methyl-phenyl)-isoxazol-3-ylmethylsulfanyl]-4-methyl-4H-[1,2,4]triazol-3-yl}-pyridine, 4-{4-Ethyl-5-[5-(2-fluoro-5-methyl-phenyl)-isoxazol-3-ylmethylsulfanyl]-4H-[1,2,4]triazol-3-yl}-pyridine, 4-Ethyl-3-[5-(2-fluoro-5-methyl-phenyl)-isoxazol-3-ylmethylsulfanyl]-5-thiophen-2-yl-4H-[1,2,4]triazole, 4-Ethyl-3-[5-(2-fluoro-5-methyl-phenyl)-isoxazol-3-ylmethylsulfanyl]-5-furan-2-yl-4H-[1,2,4]triazole, 3-[5-(3-Chloro-phenyl)-isoxazol-3-ylmethylsulfanyl]-4-ethyl-5-trifluoromethyl-4H-[1,2,4]triazole, 4-Ethyl-3-(5-thiophen-3-yl-isoxazol-3-ylmethylsulfanyl)-5-trifluoromethyl-4H-[1,2,4]triazole, 3-{1-[5-(3-Chloro-phenyl)-isoxazol-3-yl]-ethylsulfanyl}-4-ethyl-5-furan-2-yl-4H-[1,2,4]triazole, 4-(5-{1-[5-(3-Chloro-phenyl)-isoxazol-3-yl]-ethylsulfanyl}-4ethyl-4H-[1,2,4]triazol-3-yl)-pyridine, 4-Ethyl-3-{1-[5-(2-fluoro-5-methyl-phenyl)-isoxazol-3-yl]-ethylsulfanyl}-5-furan-2-yl-4H-[1,2,4]triazole, 4-(4Ethyl-5-{1-[5-(2-fluoro-5-methyl-phenyl)-isoxazol-3-yl]-ethylsulfanyl}-4H-[1,2,4]triazol-3-yl)-pyridine, 4-{5-[5-(3-Chloro-phenyl)-4-methyl-isoxazol-3-ylmethylsulfanyl]-4-ethyl-4H-[1,2,4]triazol-3-yl}-pyridine, 3-[5-(3-Chloro-phenyl)-4-methyl-isoxazol-3-ylmethylsulfanyl]-4-ethyl-5-furan-2-yl-4H-[1,2,4]triazole, 4-{5-[4-Chloro-5-(3-chloro-phenyl)-isoxazol-3-ylmethylsulfanyl]-4-ethyl-4H-[1,2,4]triazol-3-yl}pyridine, 3-[4-Chloro-5-(3-chloro-phenyl)-isoxazol-3-ylmethylsulfanyl]-4-ethyl-5-furan-2-yl-4H-[1,2,4]triazole, 4-Ethyl-3-(5-phenyl-isoxazol-3-ylmethylsulfanyl)-5-thiophen-2-yl-4H-[1,2,4]triazole, 4-Methyl-3-(5-phenyl-isoxazol-3-ylmethylsulfanyl)-5-thiophen-3-yl-4H-[1,2,4]triazole, 4-Ethyl-3-furan-2-yl-5-(5-phenyl-isoxazol-3-ylmethylsulfanyl)-4H-[1,2,4]triazole, 4-[4-Ethyl-5-(5-phenyl-isoxazol-3-ylmethylsulfanyl)-4H-[1,2,4]triazol-3-yl]-pyridine, 4-[4-Methyl-5-(5-phenyl-isoxazol-3-ylmethylsulfanyl)-4H-[1,2,4]triazol-3-yl]-pyridine, 4-{5-[5-(3-Chloro-phenyl)-isoxazol-3-ylmethylsulfanyl]-4-cyclopropyl-4H-[1,2,4]triazol-3-yl}-pyridine, 3-[5-(3-Chloro-phenyl)-isoxazol-3-ylmethylsulfanyl]-4-ethyl-5-(4-methoxy-phenyl)-4H-[1,2,4]triazole, 4-{5-[5-(5-Chloro-2-fluoro-phenyl)-isoxazol-3-ylmethylsulfanyl]-4-ethyl-4H-[1,2,4]triazol-3-yl}-pyridine, 4-(5-{1-[5-(5-Chloro-2-fluoro-phenyl)-isoxazol-3-yl]-ethylsulfanyl}-4-ethyl-4H-[1,2,4]triazol-3-yl)-pyridine, 4-{5-[5-(5-Chloro-2-fluoro-phenyl)-isoxazol-3-ylmethylsulfanyl]-4-methyl-4H-[1,2,4]triazol-3-yl}-pyridine, 4-(5-{1-[5-(5-Chloro-2-fluoro-phenyl)-isoxazol-3-yl]ethylsulfanyl}-4-methyl-4H-[1,2,4]triazol-3-yl)-pyridine,4-{5-[5-(5-Chloro-2fluoro-phenyl)-isoxazol-3-ylmethylsulfanyl]-4-cyclopropyl-4H-[1,2,4]triazol-3-yl}-pyridine, 4-(5-{1-[5-(5-Chloro-2-fluoro-phenyl)-isoxazol-3-yl]-ethylsulfanyl}-4-cyclopropyl-4H-[1,2,4]triazol-3-yl)-pyridine, 3-[5-(5-Chloro-2-fluoro-phenyl)-isoxazol-3-ylmethylsulfanyl]-4-ethyl-5-furan-2yl-4H-[1,2,4]triazole, 3-{1-[5-(5-Chloro-2-fluoro-phenyl)-isoxazol-3-yl]-ethylsulfanyl}-4-ethyl-5-furan-2-yl-4H-[1,2,4]triazole, 4-(4-Cyclopropylmethyl-5-{1-[5-(2-fluoro-5-methyl-phenyl)-isoxazol-3-yl]-ethylsulfanyl}-4H-[1,2,4]triazol-3-yl)pyridine, and 4-(5-{1-[3-(3-Chloro-phenyl)-isoxazol-5-yl]-ethoxy}-4-methyl-4H-[1,2,4]triazol-3-yl)-pyridine or a salt thereof.

11. A pharmaceutical formulation comprising as active ingredient a therapeutically effective amount of a compound according to any one of claims 1 and 10 in association with one or more pharmaceutically acceptable diluent, excipients and/or inert carrier.

* * * * *

UNITED STATES PATENT AND TRADEMARK OFFICE
CERTIFICATE OF CORRECTION

PATENT NO.       : 7,456,200 B2
APPLICATION NO.  : 11/274611
DATED            : November 25, 2008
INVENTOR(S)      : Jalaj Arora et al.

Page 1 of 2

It is certified that error appears in the above-identified patent and that said Letters Patent is hereby corrected as shown below:

Column 200,
Claim 1, lines 32-40 delete

"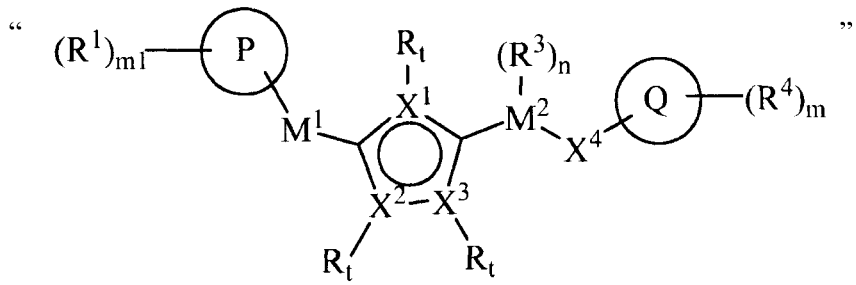"

and insert

-- 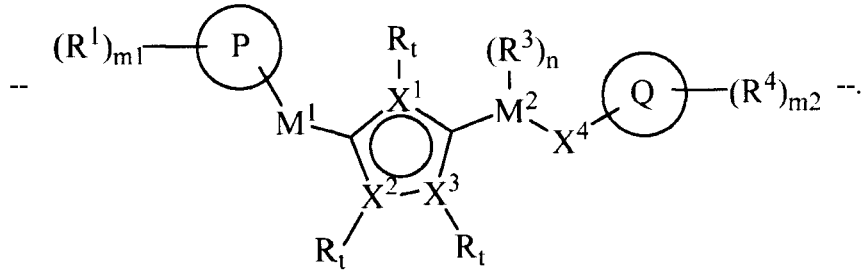 --.

Column 201,
Line 9, delete "$C^{0-3}alkyl(CO)OR^5$" and insert -- $C_{0-3}alkyl(CO)OR^5$ --.

Line 18, delete "$X^4$ is wherein" and insert -- $X^4$ is O, wherein --.

Line 22, delete "and".

Lines 28-29, delete "$C_{0-6}akylNaryl$," and insert -- $C_{0-6}alkylNaryl$, --.

Signed and Sealed this

Twenty-third Day of November, 2010

David J. Kappos
*Director of the United States Patent and Trademark Office*

CERTIFICATE OF CORRECTION (continued)
U.S. Pat. No. 7,456,200 B2

Lines 42-57, delete
"or
    ii) selected from the group consisting of tetrahydrotriazolopyridyl, tetrahydrotriazolopyrimidinyl, and pyridonyl; and
    $R^4$ is selected from the group consisting of hydrogen, hydroxy, $C_{0-6}$alkylcyano, $=NR^5$, $=NOR^5$, $C_{1-4}$alkylhalo, halo, $C_{1-6}$alkyl, $OC_{1-4}$alkyl, $OC_{0-6}$alkylaryl, $O(CO)C_{1-4}$alkyl, $C_{0-4}$alkyl(S)$C_{0-4}$alkyl, $C_{1-4}$alkyl(SO)$C_{0-4}$alkyl, $C_{1-4}$alkyl(SO$_2$)$C_{0-4}$alkyl, (SO)$C_{0-4}$alkyl, (SO$_2$)$C_{0-4}$alkyl, $C_{1-4}$alkylOR$^5$, $C_{0-4}$alkylNR$^5$R$^6$ and a 5- or 6-membered ring containing one or more atoms independently selected from C, N, O and S, which ring may optionally be fused with a 5 or 6 membered ring containing one or more atoms independently selected from the group consisting of C, N and O and wherein said ring and said fused ring may be substituted by one or two A;".